United States Patent
Jia et al.

(10) Patent No.: US 12,024,517 B2
(45) Date of Patent: Jul. 2, 2024

(54) SALTS OF AN FGFR INHIBITOR

(71) Applicant: Incyte Corporation, Wilmington, DE (US)

(72) Inventors: Zhongjiang Jia, Kennett Square, PA (US); Jiacheng Zhou, Newark, DE (US); Qun Li, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 85 days.

(21) Appl. No.: 17/503,513

(22) Filed: Oct. 18, 2021

(65) Prior Publication Data

US 2022/0153740 A1    May 19, 2022

Related U.S. Application Data

(63) Continuation of application No. 16/402,534, filed on May 3, 2019, now Pat. No. 11,174,257.

(60) Provisional application No. 62/667,040, filed on May 4, 2018.

(51) Int. Cl.
*C07D 471/14*    (2006.01)
*A61P 35/00*    (2006.01)

(52) U.S. Cl.
CPC .......... *C07D 471/14* (2013.01); *A61P 35/00* (2018.01); *C07B 2200/13* (2013.01)

(58) Field of Classification Search
CPC .................................................. C07D 471/14
See application file for complete search history.

(56) References Cited

U.S. PATENT DOCUMENTS

| | | | |
|---|---|---|---|
| 850,370 | A | 4/1907 | Hynes |
| 3,894,021 | A | 7/1975 | Denzel et al. |
| 4,271,074 | A | 6/1981 | Lohmann et al. |
| 4,339,267 | A | 7/1982 | Levitt |
| 4,347,348 | A | 8/1982 | Chernikhov et al. |
| 4,402,878 | A | 9/1983 | D'Alelio et al. |
| 4,405,519 | A | 9/1983 | D'Alelio et al. |
| 4,405,520 | A | 9/1983 | D'Alelio et al. |
| 4,405,786 | A | 9/1983 | D'Alelio et al. |
| 4,460,773 | A | 7/1984 | Suzuki et al. |
| 4,874,803 | A | 10/1989 | Baron et al. |
| 4,940,705 | A | 7/1990 | Boshagen et al. |
| 5,159,054 | A | 10/1992 | Keller |
| 5,240,941 | A | 8/1993 | Bruneau |
| 5,480,887 | A | 1/1996 | Hornback et al. |
| 5,521,184 | A | 5/1996 | Zimmermann et al. |
| 5,536,725 | A | 7/1996 | Cullen et al. |
| 5,541,324 | A | 7/1996 | TenBrink et al. |
| 5,760,068 | A | 6/1998 | Talley et al. |
| 5,783,577 | A | 7/1998 | Houghten et al. |
| 5,845,025 | A | 12/1998 | Garito et al. |
| 5,994,364 | A | 11/1999 | Njoroge et al. |
| 6,465,484 | B1 | 10/2002 | Bilodeau et al. |
| 6,998,408 | B2 | 2/2006 | Pinto |
| 7,074,801 | B1 | 7/2006 | Yoshida et al. |
| 7,125,880 | B1 | 10/2006 | Chen |
| 7,488,802 | B2 | 2/2009 | Collins et al. |
| 7,589,101 | B2 | 9/2009 | Okram et al. |
| 7,618,975 | B2 | 11/2009 | Cai et al. |
| 7,642,255 | B2 | 1/2010 | Sim |
| 7,648,973 | B2 | 1/2010 | DeLuca et al. |
| 7,846,923 | B2 | 12/2010 | Ren et al. |
| 7,868,018 | B2 | 1/2011 | Xie et al. |
| 7,943,743 | B2 | 5/2011 | Korman et al. |
| 8,008,449 | B2 | 8/2011 | Korman et al. |
| 8,119,655 | B2 | 2/2012 | Dong et al. |
| 8,168,757 | B2 | 5/2012 | Finnefrock et al. |
| 8,183,248 | B2 | 5/2012 | Nagle et al. |
| 8,217,149 | B2 | 7/2012 | Irving et al. |
| 8,426,411 | B2 | 4/2013 | Wishart et al. |
| 8,461,328 | B2 | 6/2013 | Babu et al. |
| 8,759,398 | B2 | 1/2014 | Nelson |
| 8,754,114 | B2 | 6/2014 | Yao et al. |
| 8,889,711 | B2 | 11/2014 | Bedjeguelal |
| 9,266,892 | B2 | 2/2016 | Zhuo et al. |
| 9,388,185 | B2 | 7/2016 | Lu et al. |
| 9,440,976 | B2 | 9/2016 | Dyke et al. |
| 9,533,954 | B2 | 1/2017 | Yao et al. |
| 9,533,984 | B2 | 1/2017 | Sun et al. |
| 9,580,423 | B2 | 2/2017 | Lu et al. |
| 9,611,267 | B2 | 4/2017 | Wu et al. |
| 9,708,318 | B2 | 7/2017 | Lu et al. |
| 9,745,311 | B2 | 8/2017 | Lu et al. |
| 9,801,889 | B2 | 10/2017 | Lu et al. |
| 9,890,156 | B2 | 2/2018 | Lu et al. |
| 10,016,348 | B2 | 7/2018 | Lu et al. |
| 10,040,790 | B2 | 8/2018 | Sun et al. |
| 10,131,667 | B2 | 11/2018 | Wu et al. |
| 10,208,024 | B2 | 2/2019 | Andrews et al. |
| 10,213,427 | B2 | 2/2019 | Yao et al. |
| 10,214,528 | B2 | 2/2019 | Lu et al. |
| 10,251,892 | B2 | 4/2019 | Sokolsky et al. |
| 10,308,644 | B2 | 6/2019 | Wu et al. |
| 10,350,240 | B2 | 6/2019 | Gore et al. |
| 10,357,431 | B2 | 7/2019 | Staric et al. |

(Continued)

FOREIGN PATENT DOCUMENTS

| | | |
|---|---|---|
| CL | 2014003355 | 6/2015 |
| CL | 2015002628 | 8/2016 |

(Continued)

OTHER PUBLICATIONS

Adib et al., "FGFR2/3 genomic alterations and response to Enfortumab Vedotin in metastatic urothelial carcinoma," BJUI Compass., 2022, 3:169-172.

(Continued)

*Primary Examiner* — Rebecca L Anderson
(74) *Attorney, Agent, or Firm* — Fish & Richardson P.C.

(57) ABSTRACT

The present invention relates to salt forms of the Fibroblast Growth Factor Receptors (FGFR) inhibitor 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one, including methods of preparation thereof, where the compound is useful in the treatment of FGFR mediated diseases such as cancer.

10 Claims, 41 Drawing Sheets

Specification includes a Sequence Listing.

(56) References Cited

U.S. PATENT DOCUMENTS

| | | |
|---|---|---|
| 10,450,313 B2 | 10/2019 | Lu et al. |
| 10,611,762 B2 | 4/2020 | Jia et al. |
| 10,632,126 B2 | 4/2020 | Lu et al. |
| 10,738,048 B2 | 8/2020 | Lu et al. |
| 10,813,930 B2 | 10/2020 | Yao et al. |
| 10,851,105 B2 | 12/2020 | Wu et al. |
| 10,947,230 B2 | 3/2021 | Sun et al. |
| 11,014,923 B2 | 5/2021 | Lu et al. |
| 11,053,246 B2 | 7/2021 | Wu et al. |
| 11,173,162 B2 | 11/2021 | Sokolsky et al. |
| 11,174,257 B2 | 11/2021 | Jia et al. |
| 11,407,750 B2 | 8/2022 | Tao et al. |
| 11,466,004 B2 | 10/2022 | Burn |
| 11,472,801 B2 | 10/2022 | Pan et al. |
| 11,530,214 B2 | 12/2022 | Lu et al. |
| 11,628,162 B2 | 4/2023 | Ji et al. |
| 11,667,635 B2 | 6/2023 | Lu et al. |
| 2003/0078255 A1 | 4/2003 | Pinto |
| 2003/0078277 A1 | 4/2003 | Hibi et al. |
| 2003/0181622 A1 | 9/2003 | Chiu et al. |
| 2004/0044012 A1 | 3/2004 | Dobrusin et al. |
| 2004/0067948 A1 | 4/2004 | Hallett |
| 2004/0097493 A1 | 5/2004 | Chen et al. |
| 2004/0122029 A1 | 6/2004 | Liu et al. |
| 2004/0127538 A1 | 7/2004 | Oinuma et al. |
| 2004/0204427 A1 | 10/2004 | Chen et al. |
| 2005/0009876 A1 | 1/2005 | Bhagwat et al. |
| 2005/0070542 A1 | 3/2005 | Hodgetts et al. |
| 2005/0148603 A1 | 7/2005 | Jimenez et al. |
| 2005/0197340 A1 | 9/2005 | Arora et al. |
| 2005/0222171 A1 | 10/2005 | Bold et al. |
| 2006/0222637 A1 | 10/2006 | Bamdad |
| 2006/0270849 A1 | 11/2006 | Nishino et al. |
| 2007/0116984 A1 | 5/2007 | Park et al. |
| 2007/0197510 A1 | 8/2007 | Ohmoto et al. |
| 2007/0225286 A1 | 9/2007 | Ren et al. |
| 2007/0280943 A1 | 12/2007 | Friedman et al. |
| 2008/0221098 A1 | 9/2008 | Sim et al. |
| 2008/0249301 A1 | 10/2008 | Hornberger et al. |
| 2009/0098086 A1 | 4/2009 | Zask et al. |
| 2009/0099165 A1 | 4/2009 | Hurley et al. |
| 2009/0099190 A1 | 4/2009 | Flynn et al. |
| 2009/0105233 A1 | 4/2009 | Chua et al. |
| 2009/0131467 A1 | 5/2009 | Kanazawa et al. |
| 2009/0163545 A1 | 6/2009 | Goldfarb |
| 2009/0246198 A1 | 10/2009 | Dong et al. |
| 2010/0032626 A1 | 2/2010 | Akino |
| 2010/0099684 A1 | 4/2010 | Cook, II et al. |
| 2010/0105661 A1 | 4/2010 | Shirakami et al. |
| 2010/0143547 A1 | 6/2010 | Kriegel et al. |
| 2010/0204235 A1 | 8/2010 | Lizos |
| 2010/0210636 A1 | 8/2010 | Ishikawa et al. |
| 2010/0216798 A1 | 8/2010 | Nakai et al. |
| 2010/0239496 A1 | 9/2010 | Gangadharmath et al. |
| 2011/0045511 A1 | 2/2011 | Graus Porta et al. |
| 2011/0118230 A1 | 5/2011 | Chen et al. |
| 2011/0159604 A1 | 6/2011 | Fan et al. |
| 2011/0160203 A1 | 6/2011 | Liu et al. |
| 2011/0178053 A1 | 7/2011 | Arendt et al. |
| 2011/0195968 A1 | 8/2011 | Greul et al. |
| 2011/0212077 A1 | 9/2011 | Noronha et al. |
| 2011/0224155 A1 | 9/2011 | Tachdjian et al. |
| 2011/0262525 A1 | 10/2011 | Wang et al. |
| 2011/0313003 A1 | 12/2011 | Shi et al. |
| 2012/0035153 A1 | 2/2012 | Saxty et al. |
| 2012/0135997 A1 | 5/2012 | Kato et al. |
| 2012/0165305 A1 | 6/2012 | Yao et al. |
| 2012/0295881 A1 | 11/2012 | Lange et al. |
| 2012/0319095 A1 | 12/2012 | Tada et al. |
| 2013/0078731 A1 | 3/2013 | George et al. |
| 2013/0200356 A1 | 8/2013 | Jung et al. |
| 2013/0210825 A1 | 8/2013 | Rehwinkel et al. |
| 2013/0338134 A1 | 12/2013 | Wu et al. |
| 2014/0045814 A1 | 2/2014 | Lu et al. |
| 2014/0054564 A1 | 2/2014 | Kim et al. |
| 2014/0080892 A1 | 3/2014 | Bhanot et al. |
| 2014/0088100 A1 | 3/2014 | Bifulco, Jr. et al. |
| 2014/0103325 A1 | 4/2014 | Shin et al. |
| 2014/0117318 A1 | 5/2014 | Choi et al. |
| 2014/0148548 A1 | 5/2014 | Yamanaka et al. |
| 2014/0171405 A1 | 6/2014 | Zhuo et al. |
| 2014/0187559 A1 | 7/2014 | Miduturu |
| 2014/0194430 A1 | 7/2014 | Eis et al. |
| 2014/0228370 A1 | 8/2014 | Eis et al. |
| 2014/0243308 A1 | 8/2014 | Yao et al. |
| 2014/0288069 A1 | 9/2014 | Eis et al. |
| 2014/0296233 A1 | 10/2014 | D'Agostino et al. |
| 2014/0315902 A1 | 10/2014 | Sun et al. |
| 2014/0374722 A1 | 12/2014 | Kim et al. |
| 2014/0378468 A1 | 12/2014 | Aichholz et al. |
| 2014/0378481 A1 | 12/2014 | Bifulco, Jr. et al. |
| 2014/0378483 A1 | 12/2014 | Benazet et al. |
| 2015/0011548 A1 | 1/2015 | Linnanen et al. |
| 2015/0011560 A1 | 1/2015 | Legeai-Mallet |
| 2015/0011579 A1 | 1/2015 | Clary-Ceccato et al. |
| 2015/0038485 A1 | 2/2015 | Eis et al. |
| 2015/0197519 A1 | 7/2015 | Bifulco |
| 2016/0115164 A1 | 4/2016 | Wu et al. |
| 2016/0244448 A1 | 8/2016 | Lu et al. |
| 2016/0244449 A1 | 8/2016 | Lu et al. |
| 2016/0244450 A1 | 8/2016 | Lu et al. |
| 2016/0280713 A1 | 9/2016 | Lu et al. |
| 2017/0107216 A1 | 4/2017 | Wu et al. |
| 2017/0119782 A1 | 5/2017 | Lu et al. |
| 2017/0137424 A1 | 5/2017 | Wu et al. |
| 2017/0145025 A1 | 5/2017 | Li et al. |
| 2017/0165263 A1 | 6/2017 | Yao et al. |
| 2017/0166564 A1 | 6/2017 | Sun et al. |
| 2017/0174671 A1 | 6/2017 | Wu et al. |
| 2017/0174679 A1 | 6/2017 | Lajkiewicz et al. |
| 2017/0260168 A1 | 9/2017 | Andrews et al. |
| 2017/0290839 A1 | 10/2017 | Lu et al. |
| 2017/0320875 A1 | 11/2017 | Li et al. |
| 2017/0320877 A1 | 11/2017 | Wu et al. |
| 2017/0342060 A1 | 11/2017 | Lu et al. |
| 2017/0362253 A1 | 12/2017 | Xiao et al. |
| 2018/0008610 A1 | 1/2018 | Lu et al. |
| 2018/0016260 A1 | 1/2018 | Yu et al. |
| 2018/0057486 A1 | 3/2018 | Wu et al. |
| 2018/0072718 A1 | 3/2018 | Liu et al. |
| 2018/0177784 A1 | 6/2018 | Wu et al. |
| 2018/0177870 A1 | 6/2018 | Liu et al. |
| 2018/0179179 A1 | 6/2018 | Wu et al. |
| 2018/0179197 A1 | 6/2018 | Wu et al. |
| 2018/0179201 A1 | 6/2018 | Wu et al. |
| 2018/0179202 A1 | 6/2018 | Wu et al. |
| 2018/0244672 A1 | 8/2018 | Lu et al. |
| 2018/0273519 A1 | 9/2018 | Wu et al. |
| 2019/0040082 A1 | 2/2019 | Xiao et al. |
| 2019/0055237 A1 | 2/2019 | Pan et al. |
| 2019/0062327 A1 | 2/2019 | Sun et al. |
| 2019/0062345 A1 | 2/2019 | Xiao et al. |
| 2019/0071439 A1 | 3/2019 | Li et al. |
| 2019/0092767 A1 | 3/2019 | Li et al. |
| 2019/0127376 A1 | 5/2019 | Wu et al. |
| 2019/0127467 A1 | 5/2019 | Shah et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0240220 A1 | 8/2019 | Yao et al. |
| 2019/0241560 A1 | 8/2019 | Lu et al. |
| 2019/0269693 A1 | 9/2019 | Lu et al. |
| 2019/0284187 A1 | 9/2019 | Wu et al. |
| 2019/0300524 A1 | 10/2019 | Wu et al. |
| 2019/0337948 A1 | 11/2019 | Frietze et al. |
| 2019/0345170 A1 | 11/2019 | Wu et al. |
| 2020/0002338 A1 | 1/2020 | Jia et al. |
| 2020/0055853 A1 | 2/2020 | Ellies et al. |
| 2020/0095244 A1 | 3/2020 | Sun et al. |
| 2020/0255424 A1 | 8/2020 | Wu et al. |
| 2020/0270245 A1 | 8/2020 | Pan et al. |
| 2020/0277309 A1 | 9/2020 | Wu et al. |
| 2020/0281907 A1 | 9/2020 | Ji et al. |
| 2020/0306256 A1 | 10/2020 | Lu et al. |

(56) References Cited

U.S. PATENT DOCUMENTS

| | | | |
|---|---|---|---|
| 2020/0377504 | A1 | 12/2020 | Wu et al. |
| 2020/0399267 | A1 | 12/2020 | Lu et al. |
| 2021/0009582 | A1 | 1/2021 | Vechorkin et al. |
| 2021/0094935 | A1 | 4/2021 | Vechorkin |
| 2021/0106588 | A1 | 4/2021 | Vechorkin et al. |
| 2021/0115053 | A1 | 4/2021 | Shvartsbart et al. |
| 2021/0171522 | A1 | 6/2021 | Tao et al. |
| 2021/0171535 | A1 | 6/2021 | McCammant et al. |
| 2021/0214366 | A1 | 7/2021 | Roach et al. |
| 2021/0380587 | A1 | 12/2021 | Wu et al. |
| 2021/0395246 | A1 | 12/2021 | Sun et al. |
| 2022/0009921 | A1 | 1/2022 | Lu et al. |
| 2022/0324986 | A1 | 10/2022 | Koblish et al. |
| 2022/0411423 | A1 | 12/2022 | Tao et al. |
| 2023/0121695 | A1 | 4/2023 | Frietze et al. |
| 2023/0218591 | A1 | 7/2023 | Ji et al. |

FOREIGN PATENT DOCUMENTS

| | | |
|---|---|---|
| CL | 2017000654 | 12/2017 |
| CL | 2017001984 | 3/2018 |
| CL | 2018000089 | 5/2018 |
| CL | 2018000124 | 5/2018 |
| CL | 2017002117 | 6/2018 |
| CL | 2018000036 | 6/2018 |
| CL | 2018000128 | 6/2018 |
| CL | 2018003322 | 1/2019 |
| CN | 1863774 | 11/2006 |
| CN | 101007778 | 8/2007 |
| CN | 101679408 | 3/2010 |
| CN | 101715451 | 5/2010 |
| CN | 102399220 | 4/2012 |
| CN | 102399233 | 4/2012 |
| CN | 102666536 | 9/2012 |
| CN | 103571502 | 2/2014 |
| CN | 103588771 | 2/2014 |
| CN | 104262330 | 1/2015 |
| CN | 107652289 | 2/2018 |
| DE | 2156720 | 5/1973 |
| DE | 2934578 | 3/1981 |
| DE | 3432983 | 4/1985 |
| DE | 280853 | 7/1990 |
| DE | 3937633 | 5/1991 |
| DE | 4119767 | 12/1992 |
| DE | 19912638 | 9/2000 |
| EA | 201590005 | 5/2015 |
| EP | 0466452 | 1/1992 |
| EP | 0995751 | 4/2000 |
| EP | 1199070 | 4/2002 |
| EP | 1217000 | 6/2002 |
| EP | 1388541 | 2/2004 |
| EP | 2651404 | 10/2015 |
| EP | 3184521 | 6/2017 |
| FR | 2428654 | 1/1980 |
| FR | 2876582 | 4/2006 |
| FR | 2983196 | 5/2013 |
| FR | 2983199 | 5/2013 |
| FR | 2983200 | 5/2013 |
| JP | 62273979 | 11/1987 |
| JP | 63017882 | 1/1988 |
| JP | S 6310630 | 1/1988 |
| JP | 02009895 | 1/1990 |
| JP | H 0348656 | 3/1991 |
| JP | H 03275669 | 12/1991 |
| JP | 04179576 | 6/1992 |
| JP | H 04158084 | 6/1992 |
| JP | H 04328121 | 11/1992 |
| JP | H 05320173 | 12/1993 |
| JP | H 05320515 | 12/1993 |
| JP | H 09188812 | 7/1997 |
| JP | H 1060426 | 3/1998 |
| JP | H 11171865 | 6/1999 |
| JP | 2000123973 | 4/2000 |
| JP | 2001035664 | 2/2001 |
| JP | 2001265031 | 9/2001 |
| JP | 2002516327 | 6/2002 |
| JP | 2002296731 | 10/2002 |
| JP | 2003335788 | 11/2003 |
| JP | 2004203749 | 7/2004 |
| JP | 2004346145 | 12/2004 |
| JP | 2005015395 | 1/2005 |
| JP | 2005320288 | 11/2005 |
| JP | 2006028027 | 2/2006 |
| JP | 2006514624 | 5/2006 |
| JP | 2006284843 | 10/2006 |
| JP | 2006522756 | 10/2006 |
| JP | 2006316054 | 11/2006 |
| JP | 2007500725 | 1/2007 |
| JP | 2008198769 | 8/2008 |
| JP | 2009536959 | 10/2009 |
| JP | 2009537520 | 10/2009 |
| JP | 2010180147 | 8/2010 |
| JP | 2010248429 | 11/2010 |
| JP | 2010267847 | 11/2010 |
| JP | 2010270245 | 12/2010 |
| JP | 2010272618 | 12/2010 |
| JP | 2010272727 | 12/2010 |
| JP | 2010278114 | 12/2010 |
| JP | 2011009348 | 1/2011 |
| JP | 2011044637 | 3/2011 |
| JP | 2011116840 | 6/2011 |
| JP | 2011222650 | 11/2011 |
| JP | 2012116825 | 6/2012 |
| JP | 2012136476 | 7/2012 |
| JP | 5120580 | 1/2013 |
| JP | 2013049251 | 3/2013 |
| JP | 2013179181 | 9/2013 |
| JP | 2015517376 | 6/2015 |
| JP | 20155017376 | 6/2015 |
| JP | 2015521600 | 7/2015 |
| JP | 2018507214 | 3/2018 |
| JP | 2018511573 | 4/2018 |
| JP | 6336665 | 6/2018 |
| KR | 20010043829 | 5/2001 |
| KR | 20080045536 | 5/2008 |
| KR | 20110023190 | 3/2011 |
| KR | 20110043270 | 4/2011 |
| KR | 20120052034 | 5/2012 |
| KR | 20120078303 | 7/2012 |
| KR | 20130043460 | 4/2013 |
| KR | 20140090411 | 7/2014 |
| KR | 20140099105 | 8/2014 |
| TW | 200602319 | 1/2006 |
| TW | 201402574 | 1/2014 |
| WO | WO 1988/03025 | 5/1988 |
| WO | WO 1991/09835 | 7/1991 |
| WO | WO 1991/10172 | 7/1991 |
| WO | WO 1992/06078 | 4/1992 |
| WO | WO 1992/22552 | 12/1992 |
| WO | WO 1993/24488 | 12/1993 |
| WO | WO 1994/13669 | 6/1994 |
| WO | WO 1994/15995 | 7/1994 |
| WO | WO 1994/25438 | 11/1994 |
| WO | WO 1995/20965 | 8/1995 |
| WO | WO 1996/15128 | 5/1996 |
| WO | WO 1996/40707 | 12/1996 |
| WO | WO 1997/47601 | 12/1997 |
| WO | WO 1998/05661 | 2/1998 |
| WO | WO 1998/06703 | 2/1998 |
| WO | WO 1998/11438 | 3/1998 |
| WO | WO 1998/18781 | 5/1998 |
| WO | WO 1998/28281 | 7/1998 |
| WO | WO 1998/33798 | 8/1998 |
| WO | WO 1998/46609 | 10/1998 |
| WO | WO 1998/54156 | 12/1998 |
| WO | WO 1999/06422 | 2/1999 |
| WO | WO 1999/07732 | 2/1999 |
| WO | WO 1999/09030 | 2/1999 |
| WO | WO 1999/42442 | 8/1999 |
| WO | WO 1999/59975 | 11/1999 |
| WO | WO 1999/61444 | 12/1999 |
| WO | WO 1999/64400 | 12/1999 |
| WO | WO 2000/09495 | 2/2000 |
| WO | WO 2002/000196 | 2/2000 |

(56) References Cited

FOREIGN PATENT DOCUMENTS

| | | |
|---|---|---|
| WO | WO 2000/24744 | 5/2000 |
| WO | WO 2000/053595 | 9/2000 |
| WO | WO 2000/68186 | 11/2000 |
| WO | WO 2001/02369 | 1/2001 |
| WO | WO 2001/014402 | 3/2001 |
| WO | WO 2001/22938 | 4/2001 |
| WO | WO 2001/23386 | 4/2001 |
| WO | WO 2001/29041 | 4/2001 |
| WO | WO 2001/29042 | 4/2001 |
| WO | WO 2001/42247 | 6/2001 |
| WO | WO 2001/47892 | 7/2001 |
| WO | WO 2001/53273 | 7/2001 |
| WO | WO 2001/55148 | 8/2001 |
| WO | WO 2001/57037 | 8/2001 |
| WO | WO 2001/57038 | 8/2001 |
| WO | WO 2001/58899 | 8/2001 |
| WO | WO 2001/64655 | 9/2001 |
| WO | WO 2001/66099 | 9/2001 |
| WO | WO 2001/68647 | 9/2001 |
| WO | WO 2001/83472 | 11/2001 |
| WO | WO 2001/85722 | 11/2001 |
| WO | WO 2002/00655 | 1/2002 |
| WO | WO 2002/12442 | 2/2002 |
| WO | WO 2002/14315 | 2/2002 |
| WO | WO 2002/20011 | 3/2002 |
| WO | WO 2002/051831 | 7/2002 |
| WO | WO 2002/055082 | 7/2002 |
| WO | WO 2002/066481 | 8/2002 |
| WO | WO 2002/74754 | 9/2002 |
| WO | WO 2002/076953 | 10/2002 |
| WO | WO 2002/083648 | 10/2002 |
| WO | WO 2002/088095 | 11/2002 |
| WO | WO 2002/094825 | 11/2002 |
| WO | WO 2002/096873 | 12/2002 |
| WO | WO 2002/102793 | 12/2002 |
| WO | WO 2003/000187 | 1/2003 |
| WO | WO 2003/000688 | 1/2003 |
| WO | WO 2003/000690 | 1/2003 |
| WO | WO 2003/009852 | 2/2003 |
| WO | WO 2003/014083 | 2/2003 |
| WO | WO 2003/024967 | 3/2003 |
| WO | WO 2003/037347 | 5/2003 |
| WO | WO 2003/037891 | 5/2003 |
| WO | WO 2003/040131 | 5/2003 |
| WO | WO 2003/042402 | 5/2003 |
| WO | WO 2003/049542 | 6/2003 |
| WO | WO 2003/062236 | 7/2003 |
| WO | WO 2003/075836 | 9/2003 |
| WO | WO 2003/082871 | 10/2003 |
| WO | WO 2003/097609 | 11/2003 |
| WO | WO 2003/099771 | 12/2003 |
| WO | WO 2003/099818 | 12/2003 |
| WO | WO 2003/101985 | 12/2003 |
| WO | WO 2004/002986 | 1/2004 |
| WO | WO 2004/005281 | 1/2004 |
| WO | WO 2004/011465 | 2/2004 |
| WO | WO 2004/014382 | 2/2004 |
| WO | WO 2004/014907 | 2/2004 |
| WO | WO 2004/018472 | 3/2004 |
| WO | WO 2004/020441 | 3/2004 |
| WO | WO 2004/041821 | 5/2004 |
| WO | WO 2004/041822 | 5/2004 |
| WO | WO 2004/041823 | 5/2004 |
| WO | WO 2004/043367 | 5/2004 |
| WO | WO 2004/046120 | 6/2004 |
| WO | WO 2004/046152 | 6/2004 |
| WO | WO 2004/048343 | 6/2004 |
| WO | WO 2004/052291 | 6/2004 |
| WO | WO 2004/052862 | 6/2004 |
| WO | WO 2004/056786 | 7/2004 |
| WO | WO 2004/056822 | 7/2004 |
| WO | WO 2004/056830 | 7/2004 |
| WO | WO 2004/065378 | 8/2004 |
| WO | WO 2004/080980 | 9/2004 |
| WO | WO 2004/083177 | 9/2004 |
| WO | WO 2004/087053 | 10/2004 |
| WO | WO 2004/089955 | 10/2004 |
| WO | WO 2004/094420 | 11/2004 |
| WO | WO 2004/099209 | 11/2004 |
| WO | WO 2004/108139 | 11/2004 |
| WO | WO 2004/110487 | 12/2004 |
| WO | WO 2004/112793 | 12/2004 |
| WO | WO 2004/113307 | 12/2004 |
| WO | WO 2005/007653 | 1/2005 |
| WO | WO 2005/011597 | 2/2005 |
| WO | WO 2005/021533 | 3/2005 |
| WO | WO 2005/028434 | 3/2005 |
| WO | WO 2005/028478 | 3/2005 |
| WO | WO 2005/028480 | 3/2005 |
| WO | WO 2005/028444 | 5/2005 |
| WO | WO 2005/040119 | 5/2005 |
| WO | WO 2005/047289 | 5/2005 |
| WO | WO 2005/056524 | 6/2005 |
| WO | WO 2005/063768 | 6/2005 |
| WO | WO 2005/066162 | 7/2005 |
| WO | WO 2005/070430 | 8/2005 |
| WO | WO 2005/070929 | 8/2005 |
| WO | WO 2005/072412 | 8/2005 |
| WO | WO 2005/073232 | 8/2005 |
| WO | WO 2005/080393 | 9/2005 |
| WO | WO 2005/082903 | 9/2005 |
| WO | WO 2005/085210 | 9/2005 |
| WO | WO 2005/085248 | 9/2005 |
| WO | WO 2005/085249 | 9/2005 |
| WO | WO 2005/087765 | 9/2005 |
| WO | WO 2005/092901 | 10/2005 |
| WO | WO 2005/105097 | 11/2005 |
| WO | WO 2005/113536 | 12/2005 |
| WO | WO 2005/116035 | 12/2005 |
| WO | WO 2005/121130 | 12/2005 |
| WO | WO 2005/121142 | 12/2005 |
| WO | WO 2006/000420 | 1/2006 |
| WO | WO 2006/024486 | 3/2006 |
| WO | WO 2006/024487 | 3/2006 |
| WO | WO 2006/024834 | 3/2006 |
| WO | WO 2006/028289 | 3/2006 |
| WO | WO 2006/030031 | 3/2006 |
| WO | WO 2006/038112 | 4/2006 |
| WO | WO 2006/050076 | 5/2006 |
| WO | WO 2006/050162 | 5/2006 |
| WO | WO 2006/052712 | 5/2006 |
| WO | WO 2006/055752 | 5/2006 |
| WO | WO 2006/024524 | 6/2006 |
| WO | WO 2006/056399 | 6/2006 |
| WO | WO 2006/058120 | 6/2006 |
| WO | WO 2006/062465 | 6/2006 |
| WO | WO 2006/065703 | 6/2006 |
| WO | WO 2006/074293 | 7/2006 |
| WO | WO 2006/087230 | 8/2006 |
| WO | WO 2006/092691 | 9/2006 |
| WO | WO 2006/102588 | 9/2006 |
| WO | WO 2006/102610 | 9/2006 |
| WO | WO 2006/105448 | 10/2006 |
| WO | WO 2006/107644 | 10/2006 |
| WO | WO 2006/112666 | 10/2006 |
| WO | WO 2006/119504 | 11/2006 |
| WO | WO 2006/124462 | 11/2006 |
| WO | WO 2006/124731 | 11/2006 |
| WO | WO 2006/135821 | 12/2006 |
| WO | WO 2006/136442 | 12/2006 |
| WO | WO 2007/013964 | 2/2007 |
| WO | WO 2007/017096 | 2/2007 |
| WO | WO 2007/021795 | 2/2007 |
| WO | WO 2007/022268 | 2/2007 |
| WO | WO 2007/023105 | 3/2007 |
| WO | WO 2007/025949 | 3/2007 |
| WO | WO 2007/030366 | 3/2007 |
| WO | WO 2007/032466 | 3/2007 |
| WO | WO 2007/033780 | 3/2007 |
| WO | WO 2007/038209 | 4/2007 |
| WO | WO 2007/044698 | 4/2007 |
| WO | WO 2007/044729 | 4/2007 |
| WO | WO 2007/048802 | 5/2007 |
| WO | WO 2007/053135 | 5/2007 |

(56) References Cited

FOREIGN PATENT DOCUMENTS

| | | |
|---|---|---|
| WO | WO 2007/053452 | 5/2007 |
| WO | WO 2007/053498 | 5/2007 |
| WO | WO 2007/055418 | 5/2007 |
| WO | WO 2007/056023 | 5/2007 |
| WO | WO 2007/056075 | 5/2007 |
| WO | WO 2007/056170 | 5/2007 |
| WO | WO 2007/058392 | 5/2007 |
| WO | WO 2007/058626 | 5/2007 |
| WO | WO 2007/059108 | 5/2007 |
| WO | WO 2007/061554 | 5/2007 |
| WO | WO 2007/064883 | 6/2007 |
| WO | WO 2007/064931 | 6/2007 |
| WO | WO 2007/066189 | 6/2007 |
| WO | WO 2007/067444 | 6/2007 |
| WO | WO 2007/071752 | 6/2007 |
| WO | WO 2007/084314 | 7/2007 |
| WO | WO 2007/088999 | 8/2007 |
| WO | WO 2007/092879 | 8/2007 |
| WO | WO 2007/093901 | 8/2007 |
| WO | WO 2007/109334 | 9/2007 |
| WO | WO 2007/110868 | 10/2007 |
| WO | WO 2007/112347 | 10/2007 |
| WO | WO 2007/120097 | 10/2007 |
| WO | WO 2007/120339 | 10/2007 |
| WO | WO 2007/125351 | 11/2007 |
| WO | WO 2007/125405 | 11/2007 |
| WO | WO 2007/126841 | 11/2007 |
| WO | WO 2007/134259 | 11/2007 |
| WO | WO 2007/136465 | 11/2007 |
| WO | WO 2007/140957 | 12/2007 |
| WO | WO 2007/143600 | 12/2007 |
| WO | WO 2007/147217 | 12/2007 |
| WO | WO 2008/001070 | 1/2008 |
| WO | WO 2008/003766 | 1/2008 |
| WO | WO 2008/005877 | 1/2008 |
| WO | WO 2008/008234 | 1/2008 |
| WO | WO 2008/008747 | 1/2008 |
| WO | WO 2008/012635 | 1/2008 |
| WO | WO 2008/021389 | 2/2008 |
| WO | WO 2008/021851 | 2/2008 |
| WO | WO 2008/025556 | 3/2008 |
| WO | WO 2008/033858 | 3/2008 |
| WO | WO 2008/033999 | 3/2008 |
| WO | WO 2008/034859 | 3/2008 |
| WO | WO 2008/034860 | 3/2008 |
| WO | WO 2008/037459 | 4/2008 |
| WO | WO 2008/042639 | 4/2008 |
| WO | WO 2008/052898 | 5/2008 |
| WO | WO 2008/052934 | 5/2008 |
| WO | WO 2008/060907 | 5/2008 |
| WO | WO 2008/063583 | 5/2008 |
| WO | WO 2008/063609 | 5/2008 |
| WO | WO 2008/064157 | 5/2008 |
| WO | WO 2008/071455 | 6/2008 |
| WO | WO 2008/074068 | 6/2008 |
| WO | WO 2008/075068 | 6/2008 |
| WO | WO 2008/076278 | 6/2008 |
| WO | WO 2008/078091 | 7/2008 |
| WO | WO 2008/078100 | 7/2008 |
| WO | WO 2008/079460 | 7/2008 |
| WO | WO 2008/079933 | 7/2008 |
| WO | WO 2008/085942 | 7/2008 |
| WO | WO 2008/089105 | 7/2008 |
| WO | WO 2008/099075 | 8/2008 |
| WO | WO 2008/107436 | 9/2008 |
| WO | WO 2008/107544 | 9/2008 |
| WO | WO 2008/109181 | 9/2008 |
| WO | WO 2008/109943 | 9/2008 |
| WO | WO 2008/115974 | 9/2008 |
| WO | WO 2008/117269 | 10/2008 |
| WO | WO 2008/118454 | 10/2008 |
| WO | WO 2008/123755 | 10/2008 |
| WO | WO 2008/128141 | 10/2008 |
| WO | WO 2008/130584 | 10/2008 |
| WO | WO 2008/131972 | 11/2008 |
| WO | WO 2008/141065 | 11/2008 |
| WO | WO 2008/142720 | 11/2008 |
| WO | WO 2008/144253 | 11/2008 |
| WO | WO 2008/151184 | 12/2008 |
| WO | WO 2008/153207 | 12/2008 |
| WO | WO 2008/153852 | 12/2008 |
| WO | WO 2008/154221 | 12/2008 |
| WO | WO 2008/156712 | 12/2008 |
| WO | WO 2009/013335 | 1/2009 |
| WO | WO 2009/013354 | 1/2009 |
| WO | WO 2009/097446 | 1/2009 |
| WO | WO 2009/016253 | 2/2009 |
| WO | WO 2009/019518 | 2/2009 |
| WO | WO 2009/021083 | 2/2009 |
| WO | WO 2009/029473 | 3/2009 |
| WO | WO 2009/029625 | 3/2009 |
| WO | WO 2009/030871 | 3/2009 |
| WO | WO 2009/032861 | 3/2009 |
| WO | WO 2009/036012 | 3/2009 |
| WO | WO 2009/044788 | 4/2009 |
| WO | WO 2009/046606 | 4/2009 |
| WO | WO 2009/047255 | 4/2009 |
| WO | WO 2009/047506 | 4/2009 |
| WO | WO 2009/047522 | 4/2009 |
| WO | WO 2009/047993 | 4/2009 |
| WO | WO 2009/049018 | 4/2009 |
| WO | WO 2009/050183 | 4/2009 |
| WO | WO 2009/053737 | 4/2009 |
| WO | WO 2009/055828 | 4/2009 |
| WO | WO 2009/056886 | 5/2009 |
| WO | WO 2009/071535 | 6/2009 |
| WO | WO 2009/073153 | 6/2009 |
| WO | WO 2009/085185 | 7/2009 |
| WO | WO 2009/086130 | 7/2009 |
| WO | WO 2009/086509 | 7/2009 |
| WO | WO 2009/087238 | 7/2009 |
| WO | WO 2009/092764 | 7/2009 |
| WO | WO 2009/093209 | 7/2009 |
| WO | WO 2009/093210 | 7/2009 |
| WO | WO 2009/094528 | 7/2009 |
| WO | WO 2009/099982 | 8/2009 |
| WO | WO 2009/103652 | 8/2009 |
| WO | WO 2009/105717 | 8/2009 |
| WO | WO 2009/108332 | 9/2009 |
| WO | WO 2009/108827 | 9/2009 |
| WO | WO 2009/112826 | 9/2009 |
| WO | WO 2009/114870 | 9/2009 |
| WO | WO 2009/114874 | 9/2009 |
| WO | WO 2009/122180 | 10/2009 |
| WO | WO 2009/123967 | 10/2009 |
| WO | WO 2009/124755 | 10/2009 |
| WO | WO 2009/125808 | 10/2009 |
| WO | WO 2009/125809 | 10/2009 |
| WO | WO 2009/126584 | 10/2009 |
| WO | WO 2009/128520 | 10/2009 |
| WO | WO 2009/131687 | 10/2009 |
| WO | WO 2009/131926 | 10/2009 |
| WO | WO 2009/132980 | 11/2009 |
| WO | WO 2009/133127 | 11/2009 |
| WO | WO 2009/141386 | 11/2009 |
| WO | WO 2009/144205 | 12/2009 |
| WO | WO 2009/144302 | 12/2009 |
| WO | WO 2009/146034 | 12/2009 |
| WO | WO 2009/148887 | 12/2009 |
| WO | WO 2009/148916 | 12/2009 |
| WO | WO 2009/150150 | 12/2009 |
| WO | WO 2009/150240 | 12/2009 |
| WO | WO 2009/151997 | 12/2009 |
| WO | WO 2009/153592 | 12/2009 |
| WO | WO 2009/157423 | 12/2009 |
| WO | WO 2010/006947 | 1/2010 |
| WO | WO 2010/007099 | 1/2010 |
| WO | WO 2010/007116 | 1/2010 |
| WO | WO 2010/009155 | 1/2010 |
| WO | WO 2010/009195 | 1/2010 |
| WO | WO 2010/009207 | 1/2010 |
| WO | WO 2010/009735 | 1/2010 |
| WO | WO 2010/015643 | 2/2010 |
| WO | WO 2010/017047 | 2/2010 |

(56) References Cited

FOREIGN PATENT DOCUMENTS

| | | |
|---|---|---|
| WO | WO 2010/019210 | 2/2010 |
| WO | WO 2010/019899 | 2/2010 |
| WO | WO 2010/030027 | 3/2010 |
| WO | WO 2010/036959 | 4/2010 |
| WO | WO 2010/038081 | 4/2010 |
| WO | WO 2010/045371 | 4/2010 |
| WO | WO 2010/049731 | 5/2010 |
| WO | WO 2010/051043 | 5/2010 |
| WO | WO 2010/052448 | 5/2010 |
| WO | WO 2010/059552 | 5/2010 |
| WO | WO 2010/059658 | 5/2010 |
| WO | WO 2010/062571 | 6/2010 |
| WO | WO 2010/064621 | 6/2010 |
| WO | WO 2010/064875 | 6/2010 |
| WO | WO 2010/067886 | 6/2010 |
| WO | WO 2010/067888 | 6/2010 |
| WO | WO 2010/075074 | 7/2010 |
| WO | WO 2010/077647 | 7/2010 |
| WO | WO 2010/077680 | 7/2010 |
| WO | WO 2010/078421 | 7/2010 |
| WO | WO 2010/078427 | 7/2010 |
| WO | WO 2010/080503 | 7/2010 |
| WO | WO 2010/080712 | 7/2010 |
| WO | WO 2010/083145 | 7/2010 |
| WO | WO 2010/083283 | 7/2010 |
| WO | WO 2010/086089 | 8/2010 |
| WO | WO 2010/089411 | 8/2010 |
| WO | WO 2010/092181 | 8/2010 |
| WO | WO 2010/099938 | 9/2010 |
| WO | WO 2010/103306 | 9/2010 |
| WO | WO 2010/104047 | 9/2010 |
| WO | WO 2010/107765 | 9/2010 |
| WO | WO 2010/107768 | 9/2010 |
| WO | WO 2010/111303 | 9/2010 |
| WO | WO 2010/111573 | 9/2010 |
| WO | WO 2010/115279 | 10/2010 |
| WO | WO 2010/117425 | 10/2010 |
| WO | WO 2010/119284 | 10/2010 |
| WO | WO 2010/119285 | 10/2010 |
| WO | WO 2010/117323 | 11/2010 |
| WO | WO 2010/125216 | 11/2010 |
| WO | WO 2010/126960 | 11/2010 |
| WO | WO 2010/127212 | 11/2010 |
| WO | WO 2010/129509 | 11/2010 |
| WO | WO 2010/136031 | 12/2010 |
| WO | WO 2010/142801 | 12/2010 |
| WO | WO 2010/151689 | 12/2010 |
| WO | WO 2011/002038 | 1/2011 |
| WO | WO 2011/007819 | 1/2011 |
| WO | WO 2011/011597 | 1/2011 |
| WO | WO 2011/012816 | 2/2011 |
| WO | WO 2011/014535 | 2/2011 |
| WO | WO 2011/015037 | 2/2011 |
| WO | WO 2011/016472 | 2/2011 |
| WO | WO 2011/016528 | 2/2011 |
| WO | WO 2011/018894 | 2/2011 |
| WO | WO 2011/022439 | 2/2011 |
| WO | WO 2011/026579 | 3/2011 |
| WO | WO 2011/028947 | 3/2011 |
| WO | WO 2011/031740 | 3/2011 |
| WO | WO 2011/032050 | 3/2011 |
| WO | WO 2011/039344 | 4/2011 |
| WO | WO 2011/041143 | 4/2011 |
| WO | WO 2011/042389 | 4/2011 |
| WO | WO 2011/042474 | 4/2011 |
| WO | WO 2011/045344 | 4/2011 |
| WO | WO 2011/049825 | 4/2011 |
| WO | WO 2011/049988 | 4/2011 |
| WO | WO 2011/050245 | 4/2011 |
| WO | WO 2011/051425 | 5/2011 |
| WO | WO 2011/053518 | 5/2011 |
| WO | WO 2011/054843 | 5/2011 |
| WO | WO 2011/055911 | 5/2011 |
| WO | WO 2011/057022 | 5/2011 |
| WO | WO 2011/060295 | 5/2011 |
| WO | WO 2011/062253 | 5/2011 |
| WO | WO 2011/062885 | 5/2011 |
| WO | WO 2011/063159 | 5/2011 |
| WO | WO 2011/066342 | 6/2011 |
| WO | WO 2011/068899 | 6/2011 |
| WO | WO 2011/071821 | 6/2011 |
| WO | WO 2011/075515 | 6/2011 |
| WO | WO 2011/075620 | 6/2011 |
| WO | WO 2011/077043 | 6/2011 |
| WO | WO 2011/077044 | 6/2011 |
| WO | WO 2011/079231 | 6/2011 |
| WO | WO 2011/080755 | 7/2011 |
| WO | WO 2011/082234 | 7/2011 |
| WO | WO 2011/082266 | 7/2011 |
| WO | WO 2011/082267 | 7/2011 |
| WO | WO 2011/082400 | 7/2011 |
| WO | WO 2011/082488 | 7/2011 |
| WO | WO 2011/087776 | 7/2011 |
| WO | WO 2011/090666 | 7/2011 |
| WO | WO 2011/090738 | 7/2011 |
| WO | WO 2011/090760 | 7/2011 |
| WO | WO 2011/093672 | 8/2011 |
| WO | WO 2011/094890 | 8/2011 |
| WO | WO 2011/097717 | 8/2011 |
| WO | WO 2011/101409 | 8/2011 |
| WO | WO 2011/101806 | 8/2011 |
| WO | WO 2011/102441 | 8/2011 |
| WO | WO 2011/103196 | 8/2011 |
| WO | WO 2011/103441 | 8/2011 |
| WO | WO 2011/103460 | 8/2011 |
| WO | WO 2011/103557 | 8/2011 |
| WO | WO 2011/105161 | 9/2011 |
| WO | WO 2011/109237 | 9/2011 |
| WO | WO 2011/111880 | 9/2011 |
| WO | WO 2011/112687 | 9/2011 |
| WO | WO 2011/112995 | 9/2011 |
| WO | WO 2011/115725 | 9/2011 |
| WO | WO 2011/119894 | 9/2011 |
| WO | WO 2011/120327 | 10/2011 |
| WO | WO 2011/123493 | 10/2011 |
| WO | WO 2011/128403 | 10/2011 |
| WO | WO 2011/130390 | 10/2011 |
| WO | WO 2011/133722 | 10/2011 |
| WO | WO 2011/133750 | 10/2011 |
| WO | WO 2011/133888 | 10/2011 |
| WO | WO 2011/135376 | 11/2011 |
| WO | WO 2011/137313 | 11/2011 |
| WO | WO 2011/140338 | 11/2011 |
| WO | WO 2011/141756 | 11/2011 |
| WO | WO 2011/141848 | 11/2011 |
| WO | WO 2011/143033 | 11/2011 |
| WO | WO 2011/143318 | 11/2011 |
| WO | WO 2011/143430 | 11/2011 |
| WO | WO 2011/147198 | 12/2011 |
| WO | WO 2011/147199 | 12/2011 |
| WO | WO 2011/151360 | 12/2011 |
| WO | WO 2011/153553 | 12/2011 |
| WO | WO 2011/155983 | 12/2011 |
| WO | WO 2011/156610 | 12/2011 |
| WO | WO 2011/159877 | 12/2011 |
| WO | WO 2011/161699 | 12/2011 |
| WO | WO 2011/163330 | 12/2011 |
| WO | WO 2012/000103 | 1/2012 |
| WO | WO 2012/003544 | 1/2012 |
| WO | WO 2012/004217 | 1/2012 |
| WO | WO 2012/004731 | 1/2012 |
| WO | WO 2012/004732 | 1/2012 |
| WO | WO 2012/008563 | 1/2012 |
| WO | WO 2012/008564 | 1/2012 |
| WO | WO 2012/008999 | 1/2012 |
| WO | WO 2012/009258 | 1/2012 |
| WO | WO 2012/009309 | 1/2012 |
| WO | WO 2012/013619 | 2/2012 |
| WO | WO 2012/015274 | 2/2012 |
| WO | WO 2012/019093 | 2/2012 |
| WO | WO 2012/020133 | 2/2012 |
| WO | WO 2012/027236 | 3/2012 |
| WO | WO 2012/027239 | 3/2012 |
| WO | WO 2012/030990 | 3/2012 |

(56) References Cited

FOREIGN PATENT DOCUMENTS

| | | |
|---|---|---|
| WO | WO 2012/031004 | 3/2012 |
| WO | WO 2012/032031 | 3/2012 |
| WO | WO 2012/032065 | 3/2012 |
| WO | WO 2012/032067 | 3/2012 |
| WO | WO 2012/032334 | 3/2012 |
| WO | WO 2012/035996 | 3/2012 |
| WO | WO 2012/036233 | 3/2012 |
| WO | WO 2012/038743 | 3/2012 |
| WO | WO 2012/047699 | 4/2012 |
| WO | WO 2012/054364 | 4/2012 |
| WO | WO 2012/057260 | 5/2012 |
| WO | WO 2012/058211 | 5/2012 |
| WO | WO 2012/061156 | 5/2012 |
| WO | WO 2012/061337 | 5/2012 |
| WO | WO 2012/062462 | 5/2012 |
| WO | WO 2012/063207 | 5/2012 |
| WO | WO 2012/064715 | 5/2012 |
| WO | WO 2012/065297 | 5/2012 |
| WO | WO 2012/065546 | 5/2012 |
| WO | WO 2012/066578 | 5/2012 |
| WO | WO 2012/068343 | 5/2012 |
| WO | WO 2012/073017 | 6/2012 |
| WO | WO 2012/078777 | 6/2012 |
| WO | WO 2012/080727 | 6/2012 |
| WO | WO 2012/080729 | 6/2012 |
| WO | WO 2012/083866 | 6/2012 |
| WO | WO 2012/083953 | 6/2012 |
| WO | WO 2012/083954 | 6/2012 |
| WO | WO 2012/084704 | 6/2012 |
| WO | WO 2012/087784 | 6/2012 |
| WO | WO 2012/088266 | 6/2012 |
| WO | WO 2012/091240 | 7/2012 |
| WO | WO 2012/093731 | 7/2012 |
| WO | WO 2012/098068 | 7/2012 |
| WO | WO 2012/101239 | 8/2012 |
| WO | WO 2012/106995 | 8/2012 |
| WO | WO 2012/112961 | 8/2012 |
| WO | WO 2012/112965 | 8/2012 |
| WO | WO 2012/116237 | 8/2012 |
| WO | WO 2012/125812 | 9/2012 |
| WO | WO 2012/127012 | 9/2012 |
| WO | WO 2012/129344 | 9/2012 |
| WO | WO 2012/134943 | 10/2012 |
| WO | WO 2012/138975 | 10/2012 |
| WO | WO 2012/140114 | 10/2012 |
| WO | WO 2012/158704 | 11/2012 |
| WO | WO 2012/158795 | 11/2012 |
| WO | WO 2012/158994 | 11/2012 |
| WO | WO 2012/161812 | 11/2012 |
| WO | WO 2012/167247 | 12/2012 |
| WO | WO 2012/173370 | 12/2012 |
| WO | WO 2013/016197 | 1/2013 |
| WO | WO 2013/024002 | 2/2013 |
| WO | WO 2013/024895 | 2/2013 |
| WO | WO 2013/033981 | 3/2013 |
| WO | WO 2013/039854 | 3/2013 |
| WO | WO 2013/041634 | 3/2013 |
| WO | WO 2013/049352 | 4/2013 |
| WO | WO 2013/053051 | 4/2013 |
| WO | WO 2013/063000 | 5/2013 |
| WO | WO 2013/063003 | 5/2013 |
| WO | WO 2013/108809 | 7/2013 |
| WO | WO 2013/109027 | 7/2013 |
| WO | WO 2013/124316 | 8/2013 |
| WO | WO 2013/136249 | 9/2013 |
| WO | WO 2013/144339 | 10/2013 |
| WO | WO 2014/007951 | 1/2014 |
| WO | WO 2014/011284 | 1/2014 |
| WO | WO 2014/011900 | 1/2014 |
| WO | WO 2014/019186 | 2/2014 |
| WO | WO 2014/022528 | 2/2014 |
| WO | WO 2014/026125 | 2/2014 |
| WO | WO 2014/044846 | 3/2014 |
| WO | WO 2014/048878 | 4/2014 |
| WO | WO 2014/062454 | 4/2014 |
| WO | WO 2014/085216 | 5/2014 |
| WO | WO 2014/089913 | 6/2014 |
| WO | WO 2014/105849 | 7/2014 |
| WO | WO 2014/113191 | 7/2014 |
| WO | WO 2014/136972 | 9/2014 |
| WO | WO 2014/138485 | 9/2014 |
| WO | WO 2014/140184 | 9/2014 |
| WO | WO 2014/144737 | 9/2014 |
| WO | WO 2014/160160 | 10/2014 |
| WO | WO 2014/160478 | 10/2014 |
| WO | WO 2014/160521 | 10/2014 |
| WO | WO 2014/162039 | 10/2014 |
| WO | WO 2014/170063 | 10/2014 |
| WO | WO 2014/171755 | 10/2014 |
| WO | WO 2014/172644 | 10/2014 |
| WO | WO 2014/174307 | 10/2014 |
| WO | WO 2014/182829 | 11/2014 |
| WO | WO 2014/198942 | 12/2014 |
| WO | WO 2014/206343 | 12/2014 |
| WO | WO 2014/206344 | 12/2014 |
| WO | WO 2015/000715 | 1/2015 |
| WO | WO 2015/006492 | 1/2015 |
| WO | WO 2015/006754 | 1/2015 |
| WO | WO 2015/030021 | 3/2015 |
| WO | WO 2015/057938 | 4/2015 |
| WO | WO 2015/057963 | 4/2015 |
| WO | WO 2015/059668 | 4/2015 |
| WO | WO 2015/061572 | 4/2015 |
| WO | WO 2015/066452 | 5/2015 |
| WO | WO 2015/095492 | 6/2015 |
| WO | WO 2015/108992 | 7/2015 |
| WO | WO 2016/064960 | 4/2016 |
| WO | WO 2016/134314 | 8/2016 |
| WO | WO 2016/192680 | 12/2016 |
| WO | WO 2017/023972 | 2/2017 |
| WO | WO 2017/023988 | 2/2017 |
| WO | WO 2017/023989 | 2/2017 |
| WO | WO 2017/024003 | 2/2017 |
| WO | WO 2017/024004 | 2/2017 |
| WO | WO 2017/024015 | 2/2017 |
| WO | WO 2017/024025 | 2/2017 |
| WO | WO 2017/028314 | 2/2017 |
| WO | WO 2017/223414 | 12/2017 |
| WO | WO 2018/041091 | 3/2018 |
| WO | WO 2018/049214 | 3/2018 |
| WO | WO 2018/067512 | 4/2018 |
| WO | WO 2018/093029 | 5/2018 |
| WO | WO 2018/093215 | 5/2018 |
| WO | WO 2018/105972 | 6/2018 |
| WO | WO 2018/105973 | 6/2018 |
| WO | WO 2018/234354 | 12/2018 |
| WO | WO 2019/037640 | 2/2019 |
| WO | WO 2019/079369 | 4/2019 |
| WO | WO 2019/105886 | 6/2019 |
| WO | WO 2019/213506 | 11/2019 |
| WO | WO 2020/049017 | 3/2020 |
| WO | WO 2020/081898 | 4/2020 |
| WO | WO 2020/131627 | 6/2020 |
| WO | WO 2020/131674 | 6/2020 |
| WO | WO 2021/113462 | 6/2021 |

OTHER PUBLICATIONS

Alexander et al., "Systemtherapie des Harnblasenkarzinoms," Der Urologe, Jan. 4, 2021, 60(2):247-258 (English Abstract).
Argentina Office Action in Argentina Application No. 20180101392, dated Mar. 8, 2022, 6 pages.
Australian Allowance in Australian Application No. 2020250201, dated Jun. 23, 2022, 4 pages.
Balek, L., "ARQ 087 inhibits FGFR signaling and rescues aberrant cell proliferation and differentiation in experimental models of craniosynostoses and chondrodysplasias caused by activating mutations in FGFR1, FGFR2 and FGFR3," Bone, Dec. 2017, 105:57-66.
Bauer, "Pharmaceutical Solids—The Amorphous Phase", Journal of Validation Technology, 2009, 15(3):63-68.
Byrn et al., "Pharmacautical Solids: A Strategic Approach to Regulatory Considerations," Pharmaceutical Research., Jul. 1995, 12(7):945-954.

(56) References Cited

OTHER PUBLICATIONS

Canada Office Action in Canada Application No. 2,976,788, dated Apr. 7, 2022, 4 pages.
Canada Office Action in Canada Application No. 2,976,790, dated Apr. 25, 2022, 4 pages.
Chilean Office Action in Chilean Application No. 2839-2020, dated Jan. 31, 2022, 42 pages (with English translation).
Chilean Office Action in Chilean Application No. 2848-2020, dated Apr. 3, 2022, 23 pages.
Chilean Office Action in Chilean Application No. 3439-2019, dated Jan. 31, 2022, 15 pages.
Chinese Office Action in Chinese Application No. 201910023729.3, dated Mar. 23, 2022, 11 pages.
Colombian Office Action in Colombian Application No. NC2019/0014699, dated Jun. 6, 2022, 31 pages.
Costa Rican Office Action in Costa Rican Application No. 2019-573, dated Jul. 12, 2022, 12 pages.
De Luca et al., "FGFR Fusions in Cancer: From Diagnostic Approaches to Therapeutic Intervention," Int J Mol Sci., 2020, 21(8):6856.
Ecuador Office Action in Ecuador Application No. IEPI-2015-1225, dated May 11, 2022, 18 pages.
Ecuador Opposition in Ecuador Application No. SENADI-2020-78226, dated Jun. 2022, 19 pages.
Ecuador Opposition in Ecuador Application No. SENADI-2020-78230, dated Jun. 2022, 21 pages.
Eurasian Office Action in Eurasian Application No. 202091923, dated Apr. 5, 2022, 4 pages.
Eurasian Office Action in Eurasian Application No. 202092648, dated Feb. 8, 2022, 7 pages.
Eurasian Office Action in Eurasian Application No. 202092649/26, dated Apr. 22, 2022, 6 pages.
European Office Action in European U.S. Appl. No. 19/724,670, dated Aug. 31, 2022, 3 pages.
Hess et al., "Abstract P245: Synergistic effect of combination of pemigatinib with enfortumab vedotin (EV) in human bladder cancer models," Molecular Cancer Therapeutics, Oct. 1, 2021, 20(12 Supplement):P245.
Hess et al., "Synergistic effect of combination of pemigatinib with enfortumab vedotin (EV) in human bladder cancer models," Molecular Cancer Therapeutics, Presented at AACR-NCI-EORT Virtual International Conference on Molecular Targets and Cancer Therapeutics, presented Oct. 7-10, 2021, 9 pages.
Indian Office Action in Indian Application No. 202017052609, dated May 23, 2022, 7 pages.
Indian Office Action in Indian Application No. 202017052853, dated May 13, 2022, 6 pages.
International Preliminary Report on Patentability in International Application No. PCT/US2020/053436, dated Apr. 5, 2022, 8 pages.
International Preliminary Report on Patentability in International Application No. PCT/US2020/055547, dated Apr. 19, 2022, 7 pages.
International Preliminary Report on Patentability in International Application No. PCT/US2020/055735, dated Apr. 19, 2022, 8 pages.
International Preliminary Report on Patentability in International Application No. PCT/US2020/063038, dated Jun. 16, 2022, 8 pages.
International Preliminary Report on Patentability in International Application No. PCT/US2020/063064, dated May 17, 2022, 7 pages.
International Preliminary Report on Patentability in International Application No. PCT/US2021/013438, dated Jul. 28, 2022, 7 pages.
International Search Report and Written Opinion in International Application No. PCT/US2022/024210, dated Jun. 28, 2022, 14 pages.
Israeli Office Action in Israeli Application No. 289834 dated Jul. 14, 2022, 4 pages.
Japanese Office Action in Japanese Application No. 2019-565177, dated May 13, 2022, 11 pages.
Japanese Office Action in Japanese Application No. 2020-093529, dated Mar. 1, 2022, 5 pages.
Korean Office Action in Korean Application No. 10-2022-7018808, dated Sep. 16, 2022, 5 pages.
Mexican Office Action in Mexican Application No. MX/a/2019/014097, dated Aug. 11, 2022, 13 pages.
Mexican Office Action in Mexican Application No. MX/a/2019/014097, dated Mar. 15, 2022, 12 pages.
Philippine Allowance in Philippine Application No. 1/2015/502383, dated Jun. 6, 2022, 2 pages.
Porta, "FGFR a promising druggable target in cancer: Molecular biology and new drugs." Critical reviews in oncology hematology, 2017, 113:256-267.
Ukraine Office Action in Ukraine Application No. a202007700, dated Sep. 13, 2022, 11 pages.
Vietnamese Office Action in Vietnamese Application No. 1-2022-03016, dated Jul. 8, 2022, 2 pages.
Yu et al., "Amorphous pharmaceutical solids: preparation, characterization and stabilization," Advanced Drug Delivery Reviews, May 16, 2001, 48(1):27-42.
Australian Office Action in Australian Application No. 2022291504, dated Jul. 21, 2023, 4 pages.
Brazil Office Action in Brazil Application No. BR1120170 17727-7, dated Jun. 28, 2023, 8 pages (with machine translation).
Eurasian Office Action in Eurasian Application No. 202190877, dated Jul. 14, 2023, 5 pages.
Peru Office Action in Peru Application No. 00866-2019/DIN, dated Jun. 28, 2023, 12 pages.
"Sabiosciences.com" [online]. "FGF Pathway," 2000-2012, [retrieved on Jun. 23, 2015]. Retrieved from the Internet: URL <http://www.sabiosciences.com/pathway.php?sn=FGF_Signaling>, 3 pages.
"Substance Record for SID 240993001," Feb. 13, 2015, pp. 1-8.
Acevedo et al., "Inducible FGFR-1 Activation Leads to Irreversible Prostate Adenocarcinoma and an Epithelial-to-Mesenchymal Transition," Cancer Cell, Dec. 2007, 12: 559-571.
Ali et al., "Synthesis and structure activity relationship of substituted N,6-diphenyl-5,6-dihydrobenzo[h]quinazolin-2-amine as inhibitors of fibroblast growth factor receptors (FGFR)" Cancer Res, Apr. 15, 2012, 72; 3905.
Angevin et al., "TKI258 (dovitinib lactate) in metastatic renal cell carcinoma (mRCC) patients refractory to approved targeted therapies: A phase I/II dose finding and biomarker study," Journal of Clinical Oncology, May 20, 2009, 27:15S, 1 page.
Antonios-McCrea et al., "LHMDS mediated tandem acylation-cyclization of 2-aminobenzenecarbonitriles with 2-benzymidazol-2-ylacetates: a short and efficient route to the synthesis of 4-amino-3-benzimidazol-2-ylhydroquinolin-2-ones," Tetrahedron Letters, 2006, 657-660.
Anonymous, "American Society for Clinical Pharmacology and Therapeutics," Clin Pharma and Thera., Feb. 13, 2019, 105(S1):S5-S121.
Anonymous, "In Vitro Metabolism- and Transporter—Mediated Drug-Drug Interaction Studies Guidance for Industry", Clinical Pharmacology, Oct. 2017, 47 pages.
Arai et al., "Characterization of the cell or origin and propagation potential of the fibroblast growth factor 9-induced mouse model of lung adenocarcinoma," J. Pathol., Mar. 2015, 235(4): 593-605.
Arai et al., "Fibroblast growth factor receptor 2 tyrosine kinase fusions define a unique molecular subtype of cholangiocarcinoma," Hepatology, 2014, 59(4):1427-1434.
Argentina Office Action in Argentina Application No. 20130102068, dated Jul. 17, 2020, 10 pages.
Argentina Office Action in Argentina Application No. 20140101651, dated Nov. 21, 2019, 5 pages.
Argentina Office Action in Argentina Application No. 20140101651, dated Jul. 29, 2021, 9 pages.
Ash and Ash, "Handbook of Pharmaceutical Additives," Gower Publishing Company, 2007, 3rd ed.
Atzrodt et al., "The Renaissance of H/D Exchange," Angew Chem Int Ed., 2007, 7744-7765.
Australian Office Action in Australian Application No. 2013287176, dated Sep. 12, 2017, 4 pages.

(56) References Cited

OTHER PUBLICATIONS

Australian Office Action in Australian Application No. 2014253798, dated Jul. 31, 2017, 4 pages.
Australian Office Action in Australian Application No. 2016219816, dated Aug. 26, 2019, 3 pages.
Australian Office Action in Australian Application No. 2016219822, dated Jul. 8, 2019, 4 pages.
Australian Office Action in Australian Application No. 2018208772, dated Jul. 1, 2018, 5 pages.
Australian Office Action in Australian Application No. 2019200066, dated Aug. 27, 2019, 6 pages.
Australian Office Action in Australian Application No. 2018272013, dated Sep. 2, 2021, 4 pages.
Australian Office Action in Australian Application No. 2020250211, dated Sep. 13, 2021, 4 pages.
Australian Office Action in Australian Application No. 2020270520, dated Dec. 16, 2021, 4 pages.
Avet-Loiseau et al., "Impact of high-risk cytogenetics and prior therapy on outcomes in patients with advanced relapsed or refractory multiple myeloma treated with lenalidomide plus dexamethasone," Leukemia, 2010, 623-628.
Bai et al., "GP369, an FGFR2-IIIb specific antibody, exhibits potent antitumor activity against human cancers driven by activated FGFR2 signaling," Am. Assoc. for Cancer Research, Aug. 17, 2010, 30 pages.
Bansal et al., "Specific inhibitor of FGF receptor signaling: FGF-2-mediated effects on proliferation, differentiation, and MAPK activation are inhibited by PD173074 in oligodendrocyte-lineage cells," J. Neurosci. Res., 2003, 74: 486.
Bavin, "Polymorphism in Process Development," Chemistry & Industry, Society of Chemical Industry, Aug. 1989, 527-529.
Bazyl et al., "The selective ortho-methoxylation of pentafluorobenzoic acid—a new way to tetrafluorosalicylic acid and its derivatives," J Flour Chem., Feb. 11, 1999, 94(1):11-13.
Beekman et al., "New Molecular Targets and Novel Agents in the Treatment of Advanced Urothelial Cancer," Semin Oncol, 2007, 34: 154-164.
Bello et al., "E-3810 is a potent dual inhibitor of VEGFR and FGFR that exerts antitumor activity in multiple preclinical models," Cancer Res, 2011.
Bello et al., "E-3810 is a potent dual inhibitor of VEGFR and FGFR that exerts antitumor activity in multiple preclinical models," Cancer Res, 2011, Supplemental figures, 4 pages.
Bello et al., "E-3810 is a potent dual inhibitor of VEGFR and FGFR that exerts antitumor activity in multiple preclinical models," Cancer Res, 2011, Supplemental table, 3 pages.
Bello et al., "E-3810 is a potent dual inhibitor of VEGFR and FGFR that exerts antitumor activity in multiple preclinical models," Cancer Res, 2011, Supplementary data, 4 pages.
Benet-Pages et al., "An FGF23 missense mutation causes familial tumoral calcinosis with hyperphosphatemia," Human Molecular Genetics, 2005, 14(3):385-390.
Berge et al., "Pharmaceutical Salts", Journal of Pharmaceutical Science, 1977, 66(2):1-19.
Bergwitz and Juppner, "Regulation of Phosphate Homeostasis by PTH, Vitamin D, and FGF23," Annu. Rev. Med., 2010, 61:91-104.
Bhide et al., "Discovery and Preclinical Studies of (R )-1-(4-(4-Fluoro-2-methyl-1H-indol-5-yloxy)-5-methylpyrrolo[2,1-f][1,2,4]triazin-6-yloxy)propan-2-ol (BMS-540215), an In Vivo Active Potent VEGFR-2 Inhibitor," Journal of Medicinal Chemistry, 2006, 49(7): 2143-2146.
Billerey et al., "Frequent FGFR3 Mutations in Papillary Non-Invasive Bladder (pTa) Tumors," American Journal of Pathology, Jun. 2001, 158(6): 1955-1959.
Billottet et al., "Targets of Fibroblast Growth Factor 1 (FGF-1) and FGF-2 Signaling Involved in the Invasive and Tumorigenic Behavior of Carchinoma Cells," Molecular Biology of the Cell, Oct. 2004, 15: 4725-4734.
BioCentury, Week of Nov. 10, 2014, 52 pages.

Bisping et al., "Bortezomib, Dexamethasone, and Fibroblast Growth Factor Receptor 3-Specific Tyrosine Kinase Inhibitor in t(4;14) Myeloma," Clin Cancer Res, Jan. 2009, 15(2):520-531.
Black et al., "Targeted therapies in bladder cancer—an update," Urologic Oncology: Seminars and Original Investigations, 2007, 433-438.
Blom et al., "Optimizing Preparative LC-MS Configurations and Methods for Parallel Synthesis Purification", J Combi Chem., 2003, 5:670.
Blom et al., Preparative LC-MS Purification: Improved Compound Specific Method Optimization, J Combi Chem. 2004, 6(6):874-883.
Blom, K., "Two-Pump at Column Dilution Configuration for Preparative LC-MS", J Combi Chem., 2002, 4:295.
Bonaventure et al., "Common Mutations in the Fibroblast Growth Factor Receptor 3 (FRFR3) Gene Account for Achondroplasia, Hypochondroplasia and Thanatophoric Dwarfism," Clin Pediatr Endocrinol, 1997, 105-113.
Bono et al., "Inhibition of Tumor Angiogenesis and Growth by a Small-Molecule Multi-FGF Receptor Blocker with Allosteric Properties," Cancer Cell, Apr. 2013, 477-488.
Borad et al., "Fibroblast growth factor receptor 2 fusions as a target for treating cholangiocarcinoma," Current opinion in Gastroenterology, May 2015, 31(3):264-268.
Brooks et al., "Fibroblast growth factor signaling: a new therapeutic opportunity in cancer," Clinical Cancer Research, 2012, 1-23.
Caira, "Crystalline Polymorphism of Organic Compounds," Topics in Current Chemistry, Jan. 1, 1998, 198:163-208.
Casey et al., "Translating in vivo metabolomic analysis of succinate dehydrogenase deficient tumours into clinical utility," JCO Precis Oncol., Mar. 29, 2018, 2:1-12.
Cancer [online], [retrieved on Jul. 6, 2007] Retrieved from the Internet, URL: http://www.nlm.nih.gov/medlineplus/cancer.html.
Capelletti et al., "Identification of Recurrent FGFR3-TACC3 Fusion Oncogenes from Lung Adenocarcinoma," AACR Journals, 2014, 6551-6558.
Cappellen et al., "Frequent activating mutations of FGFR3 in human bladder and cervix carcinomas," Nature Genetics, Sep. 1999, 23: 18-20.
Carmichael et al., "Familial Tumoral Calcinosis: A Forty-Year Follow-up on One Family," The Journal of Bone & Joint Surgery, 2009, 664-671.
Cha et al., "Aberrant Receptor Internalization and Enhanced FRS2-dependent Signaling Contribute to the Transforming Activity of the Fibroblast Growth Factor Receptor 2 IIIb C3 Isoform," The Journal of Biological Chemistry, Mar. 2009, 284(10): 6227-6240.
Chandrani et al., "Drug-sensitive FGFR3 mutations in lung adenocarcinoma," Annals of Oncology, 2017, 28: 597-603.
Chase et al., "Activity of TKI258 against primary cells and cell lines with FGFR1 fusion genes associated with the 8p11 myeloproliferative syndryome," Blood, 2007, 110:3729-3734.
Chefetz and Sprecher, "Familial tumoral calcinosis and the role of O-glycosylation in the maintenance of phosphate homeostasis," Biochimica et Biophysica Acta, 2009, 847-852.
Chefetz et al., "A novel homozygous missense mutation in FGF23 causes Familial Tumoral Calcinosis associated with disseminated visceral calcification," Hum Genet, 2005, 118:261-266.
Chell et al., "Tumour cell responses to new fibroblast growth factor receptor tyrosine kinase inhibitors and identification of a gatekeeper mutation in FGFR3 as a mechanism of acquired resistance," Oncogene, 2012, 1-12.
Chen et al., "Acenaphtho[1,2-b]pyrrole-Based Selective Fibroblast Growth Factor Receptors 1 (FRGR1) Inhibitors: Design, Synthesis, and Biological Activity," Jounal of Medicinal Chemistry, 2011, 54: 3732-3745.
Chen et al., "FGFR3 as a therapeutic target of the small molecule inhibitor PKC412 in hematopoietic malignancies," Oncogene, 2005, 24: 8259-8267.
Chen et al., "Genome-Wide Loss of Heterozygosity and DNA Copy Number Aberration in HPV-Negative Oral Squamous Cell Carcinoma and Their Associations with Disease-Specific Survival," Plos One, Aug. 2015, 23 pages.

(56) References Cited

OTHER PUBLICATIONS

Cherukupalli et al., "An insight on synthetic and medicinal aspects of pyrazolo[1,5-a]pyrimidine scaffold," European Journal of Medicinal Chemistry, Nov. 10, 2016, 126:298-352.
Chesi et al., "Activated fibroblast growth factor receptor 3 is an oncogene that contributes to tumor progression in multiple myeloma," Blood, 2001, 97:729-736.
Chesi et al., "Frequent translocation t(4;14)(p16.3;q32.3) in multiple myeloma is associated with increased expression and activating mutations of fibroblast growth factor receptor 3," Nature Genetics, 1997, 260-264.
Chilean Office Action in Chilean Application No. 1984-2017, dated Sep. 12, 2019, 9 pages.
Chilean Office Action in Chilean Application No. 2015-003089, dated Apr. 24, 2017, 13 pages (English Summary).
Chilean Office Action in Chilean Application No. 2015-003089, dated Jan. 23, 2018, 8 pages.
Chilean Office Action in Chilean Application No. 2122-2017, dated Apr. 22, 2019, 25 pages.
Chilean Office Action in Chilean Application No. 2122-2017, dated Nov. 15, 2019, 15 pages.
Chilean Office Action in Chilean Application No. 3355-2014, dated Jan. 18, 2017, 17 pages (with English translation).
Chilean Office Action in Chilean Application No. 3439-2019, dated Feb. 10, 2021, 26 pages.
Chilean Opposition in Chilean Application No. 3355-2014, 3 pages (English translation only).
Chinese Office Action in Chinese Application No. 10874686.0, dated Oct. 8, 2019, 10 pages.
Chinese Office Action in Chinese Application No. 201380041027.9, dated Feb. 13, 2017, 10 pages (with English translation).
Chinese Office Action in Chinese Application No. 201380041027.9, dated Jul. 12, 2016, 11 pages (with English translation).
Chinese Office Action in Chinese Application No. 201380041027.9, dated Oct. 28, 2015, 17 pages (with English translation).
Chinese Office Action in Chinese Application No. 201480028858.7, dated Apr. 4, 2018, 10 pages (English Translation).
Chinese Office Action in Chinese Application No. 201480028858.7, dated Aug. 19, 2016, 18 pages (English Translation).
Chinese Office Action in Chinese Application No. 201480028858.7, dated Jul. 12, 2017, 10 pages (English Translation).
Chinese Office Action in Chinese Application No. 201680011332.7, dated Aug. 5, 2019, 14 pages.
Chinese Office Action in Chinese Application No. 201680011348.8, dated Aug. 2, 2019, 14 pages.
Chinese Office Action in Chinese Application No. 201710395346.X, dated Jan. 22, 2019, 17 pages.
Chinese Office Action in Chinese Application No. 201710395346.X, dated Sep. 9, 2019, 10 pages.
Chinese Office Action in Chinese Application No. 201710874686.0, dated Feb. 25, 2019, 17 pages.
Chinese Office Action in Chinese Application No. 201910023729.3, dated Mar. 3, 2021, 15 pages.
Chinese Office Action in Chinese Application No. 201910023729.3, dated Sep. 8, 2021, 11 pages.
Chng et al., "Translocation t(4;14) retains prognostic significance even in the setting of high-risk molecular signature," Leukemia, 2008, 2: 459-461.
Chuaqui et al., "Interaction Profiles of Protein Kinase—Inhibitor Complexes and Their Application to Virtual Screening," J. Med. Chem., 2005, 48: 121-133.
Ciappetti and Geithlen "Molecular Variations Based on Isosteric Replacements," The Practice of Medicinal Chemistry, 2008, Chapter 15, pp. 290-341.
ClinicalTrials.gov, "A Study to Evaluate the Efficacy and Safety of Pemigatinib Versus Cherrotherapy in Unresectable or Metastatic Chol (FIGHT-302)," NCT03656536, Mar. 6, 2019, retrieved from URL <https://www.clinicaltrials.gov/ct2/history/NCT03656536?V_5=View#StudyPageTop,>, 4 pages.

Cole et al., "Inhibition of FGFR2 and FGFR1 increases cisplatin sensitivity in ovarian cancer," Cancer Biol. Therapy, Sep. 1, 2010, 10(5):495-504.
Coleman, "Positive and negative regulation of cellular sensitivity to anti-cancer drugs by FGF-2," Drug Resistance Updates, 2003, 85-94.
Colombian Office Action in Colombian Application No. 14-275934-6, dated May 31, 2016, 3 pages (English translation only).
Colombian Office Action in Colombian Application No. 14-275934-6, dated Nov. 17, 2015, 12 pages (English translation only).
Colombian Office Action in Colombian Application No. 16100866, dated Aug. 10, 2017, 9 pages.
Colombian Office Action in Colombian Application No. NC2017/0008795, dated Nov. 29, 2018, 8 pages.
Colombian Office Action in Colombian Application No. NC2017/0008795, dated Aug. 16, 2019, 6 pages.
Colombian Office Action in Colombian Application No. NC2017/0008795, dated Aug. 29, 2017, 2 pages.
Colombian Office Action in Colombian Application No. NC2017/0008824, dated Aug. 31, 2017, 3 pages.
Colombian Office Action in Colombian Application No. NC2017/0008824, dated Nov. 29, 2018, 8 pages.
Colombian Office Action in Colombian Application No. NC2019/0009690, dated Jan. 22, 2020, 20 pages.
Colombian Opposition in Colombian Application No. NC 2021/0004568, dated Apr. 15, 2021, 21 pages.
Cordovilla et al., "The Stille Reaction, 38 Years Later," ACS Catal., Apr. 17, 2015, 5(5):3040-3053.
Corre et al., "Synthesis and biological evaluation of a triazole-based library of pyrido[2,3-d]pyrimidines as FGFR3 tyrosine kinase inhibitors," Organic & Biomolecular Chemistry, 2010, 8:2164-2173.
Costa Rican Office Action in Costa Rican Application No. 2014-0577, dated Apr. 15, 2020, 18 pages.
Costa Rican Office Action in Costa Rican Application No. 2014-0577, dated Jun. 13, 2019, 17 pages.
Costa Rican Office Action in Costa Rican Application No. 2015-0578, dated Jun. 11, 2020, 15 pages.
Costa Rican Opposition in Costa Rican Application No. PCT/US2013/045309, dated Jun. 29, 2015, 14 pages (English Translation).
Covic et al., "Vascular calcification in chronic kidney disease," Clinical Science, 2010, 119: 111-121.
Crose et al., "FGFR4 Blockade Exerts Distinct Antitumorigenic Effects in Human Embryonal versus Alveolar Rhabdomyosarcoma," Clin Cancer Res., 2012, 18:3780-3790.
Dailey et al., "Mechanisms underlying differential responses to FGF signaling," Cytokine & Growth Factor Reviews, 2005, 233-247.
Dash et al., "A Role for Neoadjuvant Gemcitabine Plus Cisplatin in Muscle-Invasive Urothelial Carcinoma o the Bladder: A Retrospective Experience," Cancer, 2008, 113(9): 2471-2477.
Desnoyers et al., "Targeting FGF19 inhibits tumor growth in colon cancer xenograft and FGF19 transgenic hepatocellular carcinoma models," Oncogene, 2008, 27:85-97.
Dey et al., "Targeting Fibroblast Growth Factor Receptors Blocks PI3K/AKT Signaling, Induces Apoptosis, and Impairs Mammary Tumor Outgrowth and Metastasis," Cancer Research, 2010, 4151-4162.
Dieci et al., "Fibroblast Growth Factor Receptor Inhibitors as a Cancer Treatment: From a Biologic Rationale to Medical Perspectives," Cancer Discovery, 2013, 1-16.
Dienstmann et al., "Genomic aberrations in the FGFR pathway: opportunities for targeted therapies in solid tumors, " Annals of Oncology, 2013, 1-12.
Diller and Li, "Kinases, Homology Models, and High Throughput Docking," J. Med. Chem., 2003, 46: 4638-4647.
Dimopoulos et al., "Lenalidomide plus Dexamethasone for Relapsed or Refractory Multiple Myeloma," The New England Journal of Medicine, 2007, 357:2123-2132.
Ding et al., "Somatic mutations affect key pathways in lung adenocarcinoma," Nature., Oct. 23, 2008, 455:1069-1075.
Dovedi and Davies, "Emerging targeted therapies for bladder cancer: a disease waiting for a drug," Cancer Metastasis Rev, 2009, 28:355-367.

(56) References Cited

OTHER PUBLICATIONS

Dring et al., "A Global Expression-based Analysis of the Consequences of the t(4;14) Translocation in Myeloma," Clinical Cancer Research, Sep. 2004, 10: 5692-5701.
Drueke et al., "Phosphate binders in CKD: bad news or good news?," Journal of the American Society of Nephrology, Aug. 2012, 23(8):1277-1280.
Dutt et al., "Drug-sensitive FGFR2 mutations in endometrial carcinoma," PNAS, Jun. 24, 2008, 105(25):8713-8717.
Dutt et al., "Drug-sensitive FGFR2 mutations in endometrial carcinoma," Supporting Information, Jun. 2008, 8 pages.
Ecuador Office Action in Ecuador Application No. IEPI-2015-1225, dated Dec. 30, 2021, 21 pages.
Edmondson et al., "Aminopiperidine-fused imidazoles as dipeptidyl peptidase-IV inhibitors," Bioorg & Med Chem Lett., 2009, 19(15):4097-4101.
Eissa, "Synthesis and evaluation of some surface active agents from long chain fatty amine," Spanish National Research Council, Jan. 2007, 58(4):379-389.
Elsheikh et al., "FGFR1 amplification in breast carcinomas: a chromogenic in situ hybridisation analysis," Breast Cancer Research, Mar. 2007, 9(2): 1-12.
Erian at al., "2-Aryl-1,1-dicyano-3-phenylsulfonylpropenes in heterocyclic synthesis. A synthetic strategy towards heterocyclic sulfones," Monatshefte fuer Chemie, 1998, 129(10):1049-1056.
Eskens and Verweij, "The clinical toxicity profile of vascular endothelial growth factor (VEGF) and vascular endothelial growth factor receptor (VEGFR) targeting angiogenesis inhibitors; A review," European Journal of Cancer, 2006, 3127-3139.
Eswarakumar and Schlessinger, "Cellular signaling by fibroblast growth factor receptors," Cytokine & Growth Factor Reviews, 2005, 139-149.
Eurasian Office Action in Eurasian Application No. 201590005, dated Oct. 21, 2015, 6 pages.
Eurasian Office Action in Eurasian Application No. 201590005, Mar. 28, 2018, 6 pages.
Eurasian Office Action in Eurasian Application No. 201791866, dated Feb. 19, 2018, 10 pages (English Translation).
Eurasian Office Action in Eurasian Application No. 201791867, dated Apr. 4, 2018, 4 pages (English Translation).
Eurasian Office Action in Eurasian Application No. 202091923, dated Jul. 27, 2021, 6 pages (English Translation).
Eurasian Office Action in Eurasian Application No. 201992794, dated Sep. 17, 2021, 7 pages.
Eurasian Office Action in Eurasian Application No. 202190877, dated Oct. 6, 2021, 4 pages.
European Communication pursuant to Article 94(3) EPC in European Application No. 13783125.1, dated Jan. 26, 2016, 4 pages.
European Office Action in European Application No. 18733045.1, dated Jan. 11, 2021, 5 pages.
European Office Action in European Application No. 20192679.7, dated Feb. 11, 2021, 7 pages.
European Office Action in European Application No. 16715139.8, dated May 18, 2021, 9 pages.
European Office Action in European Application No. 19724676.2, dated Aug. 26, 2021, 5 pages.
European Office Action in European Application No. 19724670.5, dated Nov. 9, 2021, 4 pages.
European search report in European Application No. 16203866.5, dated Mar. 1, 2017, 7 pages.
European Search Report in European Application No. 17199421.3, dated Jul. 12, 2018, 15 pages.
European Search Report in European Application No. 17199421.3, dated Mar. 12, 2018, 14 pages.
Ezzat et al., "Dual Inhibition of RET and FGFR4 Restrains Medullary Thyroid Cancer Cell Growth," Clinical Cancer Research, 2005, 11:1336-1341.
Faul et al., "FGF23 induces left ventricular hypertrophy," The Journal of Clinical Investigation, 2010, 1-16.
FDA.gov, "FDA grants accelerated approval to pemigatinib for cholangiocarcinoma with an FGFR2 rearrangement or fusion," Apr. 20, 2020, [Retrieved on Apr. 27, 2021], retrieved from URL <https://www.fda.gov/drugs/resources-information-approved-drugs/fda-grants-accelerated-approval-pemigatinib-cholangiocarcinoma-fgfr2-rearrangement-or-fusion>, 2 pages.
Feng et al., "Guidance to rational use of pharmaceuticals in gallbladder sarcomatoid carcinoma using patient-derived cancer cells and whole exome sequencing," Oncotarget, 2017, 8(3): 5349-5360.
Feng et al., "Targeting Fibroblast Growth Factor Receptor Signaling Inhibits Prostate Cancer Progression," Clinical Cancer Research, 2012, 1-9.
Ferrera et al., "Bevacizumab (Avastin), a humanized anti-VEGF monoclonal antibody for cancer therapy," Biochemical and Biophysical Research Communications, 2005, 328-335.
Fillmore et al., "Estrogen expands breast cancer stem-like cells through paracrine FGF/Tbx3 signaling," PNAS, 2010, 1-6.
Fischer et al., "Fibroblast growth factor receptor-mediated signals contribute to the malignant phenotype of non-small cell lung cancer cells: therapeutic implications and synergism with epidermal growth factor receptor inhibition," Mol Cancer Therapy, 2008, 3408-3419.
French et al., Targeting FGFR4 inhibits hepatocellular carcinoma in preclinical mouse models, PLoS One 2012;7:e36713.
Fricker, "Metal based drugs: from serendipity to design," Dalton Transactions, 2007, 43:4903-4917.
Fricker, "The therapeutic application of lanthanides," Chemical Society Reviews, 2006, 35(6):524-533.
Frishberg et al., "Hypertosis-Hyperphosphatemia Syndrome: A Congenital Disorder of O-Glycosylation Associated With Augmented Processing of Fibroblast Growth Factor 23," Journal of Bone and Mineral Research, 2007, 22(2): 235-242.
Frishberg et al., "Identification of a recurrent mutation in GALNT3 demonstrates that hyperostosis-hyperphosphatemia syndrome and familial tumoral calcinosis are allelic disorders," J Mol Med, 2005, 83:33-38.
Fu et al., "Intratumoral inorganic phosphate deprivation: A new anticancer strategy," Medical Hypotheses, Feb. 2020, 135:109497.
Fukumoto and Yamashita, "FGF23 is a hormone-regulating phophate metabolism—Unique biological characteristics of FGF23," Bone, 2007, 1190-1195.
Fun et al., "2-7(7,8-Diphenyl-1H-imidazo[4,5-f]-quinoxalin-2-yl)phenol methanol disolvate," Acta Crystallographica Section E Structure Reports Online, 2008, 64(9):01741-01742.
Furniss "Acidic/Basic characteristics for purification," Vogel's Textbook of Practical Organic Chemistry, 5th edition, 1989, 131-133, 135-143.
Galdemard et al., "Regulation of FGF-3 Gene Expression in Tumorigenic and Non-tumorigenic Clones of a Human Colon Carcinoma Cell Line," The Journal of Biological Chemistry, 2000, 275(23): 17364-17373.
Gallo et al., "Functions of Fibroblast Growth Factor Receptors in cancer defined by novel translocations and mutations," Cytokine & Growth Factor Reviews, 2015, 26(4):425-449.
Garringer et al., "Molecular genetic and biochemical analyses of FGF23 mutations in familial tumoral calcinosis," Am J Physiol Endocrinol Metab, 2008, 929-937.
Gattineni et al., "FGF23 decreases renal NaPi-2a and NaPi-2c expression and induces hypophosphatemia in vivo predominantly via FGF receptor 1," Am J Physiol Renal Physiol, 2009, 297: 282-291.
Gavine et al., "AZD4547: An Orally Bioavailable, Potent, and Selective Inhibitor of the Fibroblast Growth Factor Receptor Tyrosine Kinase Family," American Association for Cancer Research, Apr. 2012, 72(8): 2045-2056.
Gennaro et al., "Pharmaceutical Sciences," Remington's Pharmaceutical Sciences 17th Ed., Jan. 1985, 14-18 and 1409-1423.
Gerby et al., "2-Arylidenedihydroindole-3-ones: Design, synthesis, and biological activity on bladder carcinoma cell lines," Bioorganic & Medicinal Chemistry Letters, 2007, 208-213.
Ghorab et al., "Synthesis of some sulfur containing Tetrahydrobenzoabuthieno[b] Thieno(Pyridines, Quinolines, Oxazines and Pyrimidines) as possible radioprotective and Antineoplastic agents," Phosphorus, Sulfur and Silicon, Jan. 1998, 134/135:57-76.

(56) References Cited

OTHER PUBLICATIONS

Gibson, "Pharmaceutical Preformulation and Formulation," CRC Press LLC, 2009, 2nd ed, 559 pages.
Goetz et al., "Isolated C-terminal tail of FGF23 alleviates hypophosphatemia by inhibiting FGF23-FGFR-Klotho complex formation," PNAS, Jan. 2010, 107(1): 407-412.
Golub et al., "Molecular Classification of Cancer: Class Discovery and Class Prediction by Gene Expression Monitoring, " Science, 1999, 286: 531-537.
Gomez-Rivera et al., "The Tyrosine Kinase Inhibitor, AZD2171, Inhibits Vascular Endothelial Growth Factor Receptor Signaling and Growth of Anaplastic Thyroid Cancer in an Orthotopic Nude Mouse Model," Clin Cancer Res, Aug. 2007, 4519-4527.
Goyal et al., "Polyclonal Secondary FGFR2 Mutations Drive Acquired Resistance to FGFR Inhibition in Patients with FGFR2 Fusion-Positive Cholangiocarcinoma," Cancer Discov., 2016, 7(3):252-263.
Govindan, "Summary of Presentations from the Ninth Annual Targeted Therapies in Lung Cancer Symposium," Journal of Thoracic Oncology, Nov. 2009, 4(11): 1045-1089.
Gozgit et al., "Ponatinib (AP24534), a Multitargeted Pan-FGFR Inhibitor with Activity in Multiple FGFR-Amplified or Mutated Cancer Models," Mol Cancer Ther, 2012, 11: 690-699.
Granberg et al., "Strong FGFR3 staining is a marker for FGFR3 fusions in diffuse gliomas," Neuro-Oncology, 2017, 19(9): 1206-1216.
Grand et al., "Targeting FGFR3 in multiple myeloma: inhibition of t(4;14)-positive cells by SU5402 and PD173074," Leukemia, 2004, 18: 962-966.
Greene, T. W. and Wuts, P. G. M., "Protective Groups in Organic Synthesis", 3rd Ed., Wiley & Sons, Inc., New York (1999), 799 pages.
Greulich and Pollock, "Targeting mutant fibroblast growth factor receptors in cancer," Cell Press, May 2011, 17(5): 283-292.
Grose and Dickson, "Fibroblast growth factor signaling in tumorigenesis," Cytokine & Growth Factor Reviews, 2005, 179-186.
Gu et al., "Phosphotyrosine profiling identifies the KG-1 cell line as a model for the study of FGFR1 fusions in acute myeloid leukemia," Blood, Dec. 15, 2006, 108(13):4202-42040.
Guagnano et al., "Discovery of 3-(2,6-Dichloro-3,5-dimethoxy-phenyl)-1-{6-[4-(4-ethyl-piperazin-1-yl)-phenylamino]-pyrimidin-4-yl}-1-methyl-urea (NVP-BGJ398), A Potent and Selective Inhibitor of the Fibroblast Growth Factor Receptor Family of Receptor Tyrosine Kinase," J. Med. Chem., 2011, 54: 7066-7083.
Guan et al., "Design and synthesis of aminopropyl tetrahydroindole-based indolin-2-ones as selective and potent inhibitors of Src and Yes tyrosine kinase," Bioorganic & Medicinal Chemistry Letters, 2004, 187-190.
Gust et al., "Fibroblast Growth Factor Receptor 3 Is a Rational Therapeutic Target in Bladder Cancer," Molecular Cancer Therapeutics, Jul. 2013, 12(7): 1245-1254.
Haas et al., "Recent Developments in Negishi Cross-Coupling Reactions," ACS Catal., 2016, 6(3):1540-1552.
Hackam et al. "Translation of Research Evidence From Animals to Humans," JAMA, 296(14), 2006, 296(14):1731-1732.
Hafner et al., "High Frequency of FGFR3 Mutations in Adenoid Seborrheic Keratoses," Journal of Investigative Dermatology, 2006, 126: 2404-2407.
Hafner, "Seborrheic keratoses and epidermal nevi: new pathogenetic insights and therapeutic implications," Expert Rev Dermatol, 2006, 1(6): 759-761.
Hagel et al., "First Selective Small Molecule Inhibitor of FGFR4 for the Treatment of Hepatocellular Carcinomas with an Activated FGFR4 Signaling Pathway," Cancer Discovery, Apr. 2015, 1-14.
Hara and Saito, "CARD9 versus CARMA1 in innate and adaptive immunity," Cell Press, 2009, 234-242.

Heinrich et al., "Fragment-based discovery of new highly substituted 1H-pyrrolo[2,3-b]- and 3H-imidazolo[4,5-b]-pyridines as focal adhesion kinase inhibitors," J of Med Chem., Jan. 8, 2013, 56(3):1160-1170.
Heinzle C, et al., "Differential Effects of Polymorphic Alleles of FGF Receptor 4 on Colon Cancer Growth and Metastasis," Cancer Research, Nov. 2012, 72(22):5767-5777.
Heinzle et al., "Is fibroblast growth factor receptor 4 a suitable target of cancer therapy?," Cur. Pharm. Des., 2014, 20:2881-2898.
Heinzle et al., "Targeting fibroblast-growth-factor-receptor-dependent signaling for cancer therapy," Expert Opinion, 2011, 1-18.
Helsten et al., "The FGFR Landscape in Cancer: Analysis of 4,853 Tumors by Next-Generation Sequencing," Clin. Cancer Res., Jan. 2016, 22:259-267.
Hideshima and Anderson, "Preclinical Studies of Novel Targeted Therapies," Hematol Oncol Clin N Am, 2007, 1071-1091.
Ho et al., "Fibroblast growth factor receptor 4 regulates proliferation, anti apoptosis and alpha-fetoprotein secretion during hepatocellular carcinoma progression and represents a potential target for therapeutic intervention," J Hepatol, 2009, 50:118-127.
Honigberg et al., "The Bruton tyrosine kinase inhibitor PCI-32765 blocks B-cell activation and is efficacious in models of autoimmune disease and B-cell malignancy," Supporting Information, PNAS, Jul. 20, 2010, 107:29.
Hruska et al., "The Pathogenesis of Vascular Calcification in the Chronic Kidney Disease Mineral Bone Disorder (CKD-MBD): The Links Between Bone and Vasculature," Semin Nephrol, Mar. 2009, 29(2): 156-165.
Hu and Cong, "Fibroblast growth factor 19 is correlated with an unfavorable prognosis and promotes progression by activating fibroblast growth factor receptor 4 in advanced-stage serous ovarian cancer," Oncol Rep., Aug. 20, 2015, 34(5):2683-2691.
Huynh, "Tyrosine kinase inhibitors to treat liver cancer," Expert Opinion, 2010, 13-26.
Hynes and Dey, "Potential for Targeting the Fibroblast Growth Factor Receptors in Breast Cancer," Cancer Res, 2010, 70:5199-5202.
ICH Harmonised Tripartite Guideline, "Specifications: Test Procedures and Acceptance Criteria for New Drug Substances and New Drug Products Chemical Substances," ICHTRRPHU, Oct. 6, 1999, 35 pages.
Ichikawa et al., "A homozygous missense mutation in human KLOTHO causes severe tumoral calcinosis," The Journal of Clinical Investigation, Sep. 2007, 117(9): 2684-2691.
Ichikawa et al., "A Novel GALNT3 Mutation in a Pseudoautosomal Dominant Form of Tumoral Calcinosis: Evidence That the Disorder Is Autosomal Recessive," J. Clin. Endocrinol. Metab., 2005, 90:2420-2423.
Ichikawa et al., "Clinical Variability of Familial Tumoral Calcinosis Caused by Novel GALNT3 Mutations," American Journal of Medical Genetics, 2009, 896-903.
Ichikawa et al., "Novel GALNT3 Mutations Causing Hyperostosis-Hyperphosphatemia Syndrome Result in Low Intact Fibroblast Growth Factor 23 Concentrations," J. Clin. Endocrinol. Metab., 2007, 92:1943-1947.
Ichikawa et al., "Tumoral Calcinosis Presenting with Eyelid Calcifications due to Novel Missense Mutations in the Glycosyl Transferase Domain of the GALNT3 Gene," J. Clin. Endocrinol. Metab., 2006, 91: 4472-4475.
Indian Office Action in Indian Application No. 10665/DELNP/2014, dated Jun. 25, 2018, 8 pages.
Indian Office Action in Indian Application No. 201717030265, dated Dec. 12, 2019, 5 pages.
Indian Office Action in Indian Application No. 201717030267, dated Dec. 3, 2019, 7 pages.
Indian Office Action in Indian Application No. 9781/DELNP/2015, dated Jan. 18, 2019, 6 pages.
Indian Oral Hearing in Indian Application No. 201717030265, dated Jan. 13, 2022, 2 pages.
Indonesian Office Action in Indonesian Application No. P00201507153, dated Apr. 27, 2018, 5 pages (English Translation).

(56) References Cited

OTHER PUBLICATIONS

Indonesian Office Action in Indonesian Application No. PID201705977, dated Jun. 5, 2020, 5 pages.
Inokuchi et al., "Therapeutic targeting of fibroblast growth factor receptors in gastric cancer," Gastroenterol Res Pract., Apr. 27, 2015, 2015:796380, 8 pages.
International Invitation to Pay Fees in International Appln. No. PCT/US2019/030633, dated Aug. 12, 2019, 5 pages.
International Preliminary Report on Patentability and Written Opinion in International Application No. PCT/US2011/066473, dated Jun. 25, 2013, 10 pages.
International Preliminary Report on Patentability in International Application No. PCT/US2013/045309, dated Dec. 24, 2014, 11 pages.
International Preliminary Report on Patentability in International Application No. PCT/US2013/054361, dated Feb. 19, 2015, 7 pages.
International Preliminary Report on Patentability in International Application No. PCT/US2014/034662, dated Oct. 29, 2015, 12 pages.
International Preliminary Report on Patentability in International Application No. PCT/US2015/056583, dated Apr. 25, 2017, 7 pages.
International Preliminary Report on Patentability in International Application No. PCT/US2016/018737, dated Aug. 31, 2017, 8 pages.
International Preliminary Report on Patentability in International Application No. PCT/US2016/018770, dated Aug. 22, 2017, 10 pages.
International Preliminary Report on Patentability in International Application No. PCT/US2016/018787, dated Aug. 22, 2017, 7 pages.
International Preliminary Report on Patentability in International Application No. PCT/US2018/034559, dated Nov. 26, 2019, 8 pages.
International Preliminary Report on Patentability in International Application No. PCT/US2019/030578, dated Nov. 10, 2020, 14 pages.
International Preliminary Report on Patentability in International Application No. PCT/US2019/030633, dated Nov. 10, 2020, 10 pages.
International Preliminary Report on Patentability in International Application No. PCT/US2020/021313, dated Aug. 25, 2021, 11 pages.
International Preliminary Report on Patentability in International Application No. PCT/US2020/041104, dated Jan. 11, 2022, 7 pages.
International Search Report and Written Opinion for International Application No. PCT/US2015/056583, dated Dec. 15, 2015, 10 pages.
International Search Report and Written Opinion in International Application No. PCT/US2013/045309, dated Jan. 22, 2014, 19 pages.
International Search Report and Written Opinion in International Application No. PCT/US2013/054361, dated Oct. 16, 2013, 12 pages.
International Search Report and Written Opinion in International Application No. PCT/US2014/034662, dated Oct. 24, 2014, 18 pages.
International Search Report and Written Opinion in International Application No. PCT/US2016/018737, dated Jun. 2, 2016, 12 pages.
International Search Report and Written Opinion in International Application No. PCT/US2016/018770, dated Jun. 2, 2016, 14 pages.
International Search Report and Written Opinion in International Application No. PCT/US2016/018787, dated Jun. 2, 2016, 12 pages.
International Search Report and Written Opinion in International Application No. PCT/US2018/034559, dated Mar. 8, 2019, 14 pages.
International Search Report and Written Opinion in International Application No. PCT/US2019/030578, dated Jul. 11, 2019, 26 pages.
International Search Report and Written Opinion in International Application No. PCT/US2019/030633, dated Nov. 28, 2019, 21 pages.
International Search Report and Written Opinion in International Application No. PCT/US2020/021313, dated Jun. 26, 2020, 19 pages.
International Search Report and Written Opinion in International Application No. PCT/US2020/041104, dated Sep. 4, 2020, 14 pages.
International Search Report and Written Opinion in International Application. No. PCT/US2011/066473, dated Jun. 19, 2012, 15 pages.
International Search Report and Written Opinion in International Appln. No. PCT/US2020/063038, dated Mar. 15, 2021, 16 pages.
International Search Report and Written Opinion in International Appln. No. PCT/US2020/063064, dated Feb. 12, 2021, 13 pages.
International Search Report and Written Opinion in International Application No. PCT/US2020/053436, dated Dec. 4, 2020, 15 pages.
International Search Report and Written Opinion in International Application No. PCT/US2020/055735, dated Dec. 15, 2020, 16 pages.
International Search Report and Written Opinion in International Application No. PCT/US2020/055547, dated Jan. 11, 2021, 13 pages.
International Search Report and Written Opinion in International Application No. PCT/US2021/013438, dated Apr. 20, 2021, 16 pages.
Invitation to Pay Additional Fees and, Where Applicable, Protest Fee in International Application No. PCT/US2013/045309, dated Nov. 25, 2013, 5 pages.
Isakova et al., "Fibroblast Growth Factor 23 and Risks of Mortality and End-Stage Renal Disease in Patients With Chronic Kidney Disease," JAMA, Jun. 15, 2011, 305:23, 2432-2439.
Ishikawa et al., "Accelerated proliferation of myeloma cells by interleukin-6 cooperating with fibroblast growth factor receptor 3-mediated signals," Oncogene, 2005, 24:6328-6332.
Israeli Office Action in Israeli Application No. 236,078 dated Mar. 21, 2017, 10 pages (English Translation).
Jackson et al., "8p11 Myeloproliferative syndrome: a review," Human Pathology, Apr. 1, 2010, 41:461-476.
Jan de Beur, "Tumoral Calcinosis: A Look into the Metabolic Mirror of Phosphate Homeostasis," The Journal of Clinical Endocrinology & Metabolism, 2005, 90: 2469-2471.
Japanese Office Action in Japanese Application No. 2015-517376, dated Feb. 21, 2017, 5 pages (with English translation).
Japanese Office Action in Japanese Application No. 2016-509131, dated Feb. 20, 2018, 5 pages (English Translation).
Japanese Office Action in Japanese Application No. 2017-543981, dated Dec. 3, 2019, 4 pages.
Japanese Office Action in Japanese Application No. 2017-544021, dated Nov. 26, 2019, 6 pages.
Japanese Office Action in Japanese Application No. 2018-228352, dated Aug. 20, 2019, 6 pages.
Japanese Office Action in Japanese Application No. 2020-069604, dated Nov. 15, 2021, 7 pages.
Javidi-Sharifi et al., "Crosstalk between KIT and FGFR3 Promotes Gastrointestinal Stromal Tumor Cell Growth and Drug Resistance," Cancer Research, Mar. 2015, 75(5): 880-892.
Jebar et al., "FGFR3 and Ras gene mutations are mutually exclusive genetic events in urothelial cell carcinoma," Oncogene, 2005, 24: 5218-5225.
Jiang et al., "miR-99a promotes proliferation targeting FGFR3 in human epithelial ovarian cancer cells," Biomedicine & Pharmacotherapy, 2014, 68: 163-169.
Ji et al., "Embase abstract: Modeling and simulation as gating for clinical pharmacology studies of INCB054828," 119th Annual Meeting of the American Society for Clinical Pharmacology and Therapeutics, Mar. 1, 2018, 2 pages.

(56) References Cited

OTHER PUBLICATIONS

Johnson et al., "Pharmacological and Functional Comparison of the Polo-like Kinase Family: Insight into Inhibitor and Substrate Specificity," Biochemistry, 2007, 46: 9551-9563.
Jonker et al., "A phase I study to determine the safety, pharmacokinetics and pharmacodynamics of a dual VEGFR and FGFR inhibitor, brivanib, in patients with advanced or metastatic solid tumors," Annals of Oncology, 2010, 1-7.
Jordan, "Tamoxifen: A Most Unlikely Pioneering Medicine," Nature Reviews: Drug Discovery, Mar. 2003, 2:205-213.
Kang et al., FGFR3 Activates RSK2 to Mediate Hematopoietic Transformation through Tyrosine Phosphorylation of RSK2 and Activation of the MEK/ERK Pathway, Cancer Cell, Sep. 2007, 12:201-214.
Kassack et al., "Structure-activity relationships of analogues of NF449 confirm NF449 as the most potent and selective known P2X1 receptor antagonist," European Journal of Medicinal Chemisty, 2004, 345-357.
Katoh and Katoh, "FGF signaling network in the gastrointestinal tract (Review)," International Journal of Oncology, 2006, 29: 163-168.
Keats et al., "Ten years and counting: so what do we know about t(4;14) (p16;q32) multiple myeloma," Leukemia & Lymphoma, Nov. 2006, 47(11): 2289-2300.
Keer et al., "Enrolling a Rare Patient Population: Establishing Proof of Concept for FP-1039, an FGF "Trap," in Endometrial Cancer Patients with the S252W FGFR2 Mutation," Journal of Clinical Oncology, 2010 ASCO Annual Meeting Abstracts, 28:15, May 20 Supplement, 1 page.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Khojasteh et al., "Chemical inhibitors of cytochrome P450 isoforms in human liver microsomes: a re-evaluation of P450 isoform selectivity," Eur J Drug Metab Pharmacokinet., Mar. 2011, 36:1-16.
Kim et al., "Phase I/II and Pharmacodynamic Study of Dovitinib (TKI258), an Inhibitor of Fibroblast Growth Factor Receptors and VEGF Receptors, in Patients with Advanced Melanoma," Clin Cancer Res, 2011, 17: 7451-7461.
Kim et al., "The design, synthesis, and biological evaluation of potent receptor tyrosine kinase inhibitors," Bioorganic & Medicinal Chemistry Letters, 2012, 4979-4985.
Klein et al., "FGFR1 Kinase Inhibitors: Close Regioisomers Adopt Divergent Binding Modes and Display Distinct Biophysical Signatures," American Chemical Society, 2014, 166-171.
Knights and Cook, "De-regulated FGF receptors as therapeutic targets in cancer," Pharmacology & Therapeutics, 2010, 125:105-117.
Kompier et al., "Bladder cancer: Novel molecular characteristics, diagnostic, and therapeutic implications," Urologic Oncology: Seminars and Original Investigations, 2010, 91-96.
Kompier et al., "FGFR3, HRAS, KRAS, NRAS and PIK3CA Mutations in Bladder Cancer and Their Potential as Biomarkers for Surveillance and Therapy," PLoS One, Nov. 2010, 5(11): 1-13.
Kono et al., "The fibroblast growth factor receptor signaling pathway as a mediator of intrinsic resistance to EGFR-specific tyrosine kinase inhibitors in non-small cell lung cancer," Drug Resistance Updates, 2009, 95-102.
Korean Office Action in Korean Application No. 10-2015-7000701, dated Aug. 26, 2019, 19 pages.
Korean Office Action in Korean Application No. 10-2015-7032502, dated Sep. 9, 2020, 16 pages.
Korean Office Action in Korean Application No. 10-2020-7021884, dated Oct. 28, 2020, 15 pages.
Korean Office Action in Korean Application No. 10-2021-7018897, dated Oct. 1, 2021, 15 pages.
Korean Office Action in Korean Application No. 10-2020-7021884, dated Oct. 25, 2021, 6 pages.
Kotha et al., "Recent applications of the Suzuki—Miyaura cross-coupling reaction in organic synthesis," Tetrahedron, 2002, 58:9633-9695.
Koziczak and Hynes, "Cooperation between Fibroblast Growth Factor Receptor-4 and ErbB2 in Regulation of Cyclin D1 Translation," The Journal of Biological Chemistry, 2004, 279(48): 50004-50011.
Koziczak et al., "Blocking of FGFR signaling inhibits breast cancer cell proliferation through downregulation of D-type cyclins," Oncogene, 2004, 23:3501-3508.
Krejci et al., "Molecular pathology of the fibroblast growth factor family," Hum Mutat, Sep. 2009, 30(9): 1245-1255.
Krejci et al., "NF449 Is a Novel Inhibitor of Fibroblast Growth Factor Receptor 3 (FGFR3) Signaling Active in Chondrocytes and Multiple Myeloma Cells," The Journal of Biological Chemistry, Jul. 2010, 285(27): 20644-20653.
Krejci et al., "NF449 is a novel inhibitor of fibroblast growth factor receptor 3 (FGFR3) signaling active in chondrocytes and multiple myeloma cells," The American Society for Biochemistry and Molecular Biology, 2010, 1-20.
Kunii et al., "FGFR2—Amplified Gastric Cancer Cell Lines Require FGFR2 and Erbb3 Signaling for Growth and Survival," Cancer Res., Apr. 1, 2008, 68(7):2340-2348.
Kunii et al., "FGFR2—Amplified Gastric Cancer Cell Lines Require FGFR2 and Erbb3 Signaling for Growth and Survival," Cancer Res., Apr. 1, 2008, Supplemental figures, 11 pages.
Kuroso et al., "Immunohistochemical Detection of Fibroblast Growth Factor Receptor 3 in Human Breast Cancer: Correlation with Clinicopathological/Molecular Parameteres and Prognosis," Pathobiology, Mar. 2010, 77: 231-240.
Kurosu et al., "Regulation of Fibroblast Growth Factor-23 Signaling by Klotho," The Journal of Biological Chemistry, Mar. 2006, 281(10): 6120-6123.
Lala et al., "Role of nitric oxide in tumor progression: Lessons from experimental tumors," Cancer and Metastasis Reviews, 1998, 17: 91-106.
Lammoglia and Mericq, "Familial Tumoral Calcinosis Caused by a Novel FGF23 Mutation: Response to Induction of Tubular Renal Acidosis with Acetazolamide and the Non-Calcium Phosphate Binder Sevelamer," Horm Res, 2009, 71:178-184.
Lamont et al., "Small molecule FGF receptor inhibitors block FGFR—dependent urothelial carcinoma growth in vitro and in vivo," Br. J Cancer, 2010, 1-8.
Lamont et al., "Small molecule FGF receptor inhibitors block FGFR—dependent urothelial carcinoma growth in vitro and in vivo," Br. J Cancer, 2011, 104:75-82.
Le Corre et al., "Synthesis and biological evaluation of a triazole-based library of pyrido[2,3-d]pyrimidines as FGFR3 tyrosine kinase inhibitors," Org. Biomol. Chem., 2010, 8, 2164-2173.
Lee et al., "In vivo Target Modulation and Biological Activity of CHIR-258, a Multitargeted Growth Factor Receptor Kinase Inhibitor, in Colon Cancer Models," Clin Cancer Res, May 2005, 3633-3641.
L'Hote and Knowles, "Cell responses to FGFR3 signalling: growth, differentiation and apoptosis," Experimental Cell Research, 2005, 417-431.
Li et al., "Compound deletion of Fgfr3 and Fgfr4 partially rescues the Hyp mouse phenotype," Am. J. Physiology—Endocrinol Metab, Dec. 7, 2010, 300:3, 29 pages.
Liang et al., "Anticancer molecules targeting fibroblast growth factor receptors," Cell Press, 2012, 11 pages.
Liu et al., "Developing Irreversible Inhibitors of the Protein Kinase Cysteinome," Chemistry & Biology, Feb. 2013, 146-159.
Liu et al., "FRFR3 and FRFR4 Do not Mediate Renal Effects of FGF23," J Am Soc Nephrol, 2008, 19:2342-2350.
Liu et al., "Pathogenic role of Fgf23 in Hyp mice," Am J Physiol Endocrinol Metab 291, Jan. 31, 2006, E38-E49.
Lopes de Menezes et al., "CHIR-258: A Potent Inhibitor of FLT3 Kinase in Experimental Tumor Xenograft Models of Human Acute Myelogenous Leukemia," Clin Cancer Res, Jul. 2005, 5281-5291.
Luo et al., "Deficiency of metabolic regulator FGFR4 delays breast cancer progression through systemic and microenvironmental metabolic alterations," Cancer & Metabolism, 2013, 20 pages.

(56) References Cited

OTHER PUBLICATIONS

Maeda et al., "Transforming property of TEL-FGFR3 mediated through PI3-K in a T-cell lymphoma that subsequently progressed to AML," Blood, Mar. 2005, 105(5): 2115-2123.
Malaysian Office Action in Malaysian Application No. 2014003396, dated Dec. 15, 2017, 4 pages.
Marek et al., "Fibroblast Growth Factor (FGF) and FGF Receptor-Mediated Autocrine Signaling in Non-Small-Cell Lung Cancer Cells," Molecular Pharmacology, 2009, 75:196-207.
Marfe and Stefano, "in vitro Anti-leukaemia Activity of Pyrrolo[1,2-b][1,2,5]benzothiadiaze-pines (PBTDs)," Recent Patents on Anti-Cancer Drug Discovery, 2010, 58-68.
Marks et al., "Mutational Analysis of EGFR and Related Signaling Pathway Genes in Lung Adenocarcinomas Identifies a Novel Somatic Kinase Domain Mutation in FGFR4," PLoS One, May 9, 2007, 2:e426.
Marshall et al., "Fibroblast Growth Factor Receptors are Components of Autocrine Signaling Networks in Head and Neck Squamous Cell Carcinoma Cells," Clin Cancer Res., 2011, 17:5016-5025.
Martinez-Torrecuadrada et al., "Targeting the Extracellular Domain of Fibroblast Growth Factor Receptor 3 with Human Single-Chain Fv Antibodies Inhibits Bladder Carcinoma Cell Line Proliferation," Clin Cancer Res, Sep. 2005, 6280-6290.
Martino et al., "Mutant fibroblast growth factor receptor 3 induces intracellular signaling and cellular transformation in a cell type- and mutation-specific manner," Oncogene, 2009, 28: 4306-4316.
Matsuda et al., "Fibroblast Growth Factor Receptor 2 IIIc as a Therapeutic Target for Colorectal Cancer Cells," Mol Cancer Ther., 2012, 52 pages.
McConkey et al., "Molecular genetics of bladder cancer: Emerging mechanisms of tumor initiation and progression," Urologic Oncology: Seminars and Original Investigations, 2010, 429-440.
McMahon, "VEGF Receptor Signaling in Tumor Angiogenesis," Oncologist, 2000, 5(suppl 1):3-10.
Meijer et al., "Fibroblast growth factor receptor 4 predicts failure on tamoxifen therapy in patients with recurrent breast cancer," Endocrine-Related Cancer, 2008, 15:101-111.
Mellor, "Targeted inhibition of the FGF19-FGFR4 pathway in hepatocellular carcinoma; translational safety considerations," Liver International, 2013, 1-9.
Memon et al., "Does Fgf23-klotho activity influence vascular and soft tissue calcification through regulating phosphate homeostasis," Kidney Int., 2008, 74(5): 566-570.
Metzner, "Fibroblast Growth Factor Receptors as Therapeutic Targets in Human Melanoma: Synergism with BRAF Inhibition," J Investigative Dermatol., 2011, 131:2087-2095.
Mexican Office Action in Mexican Application No. MX/a/2014/015192, dated Jan. 24, 2018, 6 pages.
Miyake et al., "1-tert-Butyl-3-[6-(3,5-dimethoxy-phenyl)-2-(4-diethylamino-butylamino)-pyrido[2,3-d]pyrimidin-7-yl]-urea (PD173074), a Selective Tyrosine Kinase Inhibitor of Fibroblast Growth Factor Receptor-3 (FGFR3), Inhibits Cell Proliferation of Bladder Cancer Carrying the FGFR3 Gene Mutation along with Up-Regulation of p27/Kip1 and $G_1/G_0$ Arrest," The Journal of Pharmacology and Experimental Therapeutics, 2010, 332(3):795-802.
Mohammadi et al., "Crystal structure of an angiogenesis inhibitor bound to the FGF receptor tyrosine kinase domain, " The EMBO Journal, 1998, 5896-5904.
Mohammadi et al., "Structures of the Tyrosine Kinase Domain of Fibroblast Growth Factor Receptor in Complex with Inhibitors," Science, May 1997, 276:955-960.
Murphy et al., "Evidence for distinct alterations in the FGF axis in prostate cancer progression to an aggressive clinical phenotype," J Pathol., 2010, 220:452-460.
Naito et al., "Progressive tumoral calcinosis as the presenting feature of sarcoidosis in a patient on haemodialysis treatment," Nephrol Dial Transplant, 1999, 14:2716-2719.
Nakatani et al., "In vivo genetic evidence for klotho-dependent, fibroblast growth factor 23 (Fgf23)—mediated regulation of systemic phosphate homeostasis," The FASEB Journal, Feb. 2009, 23:433-441.
Natajaran et al., "p38 MAP kinase inhibitors. Part 3: SAR on 3,4-dihydropyrimido-[4,5-d]pyrimidin-2-ones and 3,4-dihydropyrido[4,3-d]-pyrimidin-2-ones," Bioorgan. Med. Chem. Lett., 2006, 4400-4404.
Neidle et al., "Failure Modes in the Discovery Process," Cancer Drug Design, 2008, pp. 427-431.
New Zealand Examination Report in New Zealand Application No. 743274, dated Jul. 18, 2018, 4 pages.
New Zealand Office Action in New Zealand Application No. 702747, dated Mar. 8, 2019, 2 pages.
New Zealand Office Action in New Zealand Application No. 702747, dated Sep. 16, 2016, 3 pages.
New Zealand Office Action in New Zealand Application No. 713074, dated Feb. 18, 2020, 3 pages.
New Zealand Office Action in New Zealand Application No. 743274, dated Jul. 19, 2018, 5 pages.
New Zealand Office Action in New Zealand Application No. 752422, dated Feb. 18, 2020, 2 pages.
Nitta, "Relationship between Fibroblast Growth Factor-23 and Mineral Metabolism in Chronic Kidney Disease," International Journal of Nephrology, 2010, 1-7.
Nomura et al., "FGF10/FGFR20 signal induces cell migration and invasion in pancreatic cancer," Br. J Cancer, 2008, 99:305-313.
Norman et al., "Protein-Ligand Crystal Structures Can Guide the Design of Selective Inhibitors of the FGFR Tyrosine Kinase," J. Med. Chem., 2012, 55(11):5003-5012.
Novelli, "Fosrenol (TM) reduces damaging high levels of phosphate in end-stage kidney disease patients," EurekAlert!, Nov. 2, 2002 [retrieved on Dec. 1, 2020], retrieved from URL <https://www.eurekalert.org/pub_releases/2002-11/pn-fr110202.php>, 4 pages.
Office Action from the Intellectual Property Office of the Philippines in Application No. 1-2014-502772, dated Mar. 17, 2016, 3 pages.
Ornitz et al., "Receptor Specificity of the Fibroblast Growth Factor Family," The Journal of Biological Chemistry, 1996, 271(25): 15292-15297.
Pai et al., "Antibody-Mediated Inhibition of Fibroblast Growth Factor 19 Results in Increased Bile Acids Synthesis and Ileal Malabsortion of Bile Acides in Cynomolgus Monkeys," Toxicological Sciences, 2012, 126(2): 446-456.
Pan et al., "MK-2461, a Novel Multitargeted Kinase Inhibitor, Preferentially Inhibits the Activated c-Met Receptor," Cancer Res, Feb. 2010, 1524-1533.
Pandith et al., "Oncogenic role of fibroblast growth factor receptor 3 in tumorigenesis of urinary bladder cancer," Urologic Oncology: Seminars and Original Investigations, 2010, 1-9.
Pandith et al., "Oncogenic role of fibroblast growth factor receptor 3 in tumorigenesis of urinary bladder cancer," Urologic Oncology: Seminars and Original Investigations, 2013, 31: 398-406.
Pardo et al., "The Fibroblast Growth Factor Receptor Inhibitor PD173074 Blocks Small Cell Lung Cancer Growth In vitro and In vivo," Cancer Res, Nov. 2009, 8645-8651.
Paterson et al., "Preclinical studies of fibroblast growth factor receptor 3 as a therapeutic target in multiple myeloma," British Journal of Haematology, 2004, 124:595-603.
Peruvian Office Action in Peruvian Application No. 1424, dated Mar. 12, 2021, 13 pages.
Peruvian Office Action in Peruvian Application No. 1429, dated Mar. 19, 2021, 12 pages.
Peruvian Office Action in Peruvian Application No. 2433, dated Nov. 27, 2018, 13 pages.
Philippine Office Action in Philippine Application No. 1/2017/501483, dated Dec. 12, 2019, 5 pages.
Philippine Office Action in Philippine Application No. 1-2017-501481, dated Oct. 29, 2019, 4 pages.
Philippine Office Action in Philippine Application No. 1/2015/502383, dated Jul. 8, 2019, 7 pages.
Philippine Office Action in the Philippine Application No. 1/2017/501483, dated Aug. 31, 2020, 4 pages.

(56) References Cited

OTHER PUBLICATIONS

Philippine Office Action in Philippine Application No. 1/2015/502383, dated Nov. 11, 2021, 4 pages.
Philippine Office Action in Philippine Application No. 1/2019/502810, dated Dec. 7, 2021, 4 pages.
Piazza et al., "Towards a new age in the treatment of multiple myeloma," Ann Hematol, 2007, 86:159-172.
Pinedo and Slamon, "Translational Research: The Role of VEGF in Tumor Angiogenesis," Oncologist, 2000, 5(suppl 1):1-2.
Piro et al., "An FGFR3 Autocrine Loop Sustains Acquired Resistance to Trastuzumab in Gastric Cancer Patients," Clinical Cancer Research, Dec. 2016, 22(24): 6164-6175.
Platt et al., "Spectrum of Phosphatidylinositol 3-Kinase Pathway Gene Alterations in Bladder Cancer," Clin Cancer Res, Oct. 2009, 6008-6017.
Pliarchopoulou et al., "Current chemotherapeutic options for the treatment of advanced bladder cancer: A review," Urologic Oncology: Seminars and Original Investigations, 2010, 1-9.
Plowright et al., "Ectopic expression of fibroblast growth factor receptor 3 promotes myeloma cell proliferation and prevents apoptosis," Blood, Feb. 2000, 95(3): 992-998.
Podar et al., "Emerging therapies for multiple myeloma," Expert Opin. Emerging Drugs, 2009, 14(1):9-127.
Podar et al., "Targeting signalling pathways for the treatment of multiple myeloma," Expert Opin. Ther. Targets, 2005, 359-381.
Pollett et al., "Overexpression of the myeloma-associated oncogene fibroblast growth factor receptor 3 confers dexamethasone resistance," Blood, Nov. 2002, 100(10): 3819-3821.
Pollock et al., "Frequent activating FGFR2 mutations in endometrial carcinomas parallel germline mutations associated with craniosynostosis and skeletal dysplasia syndromes," Oncogene, 2007, 26:7158-7162.
Propper et al., "Phase I and Pharmacokinetic Study of PKC412, an Inhibitor of Protein Kinase C," J Clin Oncol, 2001, 19(5):1485-1492.
Qian et al., "Targeting Tumor Angiogenesis with Histone Deacetylase Inhibitors: the Hydroxamic Acid Derivative LBH589," Clin Cancer Res, Jan. 2006, 634-642.
Qing et al., "Antibody-based targeting of FGFR3 in bladder carcinoma and t(4;14)—positive multiple myeloma in mice," The Journal of Clinical Investigation, May 2009, 119(5): 1216-1229.
Qing et al., "Antibody-based targeting of FGFR3 in bladder carcinoma and t(4;14)—positive multiple myeloma in mice," The Journal of Clinical Investigation, May 2009, Supplemental Table 1: Summary of crystallographic analysis, 21 pages.
Qiu et al., "Over-expression of fibroblast growth factor receptor 3 in human hepatocellular carcinoma," World J Gastroenterol, 2005, 11(34): 5266-5272.
Raab et al., "Multiple myeloma," Lancet, 2009, 374: 324-339.
Ravindranathan et al., "Discovery of Novel Fibroblast Growth Factor Receptor 1 Kinase Inhibitors by Structure-Based Virtual Screening," J. Med. Chem., 2010, 53: 1662-1672.
Razzaque, "FGF23-mediated regulation of systemic phosphate homeostasis: is Klotho an essential player?," Am J Physiol Renal Physiol, 2009, 470-476.
Reimers et al., "NoBP, a Nuclear Fibroblast Growth Factor 3 Binding Protein, Is Cell Cycle Regulated and Promotes Cell Growth," Molecular and Cellular Biology, Aug. 2001, 21(15): 4996-5007.
Reis-Filho et al., "FGFR1 Emerges as a Potential Therapeutic Target for Lobular Breast Carcinomas," Clin Cancer Res, Nov. 2006, 6652-6662.
Reiter et al., "Consistent Fusion of ZNF198 to the Fibroblast Growth Factor Receptor-1 in the t(8;13)(p11;q12) Myeloproliferative Syndrome," Blood, Sep. 1998, 92(5): 1735-1742.
Remington, "The Science and Practice of Pharmacy," Lippincott Williams & Wilkins, 2005, 21st edition.
Remington's Pharmaceutical Sciences, 17th ed., Mack Publishing Company, Easton, Pa., 1985, p. 1418*.
Renhowe et al., "Design, Structure—Activity Relationships and in Vivo Characterization of 4-Amino-3-benzimidazol-2-ylhydroquinolin-2-ones: A Novel Class of Receptor Tyrosine Kinase Inhibitors," J. Med. Chem., 2009, 52: 278-292.
Ribatti et al., "The discovery of basic fibroblast growth factor/fibroblast growth factor-2 and its role in haematological malignancies," Cytokine & Growth Factor Reviews, 2007, 18: 327-334.
Ribatti, "Tyrosine Kinase Inhibitors as Antiangiogenic Drugs in Multiple Myeloma," Pharmaceuticals, 2010, 3: 1225-1231.
Roidl et al., "Resistance to Chemotherapy Is Associated with Fibroblast Growth Factor Receptor 4 Up-Regulation," Clin Cancer Res, Mar. 2009, 2058-2066.
Ronchetti et al., "Deregulated FGFR3 mutants in multiple myeloma cell lines with t(4;14): comparative analysis of Y373C, K650E and the novel G384D mutations," Oncogene, 2001, 20: 3553-3562.
Roumiantsev et al., "Distinct stem cell myeloproliferative/T lymphoma syndromes induced by ZNF198-FGFR1 and BCR-FGFR1 fusion genes from 8p11 translocations," Cancer Cell, Mar. 2004, 5: 287-298.
Rowe et al., "Handbook of Pharmaceutical Additives," The Pharmaceutical Press and the American Pharmaceutical Association, 2009, 3rd ed.
Rowe et al., "Handbook of Pharmaceutical Excipients," The Pharmaceutical Press and the American Pharmaceutical Association, 2009, 6th Edition, 917 pages.
Ryan et al., "Toxicologic Pathology of Unique Biotechnology Agents and Biotherapies," Toxicologic Pathology, 1999, 27(1): 78-86.
Sakurai et al., "A novel angiogenesis inhibitor, Ki23057, is useful for preventing the progression of colon cancer and the spreading of cancer cells to the liver," European Journal of Cancer, 2007, 2612-2620.
Sarker et al., "A Phase I Pharmacokinetic and Pharmacodynamic Study of TKI258, an Oral, Multitargeted Receptor Tyrosine Kinase Inhibitor in Patients with Advanced Solid Tumors," Clin Cancer Res, Apr. 2008, 2075-2081.
Saxty et al., "Fragment-based drug discovery of selective inhibitors of fibroblast growth factor receptor (FGFr)," Cancer Res, Apr. 15, 2010, 70, 5778.
Schenone et al., "Small Molecules ATP-Competitive Inhibitors of FLT3: A Chemical Overview," Current Medicinal Chemistry, 2008, 15(29): 3113-3132.
Schlapbach et al., "A novel Pd-catalyzed cyclization rection of ureas for the synthesis of dihydroquinazolinone p38 kinase inhibitors," Bioorg. Med. Chem. Lett., 2004, 357-360.
Science IP Order 3032627, Chemical Structure Search, Science IP, Apr. 2012, 78 pages.
Science IP Order 3101926, Chemical Structure Search, Science IP, Jan. 2015, 50 pages.
Science IP Order 3101983, Chemical Structure Search, Science IP, Jan. 2015, 70 pages.
Science IP Order 3104564, Patent Chemical Structure Search, Science IP, Mar. 2015, 90 pages.
Science IP Order 3104565, Patent Chemical Structure Search, Science IP, Mar. 2015, 521 pages.
Segev et al., "Restrained chondrocyte proliferation and maturation with abnormal growth plate vascularization and ossification in human FRFR-3$^{G380R}$ transgenic mice," Human Molecular Genetics, 2000, 9(2): 249-258.
Seitzer et al., "A single nucleotide change in the mouse genome accelerates breast cancer progression," Cancer Res., Jan. 2010, 70(2):802-812.
Shariat et al., "Association of Angiogenesis Related Markers With Bladder Cancer Outcomes and Other Molecular Markers," The Journal of Urology, May 2010, 183: 1744-1750.
Sharkey et al., "PKC412 demonstrates JNK-dependent activity against human multiple myeloma cells," Blood, Feb. 2007, 109(4): 1712-1719.
Shi et al., "High Expression of FGFR4 Enhances Tumor Growth and Metastasis in Nasopharyngeal Carcinoma," Journal of Cancer, 2015, 6(12): 1245-1254.

(56) References Cited

OTHER PUBLICATIONS

Shinya et al., "Fgf signalling through MAPK cascade is required for development of the subpallial telencephalon in zebrafish embryos," Development, 2001, 4153-4164.
sigmaaldrich.com, "4-Chloro-1H-pyrrolo[2,3-b]pyridine-5-carbaldehyde," CAS # 958230-19-8, [retrieved on Feb. 4, 2021] retrieved from URL <https://www.sigmaaldrich.com/catalog/product/aldrich/ade000976?lang-en®ion=US>, 2 pages.
Singh et al., "Transforming Fusions of FGFR and TACC Genes in Human Glioblastoma," Science, Sep. 2012, 337:1231-1235.
Slavin et al., "Familial Tumoral Calcinosis," The American Journal of Surgican Pathology, 1993, 17(8): 188-802.
Smith et al., "Circulating αKlotho influences phosphate handling by controlling FGF23 production," The Journal of Clinical Investigation, Dec. 2012, 122(12): 4710-4715.
Song et al., "Fibroblast growth factors: An epigenetic mechanism of broad spectrum resistance to anticancer drugs," PNAS, Jul. 2000, 97(15): 8658-8663.
Sonvilla et al., "Fibroblast growth factor receptor 3-IIIc mediates colorectal cancer growth and migration," British Journal of Cancer, 2010, 1-12.
Soria, "FGFR inhibition overview of clinical development programs," Presentation, presented at TAT in Washington DC on Mar. 5-7, 2014, 54 pages.
Soverini et al., "Novel mutation and RNA splice variant of fibroblast growth factor receptor 3 in multiple myeloma patients at diagnosis," Haematologica, 2002, 87: 1036-1040.
Specktor et al., "Hyperphosphatemic familial tumoral calcinosis caused by a mutation in GALNT3 in a European kindred," J Hum Genet, 2006, 51:487-490.
Squires et al., "Development of inhibitors of the fibroblast growth factor receptor (FGFR) kinase using a fragment based approach," Cancer Res 70, Apr. 15, 2010, 3626.
Squires et al., "Development of inhibitors of the fibroblast growth factor receptor (FGFR) kinase using a fragment based approach," Cancer Res, 2008, 1 page.
Staerk et al., "Pan-Src Family Kinase Inhibitors Replace Sox2 during the Direct Reprogramming of Somatic Cells," Angewandte Chem., Jun. 14, 2011, 50(25):5734-5736.
STN International Search Report for CAS RN 2380276-25-3, dated Nov. 20, 2019, 11 pages.
STN Search Report dated Jan. 6, 2020, 88 pages.
STN Search Report, dated Sep. 11, 2019, 31 pages.
Sun et al., "Design, Synthesis, and Evaluations of Substituted 3-[(3- or 4-Carboxyethylpyrrol-2-yl)methylidenyl]indolin-2-ones as Inhibitors of VEGF, FGF, and PDGF Receptor Tyrosine Kinases," J. Med. Chem., 1999, 42: 5120-5130.
Sun et al., "Identification of Substituted 3-[(4,5,6,7-Tetrahydro-1H-indol-2-yl)methylene]-1,3-dihydroindol-2-ones as Growth Factor Receptor Inhibitors for VEGF-R2 (Flk-1/KDR), FGF-R1, and PDGF-RB Tyrosine Kinases," J. Med. Chem., 2000, 43: 2655-2663.
Sun et al., "Synthesis and Biological Evaluations of 3-Substituated Indolin-2-ones: A Novel Class of Tyrosine Kinase Inhibitors That Exhibit Selectivity toward Particular Receptor Tyrosine Kinases," J. Med. Chem., 1998, 41: 2588-2603.
Surry et al., "Dialkylbiaryl Phosphines in Pd-Catalyzed Amination: A User's Guide," Chem Sci., 2011, 2(1):27-50.
Taiwan Office Action in Taiwan Application No. 103114284, dated Apr. 9, 2018, 4 pages (English Search Report).
Taiwan Office Action in Taiwan Application No. 105104993, dated Feb. 11, 2020, 9 pages.
Taiwan Office Action in Taiwan Application No. 105105018, dated Oct. 22, 2019, 7 pages.
Taiwan Office Action in Taiwan Application No. 107146498, dated Dec. 19, 2019, 7 pages.
Taiwanese Office Action in Taiwan Application No. 102120946, dated Nov. 9, 2016, 9 pages (with English translation).
Taiwanese Office Action in Taiwanese Application No. 102120946, dated Jul. 13, 2017, 7 pages (English Translation).
Taiwan Office Action in Taiwan Application No. 109132389, dated Aug. 23, 2021, 4 pages.
Takeda et al., "AZD2171 Shows Potent Antitumor Activity Against Gastric Cancer Over-Expressing Fibroblast Growth Factor Receptor 2/Keratinocyte Growth Factor Receptor," Clin Cancer Res, May 2007, 3051-3057.
Takii et al., "Serotonin Derivative, N-(p-Coumaroyl)serotonin, Isolated from Safflower (Carthamus tinctorius L.) Oil Cake Augments the Proliferation of Normal Human and Mouse Fibroblasts in Synergy with Basic Fibroblast Growth Factor (bFGF) or Epidermal Growth Factor (EGF)", J Biochem., 1995, 125(5):910-915.
Tan et al., "Development of covalent inhibitors that can overcome resistance to first-generation FGFR kinase inhibitors," PNAS, Oct. 2014, E4869-E4877.
Tang et al., "Role of fibroblast growth factor receptor 4 in cancer," Cancer Science, Oct. 2018, 109(10):3024-3031.
Taylor et al., "Identification of FGFR4-activating mutations in human rhabdomyasarcomas that promote metastasis in xenotransplanted models," J Clin Invest., Nov. 2009, 119(11):3395-3407.
Taylor, "Inhibitor PD-173074 Bound to the Tyrosine Kinase Domain of FGFR 1," Molecular & Behavioral Neuroscience Institute , Feb. 2006, 1 page.
Taylor, "Inhibitor SU-5402 Bound to the Tyrosine Kinase Domain of FGFR 1," Molecular & Behavioral Neuroscience Institute , Apr. 2006, 1 page.
Terai et al., "Vascular calcification and secondary hyperparathyroidism of severe chronic kidney disease and its relation to serum phosphate and calcium levels," British Journal of Pharmacology, 2009, 156: 1267-1278.
Thai Office Action in Thai Application No. 1401007417, dated Jun. 5, 2016, 7 pages (with English translation).
The Cancer Genome Atlas Research Network, "Comprehensive molecular characterization of urothelial bladder carcinoma," Nature, 2014, 507: 315-22.
Thome and Weil, "Post-translational modifications regulate distinct functions of CARMA1 and BCL10," Trends in Immunology, 2007, 28(6): 281-288.
Thompson et al., "3-(3,5-Dimethoxyphenyl)-1,6-naphthyridine-2,7-diamines and Related 2-Urea Derivatives Are Potent and Selective Inhibitors of the FGF Receptor-1 Tyrosine Kinase," J. Med. Chem., 2000, 43: 4200-4211.
Thompson et al., "Photochemical Preparation of a Pyridone Containing Tetracycle: A Jak Protein Kinase Inhibitor," Bioorganic & Medicinal Chemistry Letters 12:1219-1223, 2002.
Thompson et al., "Synthesis and Structure—Activity Relationships of Soluble 7-Substituted 3-(3,5-Dimethoxyphenyl)-1,6-naphthyridin-2-amines and Related Ureas as Dual Inhibitors of the Fibroblast Growth Factor Receptor-1 and Vascular Endothelial Growth Factor Receptor-2 Tyrosine Kinases," J. Med. Chem., 2005, 48: 4628-2653.
Thussbas et al., "FGFR4 Arg388 Allele Is Associated With Resistance to Adjuvant Therapy in Primary Breast Cancer," J. Clin. Oncol., Aug. 10, 2006, 23:3747-3755.
Tolcher et al., "381 Preliminary results of a dose escalation study of the Fibroblast Growth Factor (FGF) "trap" FP-1039 (FGFR1:Fc) in patients with advanced malignancies," EJC Supplements, Nov. 2010, 8:7, p. 121.
Tomlinson et al., "FGFR3 protein expression and its relationship to mutation status and prognostic variables in bladder cancer," J Pathol, Sep. 2007, 213(1): 91-98.
Tomlinson et al., "Fibroblast Growth Factor Receptor 1 Promotes Proliferation and Survival via Activation of the Mitogen-Activated Protein Kinase Pathway in Bladder Cancer," Cancer Res, 2009, 4613-4620.
Tomlinson et al., "Knockdown by shRNA identifies S249C mutant FGFR3 as a potential therapeutic target in bladder cancer," Oncogene, 2007, 26: 5889-5899.
Topaz et al., "Mutations in GALNT3, encoding a protein involved in O-linked glycosylation, cause familial tumoral calcinosis," Nature Genetics, 2004, 1-3.
Traxler and Furet, "Strategies toward the Design of Novel and Selective Protein Tyrosine Kinase Inhibitors," Pharmacol. Ther., 1999, 82(2-3): 195-206.

(56) References Cited

OTHER PUBLICATIONS

Trudel et al., "CHIR-258, a novel, multitargeted tyrosine kinase inhibitor for the potential treatment of t(4;14) multiple myeloma," Blood, Apr. 2005, 105(7): 2941-2948.

Trudel et al., "Inhibition of fibroblast growth factor receptor 3 induces differentiation and apoptosis in t(4;14) myeloma," Blood, May 2004, 103(9):3521-3528.

Trudel et al., "The inhibitory anti-FGFR3 antibody, PRO-001, is cytotoxic to t(4;14) multiple myeloma cells," Blood, May 2006, 107(10): 4039-4046.

Trudel, "CHIR-258, a Novel Multi-targeted Tyrosine KinaseInhibitor, for the Treatment of t(4;14) Multiple Myeloma," Presentation, Presented at International Myeloma Foundation, Apr. 2005, 18 pages.

Turkington et al., "Fibroblast growth factor receptor 4 (FGFR4): a targetable regulator of drug resistance in colorectal cancer," Cell Death Dis., Feb. 6, 2014, 5:e1046.

Turner and Grose, "Fibroblast growth factor signalling: from development to cancer," Nature Reviews Cancer, 2010, 10:116-129.

Turner et al., "FGFR1 Amplification Drives Endocrine Therapy Resistance and Is a Therapeutic Target in Breast Cancer," Cancer Res., Mar. 2010, 2085-2094.

Tvorogov et al., "Effective Suppression of Vascular Network Formation by Combination of Antibodies Blocking VEGFR Ligand Binding and Receptor Dimerization," Cancer Cell, Dec. 2010, 18: 630-640.

Ueno et al., "Enhanced Expression of Fibroblast Growth Factor Receptor 3 IIIc Promotes Human Esophageal Carcinoma Cell Proliferation," Journal of Histochemistry & Cytochemistry, 2016, 64(1): 7-17.

Ukraine Office Action in Ukraine Application No. a201500191, dated Dec. 13, 2016, 10 pages (with English translation).

Ukraine Office Action in Ukraine Application No. a201511370, dated Nov. 12, 2018, 6 pages (with English translation).

Ukraine Office Action in Ukraine Application No. a201709220, dated Dec. 9, 2019, 11 pages.

Ukraine Office Action in Ukraine Application No. a201801562, dated Jul. 28, 2021, 9 pages.

Ukraine Office Action in Ukraine Application No. a 2019 12195, dated Nov. 11, 2021, 7 pages.

Urakawa et al., "Klotho converts canonical FGF receptor into a specific receptor for FGF23," Nature, Dec. 2006, 444: 770-774.

Uzawa et al., "Targeting fibroblast growth factor receptor 3 enhances radiosensitivity in human squamous cancer cells," Oncogene, 2011, 1-6.

Van Oers et al., "FGFR3 Mutations Indicate Better Survival in Invasive Upper Urinary Tract and Bladder Tumours," European Urology, 2009, 650-658.

Våtsveen et al., "FGFR3 is expressed and is important for survival in INA-6, a human myeloma cell line without a t(4;14)," Eur. J. Haematol., 83:5, Jul. 6, 2009, 471-476.

Verstovsek et al., "Interim Results from Fight-203, a Phase 2, Open-Label, Multicenter Study Evaluating the Efficacy and Safety of Pemigatinib (INCB054828) in Patients with Myeloid/Lymphoid Neoplasms with Rearrangement of Fibroblast Growth Factor Receptor 1 (FGFR1)," Blood, Nov. 29, 2018, retrieved from URL <https://ashpublications.org/blood/article/132/Supplement%201/690/266005/Interim-Results-from-Fight203-a-Phase-2-OpenLabel>, 132(Supplement 1):690.

Vietnamese Office Action in Vietnamese Application No. 1-2015-00102, dated Mar. 18, 2015, 4 pages.

Vogt et al., "FGF23 and phosphate cardiovascular toxins in ckd," Toxins, Nov. 6, 2019, 11(11):647.

Von Massenhausen et al., "Evaluation of FGFR3 as a Therapeutic Target in Head and Neck Squamous Cell Carcinoma, "Targ. Oncol., 2016, 11: 631-642.

Walsky and Obach, "Validated assays for human cytochrome P450 activities," Drug Metab Dispos., 2004, 32(6):647-660.

Walsky et al., "Evaluation of 227 drugs for in vitro inhibition of cytochrome P450 2B6," J Clin Pharmacol., Dec. 2006, 46(12):1426-1438.

Wang and Becker, "Antisense targeting of basic fibroblast growth factor and fibroblast growth factor receptor-1 in human melanomas blocks intratumoral angiogenesis and tumor growth," Nature Medicine, Aug. 1997, 887-893.

Wang and Ding, "Fibroblast growth factor receptors in breast cancer," Tumor Biology, May 2017, 1-10.

Wang et al., "The fibroblast growth factor receptor-4 Arg388 allele is associated with prostate cancer initiation and progression," Clin Cancer Res. 2004, 10:6169-6178.

Ware et al., "Rapidly Acquired Resistance to EFGR Tyrosine Kinase Inhibitors in NSCLC Cell Lines through De-Repression of FGFR2 and FGFR3 Expression," PLoS, Nov. 2010, 5(11): 1-9.

Weiss et al., Frequent and Focal FGFR1 Amplification Associates with Therapeutically Tractable FGFR1 Dependency in Squamous Cell Lung Cancer, Sci. Transl. Med., 2010, 2(62):62ra93, pp. 1-7.

Williams et al., "Oncogenic FGFR3 gene fusions in bladder cancer," Hum Mol Genet, 2013, 22:795-803.

Wu, "Urothelial Tumorigenesis: A Tale of Divergent Pathways," Nature Reviews, Sep. 2005, 5: 713-725.

Wuts et al., "Greene's Protective Groups in Organic Synthesis," 4th Ed., 2006, Chapter 7, 696-926.

Wöhrle et al., "FGF Receptors Control Vitamin D and Phosphate Homeostasis by Mediating Renal FGF-23 Signaling and Regulating FGF-23 Expression in Bone," Journal of Bone and Mineral Research, Oct. 2011, 26(10): 2486-2497.

Wöhrle et al., "Pharmacological inhibition of FGFR signaling ameliorates FGF23-mediated hypophosphatemic rickets," Journal of Bone and Mineral Research, 2012, 1-36.

Xian et al., "Pleiotropic effects of FGFR1 on cell proliferation, survival, and migration in a 3D mammary epithelial cell model," JCB, 2005, 171(4): 663-673.

Xin et al., "CHIR-258 Is Efficacious in a Newly Developed Fibroblast Growth Factor Receptor 3-Expressing Orthotopic Multiple Myeloma Model in Mice," Clin Cancer Res, Aug. 2006, 4908-4915.

Xu et al., "Fibroblast growth factor receptor 4 promotes progression and correlates to poor prognosis in cholangiocarcinoma," Biochemical and Biophysical Research Communications, 2014, 446: 54-60.

Xu et al. "Design, synthesis and biological evaluation of deuterated nintedanib for improving pharmacokinetic properties," J Label Compd Radiopharm., 2015, 58(7):308-312.

Ye et al., "Combination of the FGFR4 inhibitor PD173074 and 5-fluorouracil reduces proliferation and promotes apoptosis in gastric cancer," Oncol Rep., Dec. 2013, 30(6):2777-2784.

Ying et al., "Genome-wide screening for genetic alterations in esophageal cancer by aCGH identifies 11q13 amplification oncogenes associated with nodal metastasis," PLoS One, Jun. 25, 2012, 7:e39797.

Yu et al., "Analysis of the Biochemical Mechanisms for the Endocrine Actions of Fibroblast Growth Factor-23," Endocrinology, Nov. 2005, 146(11): 4647-4656.

Yu et al., "FGFR-4 Arg(3)(8)(8) enhances prostate cancer progression via extracellular signal-related kinase and serum response factor signaling," Clin Cancer Res., Jul. 2011, 17:4355-4366.

Zaid et al., "Identification of FGFR4 as a Potential Therapeutic Target for Advanced-Stage, High-Grade Serous Ovarian Cancer," Clin Cancer Res, 2013, 19(4): 809-820.

Zhang et al., "AZD4547, a potent and selective FGF-receptor inhibitor induces tumor regressions in a human primary model of FGF-receptor 2 amplified gastric cancer and is efficacious in combination with chemotherapy," 2012, AstraZeneca, 1 page.

Zhang et al., "Direct Cell Cycle Regulation by the Fibroblast Growth Factor Receptor (FGFR) Kinase through Phosphorylation-dependent Release of Cks1 from FGFR Substrate 2," The Journal of Biological Chemistry, 2004, 279(53): 55348-55354.

Zhang et al., "Enhanced FGFR signalling predisposes pancreatic cancer to the effect of a potent FGFR inhibitor in preclinical models," British Journal of Cancer, 2014, 110: 320-329.

Zhang et al., "FP-1039 (FGFR1:Fc), A Soluble FGFR1 Receptor Antagonist, Inhibits Tumor Growth and Angiogenesis," Mol Cancer Ther, 6, Nov. 2007, B55.

(56) References Cited

OTHER PUBLICATIONS

Zhang et al., "Predicting Drug-Drug Interactions: An FDA Perspective," The AAPS Journal, May 6, 2009, 11(2):300-306.
Zhang et al., "Recent progress in therapeutic and diagnostic applications of lanthanides," Mini-Reviews in Medicinal Chemistry, 2011, 11(8):678-694.
Zhang et al., "Receptor Specificity of the Fibroblast Growth Factor Family," Journal of Biological Chemistry, Jun. 2006, 281(23): 15694-15700.
Zhang et al., "Translating the therapeutic potential of AZD4547 in FGFR1-amplified non-small cell lung cancer through the use of patient derived tumor xenograft (PDTX) models," Clin cancer Res, Oct. 18, 2012, 40 pages.
Zhao et al., "A Novel, Selective Inhibitor of Fibroblast Growth Factor Receptors That Shows a Potent Broad Spectrum of Antitumor Activity in Several Tumor Xenograft Models," Mol Cancer Ther, Nov. 2011, 2200-2210.
Zhao et al., "Homozygous Deletions and Chromosome Amplifications in Human Lung Carcinomas Revealed by Single Nucleotide Polymorphism Array Analysis," Cancer Res, Jul. 2005, 5561-5570.
Zhou et al., "A Structure-Guided Approach to Creating Covalent FGFR Inhibitors," Chemistry and Biology, Mar. 2010, 285-295.
Zhu et al., "Fibroblast growth factor receptor 3 inhibition by short hairpin RNAs leads to apoptosis in multiple myeloma," Mol Cancer Ther, May 2005, 787-798.
Zieger et al., "Role of Activating Fibroblast Growth Factor Receptor 3 Mutations in the Development of Bladder Tumors," Clin Cancer Res, Nov. 2005, 7709-7719.
Zingone et al., "Ectopic expression of wild-type FGFR3 cooperates with MYC to accelerate development of B-cell lineage neoplasms," Leukemia, 2010, 1171-1178.
Bazyl' et al., "The selective ortho-methoxylation of pentafluorobenzoic acid-a new way to tetrafluorosalicylic acid and its derivatives." Journal of fluorine chemistry, Feb. 11, 1999, 94(1):11-13.
Bhatia et al., "Polymorphism and its Implications in Pharmaceutical Product Development," Dosage Form Design Parameters, 2018, pp. 31-65.
Blagden et al., "Crystal engineering of active pharmaceutical ingredients to improve solubility and dissolution rates," Advanced Drug Delivery Reviews, Jul. 2007, 59(7):617-630.
Gupta et al., "Salts of Therapeutic Agents: Chemical, Physicochemical, and Biological Considerations," Molecules, Jul. 14, 2018, 23(7):1-14.
Hanna, "Clinical Overview of Enfortumab Vedotin in the Management of Locally Advanced or Metastatic Urothelial Carcinoma," Drugs, Dec. 2019, 80:1-7.
Hearing Notice in Indian Application No. 10665/DELNP/2014, dated Aug. 7, 2023, 3 pages.
Heinrich et al., "Fragment-based discovery of new highly substituted 1 H-pyrrolo [2,3-b]-and 3 H-imidazolo [4, 5-b]-pyridines as focal adhesion kinase inhibitors." Journal of medicinal chemistry, Feb. 14, 2013, 56(3):1160-70.
International Preliminary Report on Patentability in International Application No. PCT/US2020/024210, dated Oct. 12, 2023, 7 pages.
Jain et al., "Cholangiocarcinoma with FGFR Genetic Aberrations: A Unique Clinical Phenotype," JCO Precision Oncology, Jan. 17, 2018, 2:1-12.
Office Action in Argentinian Application No. 20160100442, dated Jul. 24, 2023, 11 pages (with English Translation).
Office Action in Australian Application No. 2019262195, dated Aug. 29, 2023, 6 pages.
Office Action in Australian Application No. 2019262579, dated Sep. 1, 2023, 4 pages.
Office Action in Brazil Application No. BR122020015574-4, dated Dec. 13, 2022, 12 pages (with Machine Translation).
Office Action in Chilean Application No. 202002848, dated Dec. 12, 2022, 36 pages (with machine translation).
Office Action in Chinese Application No. 201980042915, dated Jul. 14, 2023, 9 pages (with English Translation).
Office Action in Chinese Application No. 201980042917.9, dated Aug. 31, 2023, 7 pages (with English Translation).
Office Action in Chinese Application No. 201980042917.9, dated Jan. 18, 2023, 14 pages (with English translation).
Office Action in Colombia Application No. NC2020/0015228, dated Jun. 16, 2023, 21 pages (with English Translation).
Office Action in Colombian Application No. NC2019/0014699, dated Apr. 27, 2023, 30 pages (with English translation).
Office Action in Colombian Application No. NC2019/0014699, dated Oct. 31, 2022, 31 pages.
Office Action in Columbian Application No. NC2020/0015226, dated Oct. 6, 2023, 18 pages (with English Translation).
Office Action in Ecuador Application No. IEPI-2015-1225, dated Jan. 9, 2023, 30 pages (with English translation).
Office Action in Eurasian Application No. 202291810, dated Sep. 29, 2023, 8 pages (with English Translation).
Office Action in Indian Application No. 10665/DELNP/2014, dated Nov. 9, 2023, 3 pages.
Office Action in Indian Application No. 10665/DELNP/2014, dated Oct. 7, 2023, 3 pages.
Office Action in Indian Application No. 201917050123, dated Mar. 29, 2023, 5 pages.
Office Action in Indian Application No. 202017052853, dated May 17, 2023, 2 pages.
Office Action in Israeli Application No. 278289, dated Aug. 31, 2023, 4 pages.
Office Action in Japanese Application No. 2020-561731, dated Mar. 22, 2023, 8 pages (with English translation).
Office Action in Japanese Application No. 2020-561741, dated Mar. 22, 2023, 11 pages (with English translation).
Office Action in Korean Application No. 10-2019-7038203, dated Jun. 8, 2023, 15 pages (with English translation).
Office Action in Mexican Application No. MX/a/2020/011639, dated May 23, 2023, 14 pages (with machine translation).
Office Action in Mexican Application No. MX/a/2020/011639, dated Oct. 25, 2022, 13 pages.
Office Action in Mexican Application No. MX/a/2020/011718, dated Apr. 11, 2023, 12 pages (with machine translation).
Office Action in Mexican Application No. MX/a/2020/011718, dated Sep. 26, 2023, 15 pages (with English Translation).
Office Action in Philippines Application No. 1-2019-502809, dated Jun. 1, 2023, 4 pages.
Office Action in Philippines Application No. 1-2020-551843, dated Aug. 24, 2023, 7 pages.
Office Action in Taiwan Application No. 11107608, dated Dec. 26, 2022, 7 pages (with English Translation).
Office Action in Taiwanese Application No. 108115462, dated Jan. 10, 2023, 12 pages (with English translation).
Office Action in Taiwanese Application No. 108115470, dated Mar. 21, 2023, 13 pages (with machine translation).
Office Action in Taiwanese Application No. 110132234, dated Nov. 25, 2022, 8 pages (with English translation).
Office Action in Ukraine Application No. a201912195, dated Jun. 14, 2023, 12 pages (with English Translation).
Office Action in Ukraine Application No. a202007685, dated Oct. 31, 2022, 13 pages.
Opposition in Indian Application No. 202017052853, dated Sep. 2, 2023, 1167 pages.
Parmar et al., "Hydrochloride salt co-crystals: preparation, characterization and physicochemical studies," Pharmaceutical Development and Technology, 2013, 18(2):443-453.
Peterson et al., "Expanding the Scope of Crystal Form Evaluation in Pharmaceutical Science," J Pharm Pharmaceut Sci., Feb. 2006, 9(3): 317-326.
Pindelska et al., "Pharmaceutical cocrystals, salts and polymorphs: Advanced characterization techniques," Advanced Drug Delivery Reviews, 2017, 117:111-146.
Serajuddin, "Salt formation to improve drug solubility," Adv Drug Deliv Rev, Jul. 2007, 59(7):603-616.
Summons to attend oral proceedings pursuant to Rule 115(1) EPC in European Application No. 19724676.2, dated Feb. 22, 2023, 5 pages.

(56) References Cited

OTHER PUBLICATIONS

Thakuria et al., "Crystal Polymorphism in Pharmaceutical Science," Comprehensive Supramolecular Chemistry II, Jun. 2017, vol. 5, chapter 22, pp. 283-309.

SALTS OF AN FGFR INHIBITOR

FIELD OF THE INVENTION

The present invention relates to salt forms of the Fibroblast Growth Factor Receptors (FGFR) inhibitor 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one, including methods of preparation thereof, where the compound is useful in the treatment of FGFR mediated diseases such as cancer.

BACKGROUND OF THE INVENTION

The Fibroblast Growth Factor Receptors (FGFR) are receptor tyrosine kinases that bind to fibroblast growth factor (FGF) ligands. There are four FGFR proteins (FGFR1-4) that are capable of binding ligands and are involved in the regulation of many physiological processes including tissue development, angiogenesis, wound healing, and metabolic regulation. Upon ligand binding, the receptors undergo dimerization and phosphorylation leading to stimulation of the protein kinase activity and recruitment of many intracellular docking proteins. These interactions facilitate the activation of an array of intracellular signaling pathways including Ras-MAPK, AKT-PI3K, and phospholipase C that are important for cellular growth, proliferation and survival (Reviewed in Eswarakumar et al. Cytokine & Growth Factor Reviews, 2005).

Aberrant activation of this pathway either through overexpression of FGF ligands or FGFR or activating mutations in the FGFRs can lead to tumor development, progression, and resistance to conventional cancer therapies. In human cancer, genetic alterations including gene amplification, chromosomal translocations and somatic mutations that lead to ligand-independent receptor activation have been described. Large scale DNA sequencing of thousands of tumor samples has revealed that components of the FGFR pathway are among the most frequently mutated in human cancer. Many of these activating mutations are identical to germline mutations that lead to skeletal dysplasia syndromes. Mechanisms that lead to aberrant ligand-dependent signaling in human disease include overexpression of FGFs and changes in FGFR splicing that lead to receptors with more promiscuous ligand binding abilities (Reviewed in Knights and Cook Pharmacology & Therapeutics, 2010; Turner and Grose, Nature Reviews Cancer, 2010). Therefore, development of inhibitors targeting FGFR may be useful in the clinical treatment of diseases that have elevated FGF or FGFR activity.

The cancer types in which FGF/FGFRs are implicated include, but are not limited to: carcinomas (e.g., bladder, breast, cervical, colorectal, endometrial, gastric, head and neck, kidney, liver, lung, ovarian, prostate); hematopoietic malignancies (e.g., multiple myeloma, chronic lymphocytic lymphoma, adult T cell leukemia, acute myelogenous leukemia, non-Hodgkin lymphoma, myeloproliferative neoplasms, and Waldenstrom's Macroglubulinemia); and other neoplasms (e.g., glioblastoma, melanoma, and rhabdosarcoma). In addition to a role in oncogenic neoplasms, FGFR activation has also been implicated in skeletal and chondrocyte disorders including, but not limited to, achrondroplasia and craniosynostosis syndromes. The FGFR4-FGF19 signaling axis, specifically, has been implicated in the pathogenesis of a number of cancers including hepatocellular carcinoma (Heinzle et al., Cur. Pharm. Des. 2014, 20:2881). Ectopic expression of FGF19 in transgenic mice was shown to lead to tumor formation in the liver and a neutralizing antibody to FGF19 was found to inhibit tumor growth in mice. In addition, overexpression of FGFR4 has been observed in a multiple tumor types including hepatocellular carcinoma, colorectal, breast, pancreatic, prostate, lung, and thyroid cancers. Furthermore, activating mutations in FGFR4 have been reported in rhabdomyosarcoma (Taylor et al. JCI 2009, 119:3395).

Inhibitors of FGFR are currently being developed for the treatment of cancer. For example, the molecule 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one and other small molecule inhibitors of FGFR are reported in e.g., US Publication Nos.: 2012/0165305; 2014/0045814; 2013-0338134; 2014/0171405; 2014/0315902; 2016/0115164; 2016/0244448; 2016/0244449; and 2016/0244450. Accordingly, there is a need for new salts of FGFR-inhibiting molecules for preparing pharmaceutically useful formulations and dosage forms with suitable properties related to, for example, facilitating the manufacture of safe, effective, and high quality drug products.

SUMMARY OF THE INVENTION

The present invention is directed to salts of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the D-(−)-tartaric acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the L-(+)-tartaric acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the salicylic acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the hydrochloric acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the hydrobromic acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the fumaric acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the phosphoric acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the benzenesulfonic acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the ethanesulfonic acid salt of 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one.

The present invention is further directed to the maleic acid salt of 3-(2,6-difluoro-3,5-dimethoxyphenyl)-1-ethyl-8-

(morpholin-4-ylmethyl)-1,3,4,7-tetrahydro-2H-pyrrolo[3', 2':5,6]pyrido[4,3-d]pyrimidin-2-one.

The present invention is further directed to the adipic acid salt of 3-(2,6-difluoro-3,5-dimethoxyphenyl)-1-ethyl-8-(morpholin-4-ylmethyl)-1,3,4,7-tetrahydro-2H-pyrrolo[3', 2':5,6]pyrido[4,3-d]pyrimidin-2-one.

The present invention is further directed to crystalline forms of the salts described herein.

The present invention is further directed to pharmaceutical compositions comprising a salt or crystalline form described herein, and at least one pharmaceutically acceptable carrier.

The present invention is further directed to therapeutic methods of using the salts and crystalline forms described herein. The present disclosure also provides uses of the salts and crystalline forms described herein in the manufacture of a medicament for use in therapy. The present disclosure also provides the salts and crystalline forms described herein for use in therapy.

The present invention is further directed to processes for preparing the salts and crystalline forms described herein.

DETAILED DESCRIPTION

Figure 1:
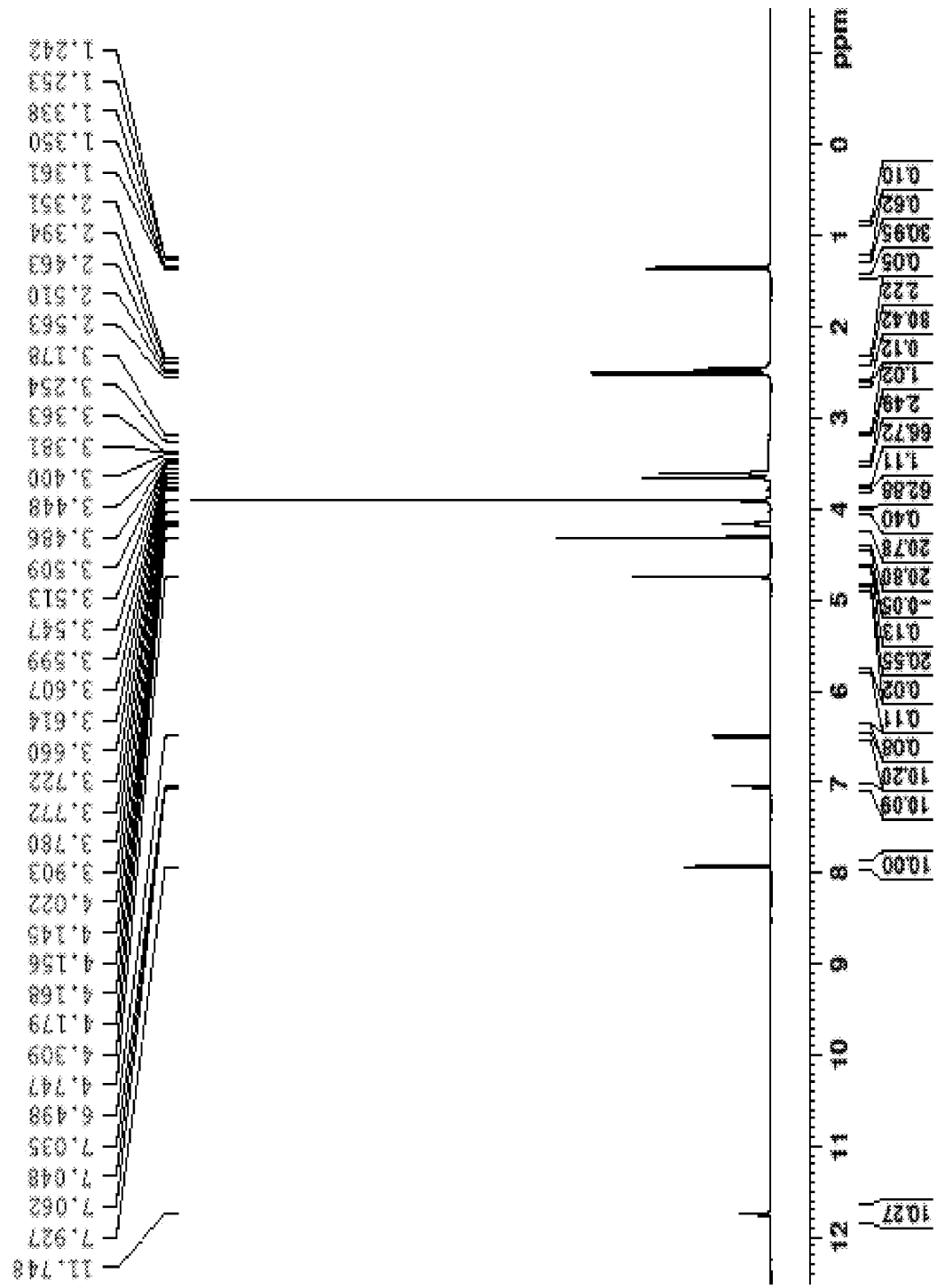
FIG. 1 shows the $^1$H NMR of Compound 1 D-(−)-tartaric acid salt.

The present invention is directed to, inter alia, salts of 3-(2,6-difluoro-3,5-dimethoxyphenyl)-1-ethyl-8-(morpholin-4-ylmethyl)-1,3,4,7-tetrahydro-2H-pyrrolo[3',2':5,6] pyrido[4,3-d]pyrimidin-2-one (Compound 1), the structure of which is shown below.

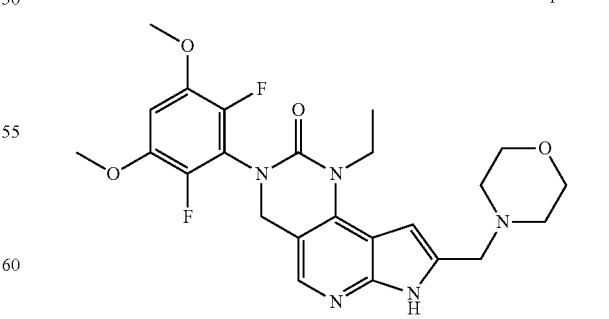

Compound 1

Compound 1 is described in U.S. Pat. No. 9,611,267, the entirety of which is incorporated herein by reference. Also provided herein are hydrates and solvates of salts of Compound 1.

Compound 1 and its salts can be isolated as one or more solid forms. The solid forms (e.g., crystalline forms) described herein have many advantages, for example they have desirable properties, such as ease of handling, ease of processing, storage stability, and ease of purification. Moreover, the crystalline forms can be useful for improving the performance characteristics of a pharmaceutical product such as dissolution profile, shelf-life and bioavailability.

In some embodiments, the salt of Compound 1 is an acid salt of Compound 1. In some embodiments, the acid is selected from L-(+)-tartaric acid, D-(+)-tartaric acid, salicylic acid, fumaric acid, benzenesulfonic acid, ethanesulfonic acid, hydrochloric acid, hydrobromic acid and phosphoric acid.

In some embodiments, the salt of the invention is a tartaric acid salt of Compound 1, such as D-(−)-tartaric acid salt form or D-tartaric acid salt form. The D-tartaric acid salt form of Compound 1 is referred to herein as "Compound 1 D-tartaric acid salt," "Compound 1 D-(+)-tartaric acid salt form," "Compound 1 D-tartaric acid," or "Compound 1 D-tartrate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one D-tartrate.

In some embodiments, the salt of the invention is a tartaric acid salt of Compound 1, such as L-(+)-tartaric acid salt form or L-tartaric acid salt form. The L-tartaric acid salt form of Compound 1 is referred to herein as "Compound 1 L-tartaric acid salt," "Compound 1 L-(+)-tartaric acid salt form," "Compound 1 L-tartaric acid," or "Compound 1 L-tartrate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one L-tartrate.

In some embodiments, the salt of the invention is a salicylic acid salt of Compound 1. The salicylic acid salt form of Compound 1 is referred to herein as "Compound 1 salicylic acid salt," "Compound 1 salicylic acid," or "Compound 1 salicylate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one salicylate.

In some embodiments, the salt of the invention is a hydrochloric acid salt of Compound 1, such as a hydrochloric acid salt form. The hydrochloric acid salt form of Compound 1 is referred to herein as "Compound 1 hydrochloric acid salt," "Compound 1 hydrochloric acid," or "Compound 1 hydrochloride." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one hydrochloride.

In some embodiments, the salt of the invention is a hydrobromic acid salt of Compound 1. The hydrobromic acid salt form of Compound 1 is referred to herein as "Compound 1 hydrobromic acid salt," "Compound 1 hydrobromic acid," or "Compound 1 hydrobromide." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one hydrobromide.

In some embodiments, the salt of the invention is a fumaric (trans-butenedioic) acid salt of Compound 1. The fumaric acid salt form of Compound 1 is referred to herein as "Compound 1 fumaric acid salt," "Compound 1 fumaric acid," or "Compound 1 fumarate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one fumarate.

In some embodiments, the salt of the invention is a phosphoric acid salt of Compound 1. The phosphoric acid salt form of Compound 1 is referred to herein as "Compound 1 phosphoric acid salt," "Compound 1 phosphoric acid," or "Compound 1 phosphate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6] pyrido[4,3-d]pyrimidin-2-one phosphate.

In some embodiments, the salt of the invention is a benzenesulfonic acid salt of Compound 1. The benzenesulfonic acid salt form of Compound 1 is referred to herein as "Compound 1 benzenesulfonic acid salt," "Compound 1 benzenesulfonic acid," or "Compound 1 besylate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one besylate.

In some embodiments, the salt of the invention is an ethanesulfonic acid salt of Compound 1. The ethanesulfonic acid salt form of Compound 1 is referred to herein as "Compound 1 ethanesulfonic acid salt," "Compound 1 ethanesulfonic acid," or "Compound 1 esylate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one esylate.

In some embodiments, the salt of the invention is a maleic acid salt of Compound 1. The maleic acid salt form of Compound 1 is referred to herein as "Compound 1 maleic acid salt," "Compound 1 maleic acid," or "Compound 1 maleate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one maleate.

In some embodiments, the salt of the invention is an adipic acid salt of Compound 1. The adipic acid salt form of Compound 1 is referred to herein as "Compound 1 adipic acid salt," "Compound 1 adipic acid," or "Compound 1 adipate." An alternative name for the salt is 3-(2,6-difluoro-3,5-dimethoxyphenyl)-1-ethyl-8-(morpholin-4-ylmethyl)-1,3,4,7-tetrahydro-2H-pyrrolo[3',2':5,6]pyrido[4,3-d]pyrimidin-2-one adipate.

The salts of the invention can be isolated as one or more solid forms. As used herein, the phrase "solid form" refers to a salt of the invention in either an amorphous state or a crystalline state ("crystalline form" or "crystalline solid"), whereby a salt of the invention in a crystalline state may optionally include solvent or water within the crystalline lattice, for example, to form a solvated or hydrated crystalline form. In some embodiments, the salt of the present invention is in a crystalline state as described herein. The term "hydrated," as used herein, is meant to refer to a crystalline form that includes one or more water molecules in the crystalline lattice. Example "hydrated" crystalline forms include hemihydrates, monohydrates, dihydrates, and the like. Other hydrated forms such as channel hydrates and the like are also included within the meaning of the term.

In some embodiments, salts of the invention can be prepared by any suitable method for the preparation of acid addition salts. For example, the free base Compound 1 can be combined with the desired acid in a solvent or in a melt. Alternatively, an acid addition salt of Compound 1 can be converted to a different acid addition salt by anion exchange. Salts of the invention which are prepared in a solvent system can be isolated by precipitation from the solvent. Precipitation and/or crystallization can be induced, for example, by evaporation, reduction of temperature, addition of antisolvent, or combinations thereof.

In some embodiments, the salts of the invention are crystalline, including crystalline forms which are anhydrous, hydrated, non-solvated, or solvated. Example hydrates include hemihydrates, monohydrates, dihydrates, and the like. In some embodiments, the crystalline salts are anhydrous and non-solvated. By "anhydrous" is meant that the crystalline salt contains no bound water in the crystal lattice structure, i.e., the compound does not form a crystalline hydrate.

In some embodiments, the salts of the invention are substantially isolated. By "substantially isolated" is meant that the salt is at least partially or substantially separated from the environment in which it was formed or detected. Partial separation can include, for example, a composition enriched in the salt of the invention. Substantial separation can include compositions containing at least about 50%, at least about 60%, at least about 70%, at least about 80%, at least about 90%, at least about 95%, at least about 97%, or at least about 99% by weight of the salt.

Salts of the invention also include all isotopes of atoms occurring in the salts. Isotopes include those atoms having the same atomic number but different mass numbers. For example, isotopes of hydrogen include tritium and deuterium.

The salt forms of the invention were found to be highly crystalline, a desirable property which can facilitate, for example, purification of the drug such as by crystallization and recrystallization as necessary. Further, a crystalline form tends to be more stable and can be easier to mill or micronize when formulating a drug. Crystalline salts also tend have excellent properties with respect to solubility and can be more suitable to be manufactured reproducibly in a clear acid/base ratio, facilitating the preparation of liquid formulations for oral as well as for intravenous applications.

As used herein, the term "crystalline" or "crystalline form" refers to a crystalline solid form of a chemical compound, including, but not limited to, a single-component or multiple-component crystal form, e.g., including solvates, hydrates, clathrates, and a co-crystals. As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (XRPD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

As used herein, the term "substantially crystalline," means a majority of the weight of a sample or preparation of a salt (or hydrate or solvate thereof) of the invention is crystalline and the remainder of the sample is a non-crystalline form (e.g., amorphous form) of the same compound. In some embodiments, a substantially crystalline sample has at least about 95% crystallinity (e.g., about 5% of the non-crystalline form of the same compound), preferably at least about 96% crystallinity (e.g., about 4% of the non-crystalline form of the same compound), more preferably at least about 97% crystallinity (e.g., about 3% of the non-crystalline form of the same compound), even more preferably at least about 98% crystallinity (e.g., about 2% of the non-crystalline form of the same compound), still more preferably at least about 99% crystallinity (e.g., about 1% of the non-crystalline form of the same compound), and most preferably about 100% crystallinity (e.g., about 0% of the non-crystalline form of the same compound). In some embodiments, the term "fully crystalline" means at least about 99% or about 100% crystallinity.

Crystalline forms are most commonly characterized by XRPD. An XRPD pattern of reflections (peaks) is typically considered a fingerprint of a particular crystalline form. It is well known that the relative intensities of the XRPD peaks can widely vary depending on, inter alia, the sample preparation technique, crystal size distribution, filters, the sample mounting procedure, and the particular instrument employed. In some instances, new peaks may be observed or existing peaks may disappear, depending on the type of instrument or the settings (for example, whether a Ni filter is used or not). As used herein, the term "peak" refers to a reflection having a relative height/intensity of at least about 4% of the maximum peak height/intensity. Moreover, instrument variation and other factors can affect the 2-theta values. Thus, peak assignments, such as those reported herein, can vary by plus or minus about 0.2° (2-theta), and the term "substantially" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. For example, with DSC it is known that the temperatures observed will depend on the rate of the temperature change as well as the sample preparation technique and the particular instrument employed. Thus, the values reported herein related to DSC thermograms can vary, as indicated above, by ±3° C. Accordingly, a crystalline form reported herein having a DSC thermogram "substantially" as shown in any of the Figures is understood to accommodate such variation.

The salts and compounds disclosed herein can include all isotopes of atoms occurring within them. Isotopes include those atoms having the same atomic number but different mass numbers. For example, isotopes of hydrogen include tritium and deuterium. Salts and compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

As used herein, and unless otherwise specified, the term "about", when used in connection with a numeric value or range of values which is provided to describe a particular solid form (e.g., a specific temperature or temperature range, such as describing a melting, dehydration, or glass transition; a mass change, such as a mass change as a function of temperature or humidity; a solvent or water content, in terms of, for example, mass or a percentage; or a peak position, such as in analysis by, for example, $^{13}C$ NMR, DSC, TGA and XRPD), indicate that the value or range of values may deviate to an extent deemed reasonable to one of ordinary skill in the art while still describing the particular solid form. Specifically, the term "about", when used in this context, indicates that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values while still describing the particular solid form. The term "about", when used in reference to a degree 2-theta value refers to +/−0.2 degrees 2-theta.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "melting point" refers to an endothermic event or endothermal event observed in e.g., a DSC experiment. An endothermic event is a process or reaction in which a sample absorbs energy from its surrounding in the form of e.g., heat as in a DSC experiment. An exothermic event is a process or reaction in which a sample releases energy. The process of heat absorption and release can be detected by DSC. In some embodiments, the term "melting point" is used to describe the major endothermic event revealed on a particular DSC thermogram.

The term "room temperature" as used herein, is understood in the art, and refers generally to a temperature, e.g., a reaction temperature, that is about the temperature of the room in which the reaction is carried out, for example, a temperature from about 20° C. to about 30° C. The term "elevated temperature" as used herein, is understood in the art, and refer generally to a temperature, e.g., a reaction temperature, that is above room temperature, e.g., above 30° C.

D-(−)-Tartaric Acid Salts

The D-(−)-tartaric acid salt of Compound 1 can be prepared by any suitable method for preparation of D-(−)-tartaric acid addition salts. For example, Compound 1 can be combined with D-(−)-tartaric acid (e.g., about 1.0 molar eq or more) in a crystallizing solvent and the resulting salt can be isolated by filtering the salt from solution. In certain embodiments, Compound 1 is combined with about 1 to about 2 molar equivalents of D-(−)-tartaric acid. In certain embodiments, Compound 1 is combined with about 1 to about 1.5 molar equivalents of D-(−)-tartaric acid. In certain embodiments, Compound 1 is combined with about 1.1 molar equivalents of D-(−)-tartaric acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is a 1:1 v/v mixture of methanol and dichloromethane.

In some embodiments, the crystallizing solvent is heated to a temperature of at least about 50° C. In some embodiments, a temperature from about 50° C. to about 80° C. is used. For example, a temperature from about 40° C. to about 60° C. is used. In some embodiments, a temperature from about 45° C. to about 55° C. is used. In some embodiments, a temperature of about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 48 hours, but longer and shorter periods are possible depending on the choice of crystallizing solvent and temperature.

The precipitation and/or crystallization of the D-(−)-tartaric acid salt, in some embodiments, is carried out by filtering the salt from solution.

Crystalline D-(−)-tartaric acid salt forms of Compound 1 can be identified by their unique signatures with respect to, for example, X-ray powder diffraction, differential scanning calorimetry (DSC), thermogravimetric analysis (TGA), and solid state NMR.

Figure 2:
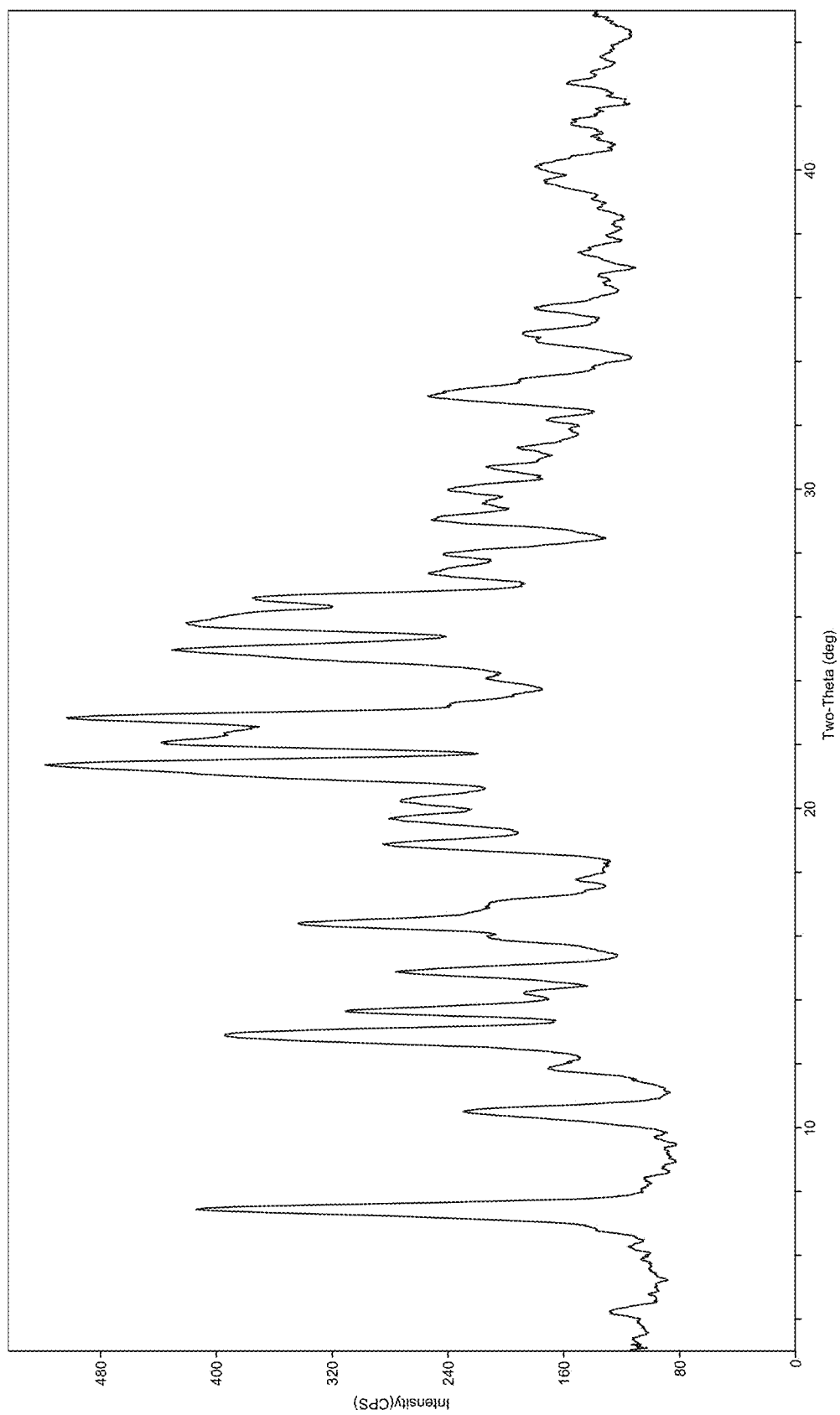
FIG. 2 shows the XRPD pattern of Compound 1 D-(−)-tartaric acid salt.

In some embodiments, the crystalline D-(−)-tartaric acid salt can be characterized by the X-ray powder diffraction (XRPD) pattern substantially as shown in FIG. 2.

In some embodiments, the D-(−)-tartaric acid salt of Compound 1 has at least one characteristic XRPD peaks selected from about 7.4, about 10.5, about 12.9, about 13.6, about 14.8, and about 16.4 degrees 2-theta.

In some embodiments, D-(−)-tartaric acid salt of Compound 1 has at least two characteristic XRPD peaks selected from about 7.4, about 10.5, about 12.9, about 13.6, about 14.8, and about 16.4 degrees 2-theta.

In some embodiments, D-(−)-tartaric acid salt of Compound 1 has at least three characteristic XRPD peaks selected from about 7.4, about 10.5, about 12.9, about 13.6, about 14.8, and about 16.4 degrees 2-theta.

In some embodiments, the D-(−)-tartaric acid salt of Compound 1 has at least one characteristic XRPD peak selected from about 7.4, about 10.5, about 12.9, about 13.6, about 14.8, about 16.4, about 18.9, about 21.3, about 22.1, about 22.8, about 25.0, about 25.8, about 26.6, and about 27.4 degrees 2-theta.

In some embodiments, D-(−)-tartaric acid salt of Compound 1 has at least two characteristic XRPD peaks selected from about 7.4, about 10.5, about 12.9, about 13.6, about 14.8, about 16.4, about 18.9, about 21.3, about 22.1, about 22.8, about 25.0, about 25.8, about 26.6, and about 27.4 degrees 2-theta.

In some embodiments, D-(−)-tartaric acid salt of Compound 1 has at least three characteristic XRPD peaks selected from about 7.4, about 10.5, about 12.9, about 13.6, about 14.8, about 16.4, about 18.9, about 21.3, about 22.1, about 22.8, about 25.0, about 25.8, about 26.6, and about 27.4 degrees 2-theta.

Figure 3:
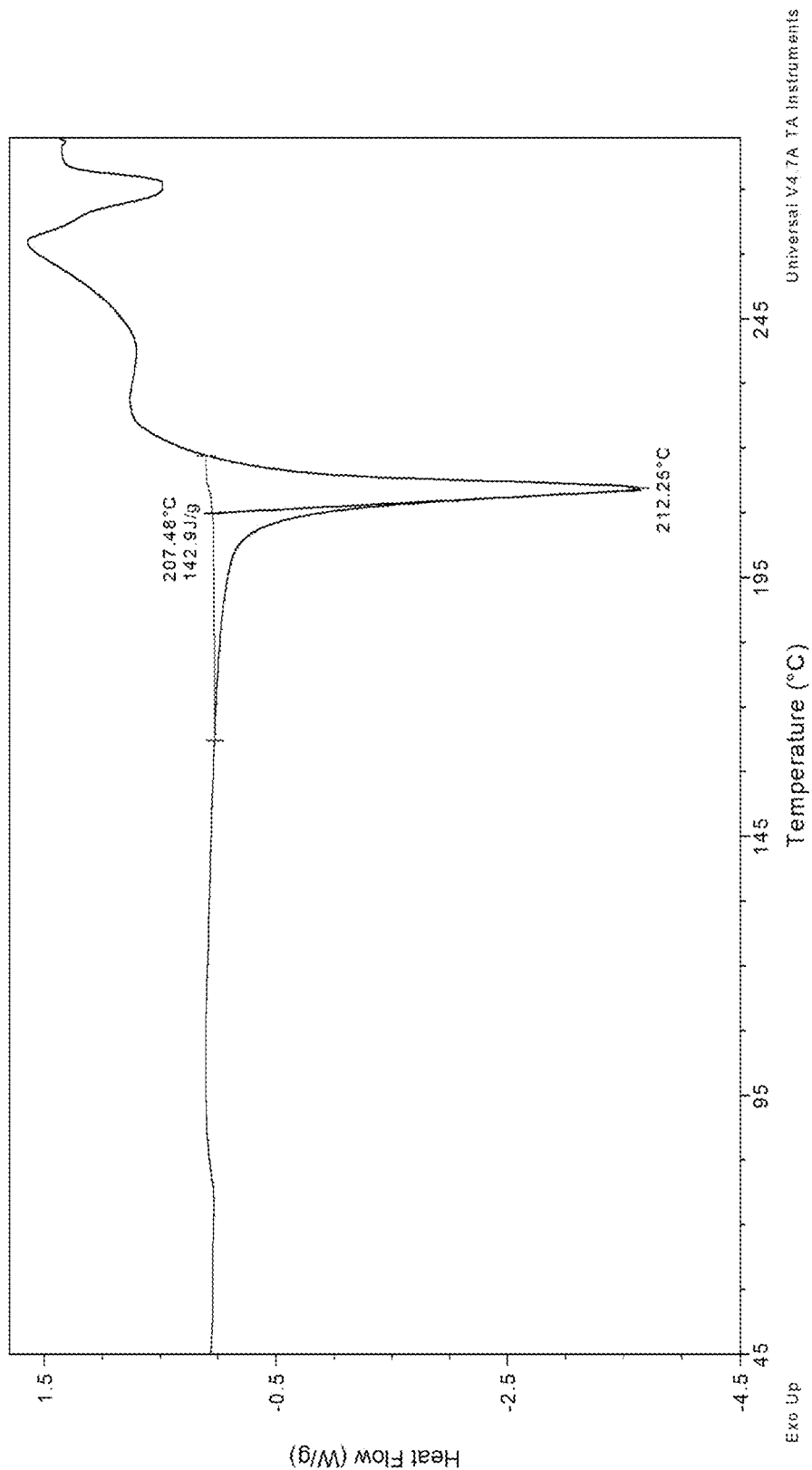
FIG. 3 shows the DSC thermogram of Compound 1 D-(−)-tartaric acid salt.
Figure 4:
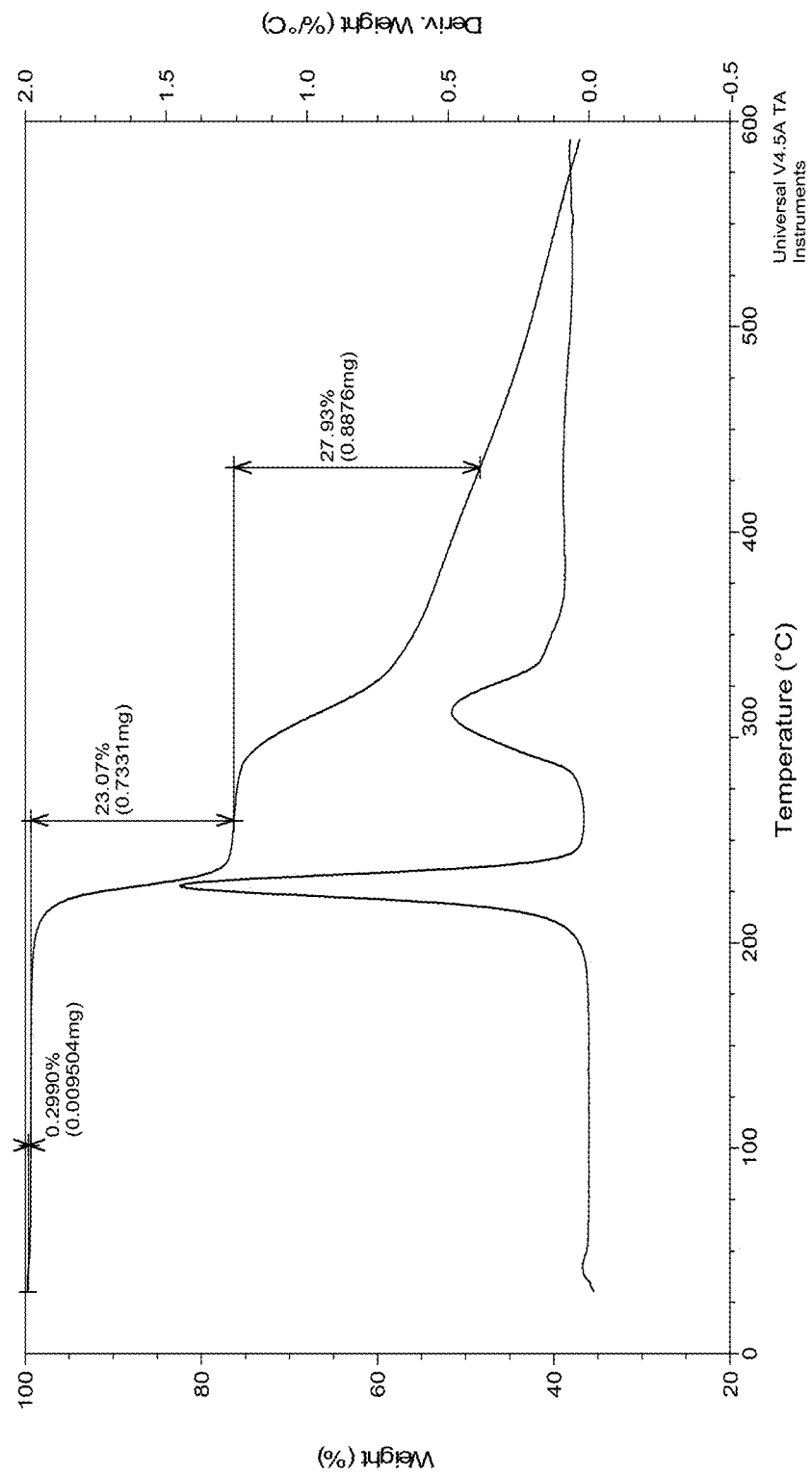
FIG. 4 shows the TGA thermogram of Compound 1 D-(−)-tartaric acid salt.

In some embodiments, the D-(−)-tartaric acid salt exhibits a DSC thermogram having an endothermic peak at a temperature of about 276° C. In some embodiments, the D-(−)- tartaric acid salt has a DSC thermogram substantially as depicted in FIG. 3. In some embodiments, the D-(−)tartaric acid salt has a TGA thermogram substantially as depicted in FIG. 4.

In some embodiments, the D-(−)-tartaric acid salt of Compound 1 has at least one characteristic XRPD peak selected from about 7.4, about 10.5, about 12.9, about 13.6, about 14.8, and about 16.4; and exhibits a DSC thermogram having an endothermic peak at a temperature of about 276° C.

In some embodiments, the D-(−)-tartaric acid salt of Compound 1 is substantially crystalline. In some embodiments, the salt is crystalline. In some embodiments, the salt is a hydrate. In some embodiments, the salt is a solvate.

L-(+)-Tartaric Acid Salts

The L-(+)-tartaric acid salt of Compound 1 can be prepared by any suitable method for preparation of L-(+)-tartaric acid addition salts. For example, Compound 1 can be combined with L-(+)-tartaric acid (e.g., about 1.0 molar eq or more) in a crystallizing solvent and the resulting salt can be isolated by filtering the salt from solution. In certain embodiments, Compound 1 is combined with about 1 to about 2 molar equivalents of L-(+)-tartaric acid. In certain embodiments, Compound 1 is combined with about 1 to about 1.5 equivalents of molar L-(+)-tartaric acid. In certain embodiments, Compound 1 is combined with about 1.1 molar equivalents of L-(+)-tartaric acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is a 1:1 v/v mixture of methanol and dichloromethane.

In some embodiments, the crystallizing solvent is heated to a temperature of at least about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 48 hours, but longer and shorter periods are possible depending on the choice of crystallizing solvent and temperature.

The precipitation and/or crystallization of the L-(+)-tartaric acid salt, in some embodiments, is carried out by filtering the salt from solution.

Crystalline L-(+)-tartaric acid salt forms of Compound 1 can be identified by their unique signatures with respect to, for example, X-ray powder diffraction, differential scanning calorimetry (DSC), thermogravimetric analysis (TGA), and solid state NMR.

Figure 6:
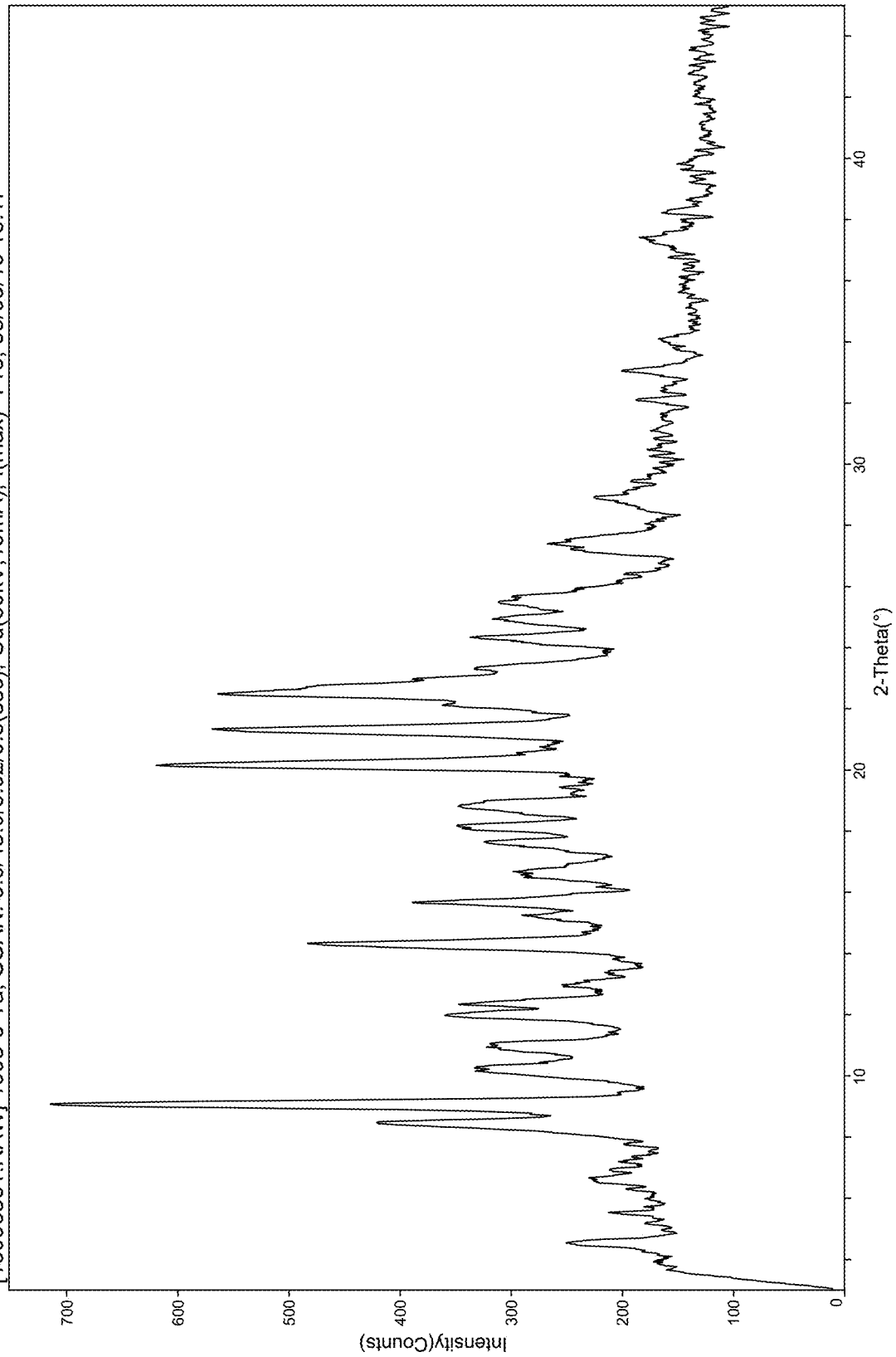
FIG. 6 shows the XRPD pattern of Compound 1 L-(+)-tartaric acid salt.

In some embodiments, the crystalline L-(+)-tartaric acid salt can be characterized by the X-ray powder diffraction (XRPD) pattern substantially as shown in FIG. 6.

In some embodiments, the L-(+)-tartaric acid salt of Compound 1 has at least one characteristic XRPD peak selected from about 3.8, about 8.5, about 9.1, about 10.3, and about 12.0 degrees 2-theta.

In some embodiments, L-(+)-tartaric acid salt of Compound 1 has at least two characteristic XRPD peaks selected from about 3.8, about 8.5, about 9.1, about 10.3, and about 12.0 degrees 2-theta.

In some embodiments, L-(+)-tartaric acid salt of Compound 1 has at least three characteristic XRPD peaks selected from about 3.8, about 8.5, about 9.1, about 10.3, and about 12.0 degrees 2-theta.

In some embodiments, the L-(+)-tartaric acid salt of Compound 1 has at least one characteristic XRPD peak selected from about 3.8, about 4.5, about 8.5, about 9.1, about 10.3, about 12.0, about 12.3, about 14.3, about 15.7, about 18.2, about 18.8, about 20.2, about 21.3, and about 22.5 degrees 2-theta.

In some embodiments, L-(+)-tartaric acid salt of Compound 1 has at least two characteristic XRPD peaks selected from about 3.8, about 4.5, about 8.5, about 9.1, about 10.3, about 12.0, about 12.3, about 14.3, about 15.7, about 18.2, about 18.8, about 20.2, about 21.3, and about 22.5 degrees 2-theta.

In some embodiments, L-(+)-tartaric acid salt of Compound 1 has at least three characteristic XRPD peaks selected from about 3.8, about 4.5, about 8.5, about 9.1, about 10.3, about 12.0, about 12.3, about 14.3, about 15.7, about 18.2, about 18.8, about 20.2, about 21.3, and about 22.5 degrees 2-theta.

Figure 7:
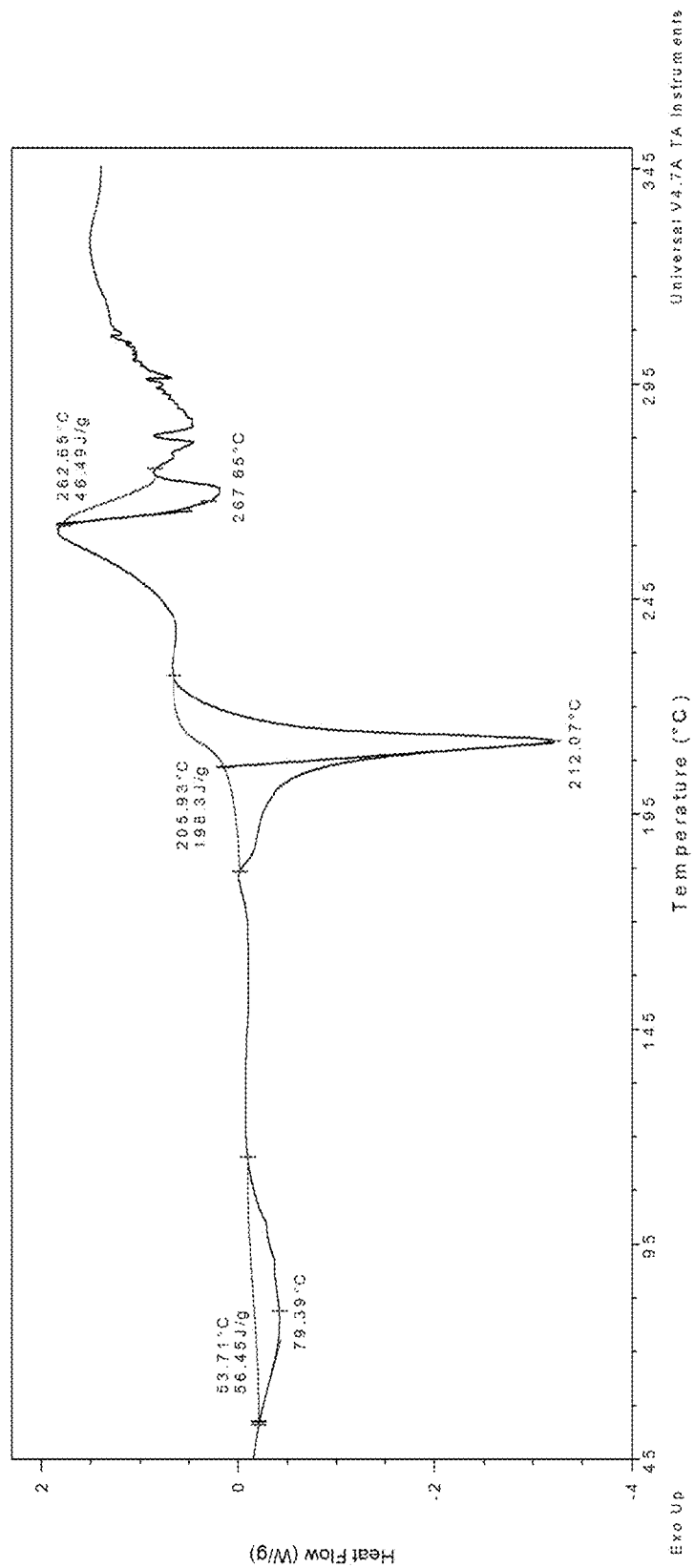
FIG. 7 shows the DSC thermogram of Compound 1 L-(+)-tartaric acid salt.
Figure 8:
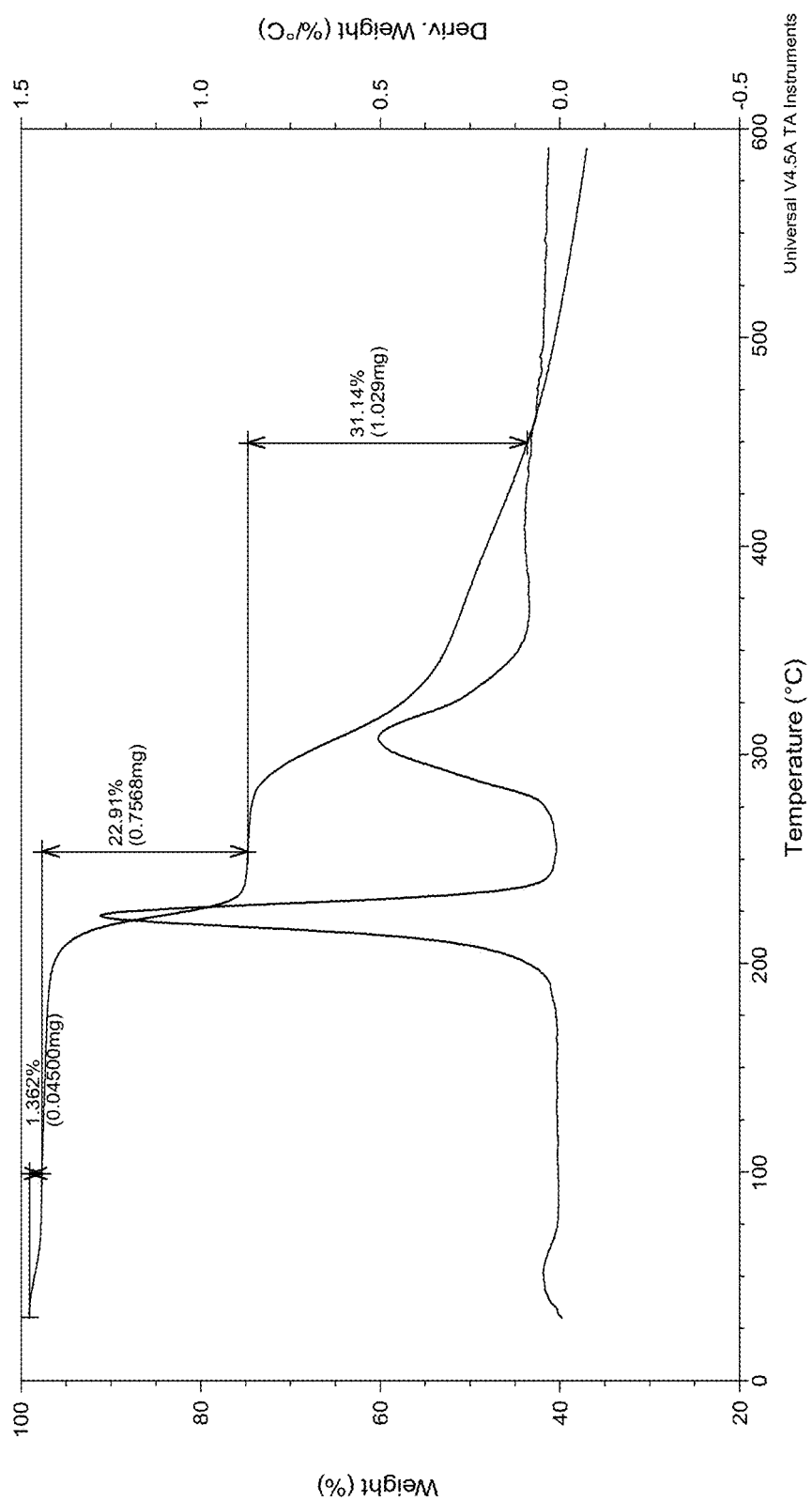
FIG. 8 shows the TGA thermogram of Compound 1 L-(+)-tartaric acid salt.

In some embodiments, the L-(+)-tartaric acid salt exhibits a DSC thermogram having endothermic peaks at temperatures of about 90° C., about 211° C., and about 266° C. In some embodiments, the endothermic peak is at a temperature of about 90° C. In some embodiments, the endothermic peak is at a temperature of about 211° C. In some embodiments, the endothermic peak is at a temperature of about 266° C. In some embodiments, the L-(+)-tartaric acid salt has a DSC thermogram substantially as depicted in FIG. 7. In some embodiments, the L-(+)-tartaric acid salt has a TGA thermogram substantially as depicted in FIG. 8.

In some embodiments, the L-(+)-tartaric acid salt of Compound 1 has at least one characteristic XRPD peak selected from about 3.8, about 8.5, about 9.1, about 10.3, and about 12.0; and the L-(+)-tartaric acid salt exhibits a DSC thermogram having endothermic peaks at temperatures of about 90° C., about 211° C., and about 266° C.

In some embodiments, the L-(+)-tartaric acid salt of Compound 1 is substantially crystalline. In some embodiments, the salt is crystalline. In some embodiments, the salt is a hydrate. In some embodiments, the salt is a solvate.

Salicylic Acid Salts

The salicylic acid salt of Compound 1 can be prepared by any suitable method for preparation of salicylic acid addition salts. For example, Compound 1 can be combined with salicylic acid (e.g., about 1.0 molar eq or more) in a crystallizing solvent and the resulting salt can be isolated by filtering the salt from solution. In certain embodiments, Compound 1 is combined with about 1 to about 2 molar equivalents of salicylic acid. In certain embodiments, Compound 1 is combined with about 1 to about 1.5 molar equivalents of salicylic acid. In certain embodiments, Compound 1 is combined with about 1.2 molar equivalents of salicylic acid. In some embodiments, Compound 1 is combined with about 1.3 molar equivalents of salicylic acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is methanol.

In some embodiments, the crystallizing solvent is heated to a temperature of at least about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 48 hours, but longer and shorter periods are possible depending on the choice of crystallizing solvent and temperature.

The precipitation and/or crystallization of the salicylic acid salt, in some embodiments, is carried out by filtering the salt from solution.

Crystalline salicylic acid salt forms of Compound 1 can be identified by their unique signatures with respect to, for example, X-ray powder diffraction, differential scanning calorimetry (DSC), thermogravimetric analysis (TGA), and solid state NMR.

Figure 10:
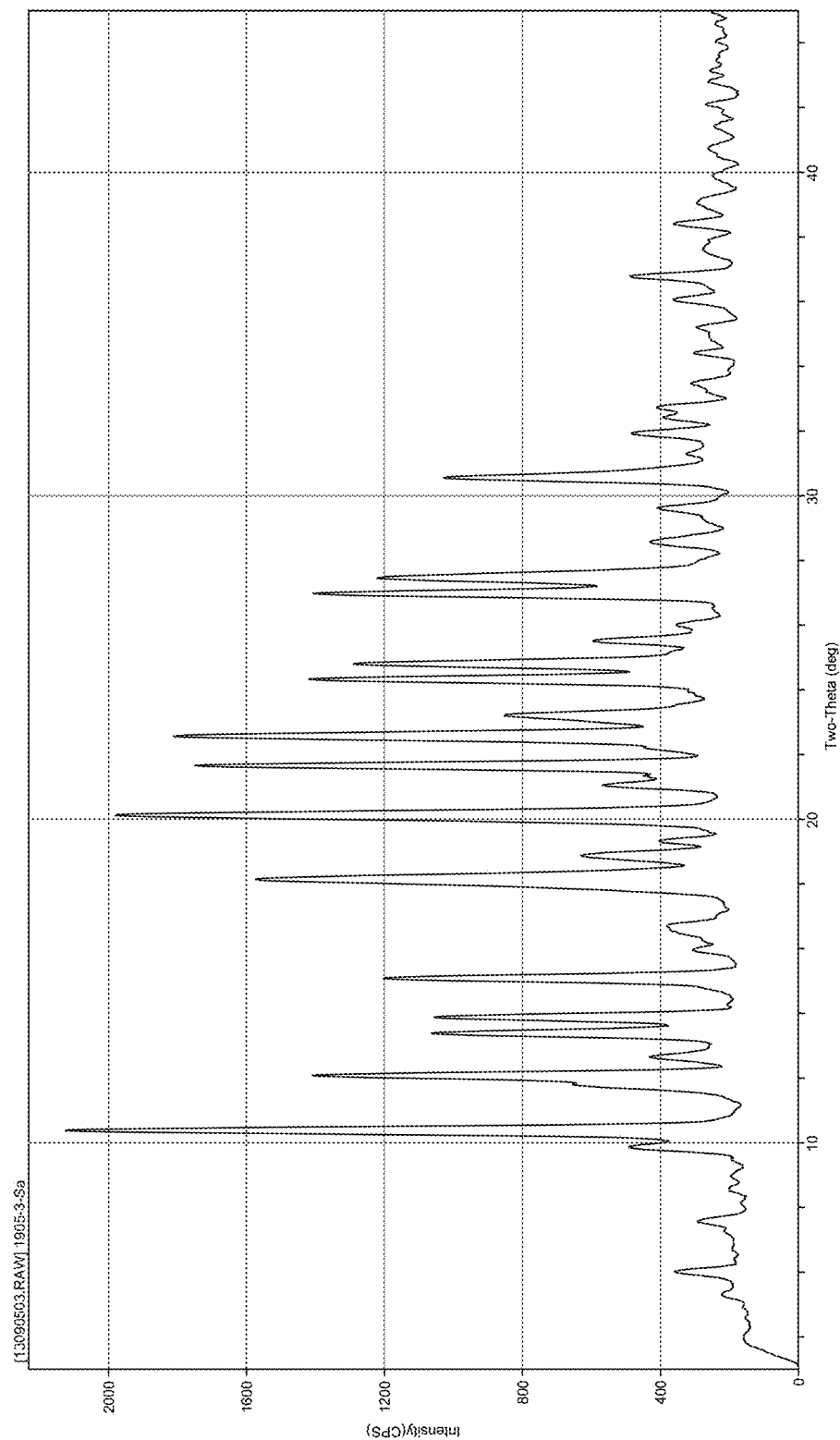
FIG. 10 shows the XRPD pattern of Compound 1 salicylic acid salt.

In some embodiments, the crystalline salicylic acid salt can be characterized by the X-ray powder diffraction (XRPD) pattern substantially as shown in FIG. 10.

In some embodiments, the salicylic acid salt of Compound 1 has at least one characteristic XRPD peak selected from about 10.4, about 11.8, about 12.1, about 13.4, and about 13.9 degrees 2-theta.

In some embodiments, salicylic acid salt of Compound 1 has at least two characteristic XRPD peaks selected from about 10.4, about 11.8, about 12.1, about 13.4, and about 13.9 degrees 2-theta.

In some embodiments, salicylic acid salt of Compound 1 has at least three characteristic XRPD peaks selected from about 10.4, about 11.8, about 12.1, about 13.4, and about 13.9 degrees 2-theta.

In some embodiments, the salicylic acid salt of Compound 1 has at least one characteristic XRPD peak selected from about 10.4, about 11.8, about 12.1, about 13.4, about 13.9, about 15.1, about 18.2, about 20.1, about 21.7, about 22.6, about 23.2, about 24.3, about 24.8, about 27.0, and about 27.4 degrees 2-theta.

In some embodiments, salicylic acid salt of Compound 1 has at least two characteristic XRPD peaks selected from about 10.4, about 11.8, about 12.1, about 13.4, about 13.9, about 15.1, about 18.2, about 20.1, about 21.7, about 22.6, about 23.2, about 24.3, about 24.8, about 27.0, and about 27.4 degrees 2-theta.

In some embodiments, salicylic acid salt of Compound 1 has at least three characteristic XRPD peaks selected from about 10.4, about 11.8, about 12.1, about 13.4, about 13.9, about 15.1, about 18.2, about 20.1, about 21.7, about 22.6, about 23.2, about 24.3, about 24.8, about 27.0, and about 27.4 degrees 2-theta.

Figure 11:
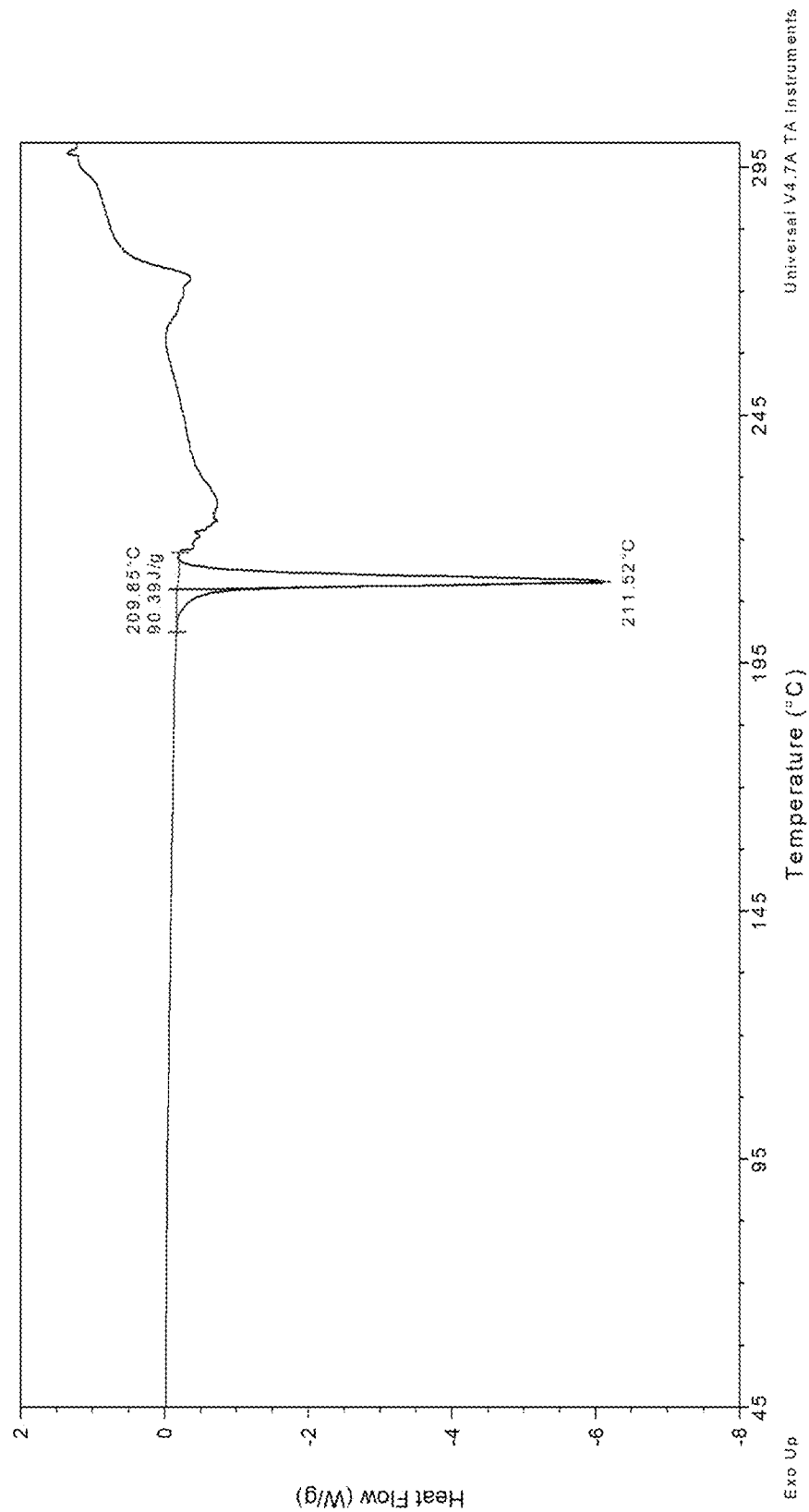
FIG. 11 shows the DSC thermogram of Compound 1 salicylic acid salt.
Figure 12:
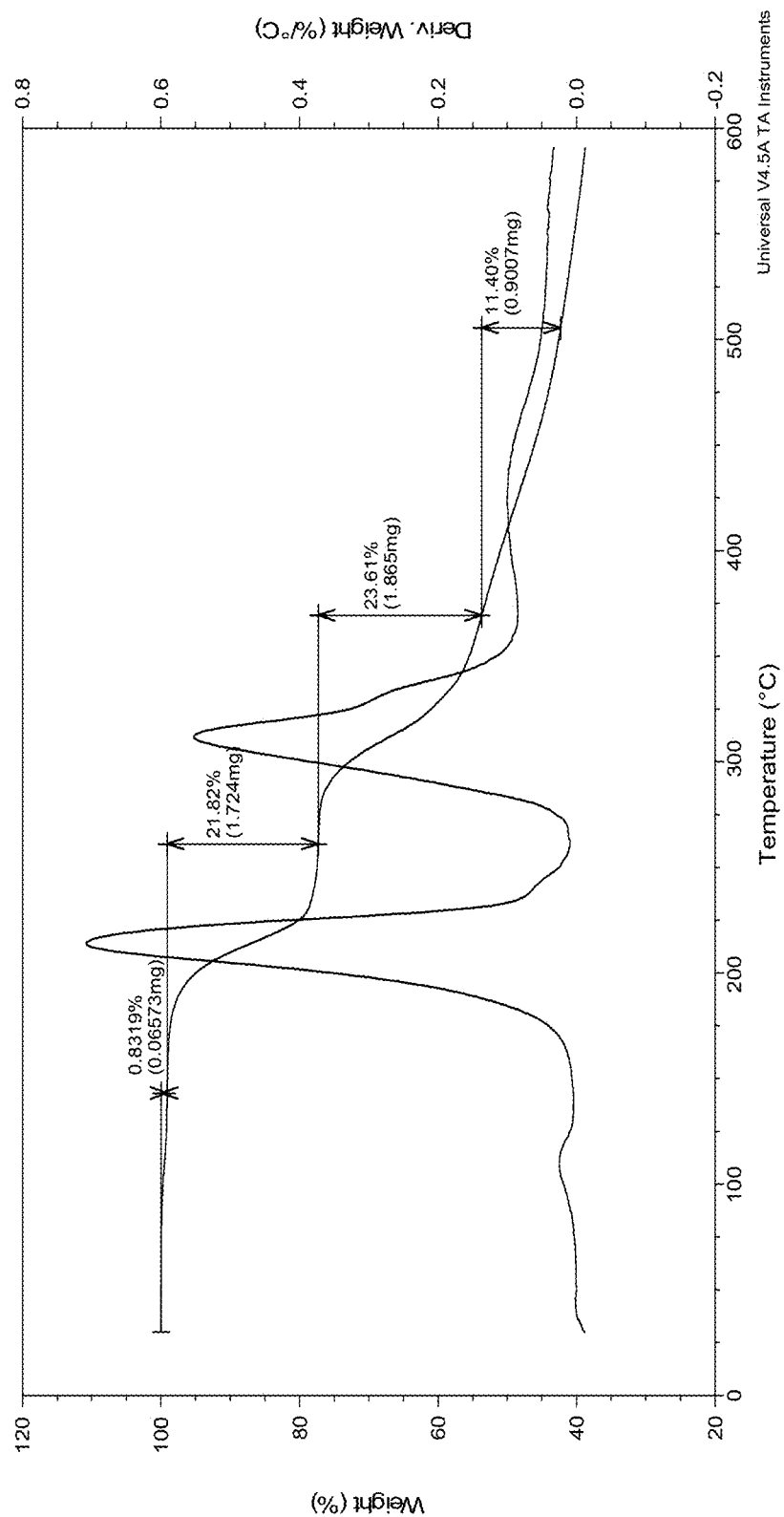
FIG. 12 shows the TGA thermogram of Compound 1 salicylic acid salt.

In some embodiments, the salicylic acid salt exhibits a DSC thermogram having an endothermic peak at a temperature of about 212° C. In some embodiments, the salicylic acid salt has a DSC thermogram substantially as depicted in FIG. 11. In some embodiments, the salicylic acid salt has a TGA thermogram substantially as depicted in FIG. 12.

In some embodiments, the salicylic acid salt of Compound 1 has at least one characteristic XRPD peak selected from about 10.4, about 11.8, about 12.1, about 13.4, and about 13.9; and the salicylic acid salt exhibits a DSC thermogram having an endothermic peak at a temperature of about 212° C.

In some embodiments, the salicylic acid salt of Compound 1 is substantially crystalline. In some embodiments, the salt is crystalline. In some embodiments, the salt is a hydrate. In some embodiments, the salt is a solvate.

Hydrochloric Acid Salts

The hydrochloric acid salt of Compound 1 can be prepared by any suitable method for preparation of hydrochloric acid addition salts. For example, Compound 1 can be combined with hydrochloric acid (e.g., about 1.0 molar eq or more) in a crystallizing solvent and the resulting salt can be isolated by filtering the salt from solution. In certain embodiments, Compound 1 is combined with about 1 to about 2 molar equivalents of hydrochloric acid. In certain embodiments, Compound 1 is combined with about 1 to about 1.5 molar equivalents of hydrochloric acid. In certain embodiments, Compound 1 is combined with about 1.25 equivalents of hydrochloric acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is methanol.

In some embodiments, the crystallizing solvent is heated to a temperature of at least about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 48 hours, but longer and shorter periods are possible depending on the choice of crystallizing solvent and temperature.

The precipitation and/or crystallization of the hydrochloric acid salt, in some embodiments, is carried out by filtering the salt from solution.

Crystalline hydrochloric acid salt forms of Compound 1 can be identified by their unique signatures with respect to, for example, X-ray powder diffraction, differential scanning calorimetry (DSC), thermogravimetric analysis (TGA), and solid state NMR.

Figure 13:
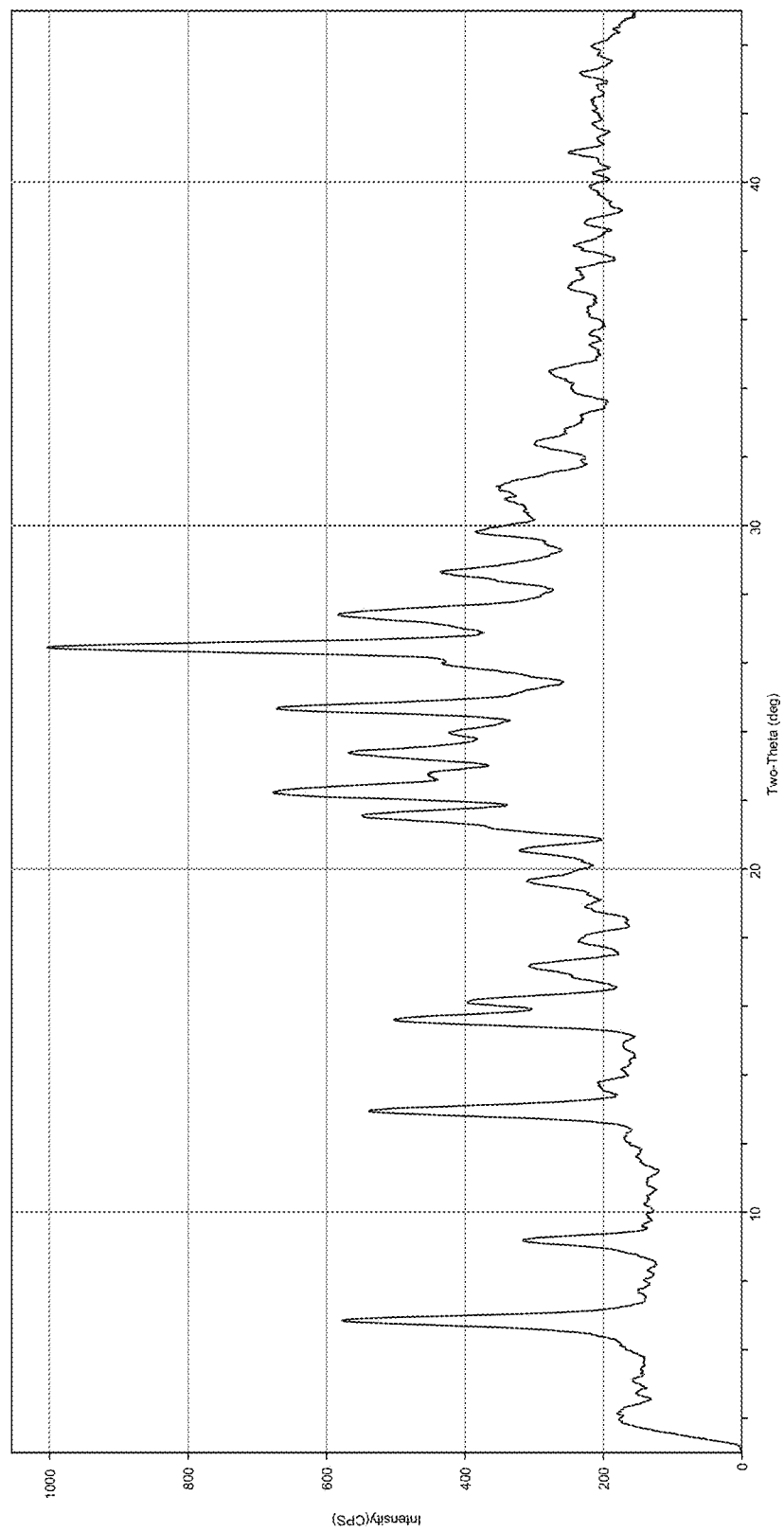
FIG. 13 shows the XRPD pattern of Compound 1 hydrochloric acid salt.

In some embodiments, the crystalline hydrochloric acid salt can be characterized by the X-ray powder diffraction (XRPD) pattern substantially as shown in FIG. 13.

In some embodiments, the hydrochloric acid salt of Compound 1 has at least one characteristic XRPD peak selected from about 6.8, about 9.2, about 12.9, about 15.6, and about 16.1 degrees 2-theta.

In some embodiments, hydrochloric acid salt of Compound 1 has at least two characteristic XRPD peaks selected from about 6.8, about 9.2, about 12.9, about 15.6, and about 16.1 degrees 2-theta.

In some embodiments, hydrochloric acid salt of Compound 1 has at least three characteristic XRPD peaks selected from about 6.8, about 9.2, about 12.9, about 15.6, and about 16.1 degrees 2-theta.

In some embodiments, the hydrochloric acid salt of Compound 1 has at least one characteristic XRPD peak selected from about 4.2, about 6.8, about 9.2, about 12.9, about 15.6, about 16.1, about 17.2, about 21.6, about 22.2, about 23.4, about 24.7, about 26.5 and about 27.4 degrees 2-theta.

In some embodiments, hydrochloric acid salt of Compound 1 has at least two characteristic XRPD peaks selected from about 4.2, about 6.8, about 9.2, about 12.9, about 15.6, about 16.1, about 17.2, about 21.6, about 22.2, about 23.4, about 24.7, about 26.5 and about 27.4 degrees 2-theta.

In some embodiments, hydrochloric acid salt of Compound 1 has at least three characteristic XRPD peaks selected from about 4.2, about 6.8, about 9.2, about 12.9, about 15.6, about 16.1, about 17.2, about 21.6, about 22.2, about 23.4, about 24.7, about 26.5 and about 27.4 degrees 2-theta.

Figure 14:
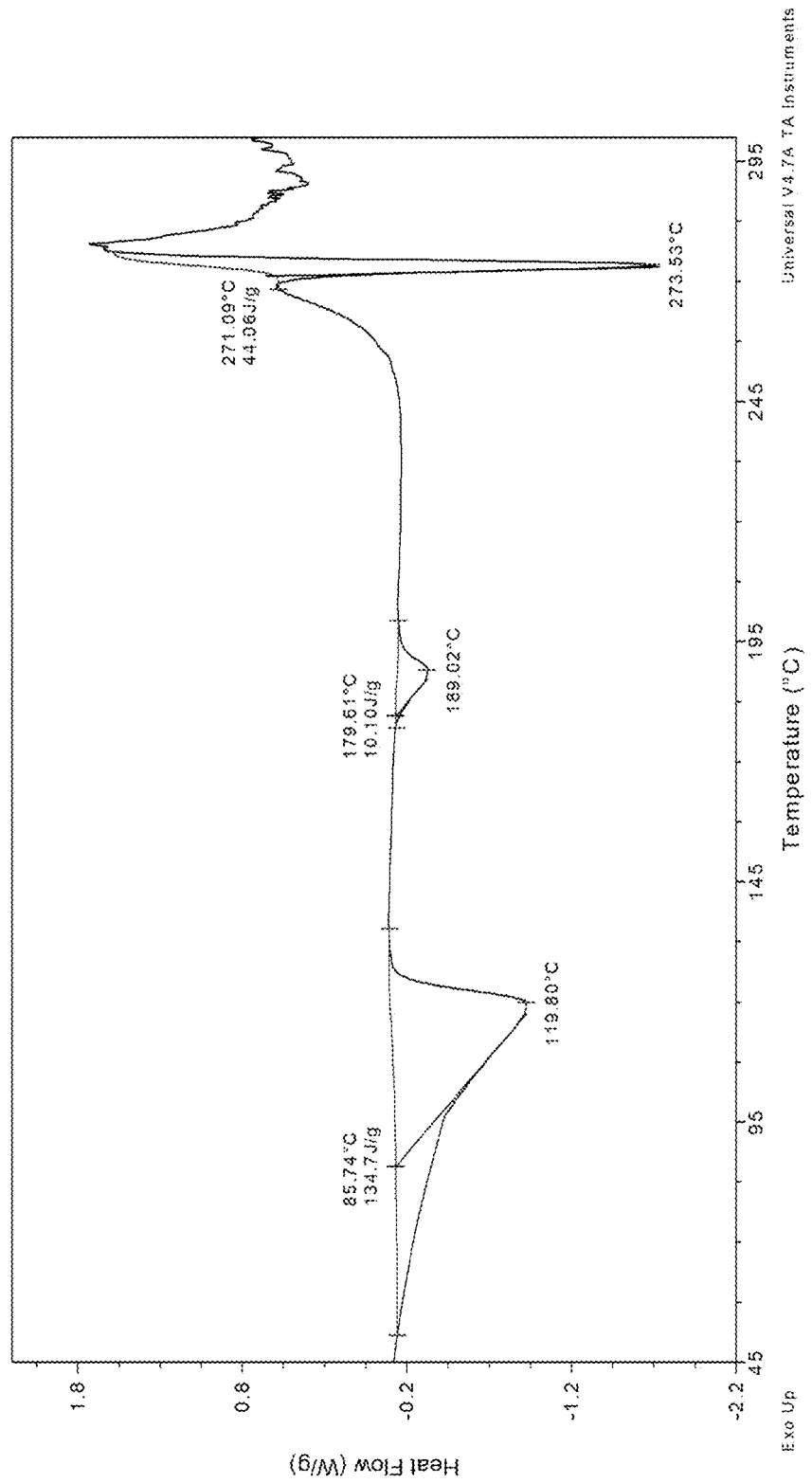
FIG. 14 shows the DSC thermogram of Compound 1 hydrochloric acid salt.
Figure 15:
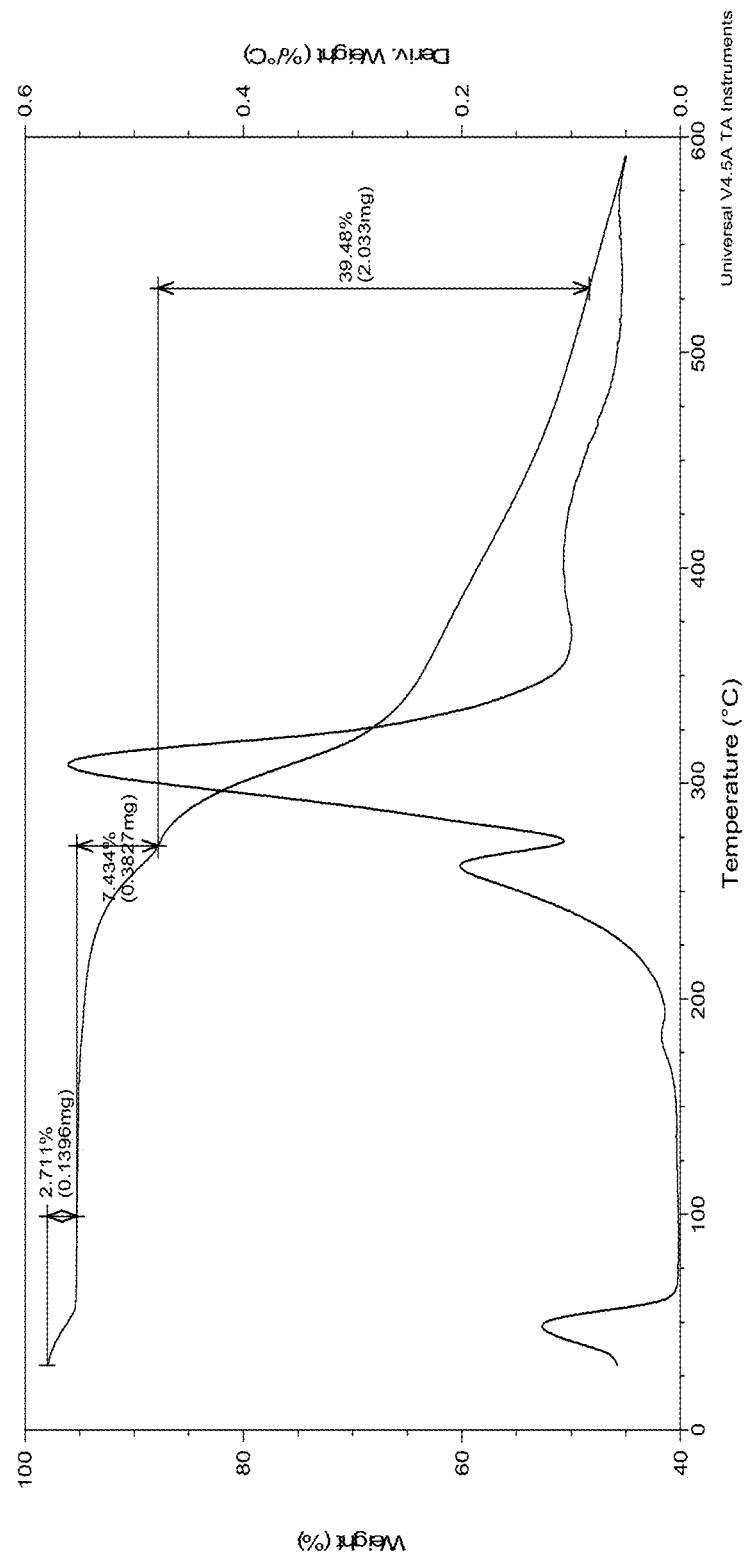
FIG. 15 shows the TGA thermogram of Compound 1 hydrochloric acid salt.

In some embodiments, the hydrochloric acid salt exhibits a DSC thermogram having endothermic peaks at temperatures of about 120° C., about 189° C., and about 274° C. In some embodiments, the hydrochloric acid salt exhibits a DSC thermogram having an endothermic peak at a temperature of about 120° C. In some embodiments, the hydrochloric acid salt exhibits a DSC thermogram having an endothermic peak at a temperature of about 189° C. In some embodiments, the hydrochloric acid salt exhibits a DSC thermogram having an endothermic peak at a temperature of about 274° C. In some embodiments, the hydrochloric acid salt has a DSC thermogram substantially as depicted in FIG. 14. In some embodiments, the hydrochloric acid salt has a TGA thermogram substantially as depicted in FIG. 15.

In some embodiments, hydrochloric acid salt of Compound 1 has at least three characteristic XRPD peaks selected from about 6.8, about 9.2, about 12.9, about 15.6, and about 16.1; and the hydrochloric acid salt exhibits a DSC thermogram having endothermic peaks at temperatures of about 120° C., about 189° C., and about 274° C.

In some embodiments, the hydrochloric acid salt of Compound 1 is substantially crystalline. In some embodiments, the salt is crystalline. In some embodiments, the salt is a hydrate. In some embodiments, the salt is a solvate.

Hydrobromic Acid Salts

The hydrobromic acid salt of Compound 1 can be prepared by any suitable method for preparation of hydrobromic acid addition salts. For example, Compound 1 can be combined with hydrobromic acid (e.g., about 1.0 molar eq or more) in a crystallizing solvent and the resulting salt can be isolated by filtering the salt from solution. In certain embodiments, Compound 1 is combined with about 1 to about 2 molar equivalents of hydrobromic acid. In certain embodiments, Compound 1 is combined with about 1 to about 1.5 molar equivalents of hydrobromic acid. In certain embodiments, Compound 1 is combined with about 1.2 molar equivalents of hydrobromic acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is methanol.

In some embodiments, the crystallizing solvent is heated to a temperature of about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 45° C., about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 24 hours, but longer and shorter periods are possible depending on the choice of crystallizing solvent and temperature.

The precipitation and/or crystallization of the hydrobromic acid salt, in some embodiments, is carried out by filtering the salt from solution.

Crystalline hydrobromic acid salt forms of the compound of Compound 1 can be identified by their unique signatures with respect to, for example, X-ray powder diffraction, differential scanning calorimetry (DSC), thermogravimetric analysis (TGA), and solid state NMR.

Figure 17:
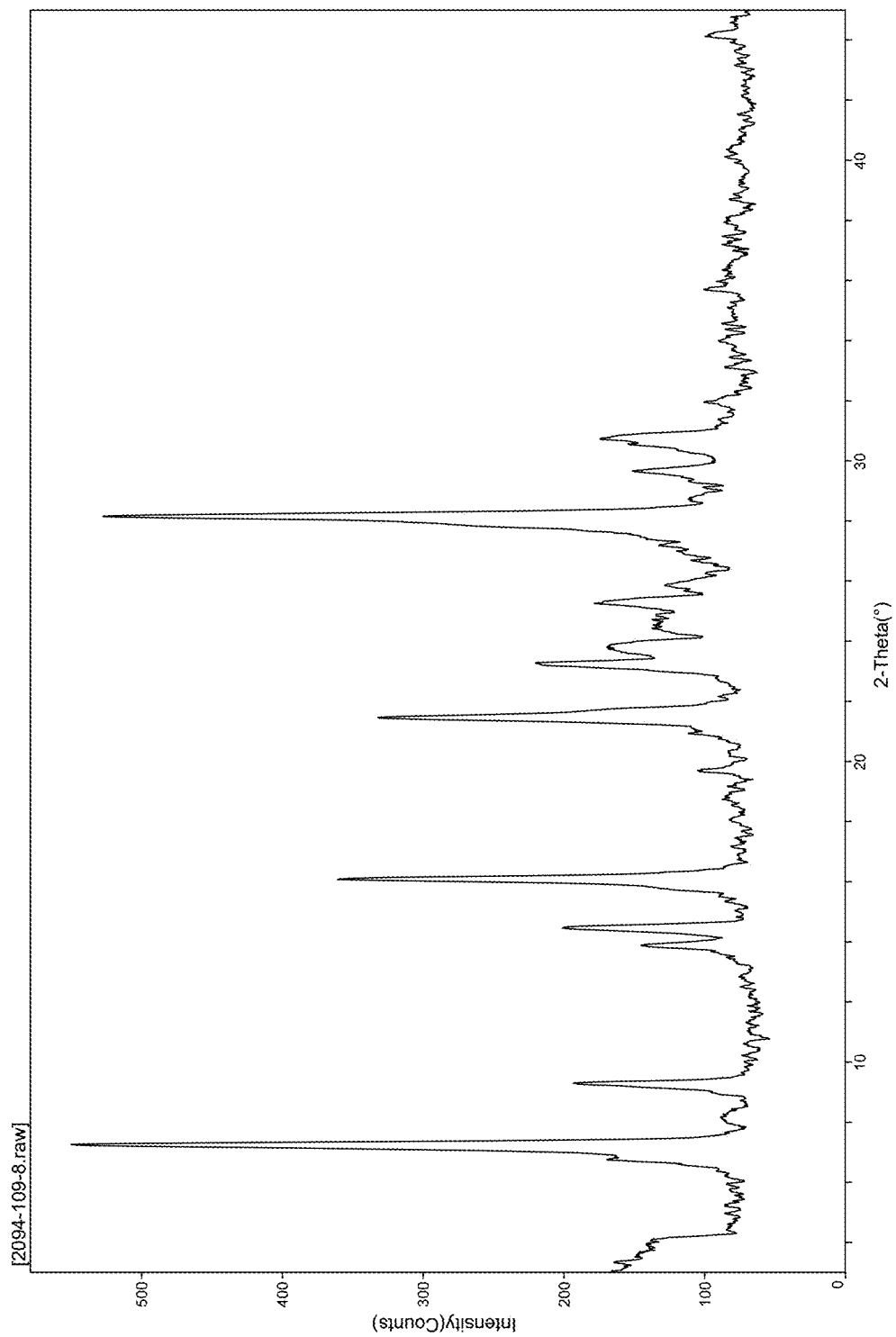
FIG. 17 shows the XRPD pattern of Compound 1 hydrobromic acid salt.

In some embodiments, the crystalline hydrobromic acid salt can be characterized by the X-ray powder diffraction (XRPD) pattern substantially as shown in FIG. 17.

In some embodiments, the hydrobromic acid salt of Compound 1 has at least one characteristic XRPD peak selected from about 7.3, about 9.3, about 13.9, about 14.5, and about 16.1 degrees 2-theta.

In some embodiments, hydrobromic acid salt of Compound 1 has at least two characteristic XRPD peaks selected from about 7.3, about 9.3, about 13.9, about 14.5, and about 16.1 degrees 2-theta.

In some embodiments, hydrobromic acid salt of Compound 1 has at least three characteristic XRPD peaks selected from about 7.3, about 9.3, about 13.9, about 14.5, and about 16.1 degrees 2-theta.

In some embodiments, the hydrobromic acid salt of Compound 1 has at least one characteristic XRPD peak selected from about 6.8, about 7.3, about 9.3, about 13.9, about 14.5, about 16.1, about 21.5, about 23.3, about 23.8, about 25.3, and about 28.1 degrees 2-theta.

In some embodiments, hydrobromic acid salt of Compound 1 has at least two characteristic XRPD peaks selected from about 6.8, about 7.3, about 9.3, about 13.9, about 14.5, about 16.1, about 21.5, about 23.3, about 23.8, about 25.3, and about 28.1 degrees 2-theta.

In some embodiments, hydrobromic acid salt of Compound 1 has at least three characteristic XRPD peaks selected from about 6.8, about 7.3, about 9.3, about 13.9, about 14.5, about 16.1, about 21.5, about 23.3, about 23.8, about 25.3, and about 28.1 degrees 2-theta.

Figure 18:
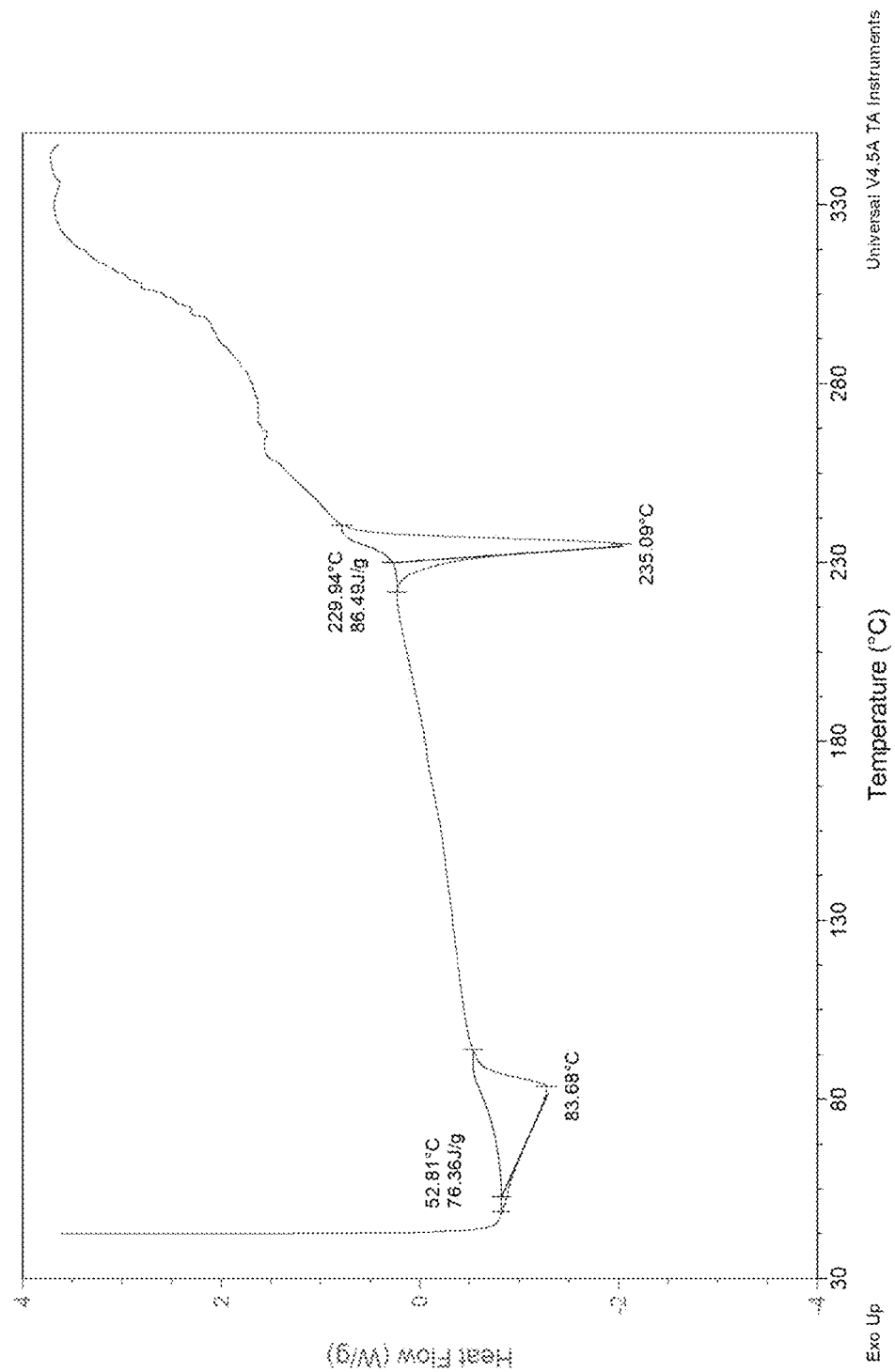
FIG. 18 shows the DSC thermogram of Compound 1 hydrobromic acid salt.
Figure 19:
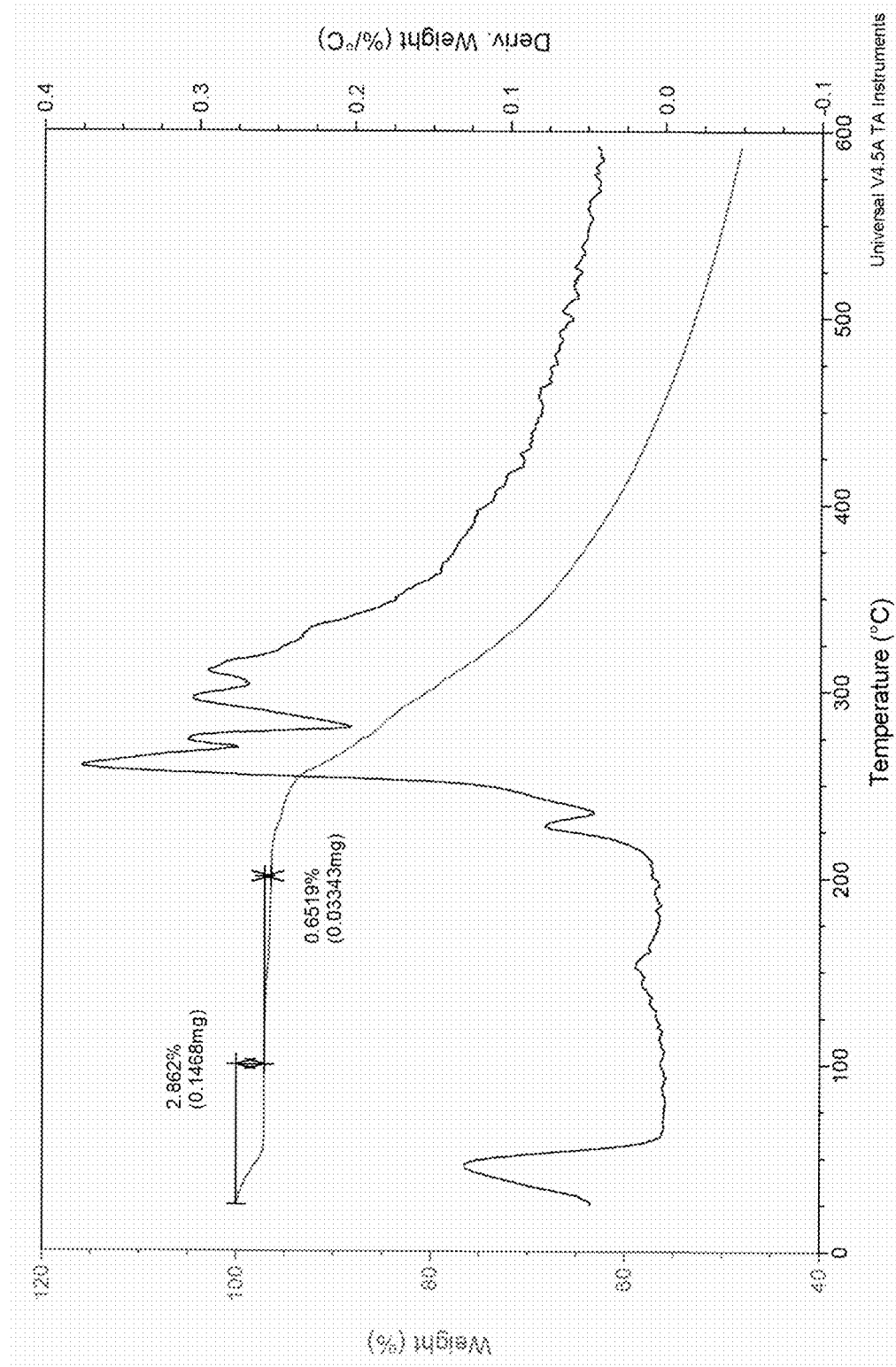
FIG. 19 shows the TGA thermogram of Compound 1 hydrobromic acid salt.

In some embodiments, the hydrobromic acid salt exhibits a DSC thermogram having endothermic peaks at temperatures of about 84° C. and about 235° C. In some embodiments, the hydrobromic acid salt exhibits a DSC thermogram having an endothermic peak at a temperature of about 84° C. In some embodiments, the hydrobromic acid salt exhibits a DSC thermogram having an endothermic peak at a temperature of about 235° C. In some embodiments, the hydrobromic acid salt has a DSC thermogram substantially as depicted in FIG. 18. In some embodiments, the hydrobromic acid salt has a TGA thermogram substantially as depicted in FIG. 19.

In some embodiments, the hydrobromic acid salt of Compound 1 has at least one characteristic XRPD peak selected from about 7.3, about 9.3, about 13.9, about 14.5, and about 16.1; and the hydrobromic acid salt exhibits a DSC thermogram having endothermic peaks at temperatures of about 84° C. and about 235° C.

In some embodiments, the hydrobromic acid salt of Compound 1 is substantially crystalline. In some embodiments, the salt is crystalline. In some embodiments, the salt is a hydrate. In some embodiments, the salt is a solvate.

Fumaric Acid Salts

The fumaric acid salt of Compound 1 can be prepared by any suitable method for preparation of fumaric acid addition salts. For example, Compound 1 can be combined with fumaric acid (e.g., about 1.0 molar eq or more) in a crystallizing solvent and the resulting salt can be isolated by filtering the salt from solution. In certain embodiments, Compound 1 is combined with about 1 to about 2 molar equivalents of fumaric acid. In certain embodiments, Compound 1 is combined with about 1 to about 1.5 molar equivalents of fumaric acid. In certain embodiments, Compound 1 is combined with about 1.2 molar equivalents of fumaric acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is methanol.

In some embodiments, the crystallizing solvent is heated to a temperature of about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 45° C., about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 24 hours, but longer and shorter periods are possible depending on the choice of crystallizing solvent and temperature.

The precipitation and/or crystallization of the fumaric acid salt, in some embodiments, is carried out by filtering the salt from solution.

Crystalline fumaric acid salt forms of Compound 1 can be identified by their unique signatures with respect to, for example, X-ray powder diffraction, differential scanning calorimetry (DSC), thermogravimetric analysis (TGA), and solid state NMR.

Figure 21:
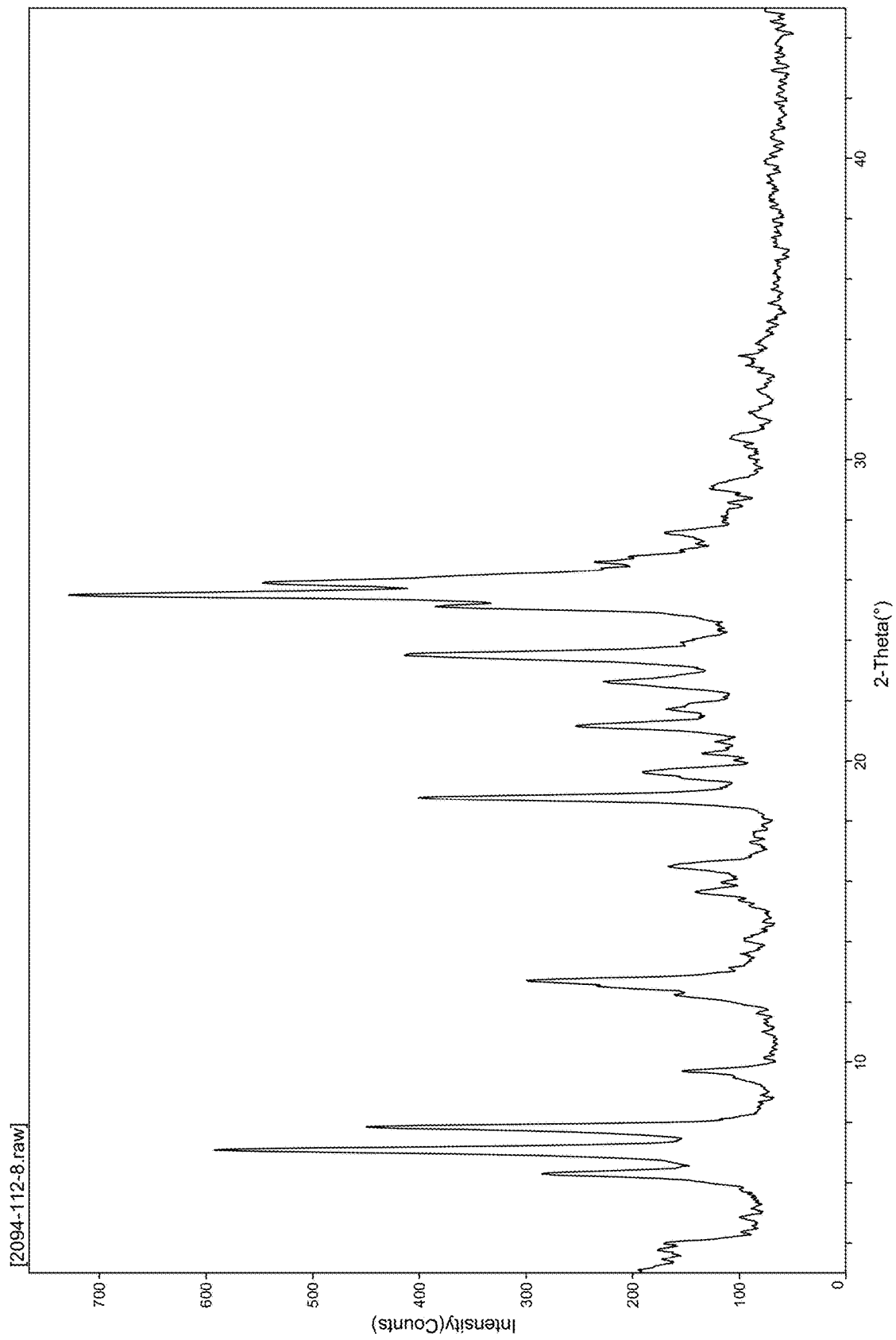
FIG. 21 shows the XRPD pattern of Compound 1 fumaric acid salt.

In some embodiments, the crystalline fumaric acid salt can be characterized by the X-ray powder diffraction (XRPD) pattern substantially as shown in FIG. 21.

In some embodiments, the fumaric acid salt of Compound 1 has at least one characteristic XRPD peak selected from about 6.3, about 7.1, about 7.8, and about 12.7 degrees 2-theta.

In some embodiments, fumaric acid salt of Compound 1 has at least two characteristic XRPD peaks selected from about 6.3, about 7.1, about 7.8, and about 12.7 degrees 2-theta.

In some embodiments, fumaric acid salt of Compound 1 has at least three characteristic XRPD peaks selected from about 6.3, about 7.1, about 7.8, and about 12.7 degrees 2-theta.

In some embodiments, the fumaric acid salt of Compound 1 has at least one characteristic XRPD peak selected from about 6.3, about 7.1, about 7.8, about 12.7, about 16.5, about 18.8, about 21.2, about 21.8, about 22.6, about 23.5, about 25.1, about 25.5, and about 25.9 degrees 2-theta.

In some embodiments, fumaric acid salt of Compound 1 has at least two characteristic XRPD peaks selected from about 6.3, about 7.1, about 7.8, about 12.7, about 16.5, about 18.8, about 21.2, about 21.8, about 22.6, about 23.5, about 25.1, about 25.5, and about 25.9 degrees 2-theta.

In some embodiments, fumaric acid salt of Compound 1 has at least three characteristic XRPD peaks selected from about 6.3, about 7.1, about 7.8, about 12.7, about 16.5, about 18.8, about 21.2, about 21.8, about 22.6, about 23.5, about 25.1, about 25.5, and about 25.9 degrees 2-theta.

Figure 22:
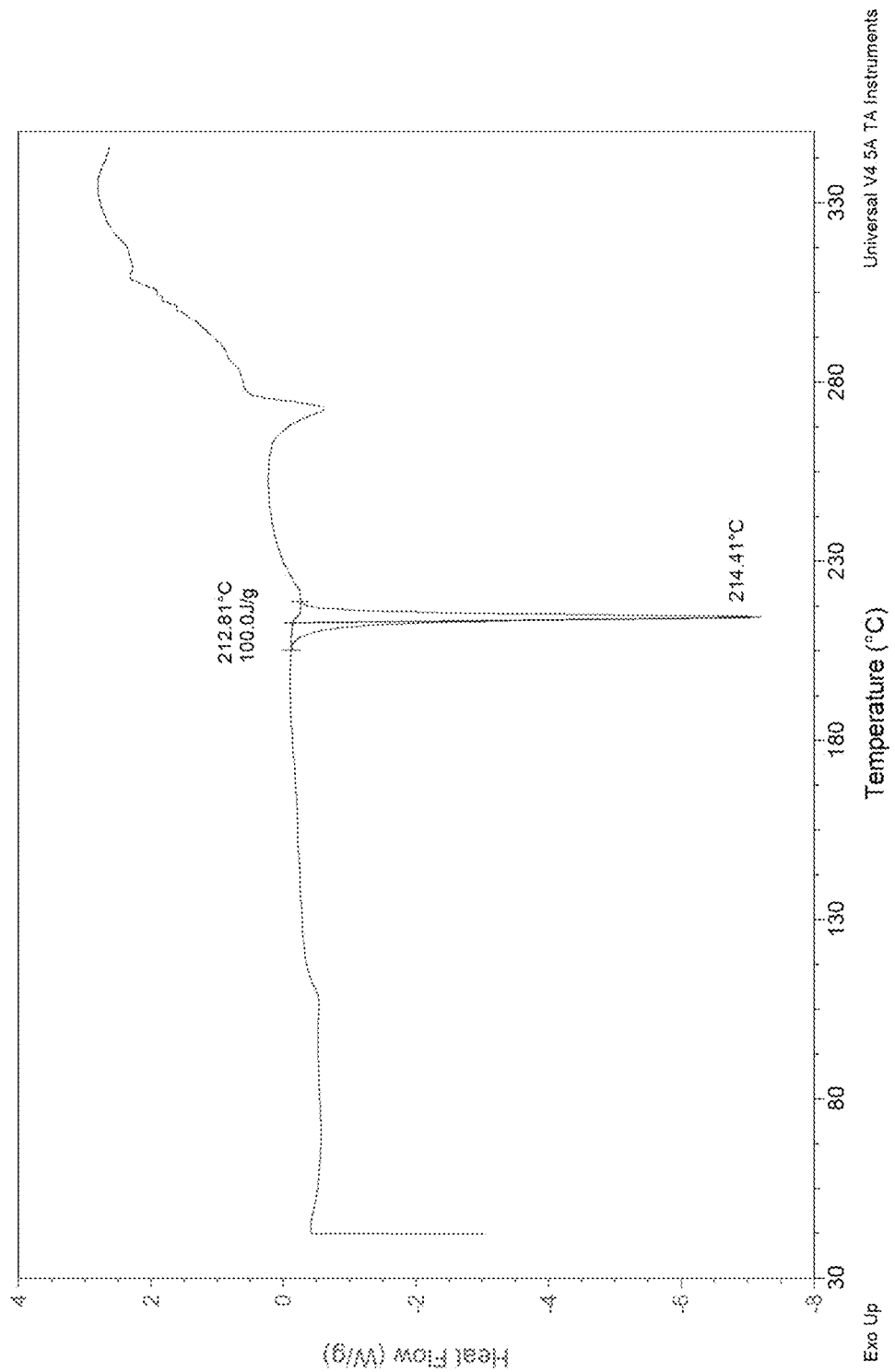
FIG. 22 shows the DSC thermogram of Compound 1 fumaric acid salt.
Figure 23:
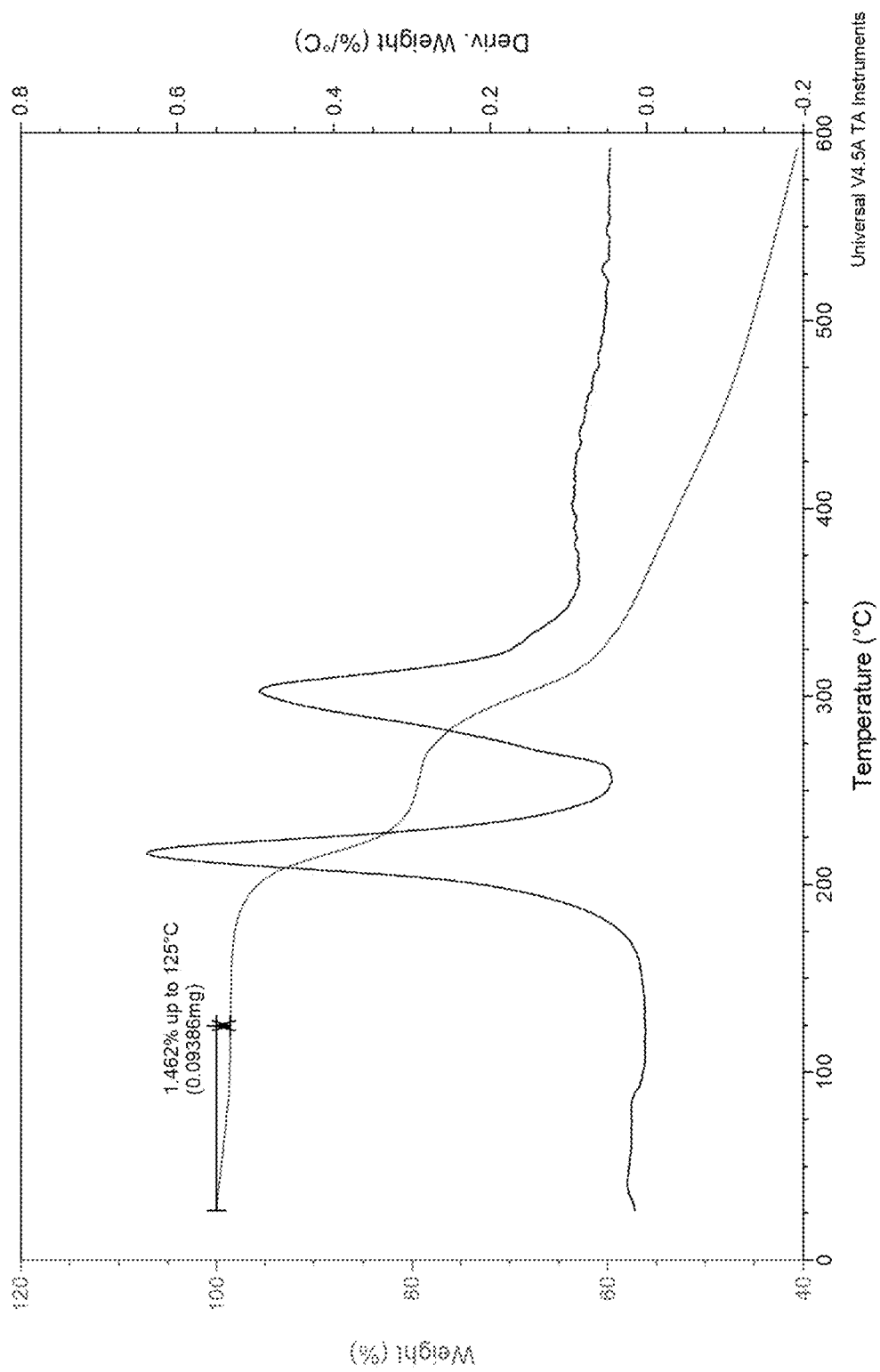
FIG. 23 shows the TGA thermogram of Compound 1 fumaric acid salt.

In some embodiments, the fumaric acid salt exhibits a DSC thermogram having an endothermic peak at a temperature of about 214° C. In some embodiments, the fumaric acid salt has a DSC thermogram substantially as depicted in FIG. 22. In some embodiments, the fumaric acid salt has a TGA thermogram substantially as depicted in FIG. 23.

In some embodiments, the fumaric acid salt of Compound 1 has at least one characteristic XRPD peak selected from about 6.3, about 7.1, about 7.8, and about 12.7; and the fumaric acid salt exhibits a DSC thermogram having an endothermic peak at a temperature of about 214° C.

In some embodiments, the fumaric acid salt of Compound 1 is substantially crystalline. In some embodiments, the salt is crystalline. In some embodiments, the salt is a hydrate. In some embodiments, the salt is a solvate.

Phosphoric Acid Salts

The phosphoric acid salt of Compound 1 can be prepared by any suitable method for preparation of phosphoric acid addition salts. For example, Compound 1 can be combined with phosphoric acid (e.g., about 1.0 molar eq or more) in a crystallizing solvent and the resulting salt can be isolated by filtering the salt from solution. In certain embodiments, Compound 1 is combined with about 1 to about 2 molar equivalents of phosphoric acid. In certain embodiments, Compound 1 is combined with about 1 to about 1.5 molar equivalents of phosphoric acid. In certain embodiments, Compound 1 is combined with about 1.2 molar equivalents of phosphoric acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is methanol.

In some embodiments, the crystallizing solvent is heated to a temperature of about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 45° C., about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 24 hours, but longer and shorter periods are possible depending on the choice of crystallizing solvent and temperature.

The precipitation and/or crystallization of the phosphoric acid salt, in some embodiments, is carried out by filtering the salt from solution.

Figure 25:
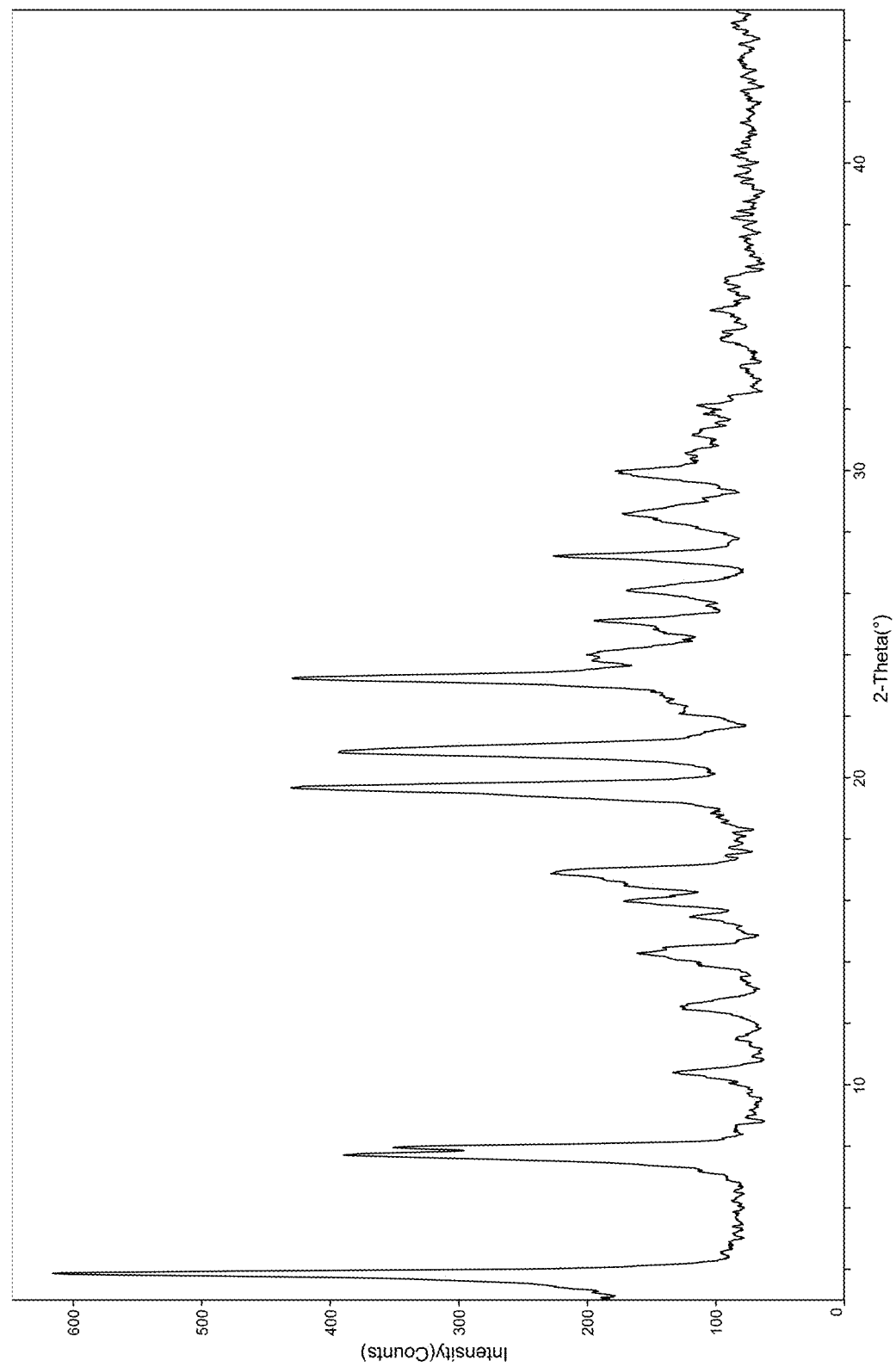
FIG. 25 shows the XRPD pattern of Compound 1 phosphoric acid salt.

Crystalline phosphoric acid salt forms of the compound of Compound 1 can be identified by their unique signatures with respect to, for example, X-ray powder diffraction, differential scanning calorimetry (DSC), thermogravimetric analysis (TGA), and solid state NMR. In some embodiments, the crystalline phosphoric acid salt can be characterized by the X-ray powder diffraction (XRPD) pattern substantially as shown in FIG. 25.

In some embodiments, the phosphoric acid salt of Compound 1 has at least one characteristic XRPD peak selected from about 3.9, about 7.7, about 10.4, and about 12.6 degrees 2-theta.

In some embodiments, phosphoric acid salt of Compound 1 has at least two characteristic XRPD peaks selected from about 3.9, about 7.7, about 10.4, and about 12.6 degrees 2-theta.

In some embodiments, phosphoric acid salt of Compound 1 has at least three characteristic XRPD peaks selected from about 3.9, about 7.7, about 10.4, and about 12.6 degrees 2-theta.

In some embodiments, the phosphoric acid salt of Compound 1 has at least one characteristic XRPD peak selected from about 3.9, about 7.7, about 10.4, about 12.6, about 14.3, about 16.9, about 19.7, about 20.8, about 23.2, about 25.1, about 27.2, about 28.6, and about 30.0 degrees 2-theta.

In some embodiments, phosphoric acid salt of Compound 1 has at least two characteristic XRPD peaks selected from about 3.9, about 7.7, about 10.4, about 12.6, about 14.3, about 16.9, about 19.7, about 20.8, about 23.2, about 25.1, about 27.2, about 28.6, and about 30.0 degrees 2-theta.

In some embodiments, phosphoric acid salt of Compound 1 has at least three characteristic XRPD peaks selected from about 3.9, about 7.7, about 10.4, about 12.6, about 14.3, about 16.9, about 19.7, about 20.8, about 23.2, about 25.1, about 27.2, about 28.6, and about 30.0 degrees 2-theta.

Figure 26:
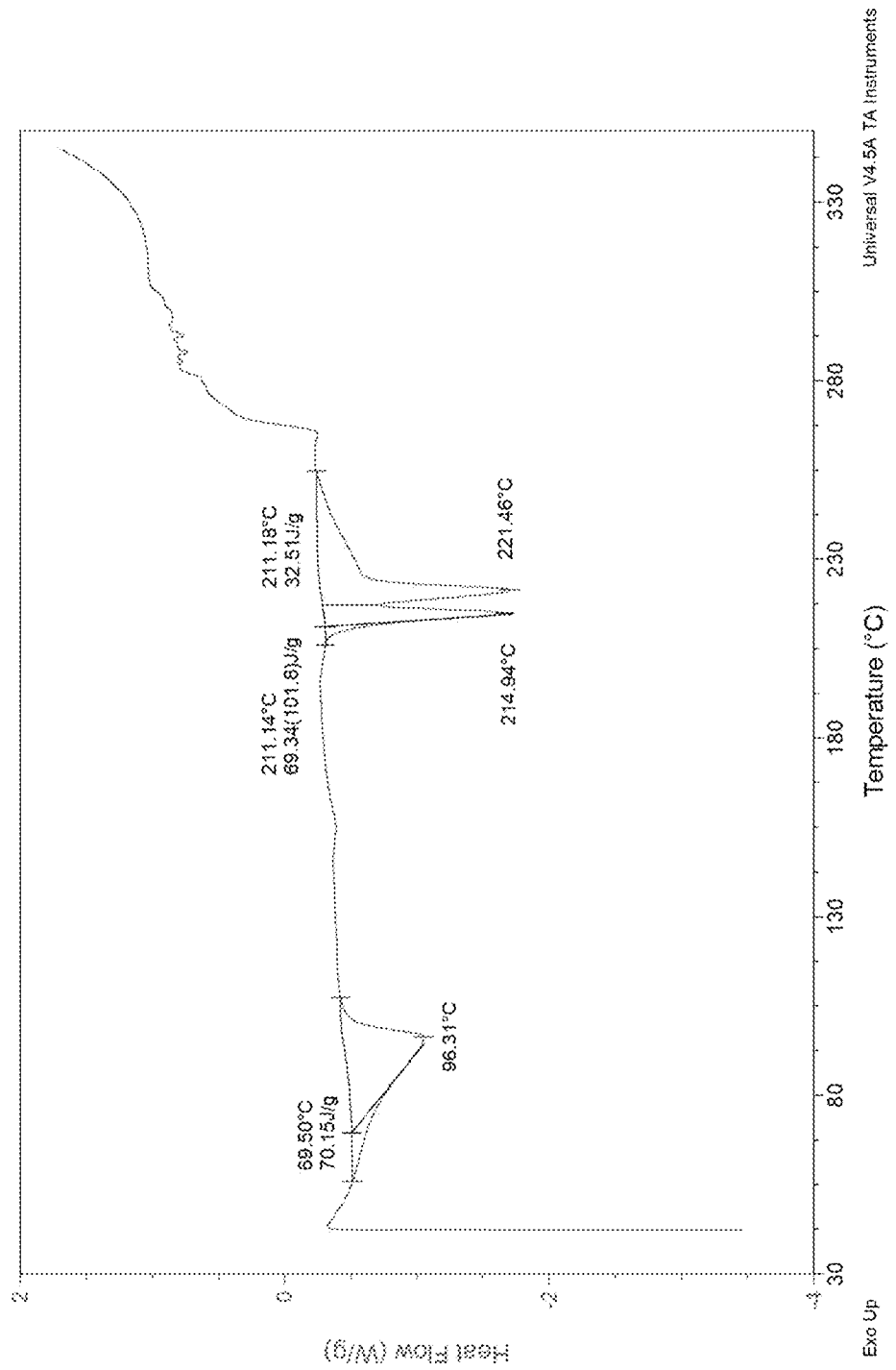
FIG. 26 shows the DSC thermogram of Compound 1 phosphoric acid salt.
Figure 27:
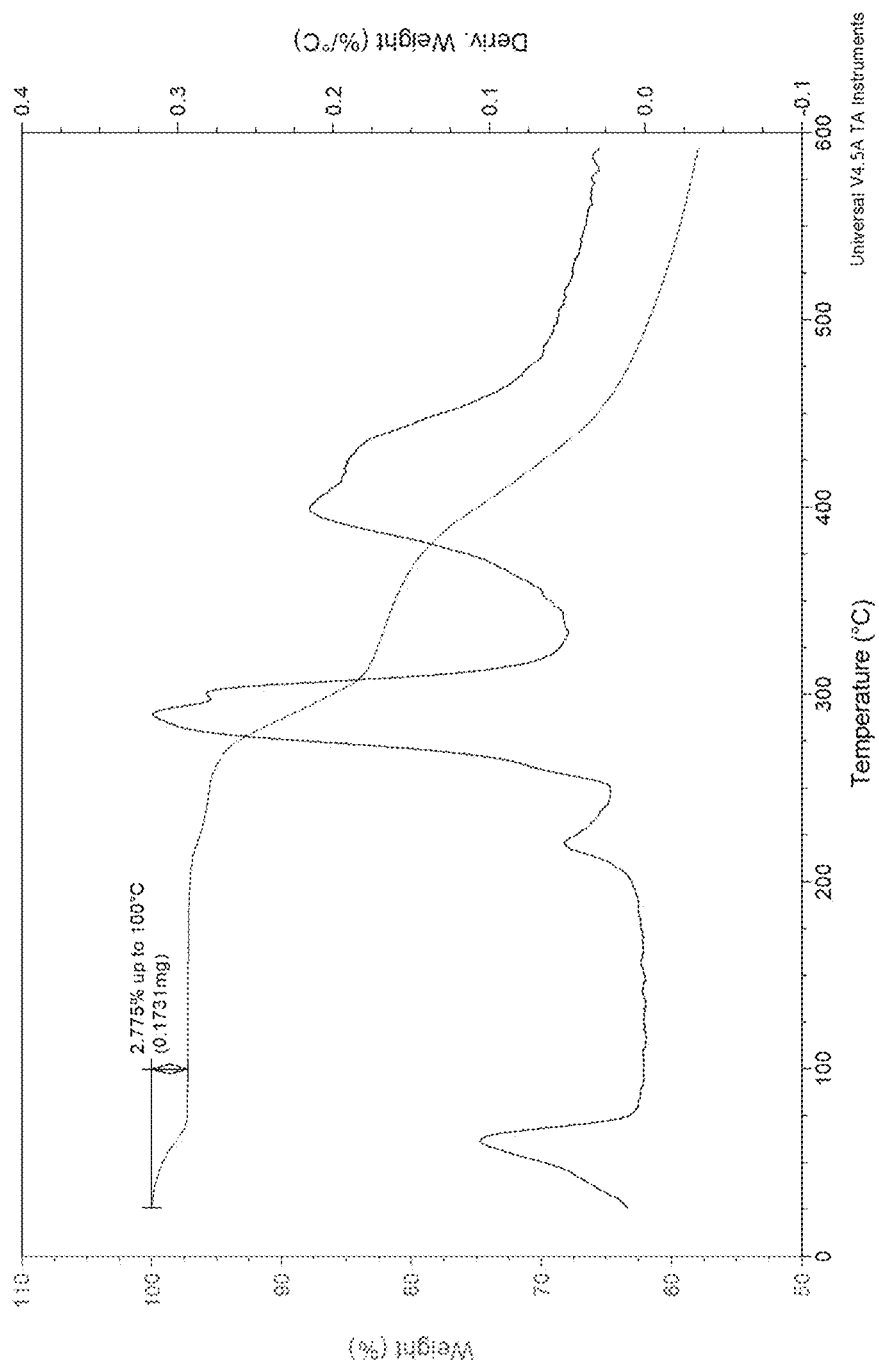
FIG. 27 shows the TGA thermogram of Compound 1 phosphoric acid salt.

In some embodiments, the phosphoric acid salt exhibits a DSC thermogram having endothermic peaks at temperatures of about 215° C. and about 221° C. In some embodiments, the phosphoric acid salt exhibits a DSC thermogram having an endothermic peak at a temperature of about 215° C. In some embodiments, the phosphoric acid salt exhibits a DSC thermogram having an endothermic peak at a temperature of about 221° C. In some embodiments, the phosphoric acid salt has a DSC thermogram substantially as depicted in FIG. 26. In some embodiments, the phosphoric acid salt has a TGA thermogram substantially as depicted in FIG. 27.

In some embodiments, the phosphoric acid salt of Compound 1 has at least one characteristic XRPD peak selected from about 3.9, about 7.7, about 10.4, and about 12.6; and the phosphoric acid salt exhibits a DSC thermogram having endothermic peaks at temperatures of about 215° C. and about 221° C.

In some embodiments, the phosphoric acid salt of Compound 1 is substantially crystalline. In some embodiments, the salt is crystalline. In some embodiments, the salt is a hydrate. In some embodiments, the salt is a solvate.

Benzenesulfonic Acid Salts

The benzenesulfonic acid salt of Compound 1 can be prepared by any suitable method for preparation of benzenesulfonic acid addition salts. For example, Compound 1 can be combined with benzenesulfonic acid (e.g., about 1.0 molar eq or more) in a crystallizing solvent and the resulting salt can be isolated by filtering the salt from solution. In certain embodiments, Compound 1 is combined with about 1 to about 2 molar equivalents of benzenesulfonic acid. In certain embodiments, Compound 1 is combined with about 1 to about 1.5 molar equivalents of benzenesulfonic acid. In certain embodiments, Compound 1 is combined with about 1.2 molar equivalents of benzenesulfonic acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is methanol.

In some embodiments, the crystallizing solvent is heated to a temperature of about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 45° C., about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 24 hours, but longer and shorter periods are possible depending on the choice of crystallizing solvent and temperature.

The precipitation and/or crystallization of the benzenesulfonic acid salt, in some embodiments, is carried out by filtering the salt from solution.

Crystalline benzenesulfonic acid salt forms of Compound 1 can be identified by their unique signatures with respect to, for example, X-ray powder diffraction, differential scanning calorimetry (DSC), thermogravimetric analysis (TGA), and solid state NMR.

Figure 29:
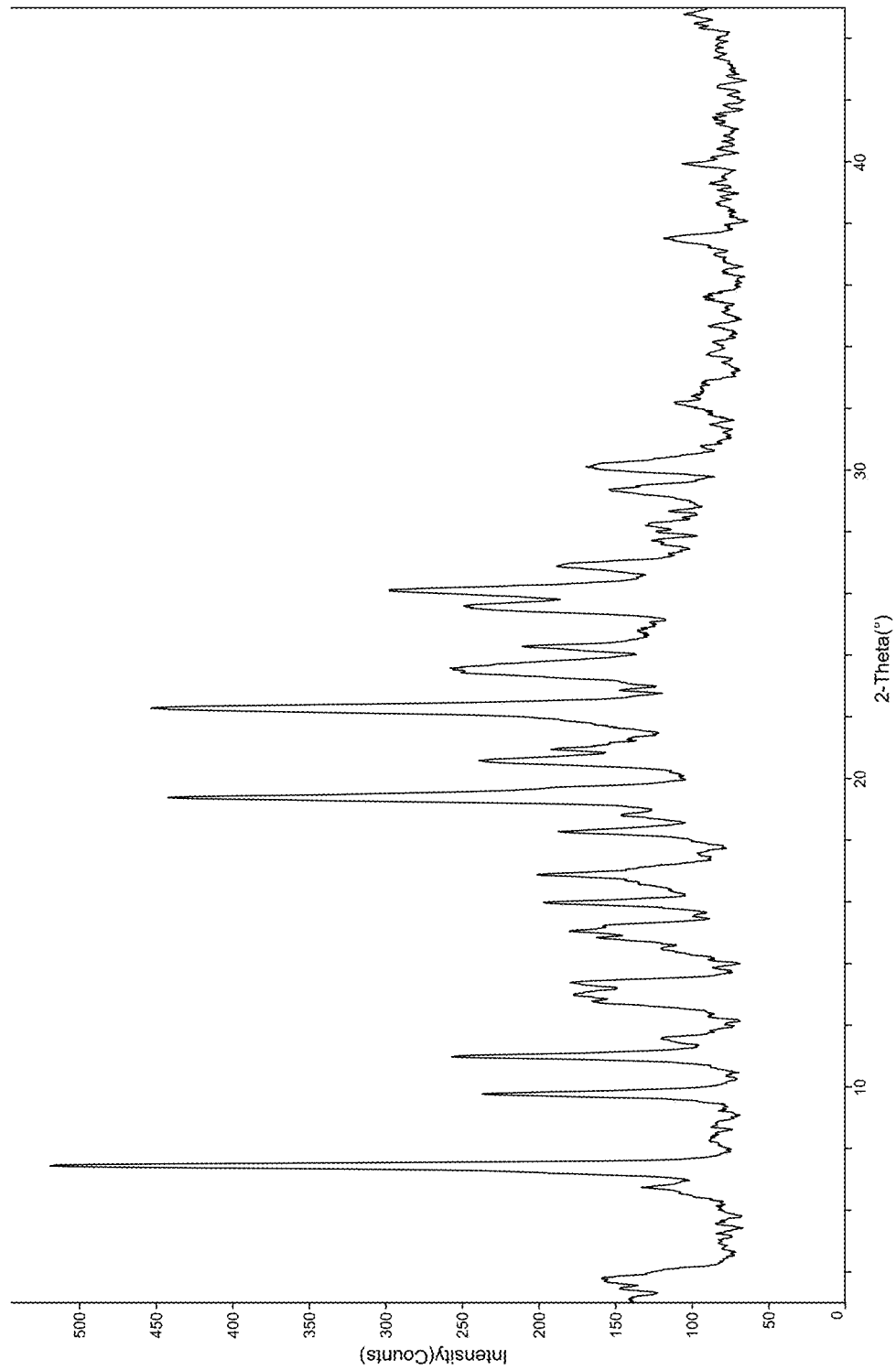
FIG. 29 shows the XRPD pattern of Compound 1 benzenesulfonic acid salt.

In some embodiments, the crystalline benzenesulfonic acid salt can be characterized by the X-ray powder diffraction (XRPD) pattern substantially as shown in FIG. 29.

In some embodiments, the benzenesulfonic acid salt of Compound 1 has at least one characteristic XRPD peak selected from about 3.8, about 6.7, about 7.4, about 9.8, about 11.0, and about 13.0 degrees 2-theta.

In some embodiments, benzenesulfonic acid salt of Compound 1 has at least two characteristic XRPD peaks selected from about 3.8, about 6.7, about 7.4, about 9.8, about 11.0, and about 13.0 degrees 2-theta.

In some embodiments, benzenesulfonic acid salt of Compound 1 has at least three characteristic XRPD peaks selected from about 3.8, about 6.7, about 7.4, about 9.8, about 11.0, and about 13.0 degrees 2-theta.

In some embodiments, the benzenesulfonic acid salt of Compound 1 has at least one characteristic XRPD peak selected from about 3.8, about 6.7, about 7.4, about 9.8, about 11.0, about 13.0, about 13.4, about 15.1, about 16.0, about 16.9, about 19.4, about 20.6, about 21.0, about 22.3, about 23.6, about 25.6, about 26.1, and about 30.1 degrees 2-theta.

In some embodiments, benzenesulfonic acid salt of Compound 1 has at least two characteristic XRPD peaks selected from about 3.8, about 6.7, about 7.4, about 9.8, about 11.0, about 13.0, about 13.4, about 15.1, about 16.0, about 16.9, about 19.4, about 20.6, about 21.0, about 22.3, about 23.6, about 25.6, about 26.1, and about 30.1 degrees 2-theta.

In some embodiments, benzenesulfonic acid salt of Compound 1 has at least three characteristic XRPD peaks selected from about 3.8, about 6.7, about 7.4, about 9.8, about 11.0, about 13.0, about 13.4, about 15.1, about 16.0, about 16.9, about 19.4, about 20.6, about 21.0, about 22.3, about 23.6, about 25.6, about 26.1, and about 30.1 degrees 2-theta.

Figure 30:
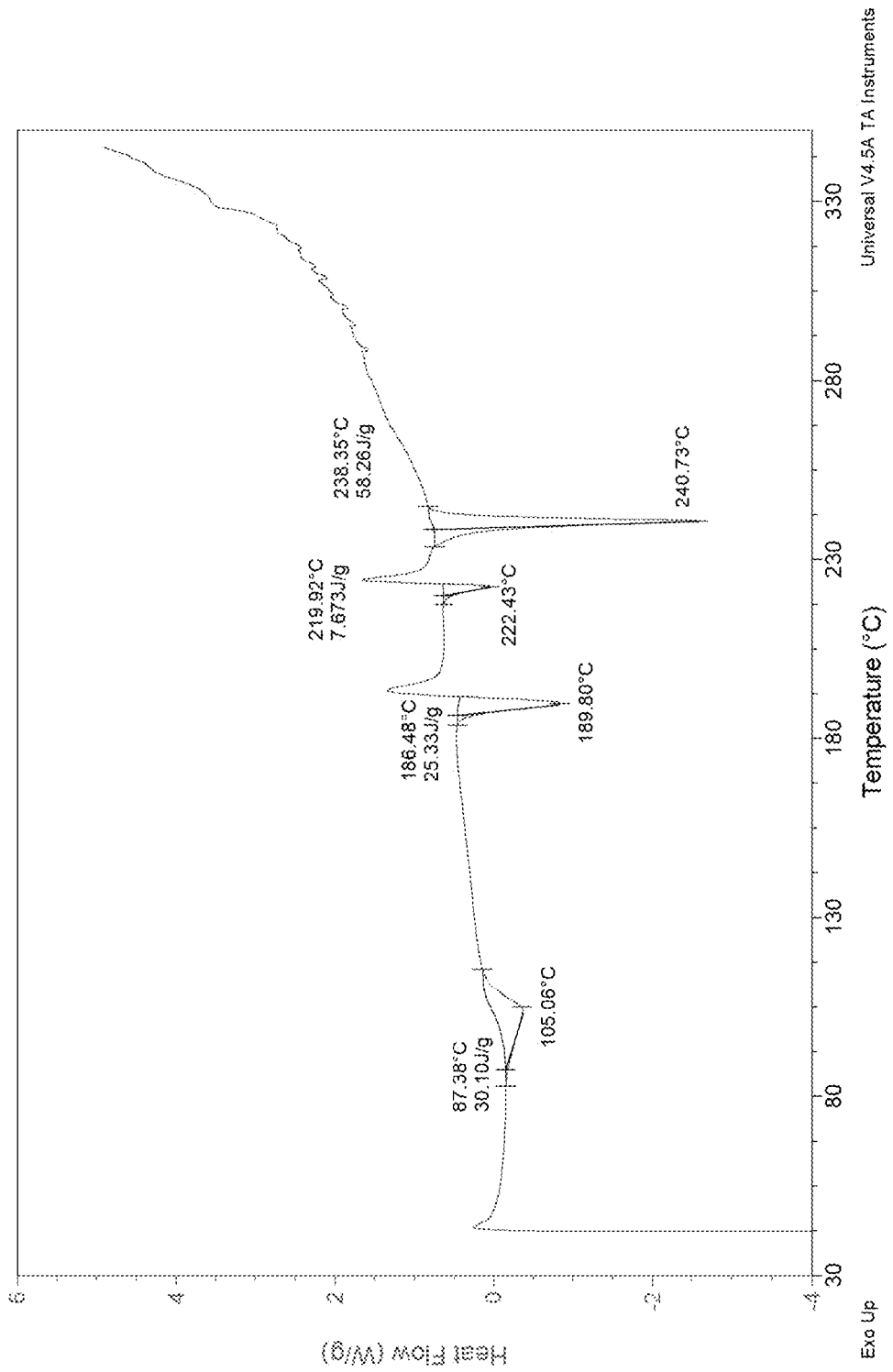
FIG. 30 shows the DSC thermogram of Compound 1 benzenesulfonic acid salt.
Figure 31:
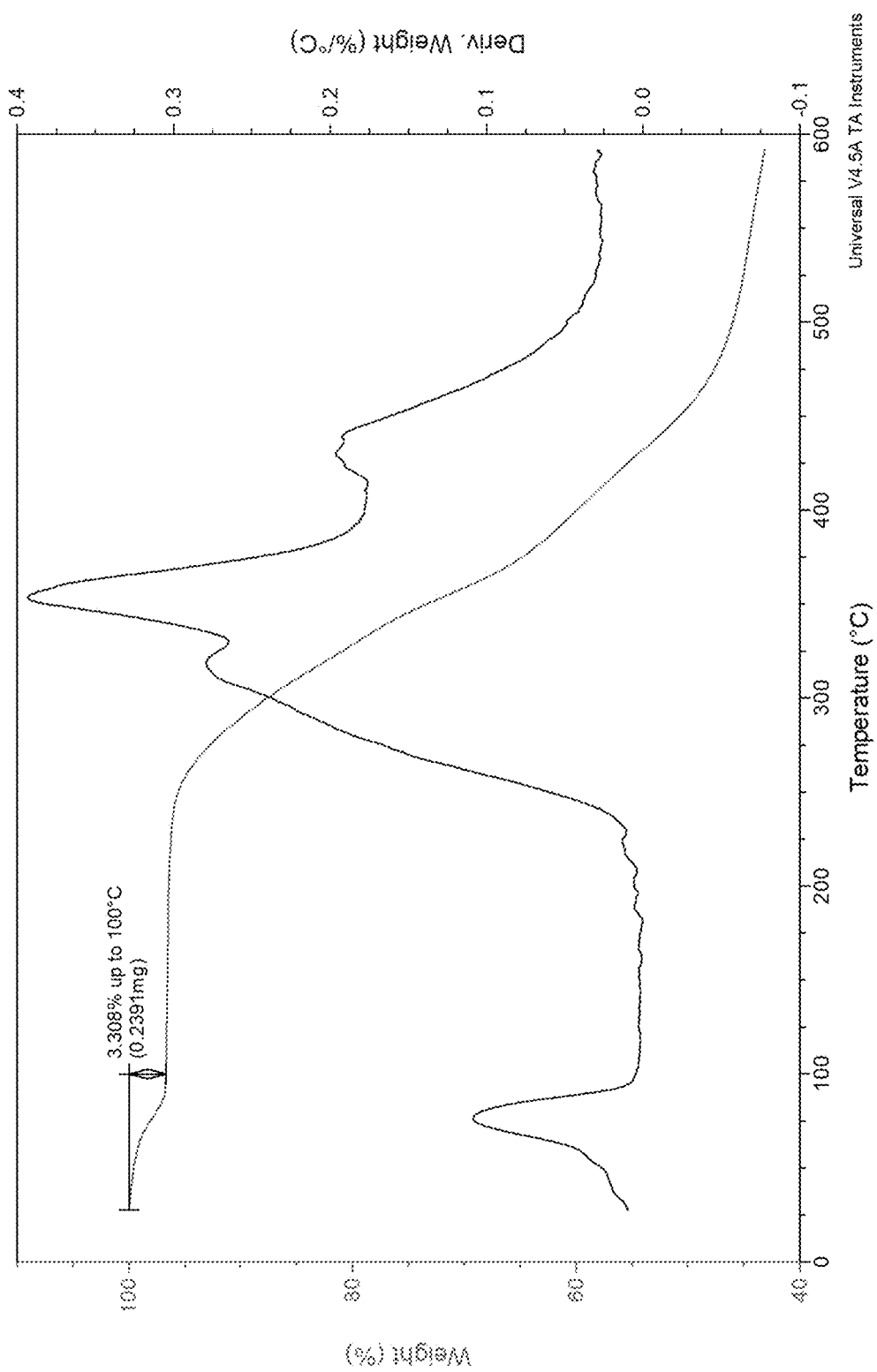
FIG. 31 shows the TGA thermogram of Compound 1 benzenesulfonic acid salt.

In some embodiments, the benzenesulfonic acid salt exhibits a DSC thermogram having endothermic peaks at temperatures of about 105° C., about 190° C., about 222° C., and about 241° C. In some embodiments, the benzenesulfonic acid salt exhibits a DSC thermogram having an endothermic peak at a temperature of about 105° C. In some embodiments, the benzenesulfonic acid salt exhibits a DSC thermogram having an endothermic peak at a temperature of about 190° C. In some embodiments, the benzenesulfonic acid salt exhibits a DSC thermogram having an endothermic peak at a temperature of about 222° C. In some embodiments, the benzenesulfonic acid salt exhibits a DSC thermogram having an endothermic peak at a temperature of about 241° C. In some embodiments, the benzenesulfonic acid salt has a DSC thermogram substantially as depicted in FIG. 30. In some embodiments, the benzenesulfonic acid salt has a TGA thermogram substantially as depicted in FIG. 31.

In some embodiments, the benzenesulfonic acid salt of Compound 1 has at least one characteristic XRPD peak selected from about 3.8, about 6.7, about 7.4, about 9.8, about 11.0, and about 13.0; and the benzenesulfonic acid salt exhibits a DSC thermogram having endothermic peaks at temperatures of about 105° C., about 190° C., about 222° C., and about 241° C.

In some embodiments, the benzenesulfonic acid salt of Compound 1 is substantially crystalline. In some embodiments, the salt is crystalline. In some embodiments, the salt is a hydrate. In some embodiments, the salt is a solvate.

Ethanesulfonic Acid Salts

The ethanesulfonic acid salt of Compound 1 can be prepared by any suitable method for preparation of ethanesulfonic acid addition salts. For example, Compound 1 can be combined with ethanesulfonic acid (e.g., about 1.0 molar eq or more) in a crystallizing solvent and the resulting salt can be isolated by filtering the salt from solution. In certain embodiments, Compound 1 is combined with about 1 to about 2 molar equivalents of ethanesulfonic acid. In certain embodiments, Compound 1 is combined with about 1 to about 1.5 molar equivalents of ethanesulfonic acid. In certain embodiments, Compound 1 is combined with about 1.2 molar equivalents of ethanesulfonic acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, ethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane. In some embodiments, the crystallizing solvent contains isopropanol.

In some embodiments, the crystallizing solvent is methanol. In some embodiments, the crystallizing solvent is a mixture of methanol and isopropanol.

In some embodiments, the crystallizing solvent is heated to a temperature of about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 45° C., about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 24 hours, but longer and shorter periods are possible depending on the choice of crystallizing solvent and temperature.

The precipitation and/or crystallization of the ethanesulfonic acid salt, in some embodiments, is carried out by filtering the salt from solution.

Crystalline ethanesulfonic acid salt forms of Compound 1 can be identified by their unique signatures with respect to, for example, X-ray powder diffraction, differential scanning calorimetry (DSC), thermogravimetric analysis (TGA), and solid state NMR.

Figure 33:
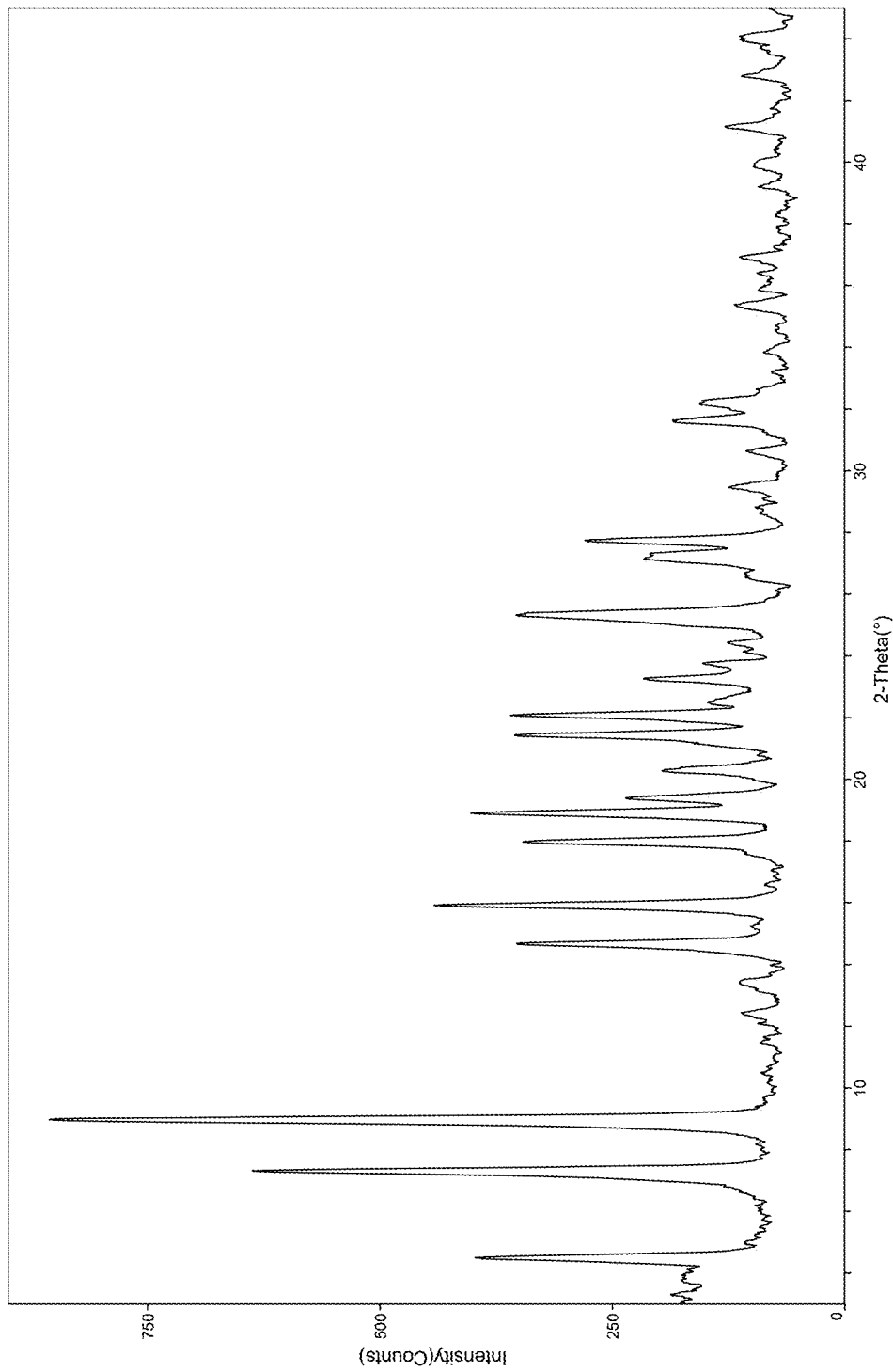
FIG. 33 shows the XRPD pattern of Compound 1 ethanesulfonic acid salt.

In some embodiments, the crystalline ethanesulfonic acid salt can be characterized by the X-ray powder diffraction (XRPD) pattern substantially as shown in FIG. 33.

In some embodiments, the ethanesulfonic acid salt of Compound 1 has at least one characteristic XRPD peak selected from about 4.5, about 7.3, about 9.0, about 14.7, and about 15.9 degrees 2-theta.

In some embodiments, ethanesulfonic acid salt of Compound 1 has at least two characteristic XRPD peaks selected from about 4.5, about 7.3, about 9.0, about 14.7, and about 15.9 degrees 2-theta.

In some embodiments, ethanesulfonic acid salt of Compound 1 has at least three characteristic XRPD peaks selected from about 4.5, about 7.3, about 9.0, about 14.7, and about 15.9 degrees 2-theta.

In some embodiments, the ethanesulfonic acid salt of Compound 1 has at least one characteristic XRPD peak selected from about 4.5, about 7.3, about 9.0, about 14.7, about 15.9, about 18.0, about 18.9, about 19.4, about 21.4, about 22.1, about 25.3, about 27.7, and about 31.6 degrees 2-theta.

In some embodiments, ethanesulfonic acid salt of Compound 1 has at least two characteristic XRPD peaks selected from about 4.5, about 7.3, about 9.0, about 14.7, about 15.9, about 18.0, about 18.9, about 19.4, about 21.4, about 22.1, about 25.3, about 27.7, and about 31.6 degrees 2-theta.

In some embodiments, ethanesulfonic acid salt of Compound 1 has at least three characteristic XRPD peaks selected from about 4.5, about 7.3, about 9.0, about 14.7, about 15.9, about 18.0, about 18.9, about 19.4, about 21.4, about 22.1, about 25.3, about 27.7, and about 31.6 degrees 2-theta.

Figure 34:
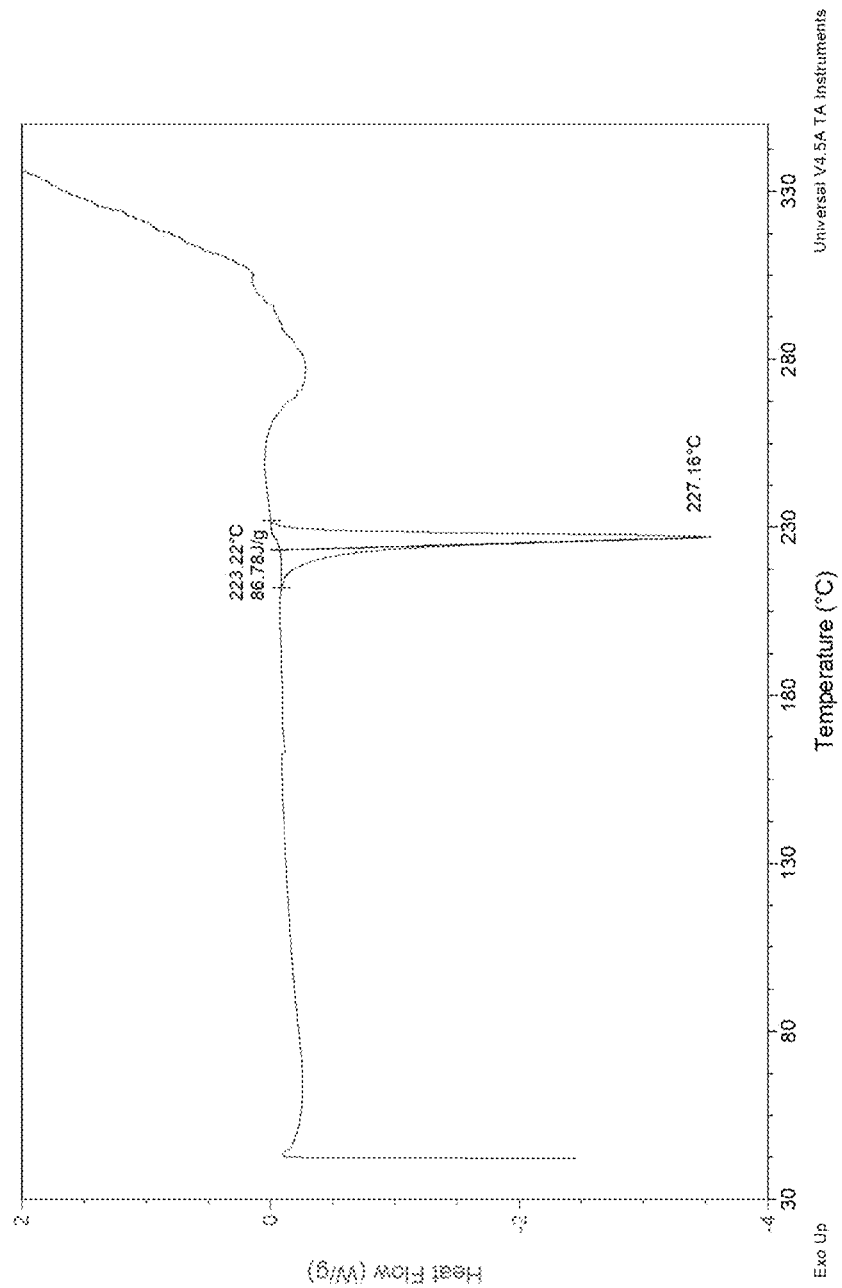
FIG. 34 shows the DSC thermogram of Compound 1 ethanesulfonic acid salt.
Figure 35:
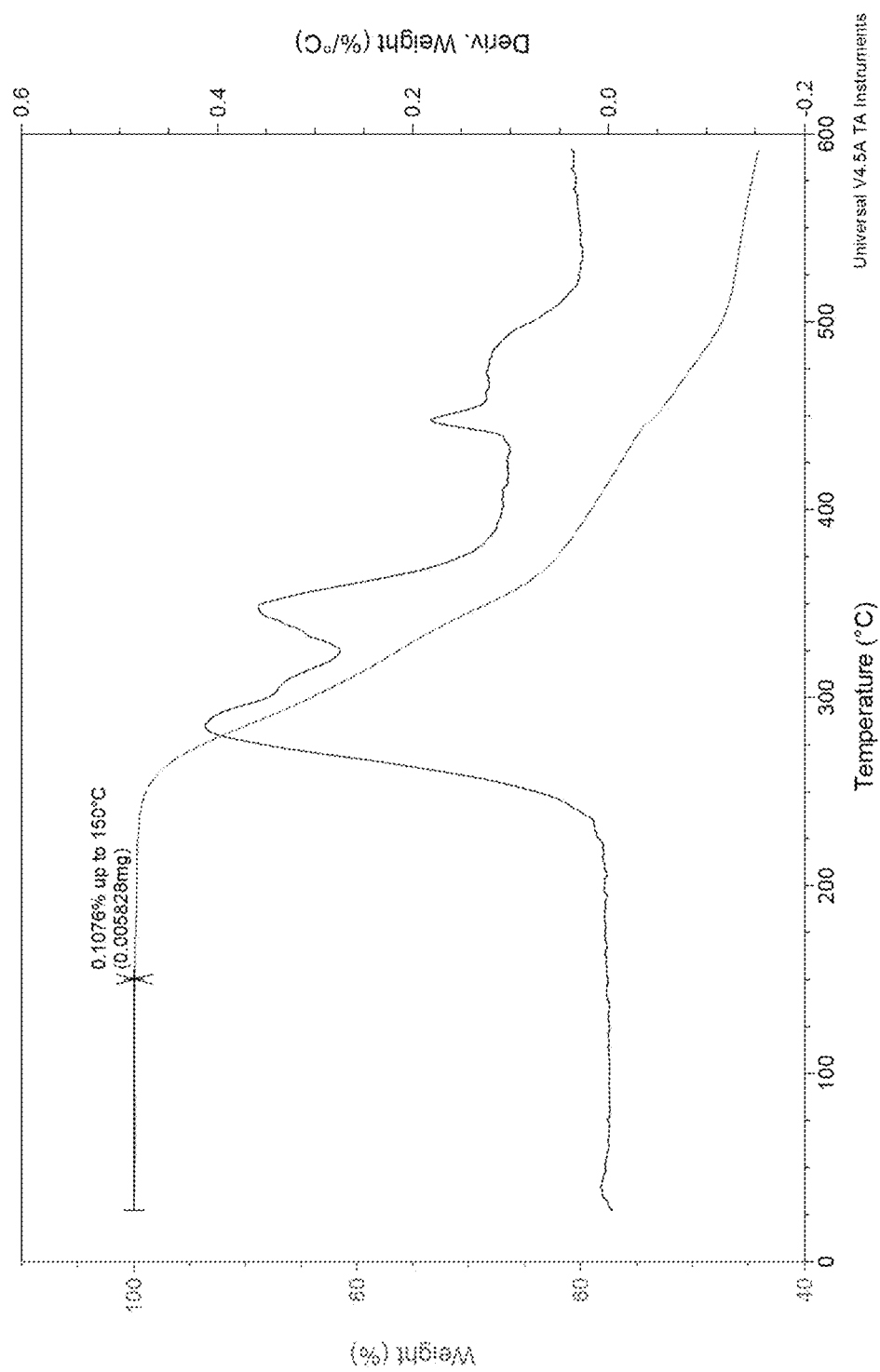
FIG. 35 shows the TGA thermogram of Compound 1 ethanesulfonic acid salt.

In some embodiments, the ethanesulfonic acid salt exhibits a DSC thermogram having an endothermic peak at a temperature of about 227° C. In some embodiments, the ethanesulfonic acid salt has a DSC thermogram substantially as depicted in FIG. 34. In some embodiments, the ethanesulfonic acid salt has a TGA thermogram substantially as depicted in FIG. 35.

In some embodiments, the ethanesulfonic acid salt of Compound 1 has at least one characteristic XRPD peak selected from about 4.5, about 7.3, about 9.0, about 14.7, and about 15.9; and the ethanesulfonic acid salt exhibits a DSC thermogram having an endothermic peak at a temperature of about 227° C.

In some embodiments, the ethanesulfonic acid salt of Compound 1 is substantially crystalline. In some embodiments, the salt is crystalline. In some embodiments, the salt is a hydrate. In some embodiments, the salt is a solvate.

Maleic Acid Salts

The maleic acid salt of Compound 1 can be prepared by any suitable method for preparation of maleic acid addition salts. For example, Compound 1 can be combined with maleic acid (e.g., about 1.0 molar eq or more) in a crystallizing solvent and the resulting salt can be isolated by filtering the salt from solution. In certain embodiments, Compound 1 is combined with about 1 to about 2 molar equivalents of maleic acid. In certain embodiments, Compound 1 is combined with about 1 to about 1.5 molar equivalents of maleic acid. In certain embodiments, Compound 1 is combined with about 1.2 molar equivalents of maleic acid.

The crystallizing solvent can contain any solvent or mixture of solvents capable of at least partially dissolving Compound 1. In some embodiments, the crystallizing solvent contains an alcohol. Suitable alcohols include methanol, ethanol, 2-nitroethanol, 2-fluoroethanol, 2,2,2-trifluoroethanol, ethylene glycol, 1-propanol, isopropanol (isopropyl alcohol, 2-propanol), 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, benzyl alcohol, phenol, or glycerol. In some embodiments, the crystallizing solvent contains dichloromethane, methanol, ethanol, 1-propanol, or isopropanol. In some embodiments, the crystallizing solvent contains dichloromethane.

In some embodiments, the crystallizing solvent is methanol.

In some embodiments, the crystallizing solvent is heated to a temperature of about 50° C. In some embodiments, a temperature from about 50° C. to about 80° C. is used. In some embodiments, a temperature from about 40° C. to about 60° C. is used. In some embodiments, a temperature from about 45° C. to about 55° C. is used. In some embodiments, a temperature of about 45° C., about 50° C., about 55° C., about 60° C., about 65° C., about 70° C., about 75° C. or about 80° C. is used.

In some embodiments, the crystallizing solvent is heated to a temperature that can induce crystallization at a practical rate. In some embodiments, crystallization is completed within about 12 to about 24 hours, but longer and shorter periods are possible depending on the choice of crystallizing solvent and temperature.

The precipitation and/or crystallization of the maleic acid salt, in some embodiments, is carried out by filtering the salt from solution.

Crystalline maleic acid salt forms of Compound 1 can be identified by their unique signatures with respect to, for example, X-ray powder diffraction, differential scanning calorimetry (DSC), thermogravimetric analysis (TGA), and solid state NMR.

Figure 37:
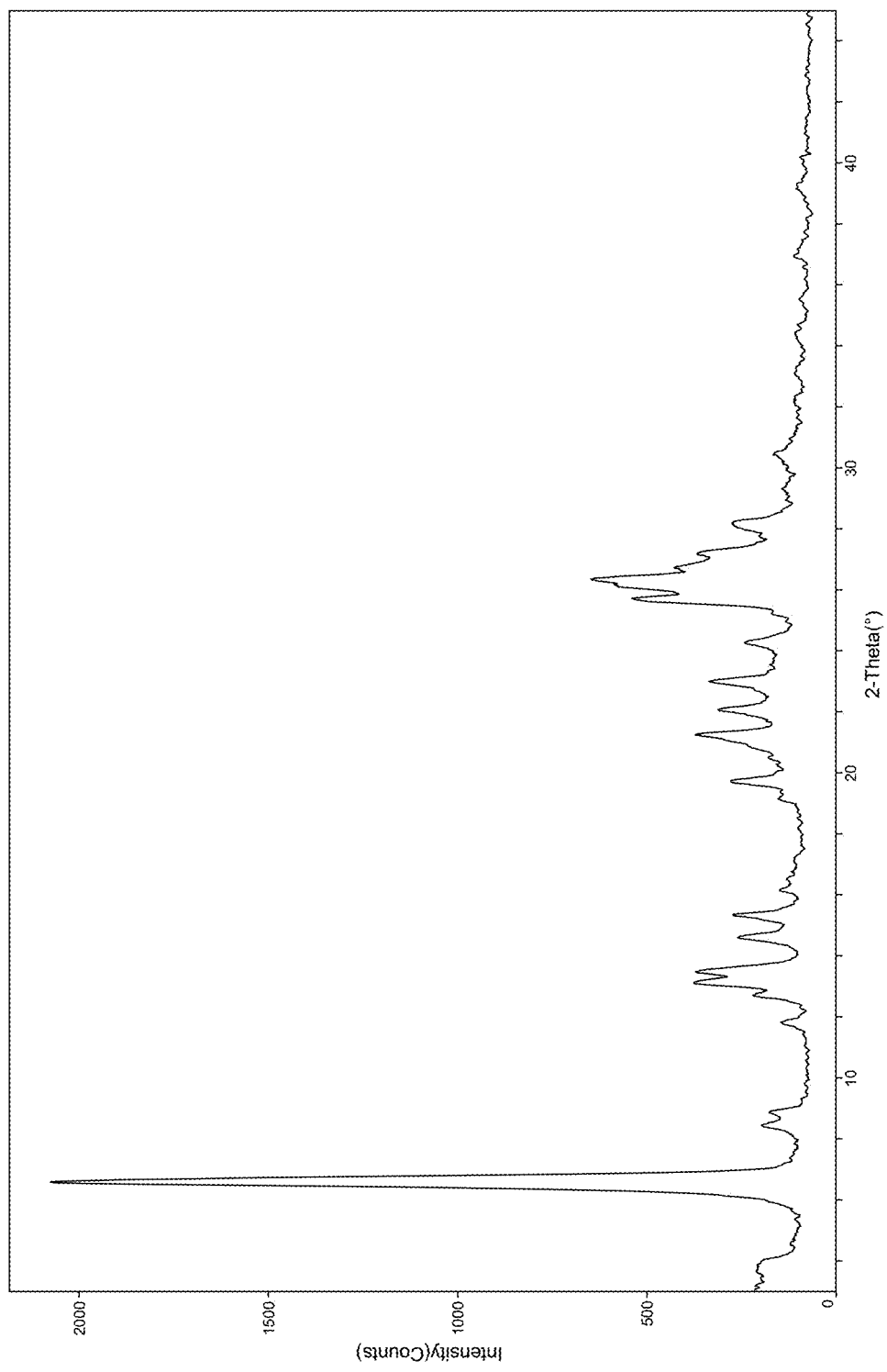
FIG. 37 shows the XRPD pattern of Compound 1 maleic acid salt.

In some embodiments, the crystalline maleic acid salt can be characterized by the X-ray powder diffraction (XRPD) pattern substantially as shown in FIG. 37.

In some embodiments, the maleic acid salt of Compound 1 has at least one characteristic XRPD peak selected from about 6.6, about 8.4, about 8.9, about 13.1, and about 13.5 degrees 2-theta.

In some embodiments, maleic acid salt of Compound 1 has at least two characteristic XRPD peaks selected from about 6.6, about 8.4, about 8.9, about 13.1, and about 13.5 degrees 2-theta.

In some embodiments, maleic acid salt of Compound 1 has at least three characteristic XRPD peaks selected from about 6.6, about 8.4, about 8.9, about 13.1, and about 13.5 degrees 2-theta.

In some embodiments, the maleic acid salt of Compound 1 has at least one characteristic XRPD peak selected from about 6.6, about 8.4, about 8.9, about 12.7, about 13.1, about 13.5, about 14.6, about 15.3, about 19.7, about 21.2, about 25.7, about 26.4, and about 26.8 degrees 2-theta.

In some embodiments, maleic acid salt of Compound 1 has at least two characteristic XRPD peaks selected from about 6.6, about 8.4, about 8.9, about 12.7, about 13.1, about 13.5, about 14.6, about 15.3, about 19.7, about 21.2, about 25.7, about 26.4, and about 26.8 degrees 2-theta.

In some embodiments, maleic acid salt of Compound 1 has at least three characteristic XRPD peaks selected from about 6.6, about 8.4, about 8.9, about 12.7, about 13.1, about 13.5, about 14.6, about 15.3, about 19.7, about 21.2, about 25.7, about 26.4, and about 26.8 degrees 2-theta.

Figure 38:
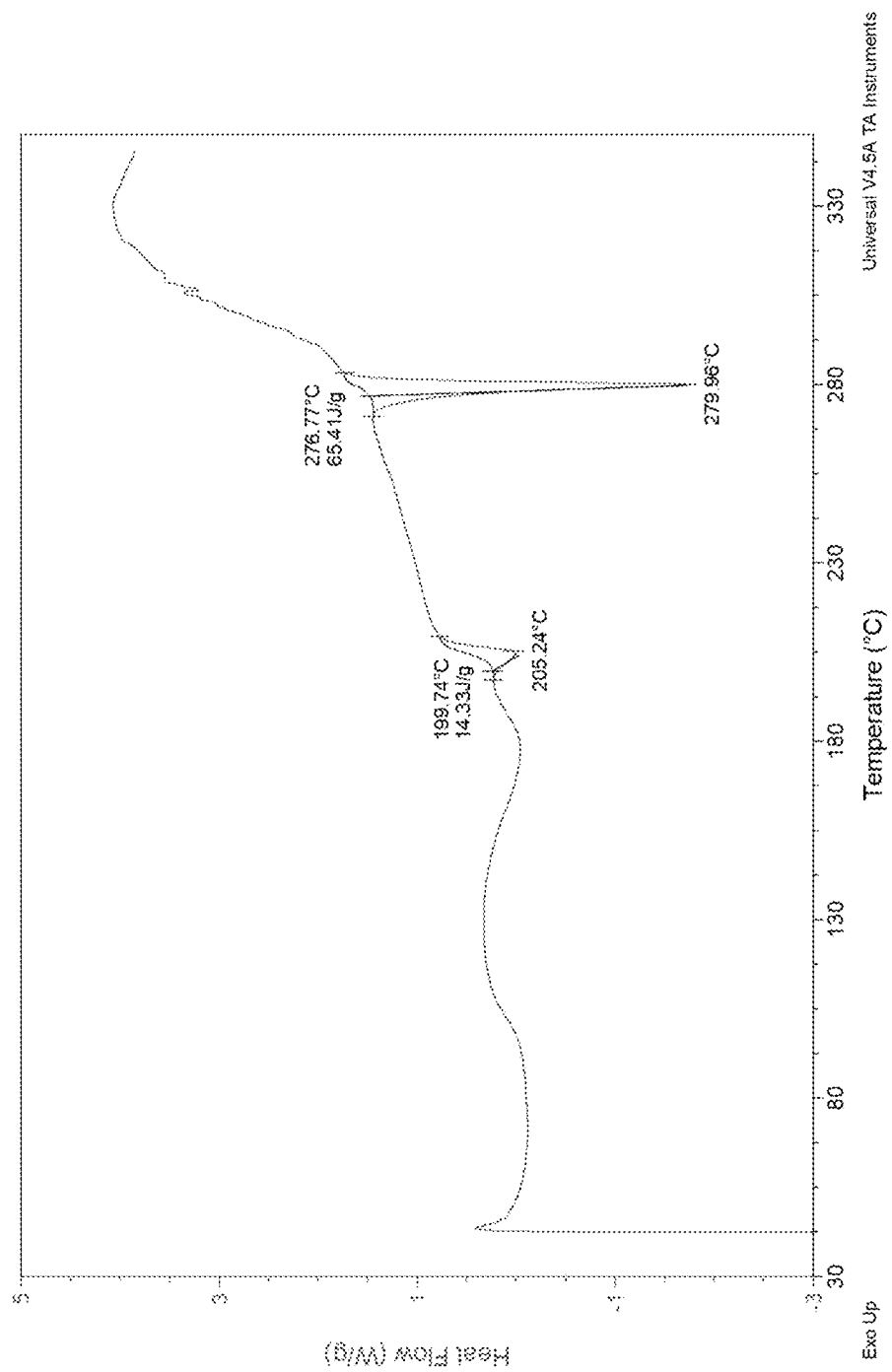
FIG. 38 shows the DSC thermogram of Compound 1 maleic acid salt.
Figure 39:
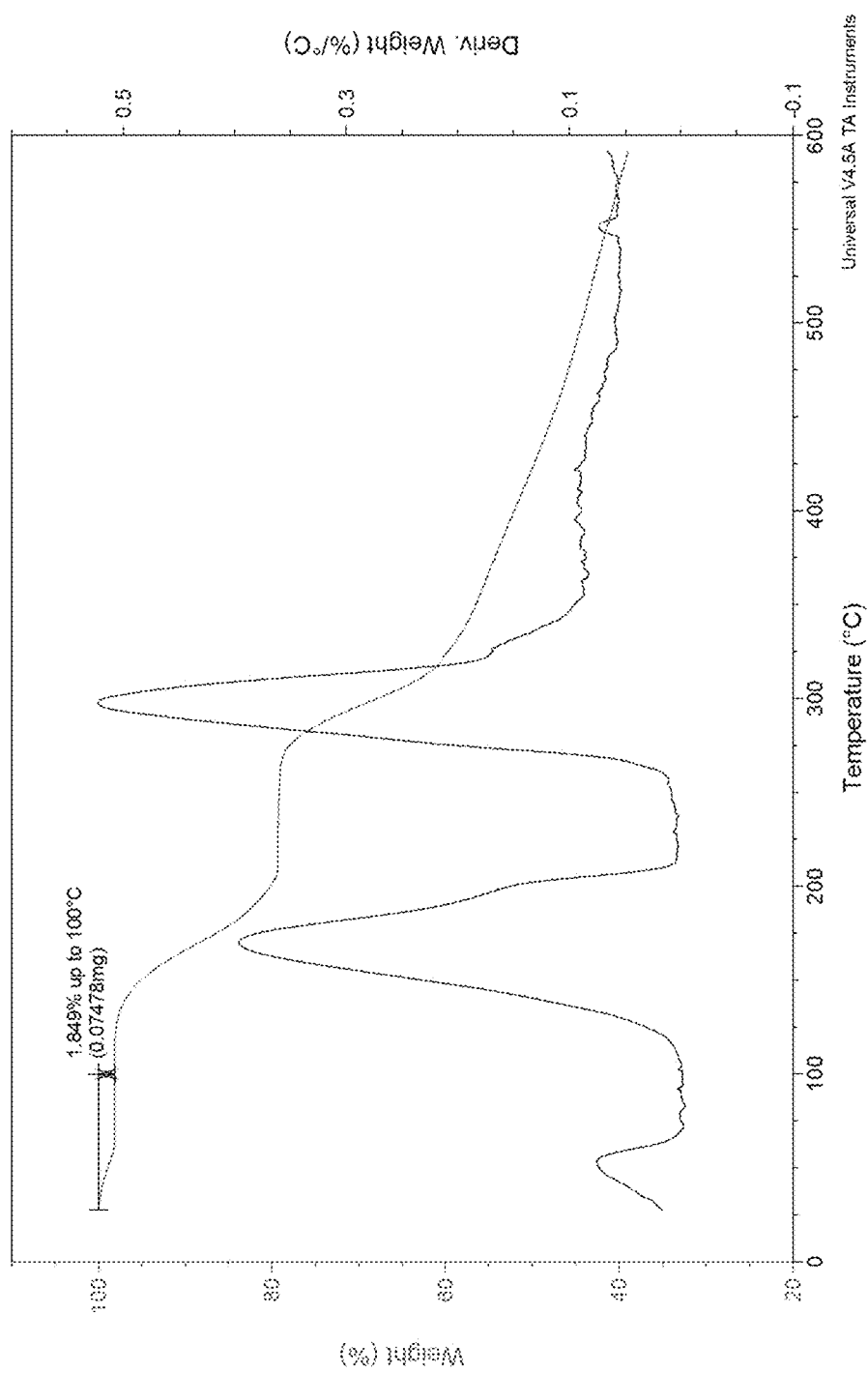
FIG. 39 shows the TGA thermogram of Compound 1 maleic acid salt.

In some embodiments, the maleic acid salt exhibits a DSC thermogram having endothermic peaks at temperatures of about 205° C. and about 280° C. In some embodiments, the maleic acid salt exhibits a DSC thermogram having an endothermic peak at a temperature of about 205° C. In some embodiments, the maleic acid salt exhibits a DSC thermogram having an endothermic peaks at a temperature of about 280° C. In some embodiments, the maleic acid salt has a DSC thermogram substantially as depicted in FIG. 38. In some embodiments, the maleic acid salt has a TGA thermogram substantially as depicted in FIG. 39. In some embodiments, the maleic acid salt of Compound 1 has at least one characteristic XRPD peak selected from about 6.6, about 8.4, about 8.9, about 13.1, and about 13.5; and the maleic acid salt exhibits a DSC thermogram having endothermic peaks at temperatures of about 205° C. and about 280° C.

In some embodiments, the maleic acid salt of Compound 1 is substantially crystalline. In some embodiments, the salt is crystalline. In some embodiments, the salt is a hydrate. In some embodiments, the salt is a solvate.

Adipic Acid Salts

The adipic salt of Compound 1 can be prepared by any suitable method for preparation of adipic acid addition salts. For example, Compound 1 can be combined with adipic acid (e.g., about 1.0 molar eq or more) in a crystallizing solvent and the resulting salt can be isolated by filtering the salt from solution. In certain embodiments, Compound 1 is combined with about 1 to about 2 molar equivalents of adipic acid. In certain embodiments, Compound 1 is combined with about 1 to about 1.5 molar equivalents of adipic acid. In certain embodiments, Compound 1 is combined with about 1 to about 1.25 molar equivalents of adipic acid.

Figure 40:
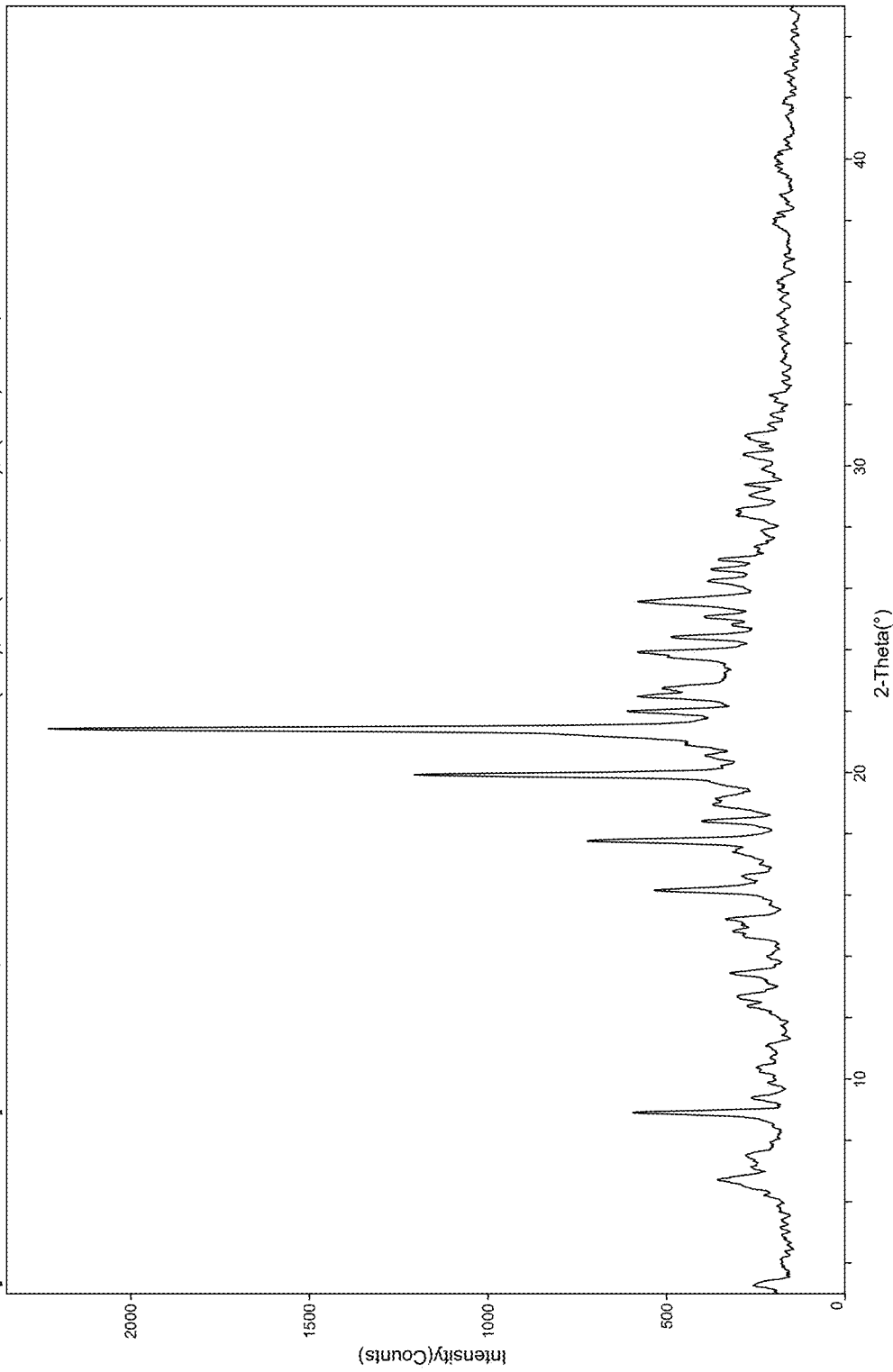
FIG. 40 shows the XRPD pattern of Compound 1 adipic acid salt.

Crystalline adipic acid salt forms of Compound 1 can be identified by their unique signatures with respect to, for example, X-ray powder diffraction, differential scanning calorimetry (DSC), thermogravimetric analysis (TGA), and solid state NMR. In some embodiments, the crystalline adipic acid salt can be characterized by the X-ray powder diffraction (XRPD) pattern substantially as shown in FIG. 40.

In some embodiments, the adipic acid salt of Compound 1 has at least one characteristic XRPD peak selected from about 6.7, about 8.9, about 16.2, and about 17.8 degrees 2-theta.

In some embodiments, adipic acid salt of Compound 1 has at least two characteristic XRPD peaks selected from about 6.7, about 8.9, about 16.2, and about 17.8 degrees 2-theta.

In some embodiments, adipic acid salt of Compound 1 has at least three characteristic XRPD peaks selected from about 6.7, about 8.9, about 16.2, and about 17.8 degrees 2-theta.

In some embodiments, the adipic acid salt of Compound 1 has at least one characteristic XRPD peak selected from about 6.7, about 8.9, about 16.2, about 17.8, about 19.9, about 21.4, about 22.0, about 22.5, about 23.9, about 24.4, and about 25.6 degrees 2-theta.

In some embodiments, adipic acid salt of Compound 1 has at least two characteristic XRPD peaks selected from about 6.7, about 8.9, about 16.2, about 17.8, about 19.9, about 21.4, about 22.0, about 22.5, about 23.9, about 24.4, and about 25.6 degrees 2-theta.

In some embodiments, adipic acid salt of Compound 1 has at least three characteristic XRPD peaks selected from about 6.7, about 8.9, about 16.2, about 17.8, about 19.9, about 21.4, about 22.0, about 22.5, about 23.9, about 24.4, and about 25.6 degrees 2-theta.

Figure 41:
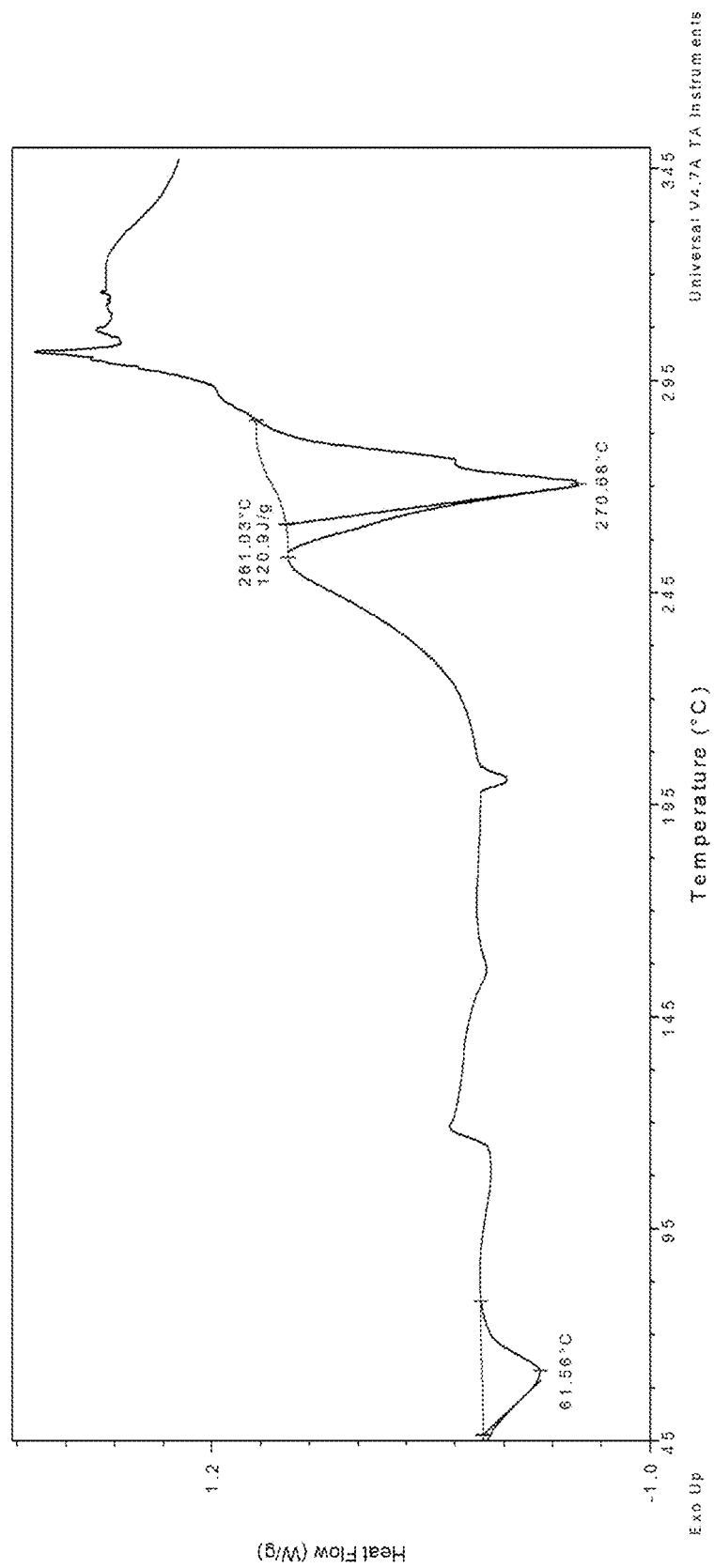
FIG. 41 shows the DSC thermogram of Compound 1 adipic acid salt.

In some embodiments, the adipic acid salt exhibits a DSC thermogram having endothermic peaks at temperatures of about 62° C. and about 271° C. In some embodiments, the adipic acid salt exhibits a DSC thermogram having an endothermic peak at a temperature of about 62° C. In some embodiments, the adipic acid salt exhibits a DSC thermogram having an endothermic peak at a temperature of about 271° C. In some embodiments, the adipic acid salt has a DSC thermogram substantially as depicted in FIG. 41.

In some embodiments, the adipic acid salt of Compound 1 has at least one characteristic XRPD peak selected from about 6.7, about 8.9, about 16.2, and about 17.8; and the adipic acid salt exhibits a DSC thermogram having endothermic peaks at temperatures of about 62° C. and about 271° C.

In some embodiments, the adipic acid salt of Compound 1 is substantially crystalline. In some embodiments, the salt is crystalline. In some embodiments, the salt is a hydrate. In some embodiments, the salt is a solvate.

Methods of Use

Compound 1 and the salts described herein can inhibit the activity of the FGFR enzyme. For example, Compound 1 can be used to inhibit activity of an FGFR enzyme in a cell or in an individual or patient in need of inhibition of the enzyme by administering an inhibiting amount of Compound 1 to the cell, individual, or patient.

As FGFR inhibitors, Compound 1 and its salts are useful in the treatment of various diseases associated with abnormal expression or activity of the FGFR enzyme or FGFR ligands. Compounds which inhibit FGFR will be useful in providing a means of preventing the growth or inducing apoptosis in tumors, particularly by inhibiting angiogenesis. It is therefore anticipated that Compound 1 and its salts will prove useful in treating or preventing proliferative disorders such as cancers. In particular tumors with activating mutants of receptor tyrosine kinases or upregulation of receptor tyrosine kinases may be particularly sensitive to the inhibitors.

In certain embodiments, the disclosure provides a method for treating a FGFR-mediated disorder in a patient in need thereof, comprising the step of administering to the patient a salt of Compound 1, or a pharmaceutical composition thereof.

For example, Compound 1, its salts, and solid forms thereof are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth; squamous head and neck cancers), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, vulvar cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., 8p11 myeloproliferative syndrome, polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

In certain embodiments, provided herein is a method of treating cancer comprising administering to a patient in need thereof a therapeutically effect amount of Compound 1, its salts, and solid forms thereof. In certain embodiments, the cancer is selected from bladder cancer, breast cancer, cervical cancer, cancer of the small intestine, colorectal cancer, endometrial cancer, gastric cancer, head and neck cancer, kidney cancer, liver cancer, lung cancer, ovarian cancer, prostate cancer, testicular cancer, uterine cancer, vulvar cancer, esophageal cancer, gall bladder cancer, pancreatic cancer, thyroid cancer, skin cancer, brain cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, myeloproliferative neoplasms, chronic myelogenic lymphoma, acute lymphoblastic lymphoma, hairy cell lymphoma, Burkett's lymphoma, glioblastoma, melanoma, rhabdosarcoma, lymphosarcoma, and osteosarcoma. In certain embodiments, the cancer is bladder cancer. In certain embodiments, the liver cancer is cholangiocellular carcinoma.

Other cancers treatable with Compound 1, its salts, or solid forms thereof include tumors of the eye, glioblastoma, melanoma, rhabdosarcoma, lymphosarcoma, and osteosarcoma.

Compound 1, its salts, or solid forms thereof can also be useful in the inhibition of tumor metastases.

In some embodiments, compound 1 or solid forms as described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the FGFR enzyme with a compound described herein (e.g., a salt of Compound 1) includes the administration of a compound described herein to an individual or patient, such as a human, having FGFR, as well as, for example, introducing a compound described herein (e.g., a salt of Compound 1) into a sample containing a cellular or purified preparation containing the FGFR enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy*, 21st ed.; Lippincott Williams & Wilkins: Philadelphia, Pa., 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, Fla., 2009.

As used herein, the term "treating" or "treatment" refers to inhibiting the disease; for example, inhibiting a disease, condition or disorder in an individual who is experiencing or displaying the pathology or symptomatology of the disease, condition or disorder (i.e., arresting further development of the pathology and/or symptomatology) or ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapies

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with Compound 1 or its salts for treatment of FGFR-associated diseases, disorders or conditions, or diseases or conditions as described herein. The agents can be combined with the present compounds in a single dosage form, or the agents can be administered simultaneously or sequentially as separate dosage forms.

The salts of the FGFR inhibitor Compound 1 as described herein can be used in combination with one or more other kinase inhibitors for the treatment of diseases, such as cancer, that are impacted by multiple signaling pathways. For example, a combination can include one or more inhibitors of the following kinases for the treatment of cancer: Akt1, Akt2, Akt3, TGF-βR, Pim, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, flt-1, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. Additionally, the salts of the FGFR inhibitor as described herein can be combined with inhibitors of kinases associated with the PIK3/Akt/mTOR signaling pathway, such as PI3K, Akt (including Akt1, Akt2 and Akt3) and mTOR kinases.

In some embodiments, the salts of Compound 1 as described herein can be used in combination with one or more inhibitors of the enzyme or protein receptors such as HPK1, SBLB, TUT4, A2A/A2B, CD47, CDK2, STING, ALK2, LIN28, ADAR1, MAT2a, RIOK1, HDAC8, WDR5, SMARCA2, and DCLK1 for the treatment of diseases and disorders. Exemplary diseases and disorders include cancer, infection, inflammation and neurodegenerative disorders.

In some embodiments, the salts of Compound 1 as described herein can be used in combination with a therapeutic agent that targets an epigenetic regulator. Examples of epigenetic regulators include bromodomain inhibitors, the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the salts of Compound 1 as described herein can be used in combination with targeted therapies, including JAK kinase inhibitors (Ruxolitinib, additional JAK1/2 and JAK1-selective, baricitinib or INCB39110), Pim kinase inhibitors (e.g., INCB53914), PI3 kinase inhibitors including PI3K-delta selective and broad spectrum PI3K inhibitors (e.g., INCB50465 and INCB54707), PI3K-gamma inhibitors such as PI3K-gamma selective inhibitors, MEK inhibitors, CSF1R inhibitors, TAM receptor tyrosine kinases inhibitors (Tyro-3, Axl, and Mer; e.g., INCB81776), angiogenesis inhibitors, interleukin receptor inhibitors, Cyclin Dependent kinase inhibitors, BRAF inhibitors, mTOR inhibitors, proteasome inhibitors (Bortezomib, Carfilzomib), HDAC-inhibitors (panobinostat, vorinostat), DNA methyl transferase inhibitors, dexamethasone, bromo and extra terminal family members inhibitors (for example, bromodomain inhibitors or BET inhibitors INCB54329 or INCB57643), LSD1 inhibitors (INCB59872 or INCB60003), arginase inhibitors (INCB1158), indoleamine 2,3-dioxygenase inhibitors (epacadostat, NLG919 or BMS-986205), and PARP inhibitors (e.g., olaparib or rucaparib).

For treating cancer and other proliferative diseases, the salts of Compound 1 as described herein can be used in combination with chemotherapeutic agents, agonists or antagonists of nuclear receptors, or other anti-proliferative agents. The salts of Compound 1 can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, baricitinib, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, niraparib, nofetumomab, olaparib, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, rucaparib, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, veliparib, talazoparib, and zoledronate.

In some embodiments, the salts of Compound 1 as described herein can be used in combination with immune checkpoint inhibitors. Exemplary immune checkpoint inhibitors include inhibitors against immune checkpoint molecules such as CD20, CD28, CD40, CD122, CD96, CD73, CD47, GITR, CSF1R, JAK, PI3K delta, PI3K gamma, TAM, arginase, HPK1, CD137 (also known as 4-1BB), ICOS, B7-H3, B7-H4, BTLA, CTLA-4, LAG3, TIM3, VISTA, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds of the disclosure provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is a small molecule PD-L1 inhibitor. In some embodiments, the small molecule PD-L1 inhibitor has an IC50 less than 1 µM, less than 100 nM, less than 10 nM or less than 1 nM in a PD-L1 assay described in US Patent Publication Nos. US 20170107216, US 20170145025, US 20170174671, US 20170174679, US 20170320875, US 20170342060, US 20170362253, and US 20180016260, each of which is incorporated by reference in its entirety for all purposes.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), durvalumab (Imfinzi®), pidilizumab, SHR-1210, PDR001, MGA012, PDR001, AB122, or AMP-224. In some embodiments, the anti-PD-1 monoclonal antibody is nivolumab or pembrolizumab. In some embodiments, the anti-PD1 antibody is pembrolizumab. In some embodiments, the anti-PD-1 monoclonal antibody is MGA012. In some embodiments, the anti-PD1 antibody is SHR-1210. Other anti-cancer agent(s) include antibody therapeutics such as 4-1BB (e.g. urelumab, utomilumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of PD-1 and PD-L1, e.g., an anti-PD-1/PD-L1 monoclonal antibody. In some embodiments, the anti-PD-1/PD-L1 is MCLA-136.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518, MK-4166, INCAGN1876, MK-1248, AMG228, BMS-986156, GWN323, or MEDI1873.

In some embodiments, the inhibitor of an immune checkpoint molecule is an agonist of OX40, e.g., OX40 agonist antibody or OX40L fusion protein. In some embodiments, the anti-OX40 antibody is MEDI0562, MOXR-0916, PF-04518600, GSK3174998, or BMS-986178. In some embodiments, the OX40L fusion protein is MEDI6383.

In some embodiments, the inhibitor of an immune checkpoint molecule is an inhibitor of CD20, e.g., an anti-CD20 antibody. In some embodiments, the anti-CD20 antibody is obinutuzumab or rituximab.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the compounds of the disclosure can be used in combination with one or more metabolic enzyme inhibitors. In some embodiments, the metabolic enzyme inhibitor is an inhibitor of IDOL TDO, or arginase. Examples of IDO1 inhibitors include epacadostat, NLG919, BMS-986205, PF-06840003, IOM2983, RG-70099 and LY338196.

As provided throughout, the additional compounds, inhibitors, agents, etc. can be combined with the present compound in a single or continuous dosage form, or they can be administered simultaneously or sequentially as separate dosage forms. In some embodiments, the salts of Compound 1 as described herein can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Suitable antiviral agents contemplated for use in combination with Compound 1 or its salts can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

Suitable agents for use in combination with Compound 1 or its salts for the treatment of cancer include chemotherapeutic agents, targeted cancer therapies, immunotherapies or radiation therapy. Compound 1 and its salts may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with Compound 1 and its salts. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compound 1 and its salts may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with FGFR inhibitors. These include onartumzumab, tivantnib, and INC-280. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with Compound 1 or its salts include inhibitors of the PI3K-AKT-mTOR pathway, inhibitors of the Raf-MAPK pathway, inhibitors of JAK-STAT pathway, and inhibitors of protein chaperones and cell cycle progression.

Agents against the PI3 kinase include but are not limited topilaralisib, idelalisib, buparlisib. Inhibitors of mTOR such as rapamycin, sirolimus, temsirolimus, and everolimus may be combined with FGFR inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, tofacitinib), Hsp90 (e.g., tanespimycin), cyclin dependent kinases (e.g., palbociclib), HDACs (e.g., panobinostat), PARP (e.g., olaparib), and proteasomes (e.g., bortezomib, carfilzomib) can also be combined with Compound 1 or its salts. In some embodiments, the JAK inhibitor is selective for JAK1 over JAK2 and JAK3.

Other suitable agents for use in combination with Compound 1 or its salts include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with Compound 1 or its salts include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compound 1 may also be combined with immunotherapy drugs, including cytokines such as interferon alpha, interleukin 2, and tumor necrosis factor (TNF) in.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-L1 and PD-1 antibodies, or antibodies to cytokines (IL-10, TGF-β, etc.).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Formulation, Dosage Forms and Administration

When employed as pharmaceuticals, salts of the invention as described herein can be administered in the form of pharmaceutical compositions which refers to a combination of a salt of Compound 1 as described herein, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, a salt of Compound 1 in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a salt of Compound 1. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the salt of Compound 1, or compositions as described herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a salt of Compound 1 can vary according to, for example, the particular use for which the treatment is made, the manner of administration of the compound, the health and condition of the patient, and the judgment of the prescribing physician. The proportion or concentration of the salt of Compound 1 in a pharmaceutical composition can vary depending upon a number of factors including dosage, chemical characteristics (e.g., hydrophobicity), and the route of administration. For example, a salt of Compound 1 can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Salts of compound 1 can also be formulated in combination with one or more additional active ingredients which can include any pharmaceutical agent such as anti-viral agents, vaccines, antibodies, immune enhancers, immune suppressants, anti-inflammatory agents and the like.

EXAMPLES

Example 1

Experimental Methods

In the below examples, X-Ray Powder Diffraction analysis was carried out on a Rigaku MiniFlex X-ray Powder Diffractometer (XRPD) instrument. The general experimental procedures for XRPD were: (1) X-ray radiation from copper at 1.054056 Å with $K_\beta$ filter; (2) X-ray power at 30 KV, 15 mA; and (3) the sample powder was dispersed on a zero-background sample holder. The general measurement conditions for XRPD were: Start Angle 3 degrees; Stop Angle 45 degrees; Sampling 0.02 degrees; and Scan speed 2 degree/min.

Differential Scanning calorimetry (DSC) was carried out on a TA Instruments Differential Scanning calorimetry, Model Q200 with autosampler. The DSC instrument conditions were as follows: 30-300° C. at 10° C./min; Tzero aluminum sample pan and lid; and nitrogen gas flow at 50 mL/min.

Thermogravimetric analysis (TGA) was carried out on a TA Instrument Thermogravimetric Analyzer, Model Q500. The general experimental conditions for TGA were: ramp from 20° C.-600° C. at 20° C./min; nitrogen purge, gas flow at 40 mL/min followed by balance of the purge flow; sample purge flow at 60 mL/min; platinum sample pan.

Example 2

Preparation of the D-(−)-Tartaric Acid Salt

D-(−)-tartaric acid (32.55 mg, 0.217 mmol, 1.12 eq.) was added to a solution of Compound 1 (94.55 mg, 0.194 mmol) in a 1:1 v/v mixture of methanol and dichloromethane (2.4 mL). The reaction mixture was stirred to give a thick slurry. The slurry was stirred for 1.5 h at 50° C. for 65 min, and then cooled to room temperature and stirred overnight. The slurry was filtered, and the solids were dried under vacuum at 36-40° C. overnight (16 h) to provide Compound 1 D-(−)-tartaric acid salt (104.6 mg, 84% yield).

The stoichiometric ratio between Compound 1 and D-(−)-tartaric acid was determined as 1:1 by $^1$H NMR (FIG. 1). The crystallinity of the Compound 1 D-(−)-tartrate was confirmed by XRPD (FIG. 2) and further supported by DSC (FIG. 3) and TGA (FIG. 4). Analytical data collected on the product, including characterization by XRPD, DSC, and TGA were performed as described in Example 1. The D-(−)-tartaric acid salt exhibits a DSC thermogram having an endothermic peak at a temperature of about 276° C.

TABLE 1

XRPD Peak Data for the D-(−)-Tartaric Acid Salt

| 2-Theta | Height | I % |
|---|---|---|
| 7.4 | 317 | 100 |
| 10.5 | 144 | 45.4 |
| 11.9 | 45 | 14.2 |
| 12.9 | 236 | 74.4 |
| 13.6 | 151 | 47.6 |
| 14.8 | 140 | 44.2 |
| 16.4 | 204 | 64.4 |
| 17.0 | 52 | 16.4 |
| 18.9 | 113 | 35.6 |
| 19.7 | 83 | 26.2 |
| 20.2 | 61 | 19.2 |
| 21.3 | 294 | 92.7 |
| 22.1 | 198 | 62.5 |
| 22.8 | 277 | 87.4 |
| 25.0 | 203 | 64 |
| 25.8 | 166 | 52.4 |
| 26.6 | 106 | 33.4 |
| 27.4 | 79 | 24.9 |
| 28.0 | 95 | 30 |
| 29.0 | 77 | 24.3 |
| 30.0 | 60 | 18.9 |

TABLE 1-continued

XRPD Peak Data for the D-(−)-Tartaric Acid Salt

| 2-Theta | Height | I % |
|---|---|---|
| 30.7 | 50 | 15.8 |
| 33.0 | 119 | 37.5 |
| 34.9 | 64 | 20.2 |
| 35.7 | 53 | 16.7 |
| 40.2 | 51 | 16.1 |
| 41.5 | 39 | 12.3 |

Example 3

Preparation of the L-(+)-Tartaric Acid Salt

L-(−)-tartaric acid (32.85 mg, 0.218 mmol, 1.25 eq.) was added to a solution of Compound 1 (85.01 mg, 0.174 mmol) in a 1:1 mixture of methanol and dichloromethane (2.4 mL). The reaction mixture was stirred to give a slurry. The slurry was stirred for 50 min at 50° C. for 65 min, and then cooled to room temperature and stirred overnight. The slurry was filtered, and the solids were washed with methyl t-butyl ether, and dried under vacuum at 36-40° C. overnight (16 h) to provide Compound 1 L-(−)-tartaric acid salt (104.6 mg, 84% yield).

Figure 5:
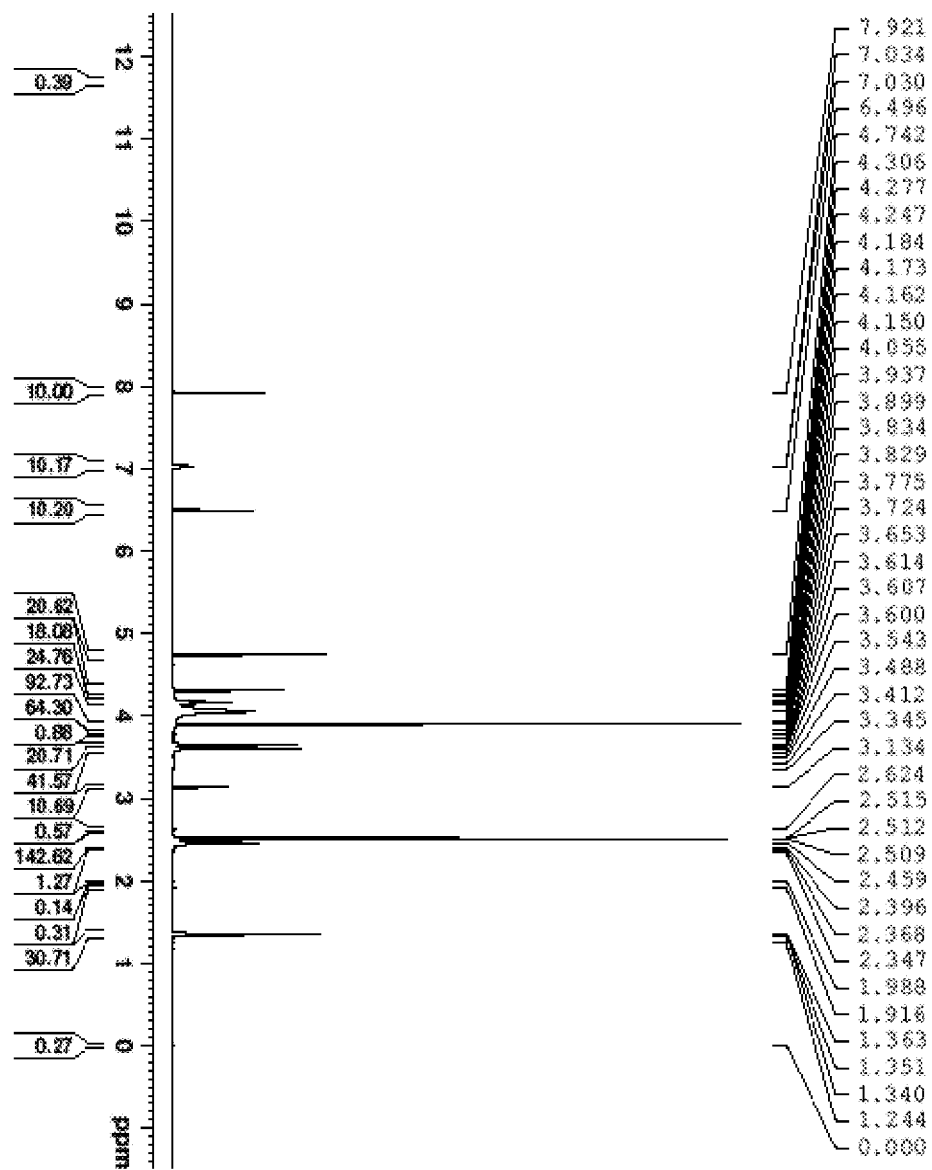
FIG. 5 shows the $^1$H NMR of Compound 1 L-(+)-tartaric acid salt.

The stoichiometric ratio between Compound 1 and L-(+)-tartaric acid was 1:1 by $^1$H NMR (FIG. 5). The crystallinity of Compound 1 L-(+)-tartrate was confirmed by XRPD (FIG. 6) and further supported by DSC (FIG. 7). TGA of the salt is provided in FIG. 8. Analytical data collected on the product, including characterization by XRPD, DSC, and TGA were performed as described in Example 1. The L-(+)-tartaric acid salt exhibits a DSC thermogram having endothermic peaks at temperatures of about 90° C., 211° C., and 266° C.

TABLE 2

XRPD Peak Data for the L-(+)-Tartaric Acid Salt

| 2-Theta | Height | I % |
|---|---|---|
| 3.8 | 151 | 29.4 |
| 4.5 | 100 | 19.5 |
| 5.5 | 51 | 9.9 |
| 6.7 | 61 | 11.9 |
| 8.5 | 238 | 46.3 |
| 9.1 | 514 | 100 |
| 10.3 | 135 | 26.3 |
| 10.9 | 90 | 17.5 |
| 12.0 | 149 | 29 |
| 12.3 | 143 | 27.8 |
| 14.3 | 277 | 53.9 |
| 15.3 | 73 | 14.2 |
| 15.7 | 180 | 35 |
| 16.7 | 91 | 17.7 |
| 17.7 | 97 | 18.9 |
| 18.2 | 119 | 23.2 |
| 18.8 | 103 | 20 |
| 20.2 | 376 | 73.2 |
| 21.3 | 313 | 60.9 |
| 22.5 | 305 | 59.3 |
| 24.3 | 107 | 20.8 |
| 24.9 | 89 | 17.3 |
| 25.7 | 98 | 19.1 |
| 27.5 | 94 | 18.3 |
| 28.9 | 68 | 13.2 |
| 33.1 | 59 | 11.5 |
| 37.4 | 53 | 10.3 |

Example 4

Preparation of the Salicylic Acid Salt

Salicylic acid (33.8, 0.245 mmol, 1.26 eq.) was added to a solution of Compound 1 (94.42 mg, 0.193 mmol) in a mixture of dichloromethane (1.5 mL) and methanol (1.0 mL). The reaction mixture was stirred to give a clear solution. The solution was evaporated to remove dichloromethane to give a slurry. The slurry was stirred for 50 min at 50° C., and then cooled to room temperature and stirred overnight. The slurry was filtered and the solids washed with methyl t-butyl ether. The solids were dried under vacuum at 36-40° C. overnight (16 h) to provide Compound 1 salicylic acid salt (111.7 mg, 92% yield).

Figure 9:
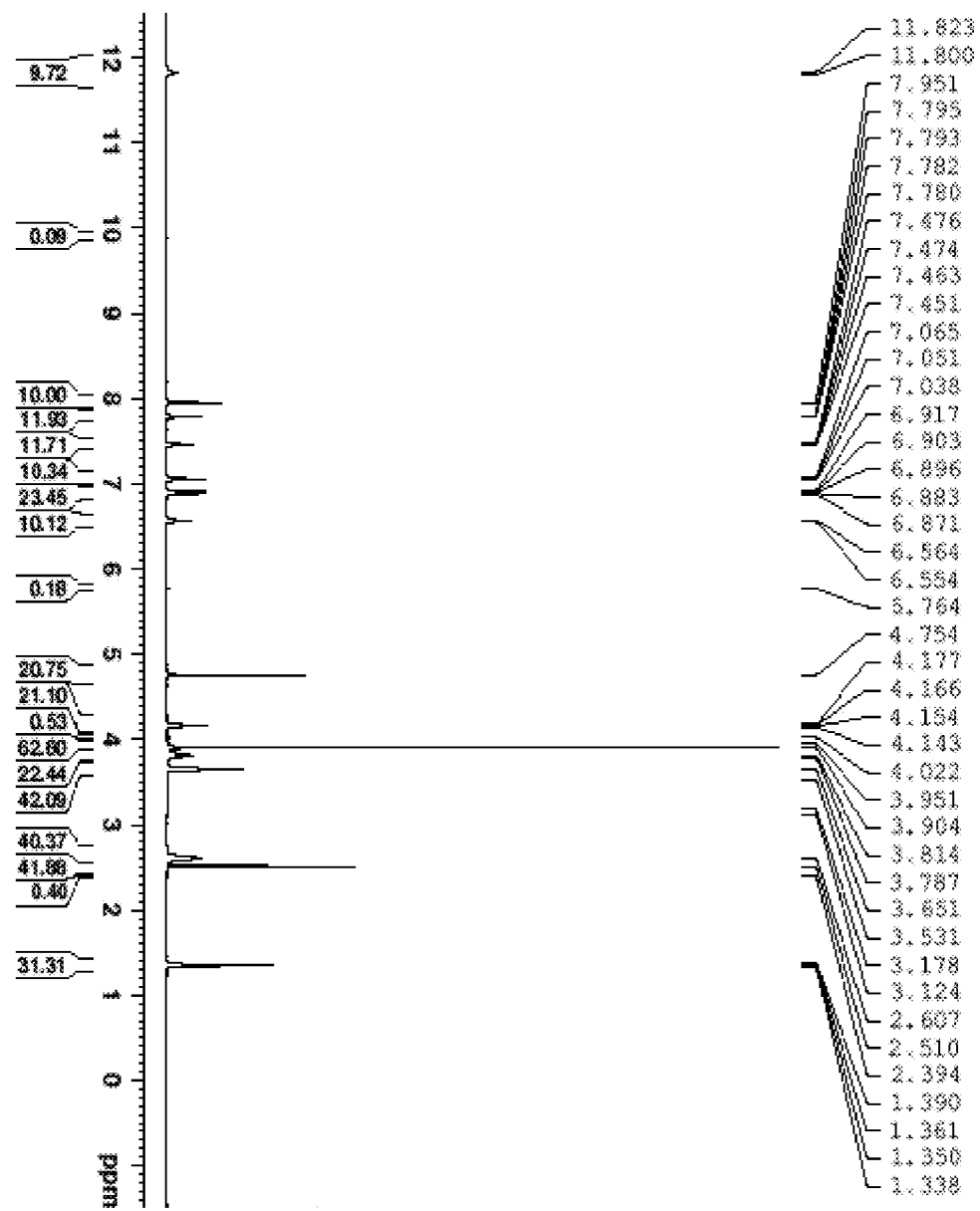
FIG. 9 shows the $^1$H NMR of Compound 1 salicylic acid salt.

The stoichiometric ratio between Compound 1 and salicylic acid was determined by $^1$H NMR (FIG. 9) as 1:1. The crystallinity of the Compound 1 salicylate was confirmed by XRPD (FIG. 10) and further supported by DSC (FIG. 11). TGA of the salicylic acid salt is provided in FIG. 12. Analytical data collected on the product, including characterization by XRPD, DSC, and TGA were performed as described in Example 1. The salicylic acid salt exhibits a DSC thermogram having an endothermic peak at a temperatures of about 212° C.

TABLE 3

XRPD Peak Data for the Salicylic Acid Salt

| 2-Theta | Height | I % |
|---|---|---|
| 5.3 | 71 | 3.4 |
| 6.0 | 200 | 9.6 |
| 7.6 | 130 | 6.3 |
| 8.6 | 54 | 2.6 |
| 9.9 | 339 | 16.3 |
| 10.4 | 2079 | 100 |
| 11.8 | 430 | 20.7 |
| 12.1 | 1263 | 60.8 |
| 12.7 | 193 | 9.3 |
| 13.4 | 908 | 43.7 |
| 13.9 | 901 | 43.3 |
| 15.1 | 1096 | 52.7 |
| 16.0 | 115 | 5.5 |
| 16.7 | 198 | 9.5 |
| 18.2 | 1346 | 64.7 |
| 18.9 | 326 | 15.7 |
| 19.3 | 142 | 6.8 |
| 20.1 | 1782 | 85.7 |
| 21.1 | 340 | 16.4 |
| 21.7 | 1548 | 74.5 |
| 22.6 | 1493 | 71.8 |
| 23.2 | 491 | 23.6 |
| 24.3 | 1188 | 57.1 |
| 24.8 | 1015 | 48.8 |
| 25.5 | 319 | 15.3 |
| 26.0 | 79 | 3.8 |
| 27.0 | 1212 | 58.3 |
| 27.4 | 997 | 48 |
| 28.6 | 215 | 10.3 |
| 29.6 | 208 | 10 |
| 30.6 | 823 | 39.6 |
| 31.9 | 230 | 11.1 |
| 32.4 | 134 | 6.4 |
| 32.8 | 173 | 8.3 |
| 33.5 | 105 | 5.1 |
| 34.4 | 134 | 6.4 |
| 35.2 | 110 | 5.3 |
| 36.1 | 173 | 8.3 |
| 36.8 | 303 | 14.6 |
| 37.6 | 86 | 4.1 |
| 38.4 | 158 | 7.6 |
| 39.1 | 100 | 4.8 |
| 39.9 | 70 | 3.4 |

TABLE 3-continued

XRPD Peak Data for the Salicylic Acid Salt

| 2-Theta | Height | I % |
|---|---|---|
| 40.7 | 76 | 3.7 |
| 41.5 | 61 | 2.9 |
| 42.1 | 83 | 4 |
| 42.8 | 80 | 3.8 |

Example 5

Preparation of the Hydrochloric Acid Salt

Hydrochloric acid (0.25 mL, 1 M in 2-propanol/water, 0.25 mmol, 1.25 eq.) was added to a solution of Compound 1 (94.49 mg, 0.194 mmol) in a mixture of dichloromethane (1.5 mL) and methanol (1.0 mL). The reaction mixture was stirred to give a clear solution. The solution was evaporated to remove dichloromethane to give a slurry. The slurry was stirred for 50 min at 50° C., and then cooled to room temperature and stirred overnight. The slurry was filtered and the solids washed with methyl t-butyl ether. The solids were dried under vacuum at 36-40° C. overnight (16 h) to provide Compound 1 hydrochloric acid salt (88.2 mg, 87% yield).

The crystallinity of Compound 1 hydrochloride was confirmed by XRPD (FIG. 13) and further supported by DSC (FIG. 14). FIG. 15 shows the result of TGA. Analytical data collected on the product, including characterization by XRPD, DSC, and TGA were performed as described in Example 1. The hydrochloric acid salt exhibits a DSC thermogram having endothermic peaks at temperatures of about 120° C., 189° C., and 274° C.

TABLE 4

XRPD Peak Data for the Hydrochloric Acid Salt

| 2-Theta | Height | I % |
|---|---|---|
| 4.2 | 176 | 26 |
| 6.8 | 454 | 67.2 |
| 9.2 | 196 | 29 |
| 12.9 | 374 | 55.3 |
| 15.6 | 336 | 49.7 |
| 16.1 | 226 | 33.4 |
| 17.2 | 128 | 18.9 |
| 17.9 | 63 | 9.3 |
| 19.7 | 108 | 16 |
| 20.6 | 109 | 16.1 |
| 21.6 | 234 | 34.6 |
| 22.2 | 330 | 48.8 |
| 22.7 | 100 | 14.8 |
| 23.4 | 210 | 31.1 |
| 23.9 | 76 | 11.2 |
| 24.7 | 374 | 55.3 |
| 26.0 | 115 | 17 |
| 26.5 | 676 | 100 |
| 27.4 | 245 | 36.2 |
| 28.6 | 176 | 26 |
| 29.6 | 98 | 14.5 |
| 31.2 | 94 | 13.9 |
| 32.4 | 90 | 13.3 |
| 34.0 | 55 | 8.1 |
| 34.5 | 80 | 11.8 |
| 37.0 | 55 | 8.1 |
| 38.1 | 56 | 8.3 |
| 38.8 | 53 | 7.8 |
| 40.9 | 63 | 9.3 |

Example 6

Preparation of the Hydrobromic Acid Salt

Hydrobromic acid (48% in water, 0.084 mL, 1.2 equiv) was added to a solution of Compound 1 (0.3 g) in a mixture of dichloromethane (3.6 mL) and methanol (4.0 mL). The reaction was heated to 50° C., distilling off the dichloromethane. The mixture was stirred at 50° C. for about 1 h. The mixture was cooled to room temperature and stirred for another 1.5 h. The reaction was filtered and the solids were washed with methyl t-butyl ether (1.5 mL). The solid was dried at 40° C. under vacuum overnight to provide Compound 1 hydrobromic acid salt (0.32 g, 91.4% yield).

Figure 16:
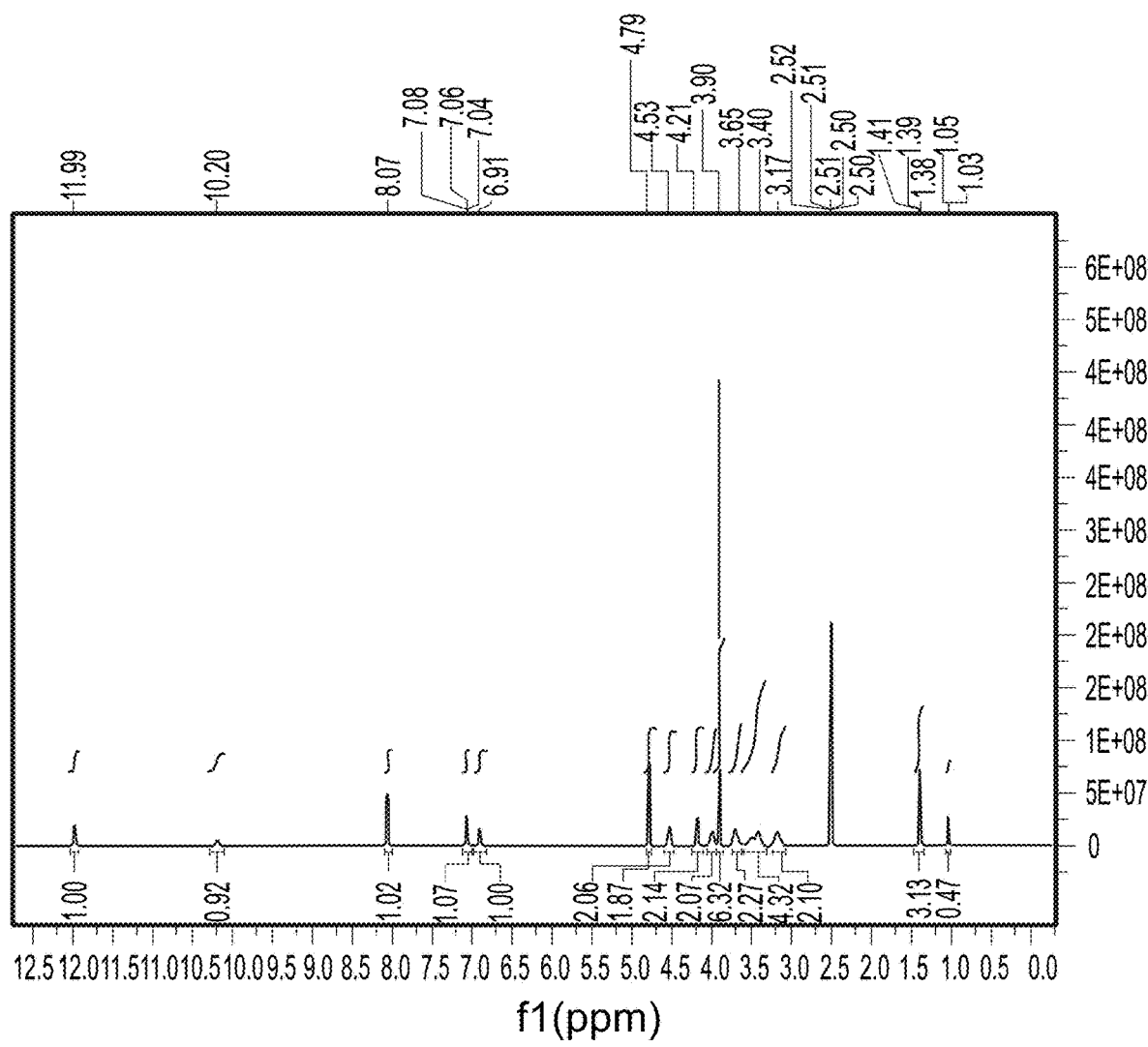
FIG. 16 shows the $^1$H NMR of Compound 1 hydrobromic acid salt.

FIG. 16 shows the $^1$H NMR of Compound 1 hydrobromic acid salt. The crystallinity of Compound 1 hydrobromic acid salt was confirmed by XRPD (FIG. 17). FIG. 18 shows the DSC thermogram of Compound 1 hydrobromic acid salt. FIG. 19 shows the TGA thermogram of Compound 1 hydrobromic acid salt. Analytical data collected on the product, including characterization by XRPD and DSC were performed as described in Example 1. The hydrobromic acid salt exhibits a DSC thermogram having endothermic peaks at temperatures of about 84° C. and about 235° C.

TABLE 5

XRPD Peak Data for the Hydrobromic Acid Salt

| 2-Theta | Height | I % |
|---|---|---|
| 6.8 | 95.0 | 20.0 |
| 7.3 | 474.0 | 100.0 |
| 9.3 | 125.0 | 26.4 |
| 13.9 | 76.0 | 16.0 |
| 14.5 | 125.0 | 26.4 |
| 16.1 | 289.0 | 61.0 |
| 21.5 | 256.0 | 54.0 |
| 23.3 | 128.0 | 27.0 |
| 23.9 | 64.0 | 13.5 |
| 25.3 | 73.0 | 15.4 |
| 28.1 | 423.0 | 89.2 |
| 29.7 | 58.0 | 12.2 |
| 30.8 | 79.0 | 16.7 |

Example 7

Preparation of the Fumaric Acid Salt

Fumaric acid (0.086 g, 1.2 equiv) was added to a solution of Compound 1 (0.3 g) in a mixture of dichloromethane (3.6 mL) and methanol (4.0 mL). The reaction was heated to 50° C., distilling off the dichloromethane. The mixture was stirred at 50° C. for about 1 h. The mixture was cooled to room temperature and stirred for another 1.5 h. The reaction was filtered and the solids were washed with methyl t-butyl ether (1.5 mL). The solid was dried at 40° C. under vacuum overnight to provide Compound 1 fumaric acid salt (0.34 g, 91.6% yield).

Figure 20:
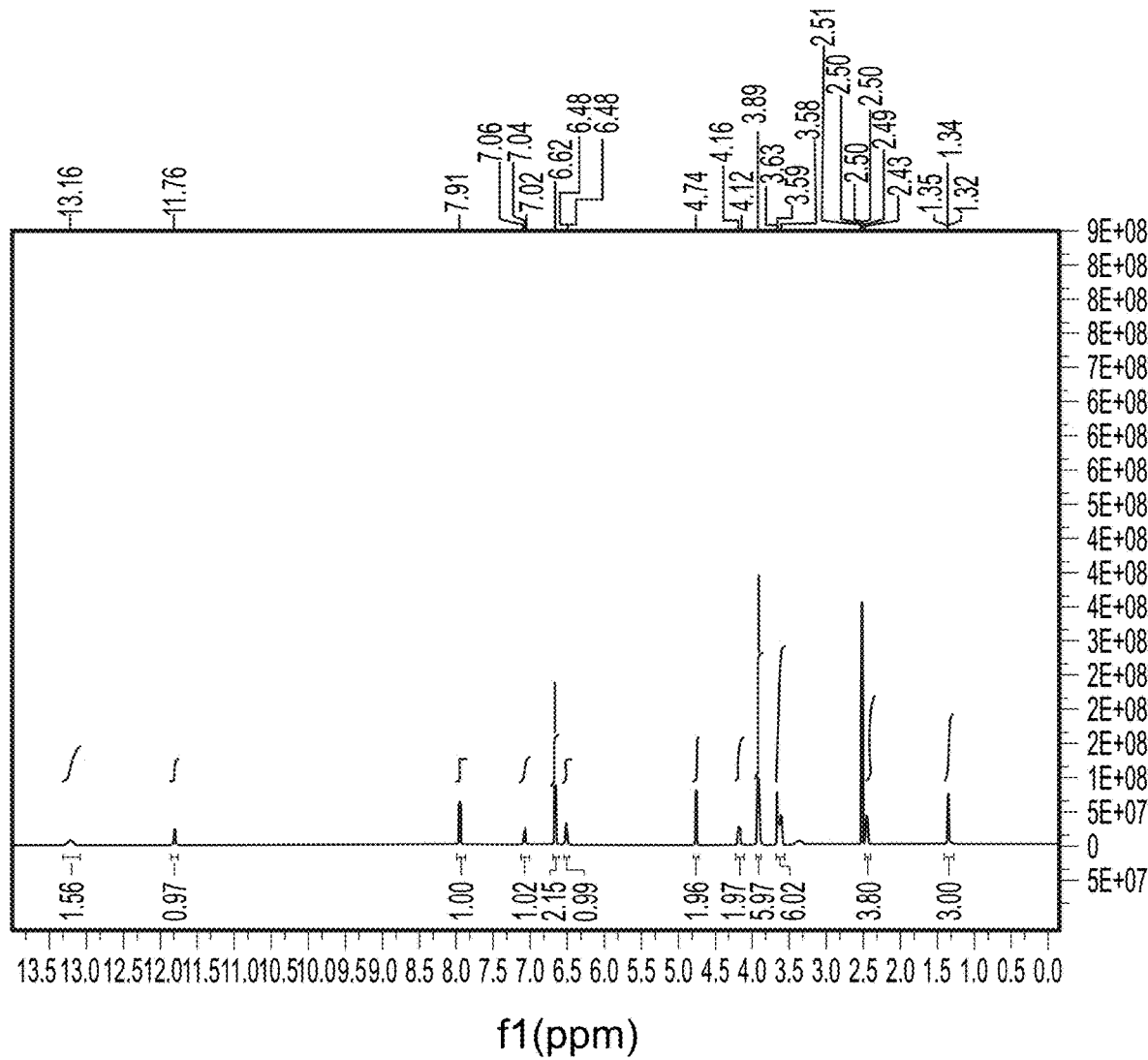
FIG. 20 shows the $^1$H NMR of Compound 1 fumaric acid salt.

FIG. 20 shows the $^1$H NMR of Compound 1 fumaric acid salt. FIG. 21 shows the XRPD pattern of Compound 1 fumaric acid salt. FIG. 22 shows the DSC thermogram of Compound 1 fumaric acid salt. FIG. 23 shows the TGA thermogram of Compound 1 fumaric acid salt. Analytical data collected on the product, including characterization by XRPD and DSC were performed as described in Example 1. The fumaric acid salt exhibits a DSC thermogram having an endothermic peak at a temperature of about 214° C.

TABLE 6

XRPD Peak Data for the Fumaric Acid Salt

| 2-Theta | Height | I % |
|---|---|---|
| 6.3 | 147.0 | 26.0 |
| 7.1 | 461.0 | 81.6 |
| 7.8 | 379.0 | 67.1 |
| 9.7 | 85.0 | 15.0 |
| 12.7 | 220.0 | 38.9 |
| 15.7 | 46.0 | 8.1 |
| 16.5 | 81.0 | 14.3 |
| 18.8 | 306.0 | 54.2 |
| 19.6 | 89.0 | 15.8 |
| 21.2 | 146.0 | 25.8 |
| 21.8 | 49.0 | 8.7 |
| 22.6 | 103.0 | 18.2 |
| 23.5 | 287.0 | 50.8 |
| 25.1 | 270.0 | 47.8 |
| 25.5 | 565.0 | 100.0 |
| 25.9 | 383.0 | 67.8 |
| 27.6 | 46.0 | 8.1 |
| 29.1 | 38.0 | 6.7 |

Example 8

Preparation of the Phosphoric Acid Salt

Phosphoric acid (85% in water, 0.051 mL, 1.2 equiv) was added to a solution of Compound 1 (0.3 g) in a mixture of dichloromethane (3.6 mL) and methanol (4.0 mL). The reaction was heated to 50° C., distilling off the dichloromethane. The mixture was stirred at 50° C. for about 1 h. The mixture was cooled to room temperature and stirred for another 1.5 h. The reaction was filtered and the solids were washed with methyl t-butyl ether (1.5 mL). The solid was dried at 40° C. under vacuum overnight to provide Compound 1 phosphoric acid salt (0.35 g, 97.2% yield).

Figure 24:
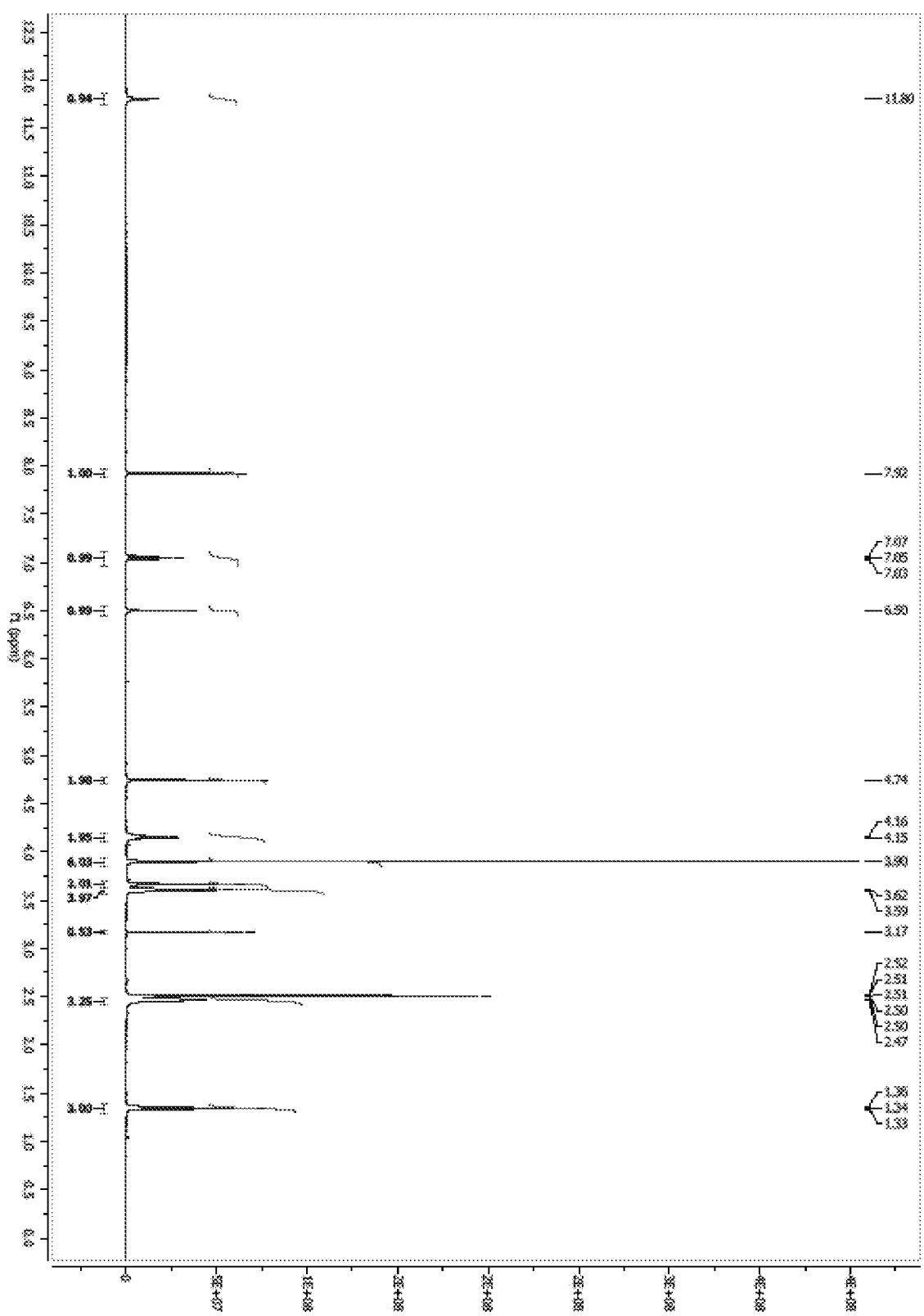
FIG. 24 shows the $^1$H NMR of Compound 1 phosphoric acid salt.

FIG. 24 shows the $^1$H NMR of Compound 1 phosphoric acid salt. FIG. 25 shows the XRPD pattern of Compound 1 phosphoric acid salt. FIG. 26 shows the DSC thermogram of Compound 1 phosphoric acid salt. FIG. 27 shows the TGA thermogram of Compound 1 phosphoric acid salt. Analytical data collected on the product, including characterization by XRPD and DSC were performed as described in Example 1. The phosphoric acid salt exhibits a DSC thermogram having endothermic peaks at temperatures of about 215° C. and about 221° C.

TABLE 7

XRPD Peak Data for the Phosphoric Acid Salt

| 2-Theta | Height | I % |
|---|---|---|
| 3.9 | 530.0 | 100.0 |
| 7.7 | 313.0 | 59.1 |
| 10.4 | 69.0 | 13.0 |
| 12.6 | 60.0 | 11.3 |
| 14.3 | 75.0 | 14.2 |
| 16.0 | 61.0 | 11.5 |
| 16.9 | 129.0 | 24.3 |
| 19.7 | 330.0 | 62.3 |
| 20.8 | 302.0 | 57.0 |
| 23.2 | 293.0 | 55.3 |
| 24.1 | 46.0 | 8.7 |
| 25.1 | 88.0 | 16.6 |
| 26.1 | 79.0 | 14.9 |
| 27.2 | 144.0 | 27.2 |
| 28.6 | 87.0 | 16.4 |
| 30.0 | 85.0 | 16.0 |

Example 9

Preparation of the Benzenesulfonic Acid Salt

Benzenesulfonic acid (94%, 0.124 g, 1.2 equiv) was added to a solution of Compound 1 (0.3 g) in a mixture of dichloromethane (3.6 mL) and methanol (4.0 mL). The reaction was heated to 50° C., distilling off the dichloromethane. The mixture was stirred at 50° C. for about 1 h. The mixture was cooled to room temperature and stirred for another 1.5 h. The reaction was filtered and the solids were washed with methyl t-butyl ether (1.5 mL). The solid was dried at 40° C. under vacuum overnight to provide Compound 1 benzenesulfonic acid salt (0.28 g, 70.5% yield).

Figure 28:
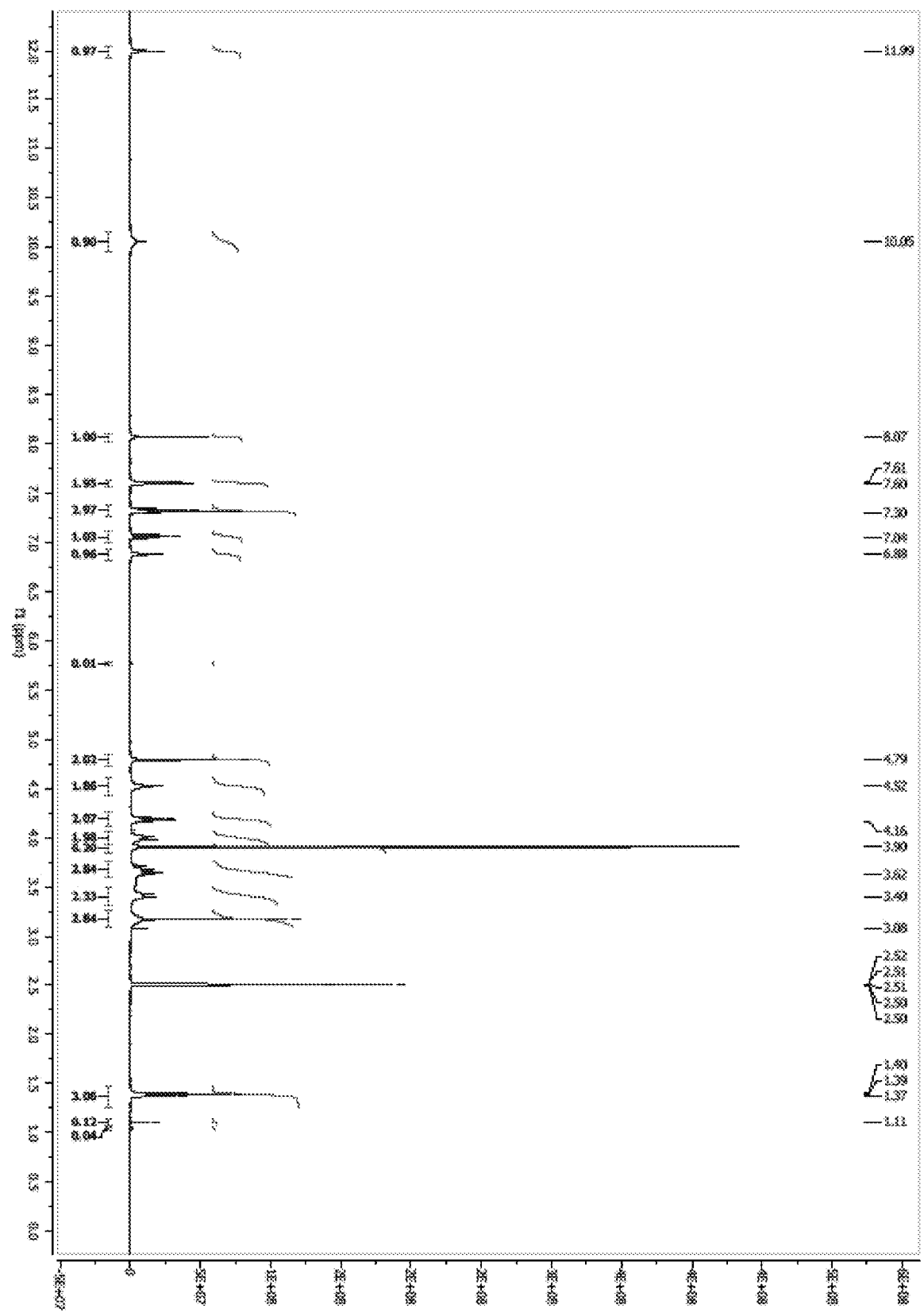
FIG. 28 shows the $^1$H NMR of Compound 1 benzenesulfonic acid salt.

FIG. 28 shows the $^1$H NMR of Compound 1 benzenesulfonic acid salt. FIG. 29 shows the XRPD pattern of a solid form of Compound 1 benzenesulfonic acid salt. FIG. 30 shows the DSC thermogram of a solid form of Compound 1 benzenesulfonic acid salt. FIG. 31 shows the TGA thermogram of a solid form of Compound 1 benzenesulfonic acid salt. Analytical data collected on the product, including characterization by XRPD, DSC, and TGA were performed as described in Example 1. The benzenesulfonic acid salt exhibits a DSC thermogram having endothermic peaks at temperatures of about 105° C., about 190° C., about 222° C., and about 241° C.

TABLE 8

XRPD Peak Data for the Benzenesulfonic Acid Salt

| 2-Theta | Height | I % |
|---|---|---|
| 3.8 | 52.0 | 11.9 |
| 6.7 | 55.0 | 12.6 |
| 7.4 | 438.0 | 100.0 |
| 9.8 | 165.0 | 37.7 |
| 11.0 | 183.0 | 41.8 |
| 11.6 | 46.0 | 10.5 |
| 13.0 | 105.0 | 24.0 |
| 13.4 | 101.0 | 23.1 |
| 15.1 | 78.0 | 17.8 |
| 16.0 | 95.0 | 21.7 |
| 16.9 | 105.0 | 24.0 |
| 18.3 | 88.0 | 20.1 |
| 19.4 | 336.0 | 76.7 |
| 20.6 | 125.0 | 28.5 |
| 21.0 | 67.0 | 15.3 |
| 22.3 | 328.0 | 74.9 |
| 23.6 | 129.0 | 29.5 |
| 24.3 | 74.0 | 16.9 |
| 25.6 | 124.0 | 28.3 |
| 26.1 | 176.0 | 40.2 |
| 26.9 | 61.0 | 13.9 |
| 29.4 | 61.0 | 13.9 |
| 30.1 | 82.0 | 18.7 |
| 37.5 | 50.0 | 11.4 |
| 39.9 | 33.0 | 7.5 |

Example 10

Preparation of the Ethanesulfonic Acid Salt

Ethanesulfonic acid (95%, 0.063 mL, 1.2 equiv) was added to a solution of Compound 1 (0.3 g) in a mixture of dichloromethane (3.6 mL) and methanol (4.0 mL). The reaction was heated to 50° C., distilling off the dichloromethane. Isopropyl alcohol (3 mL) was added. The mixture was stirred at 50° C. for about 1 h. The mixture was cooled to room temperature and stirred for another 1.5 h. The reaction was filtered and the solids were washed with methyl t-butyl ether (1.5 mL). The solid was dried at 40° C. under vacuum overnight to provide Compound 1 ethanesulfonic acid salt (0.27 g, 73.4% yield).

Figure 32:
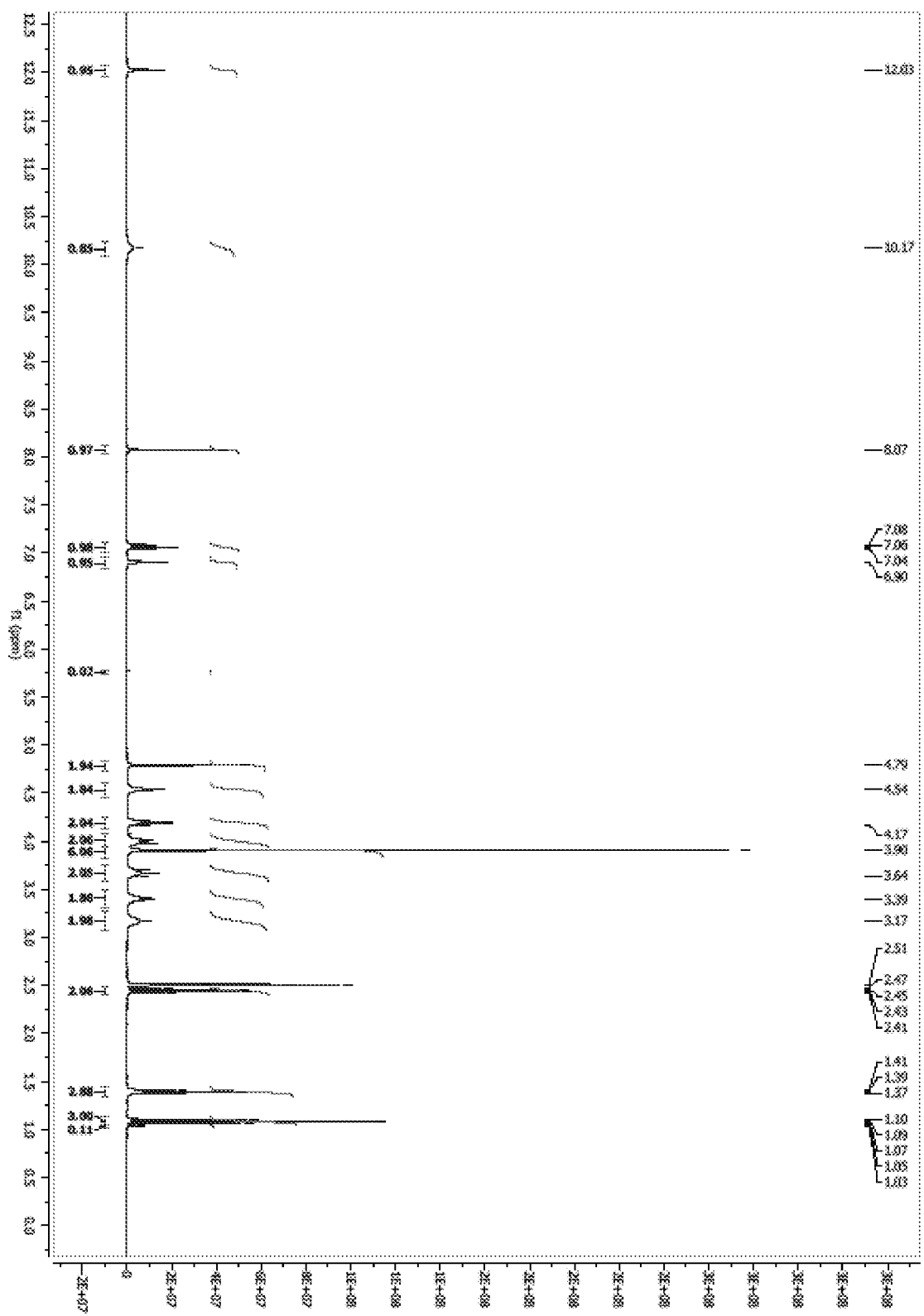
FIG. 32 shows the $^1$H NMR of Compound 1 ethanesulfonic acid salt.

FIG. 32 shows the $^1$H NMR of Compound 1 ethanesulfonic acid salt. FIG. 33 shows the XRPD pattern of Compound 1 ethanesulfonic acid salt. FIG. 34 shows the DSC thermogram of a solid form of Compound 1 ethanesulfonic acid salt. FIG. 35 shows the TGA thermogram of a solid form of Compound 1 ethanesulfonic acid salt. Analytical data collected on the product, including characterization by)(RFD, DSC, and TGA were performed as described in Example 1. The ethanesulfonic acid salt exhibits a DSC thermogram having an endothermic peak at a temperature of about 227° C.

TABLE 9

XRPD of the Ethanesulfonic Acid Salt

| 2-Theta | Height | I % |
| --- | --- | --- |
| 4.5 | 276.0 | 35.7 |
| 7.3 | 553.0 | 71.4 |
| 9.0 | 774.0 | 100.0 |
| 12.4 | 38.0 | 4.9 |
| 13.4 | 43.0 | 5.6 |
| 14.7 | 275.0 | 35.5 |
| 15.9 | 359.0 | 46.4 |
| 18.0 | 267.0 | 34.5 |
| 18.9 | 320.0 | 41.3 |
| 19.4 | 156.0 | 20.2 |
| 20.3 | 116.0 | 15.0 |
| 21.4 | 248.0 | 32.0 |
| 22.1 | 246.0 | 31.8 |
| 22.5 | 38.0 | 4.9 |
| 23.3 | 118.0 | 15.2 |
| 23.8 | 63.0 | 8.1 |
| 24.4 | 37.0 | 4.8 |
| 25.3 | 275.0 | 35.5 |
| 27.2 | 144.0 | 18.6 |
| 27.7 | 199.0 | 25.7 |
| 29.5 | 53.0 | 6.8 |
| 30.6 | 42.0 | 5.4 |
| 31.6 | 109.0 | 14.1 |
| 32.3 | 77.0 | 9.9 |
| 35.4 | 53.0 | 6.8 |
| 36.9 | 43.0 | 5.6 |
| 39.9 | 34.0 | 4.4 |
| 41.1 | 64.0 | 8.3 |
| 42.8 | 48.0 | 6.2 |
| 44.1 | 51.0 | 6.6 |

Example 11

Preparation of the Maleic Acid Salt

Maleic acid (0.086 g, 1.2 equiv) was added to a solution of Compound 1 (0.3 g) in a mixture of dichloromethane (3.6 mL) and methanol (4.0 mL). The reaction was heated to 50° C., distilling off the dichloromethane. The mixture was stirred at 50° C. for about 1 h. The mixture was cooled to room temperature and stirred for another 1.5 h. The reaction was filtered and the solids were washed with methyl t-butyl ether (1.5 mL). The solid was dried at 40° C. under vacuum overnight to provide Compound 1 maleic acid salt (0.38 g, 102.7% yield [product may contain residual solvent]).

Figure 36:
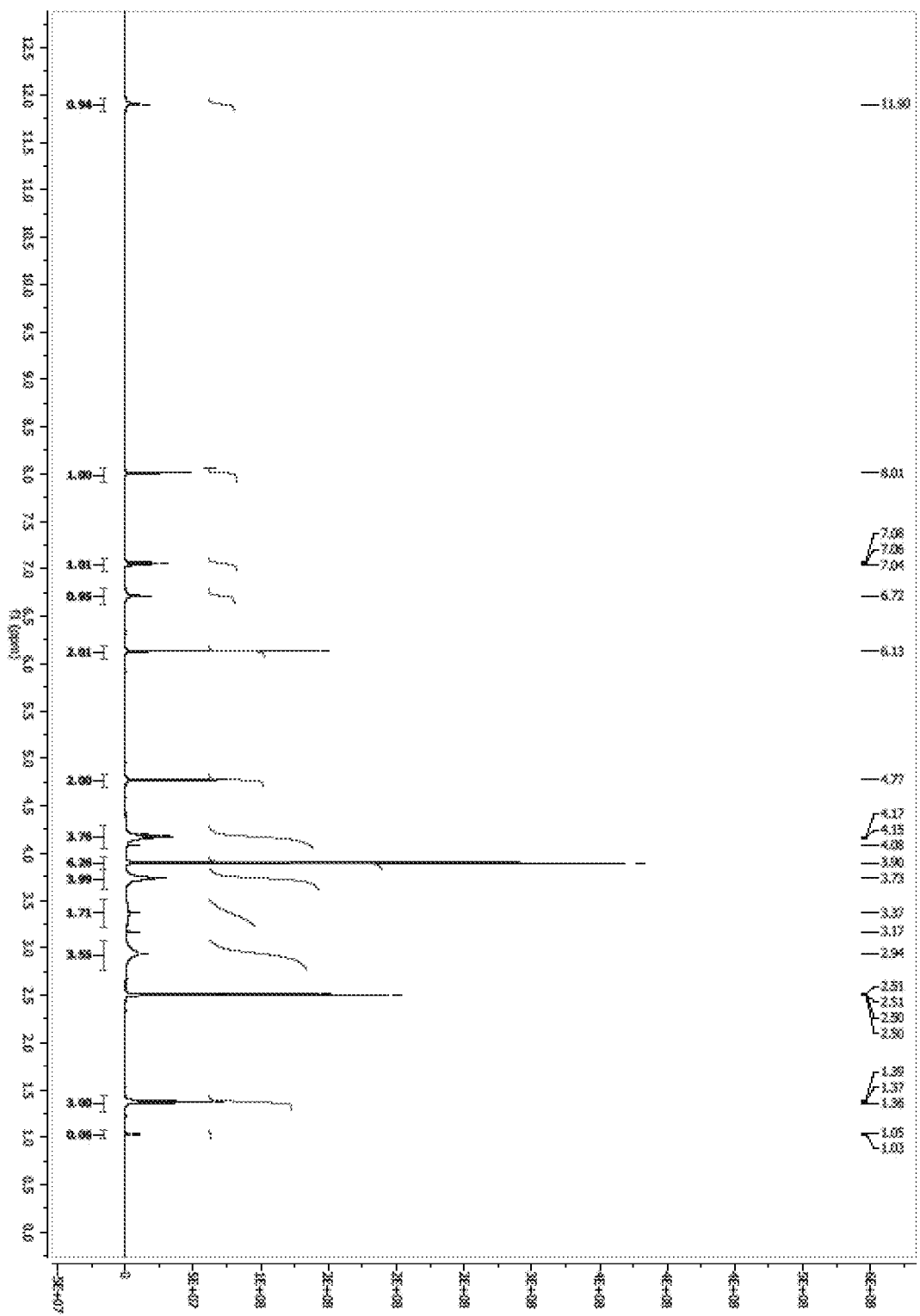
FIG. 36 shows the $^1$H NMR of Compound 1 maleic acid salt.

FIG. 36 shows the $^1$H NMR of Compound 1 maleic acid salt. FIG. 37 shows the XRPD pattern of Compound 1 maleic acid salt. FIG. 38 shows the DSC thermogram of Compound 1 maleic acid salt. FIG. 39 shows the TGA thermogram of Compound 1 maleic acid salt. Analytical data collected on the product, including characterization by XRPD, DSC, and TGA were performed as described in Example 1. The maleic acid salt exhibits a DSC thermogram having endothermic peaks at temperatures of about 205° C. and 280° C.

TABLE 10

XRPD Peak Data for the Maleic Acid Salt

| 2-Theta | Height | I % |
| --- | --- | --- |
| 6.6 | 1975.0 | 100.0 |
| 8.4 | 106.0 | 5.4 |
| 8.9 | 87.0 | 4.4 |
| 11.8 | 65.0 | 3.3 |
| 12.7 | 137.0 | 6.9 |
| 13.1 | 284.0 | 14.4 |
| 13.5 | 267.0 | 13.5 |
| 14.6 | 148.0 | 7.5 |
| 15.3 | 162.0 | 8.2 |
| 16.1 | 45.0 | 2.3 |
| 19.1 | 38.0 | 1.9 |
| 19.7 | 149.0 | 7.5 |
| 21.2 | 205.0 | 10.4 |
| 22.1 | 133.0 | 6.7 |
| 23.0 | 161.0 | 8.2 |
| 24.3 | 98.0 | 5.0 |
| 25.7 | 421.0 | 21.3 |
| 26.4 | 425.0 | 21.5 |
| 26.8 | 229.0 | 11.6 |
| 28.2 | 116.0 | 5.9 |
| 30.4 | 60.0 | 3.0 |
| 36.9 | 37.0 | 1.9 |

Example 12

Preparation of the Adipic Acid Salt

The reaction of Compound 1 with adipic acid gave the corresponding adipate. Analytical data collected on the product were performed as described in Example 1. FIG. 26 shows the XRPD pattern of a solid form of Compound 1 adipic acid salt. FIG. 27 shows the DSC thermogram of a solid form of Compound 1 adipic acid salt.

TABLE 11

XRPD Peak Data for the Adipic Acid Salt

| 2-Theta | Height | I % |
| --- | --- | --- |
| 3.3 | 72 | 3.8 |
| 6.7 | 163 | 8.6 |
| 7.5 | 62 | 3.3 |
| 8.9 | 417 | 22 |
| 9.4 | 88 | 4.6 |
| 10.4 | 82 | 4.3 |
| 12.4 | 93 | 4.9 |
| 12.7 | 116 | 6.1 |
| 13.4 | 133 | 7 |
| 14.8 | 130 | 6.9 |
| 15.2 | 149 | 7.9 |
| 16.2 | 337 | 17.8 |
| 16.6 | 83 | 4.4 |
| 17.4 | 103 | 5.4 |
| 17.8 | 512 | 27 |
| 18.4 | 183 | 9.7 |
| 19.0 | 115 | 6.1 |
| 19.9 | 908 | 47.9 |
| 21.4 | 1894 | 100 |
| 22.0 | 246 | 13 |
| 22.5 | 241 | 12.7 |
| 22.7 | 176 | 9.3 |
| 23.9 | 279 | 14.7 |
| 24.4 | 208 | 11 |
| 25.1 | 128 | 6.8 |

TABLE 11-continued

XRPD Peak Data for the Adipic Acid Salt

| 2-Theta | Height | I % |
|---|---|---|
| 25.6 | 314 | 16.6 |
| 26.2 | 124 | 6.5 |
| 26.6 | 135 | 7.1 |
| 26.9 | 124 | 6.5 |
| 28.6 | 111 | 5.9 |
| 29.0 | 78 | 4.1 |
| 29.4 | 88 | 4.6 |
| 30.4 | 91 | 4.8 |
| 31.0 | 82 | 4.3 |
| 32.3 | 48 | 2.5 |
| 37.9 | 51 | 2.7 |
| 40.1 | 43 | 2.3 |

Example A

FGFR Enzymatic Assay

The inhibitor potency of Compound 1 was measured in an enzyme assay that measures peptide phosphorylation using FRET measurements to detect product formation. Compound 1 was serially diluted in DMSO and a volume of 0.5 µL was transferred to the wells of a 384-well plate. For FGFR3, a 10 µL volume of FGFR3 enzyme (Millipore) diluted in assay buffer (50 mM HEPES, 10 mM $MgCl_2$, 1 mM EGTA, 0.01% Tween-20, 5 mM DTT, pH 7.5) was added to the plate and pre-incubated for 5-10 minutes. Appropriate controls (enzyme blank and enzyme with no inhibitor) were included on the plate. The assay was initiated by the addition of a 10 solution containing biotinylated EQEDEPEGDYFEWLE peptide substrate (SEQ ID NO: 1) and ATP (final concentrations of 500 nM and 140 µM respectively) in assay buffer to the wells. The plate was incubated at 25° C. for 1 hr. The reactions were ended with the addition of 10 µL/well of quench solution (50 mM Tris, 150 mM NaCl, 0.5 mg/mL BSA, pH 7.8; 30 mM EDTA with Perkin Elmer Lance Reagents at 3.75 nM Eu-antibody PY20 and 180 nM APC-Streptavidin). The plate was allowed to equilibrate for ~1 hr before scanning the wells on a PheraStar plate reader (BMG Labtech).

FGFR1 and FGFR2 were measured under equivalent conditions with the following changes in enzyme and ATP concentrations: FGFR1, 0.02 nM and 210 respectively and FGFR2, 0.01 nM and 100 respectively. The enzymes were purchased from Millipore or Invitrogen.

GraphPad prism3 was used to analyze the data. The $IC_{50}$ values were derived by fitting the data to the equation for a sigmoidal dose-response with a variable slope. Y=Bottom+ (Top−Bottom)/(1+10^((Log $IC_{50}$−X)*HillSlope)) where X is the logarithm of concentration and Y is the response. Compounds having an $IC_{50}$ of 1 µM or less are considered active.

Compound 1 of the invention were found to be inhibitors of one or more of FGFR1, FGFR2, and FGFR3 according to the above-described assay. $IC_{50}$ data is provided below in Table 12. The symbol "+" indicates an $IC_{50}$ less than 100 nM and the symbol "++" indicates an $IC_{50}$ of 100 to 500 nM.

TABLE 12

| | FGFR1 IC50 (nM) | FGFR2 IC50 (nM) | FGFR3 IC50 (nM) |
|---|---|---|---|
| Compound 1 | + | + | + |

Example B

FGFR Cell Proliferation/Survival Assays

The ability of the example compounds to inhibit the growth of cells dependent on FGFR signaling for survival was measured using viability assays. A recombinant cell line over-expressing human FGFR3 was developed by stable transfection of the mouse pro-B Ba/F3 cells (obtained from the Deutsche Sammlung von Mikroorganismen and Zellkulturen) with a plasmid encoding the full length human FGFR3. Cells were sequentially selected for puromycin resistance and proliferation in the presence of heparin and FGF1. A single cell clone was isolated and characterized for functional expression of FGFR3. This Ba/F3-FGFR3 clone is used in cell proliferation assays, and compounds are screened for their ability to inhibit cell proliferation/survival. The Ba/F3-FGFR3 cells are seeded into 96 well, black cell culture plates at 3500 cells/well in RPMI1640 media containing 2% FBS, 20 µg/mL Heparin and 5 ng/mL FGF1. The cells were treated with 10 µL of 10× concentrations of serially diluted compounds (diluted with medium lacking serum from 5 mM DSMO dots) to a final volume of 100 µL/well. After 72 hour incubation, 100 µL of Cell Titer Glo® reagent (Promega Corporation) that measures cellular ATP levels is added to each well. After 20 minute incubation with shaking, the luminescence is read on a plate reader. The luminescent readings are converted to percent inhibition relative to DMSO treated control wells, and the $IC_{50}$ values are calculated using GraphPad Prism software by fitting the data to the equation for a sigmoidal dose-response with a variable slope. Compounds having an $IC_{50}$ of 10 µM or less are considered active. Cell lines representing a variety of tumor types including KMS-11 (multiple myeloma, FGFR3 translocation), RT112 (bladder cancer, FGFR3 overexpression), KatoIII (gastric cancer, FGFR2 gene amplification), and H-1581 (lung, FGFR1 gene amplification) are used in similar proliferation assays. In some experiments, MTS reagent, Cell Titer 96® AQueous One Solution Reagent (Promega Corporation) is added to a final concentration of 333 µg/mL in place Cell Titer Glo and read at 490/650 nm on a plate reader. Compounds having an $IC_{50}$ of 5 µM or less are considered active.

Example C

Cell-Based FGFR Phosphorylation Assays

The inhibitory effect of compounds on FGFR phosphorylation in relevant cell lines (Ba/F3-FGFR3, KMS-11, RT112, KatoIII, H-1581 cancer cell lines and HUVEC cell line) can be assessed using immunoassays specific for FGFR phosphorylation. Cells are starved in media with reduced serum (0.5%) and no FGF1 for 4 to 18 h depending upon the cell line then treated with various concentrations of individual inhibitors for 1-4 hours. For some cell lines, such as Ba/F3-FGFR3 and KMS-11, cells are stimulated with Heparin (20 µg/mL) and FGF1 (10 ng/mL) for 10 min. Whole cell protein extracts are prepared by incubation in lysis buffer with protease and phosphatase inhibitors [50 mM HEPES (pH 7.5), 150 mM NaCl, 1.5 mM $MgCl_2$, 10% Glycerol, 1% Triton X-100, 1 mM sodium orthovanadate, 1 mM sodium fluoride, aprotinin (2 µg/mL), leupeptin (2 µg/mL), pepstatin A (2 µg/mL), and phenylmethylsulfonyl fluoride (1 mM)] at 4° C. Protein extracts are cleared of cellular debris by centrifugation at 14,000×g for 10 minutes and quantified using the BCA (bicinchoninic acid) microplate assay reagent (Thermo Scientific).

Phosphorylation of FGFR receptor in protein extracts was determined using immunoassays including western blotting, enzyme-linked immunoassay (ELISA) or bead-based immunoassays (Luminex). For detection of phosphorylated FGFR2, a commercial ELISA kit DuoSet IC Human Phospho-FGF R2a ELISA assay (R&D Systems, Minneapolis, MN) can be used. For the assay KatoIII cells are plated in 0.2% FBS supplemented Iscove's medium (50,000 cells/well/per 100 μL) into 96-well flat-bottom tissue culture treated plates (Corning, Corning, NY), in the presence or absence of a concentration range of test compounds and incubated for 4 hours at 37° C., 5% $CO_2$. The assay is stopped with addition of 200 μL of cold PBS and centrifugation. The washed cells are lysed in Cell Lysis Buffer (Cell Signaling, #9803) with Protease Inhibitor (Calbiochem, #535140) and PMSF (Sigma, #P7626) for 30 min on wet ice. Cell lysates were frozen at −80° C. before testing an aliquot with the DuoSet IC Human Phospho-FGF R2α ELISA assay kit. GraphPad prism3 was used to analyze the data. The $IC_{50}$ values were derived by fitting the data to the equation for a sigmoidal dose-response with a variable slope.

For detection of phosphorylated FGFR3, a bead based immunoassay was developed. An anti-human FGFR3 mouse mAb (R&D Systems, cat #MAB7661) was conjugated to Luminex MAGplex microspheres, bead region 20 and used as the capture antibody. RT-112 cells were seeded into multi-well tissue culture plates and cultured until 70% confluence. Cells were washed with PBS and starved in RPMI+0.5% FBS for 18 hr. The cells were treated with 10 of 10× concentrations of serially diluted compounds for 1 hr at 37° C., 5% $CO_2$ prior to stimulation with 10 ng/mL human FGF1 and 20 μg/mL Heparin for 10 min. Cells were washed with cold PBS and lysed with Cell Extraction Buffer (Invitrogen) and centrifuged. Clarified supernatants were frozen at −80° C. until analysis.

For the assay, cell lysates are diluted 1:10 in Assay Diluent and incubated with capture antibody-bound beads in a 96-well filter plate for 2 hours at room temperature on a plate shaker. Plates are washed three times using a vacuum manifold and incubated with anti-phospho-FGF R1-4 (Y653/Y654) rabbit polyclonal antibody (R&D Systems cat #AF3285) for 1 hour at RT with shaking. Plates are washed three times. The diluted reporter antibody, goat anti-rabbit-RPE conjugated antibody (Invitrogen Cat. #LHB0002) is added and incubated for 30 minutes with shaking. Plates are washed three times. The beads are suspended in wash buffer with shaking at room temperature for 5 minutes and then read on a Luminex 200 instrument set to count 50 events per sample, gate settings 7500-13500. Data is expressed as mean fluorescence intensity (MFI). MFI from compound treated samples are divided by MFI values from DMSO controls to determine the percent inhibition, and the $IC_{50}$ values are calculated using the GraphPad Prism software. Compounds having an $IC_{50}$ of 1 μM or less are considered active.

Example D

FGFR Cell-Based Signaling Assays

Activation of FGFR leads to phosphorylation of Erk proteins. Detection of pErk is monitored using the Cellu'Erk HTRF (Homogeneous Time Resolved Fluorescence) Assay (CisBio) according to the manufacturer's protocol. KMS-11 cells are seeded into 96-well plates at 40,000 cells/well in RPMI medium with 0.25% FBS and starved for 2 days. The medium is aspirated and cells are treated with 30 μL of 1× concentrations of serially diluted compounds (diluted with medium lacking serum from 5 mM DSMO dots) to a final volume of 30 μL/well and incubated for 45 min at room temperature. Cells are stimulated by addition of 10 μL of Heparin (100 μg/mL) and FGF1 (50 ng/mL) to each well and incubated for 10 min at room temperature. After lysis, an aliquot of cell extract is transferred into 384-well low volume plates, and 4 μL of detection reagents are added followed by incubation for 3 hr at room temperature. The plates are read on a PheraStar instrument with settings for HTRF. The normalized fluorescence readings are converted to percent inhibition relative to DMSO treated control wells, and the $IC_{50}$ values are calculated using the GraphPad Prism software. Compounds having an $IC_{50}$ of 1 μM or less are considered active.

Example E

VEGFR2 Kinase Assay

40 μL Enzyme reactions are run in black 384 well polystyrene plates for 1 hour at 25° C. Wells are dotted with 0.8 μL of test compound in DMSO. The assay buffer contains 50 mM Tris, pH 7.5, 0.01% Tween-20, 10 mM $MgCl_2$, 1 mM EGTA, 5 mM DTT, 0.5 μM Biotin-labeled EQEDEPEGDYFEWLE peptide substrate (SEQ ID NO: 1), 1 mM ATP, and 0.1 nM enzyme (Millipore catalogue number 14-630). Reactions are stopped by addition of 20 μL Stop Buffer (50 mM Tris, pH=7.8, 150 mM NaCl, 0.5 mg/mL BSA, 45 mM EDTA) with 225 nM LANCE Streptavidin Surelight® APC (PerkinElmer catalogue number CR130-100) and 4.5 nM LANCE Eu-W1024 anti phosphotyrosine (PY20) antibody (PerkinElmer catalogue number AD0067). After 20 minutes of incubation at room temperature, the plates are read on a PheraStar FS plate reader (BMG Labtech). $IC_{50}$ values can be calculated using GraphPad Prism by fitting the data to the equation for a sigmoidal dose-response with a variable slope. Compounds having an $IC_{50}$ of 1 μM or less are considered active.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A salt which is an acid salt of 3-(2,6-difluoro-3,5-dimethoxyphenyl)-1-ethyl-8-(morpholin-4-ylmethyl)-1,3,4,7-tetrahydro-2H-pyrrolo[3', 2':5,6]pyrido[4,3-d]pyrimidin-2-one, having the structure:

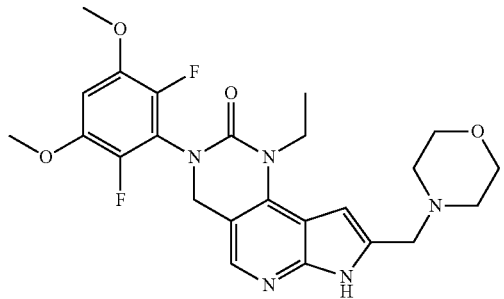 [SMILES: CCN1C(=O)N(c2c(F)c(OC)cc(OC)c2F)Cc2cnc3[nH]c(CN4CCOCC4)cc3c21]

or a hydrate or solvate thereof, wherein the acid is salicylic acid; wherein the salt is crystalline; and wherein the salt has at least one characteristic XRPD peak selected from about 10.4, about 11.8, about 12.1, about 13.4, and about 13.9 degrees 2-theta.

2. The salt of claim 1 which is a hydrate.

3. The salt of claim 1 which is a solvate.

4. The salt of claim 1, having an X-ray powder diffraction pattern with characteristic peaks as substantially shown in FIG. 10.

5. A pharmaceutical composition comprising a salt of claim 1, and a pharmaceutically acceptable carrier or excipient.

6. A solid oral dosage form comprising the pharmaceutical composition of claim 5.

7. The salt of claim 1, having at least two characteristic XRPD peaks selected from about 10.4, about 11.8, about 12.1, about 13.4, and about 13.9 degrees 2-theta.

8. The salt of claim 1, having at least three characteristic XRPD peaks selected from about 10.4, about 11.8, about 12.1, about 13.4, and about 13.9 degrees 2-theta.

9. The salt of claim 1, which exhibits a DSC thermogram having an endothermic peak at a temperature of about 212° C.

10. The salt of claim 1, having a DSC thermogram substantially as depicted in FIG. 11.

* * * * *

SEQUENCE LISTING

```
<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide
```

-continued

```
<400> SEQUENCE: 1

Glu Gln Glu Asp Glu Pro Glu Gly Asp Tyr Phe Glu Trp Leu Glu
1               5                   10                  15
```